US008821889B2

(12) United States Patent
Hennessy et al.

(10) Patent No.: US 8,821,889 B2
(45) Date of Patent: Sep. 2, 2014

(54) WEST NILE VIRUS VACCINE

(75) Inventors: Kristina J. Hennessy, Leawood, KS (US); Phillip Wayne Hayes, Maurice, IA (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 411 days.

(21) Appl. No.: 12/937,504

(22) PCT Filed: Aug. 31, 2009

(86) PCT No.: PCT/US2009/055564
§ 371 (c)(1),
(2), (4) Date: Dec. 7, 2010

(87) PCT Pub. No.: WO2010/025469
PCT Pub. Date: Mar. 4, 2010

(65) Prior Publication Data

US 2011/0159033 A1 Jun. 30, 2011

Related U.S. Application Data

(60) Provisional application No. 61/093,081, filed on Aug. 29, 2008, provisional application No. 61/117,086, filed on Nov. 21, 2008.

(51) Int. Cl.
*A61K 39/295* (2006.01)
*A61K 39/12* (2006.01)
*A61P 37/04* (2006.01)
*A61P 31/14* (2006.01)
*A61P 31/00* (2006.01)
*C12N 7/04* (2006.01)

(52) U.S. Cl.
USPC .................. 424/201.1; 424/202.1; 424/218.1; 435/236

(58) Field of Classification Search
None
See application file for complete search history.

(56) References Cited

U.S. PATENT DOCUMENTS

| | | | | |
|---|---|---|---|---|
| 6,235,282 | B1 | 5/2001 | Riviere et al. | |
| 6,812,219 | B2 | 11/2004 | LaColla et al. | |
| 6,878,372 | B2 | 4/2005 | Monath et al. | |
| 7,101,861 | B2 | 9/2006 | Sommadossi et al. | |
| 7,105,493 | B2 | 9/2006 | Sommadossi et al. | |
| 7,148,206 | B2 | 12/2006 | Sommadossi et al. | |
| 7,153,513 | B2 * | 12/2006 | Chu | 424/218.1 |
| 7,163,929 | B2 | 1/2007 | Sommadossi et al. | |
| 7,227,011 | B2 | 6/2007 | Chang | |
| 7,244,430 | B2 | 7/2007 | Throsby et al. | |
| 7,425,437 | B2 | 9/2008 | UytdeHaag et al. | |
| 7,445,787 | B2 | 11/2008 | Chu | |
| 7,455,842 | B2 | 11/2008 | Yamshchikov | |
| 7,459,163 | B2 | 12/2008 | Yamshchikov | |
| 7,482,017 | B2 | 1/2009 | Barrett et al. | |
| 7,507,415 | B2 | 3/2009 | Arroyo et al. | |
| 7,556,812 | B2 | 7/2009 | Tangy et al. | |
| 7,585,621 | B2 | 9/2009 | Beall et al. | |
| 8,133,712 | B2 * | 3/2012 | Sterner et al. | 435/235.1 |
| 2003/0091595 | A1 | 5/2003 | Chu | |
| 2003/0104008 | A1 | 6/2003 | Loosmore et al. | |
| 2003/0148261 | A1 | 8/2003 | Fikrig et al. | |
| 2008/0279891 | A1 | 11/2008 | Johnston et al. | |
| 2009/0130146 | A1 | 5/2009 | Broeker | |
| 2011/0159033 | A1 | 6/2011 | Hennessy et al. | |

FOREIGN PATENT DOCUMENTS

| | | | |
|---|---|---|---|
| WO | 02067899 | A1 | 9/2002 |
| WO | 03061555 | A2 | 7/2003 |
| WO | 2007002470 | A2 | 1/2007 |
| WO | 2007051763 | A1 | 5/2007 |
| WO | 2010025469 | A1 | 3/2010 |

OTHER PUBLICATIONS

Ebel et al., "Genetic and Phenotypic Variation of West Nile Virus in New York, 2000-2003". 2004, American Journal of Tropical Medicine and Hygiene, vol. 71, No. 4, pp. 493-500.
Hilgers et al., "Alkyl-esters of polyacrylic acid as vaccine adjuvants". 1998, Vaccine, vol. 16, No. 16, pp. 1575-1581.
Imam et al., "Challenge of Hamsters With Japanese B, St. Louis and Murray Valley Encephalitis Viruses After Immunization by West Nile Infection Plus Specific Vaccine". 1957, The Journal of Immunology, vol. 79, pp. 243-252.
Price et al., "Live and Inactivated Vaccines of Group B Arboviruses: Role of Neutralizing Antibody and Serum Protective Factor". Jun. 1969, Nature, vol. 222, pp. 1294-1295.
Snapinn et al., "Declining Growth Rate of West Nile Virus in North America". Mar. 2007, Journal of Virology, vol. 81, No. 5, pp. 2531-2534.
Steele et al., "Pathology of Fatal West Nile Virus Infections in Native and Exotic Birds during the 1999 Outbreak in New York City, New York". 2000, Veterinary Pathology, vol. 37, pp. 208-224.
Van Hoof, J. "Manufacturing Issues Related to Combining Different Antigens: An Industry Perspective". Clinical Infectious Diseases, Suppl. 4, vol. 33, 2001, p. S346-S350.
Written Opinion of the International Searching Authority for PCT/US2009/055564 mailed Dec. 3, 2009.
"West Nile Innovator + EWT"., Ft. Dodge Material Safety Data Sheet, Fort Dodge Animal Health—A Division of Wyeth Corporation, Jan. 23, 2004, pp. 1-5.
"West Nile Innovator + VEWT"., Fort Dodge Material Safety Data Sheet, Fort Dodge Animal Health, Apr. 10, 2007, pp. 1-6.
Blood-Horse Staff, "Fort Dodge Releases West Nile DNA Vaccine"., BloodHorse.com, Jul. 19, 2005, 1 page. [Accessed at http://www.bloodhorse.com/horse-racing/articles/29112/fort-dodge-releases-west-nile- . . . on Apr. 9, 2013.].

(Continued)

*Primary Examiner* — Shanon A Foley
(74) *Attorney, Agent, or Firm* — Michael P. Morris; Joyce L. Morrison

(57) ABSTRACT

The invention provides for immunogenic compositions against West Nile Virus. The immunogenic compositions, in alternate embodiments, also include other equine pathogens. The West Nile Virus composition of the present invention advantageously provides for protection against North American Dominant West Nile Virus strains or isolates.

18 Claims, 120 Drawing Sheets

(56) References Cited

OTHER PUBLICATIONS

Cohen, Bettina, "The Golden Age of Horse Health". BloodHorse.com, Nov. 22, 2004, 4 pages. [Accessed at: http://www.bloodhorse.com/horse-racing/articles/25516/the-golden-age-of-horse-healt . . . on Apr. 8, 2013.].

Kramer et al., "West Nile virus"., The Lancet Neurology, vol. 6, 2007, pp. 171-181.

Lanciotti et al., "Origin of the West Nile Virus Responsible for the Outbreak of Encephalitis in the Northeastern United States". Science, vol. 286, No. 17, Dec. 1999, pp. 2333-2337. [Accessed at www.sciencemag.org on Dec. 20, 2010].

Minke et al., "Equine viral vaccines: the past, the present and future". Veterinary Research, vol. 35, 2004, pp. 425-443.

Wilson, J.H., "Vaccine Efficacy and Controversies". American Asssociation of Equine Practicioners Annual Proceedings, vol. 51, 2005, pp. 409-420.

Davis et al., "Phylogenetic analysis of North American West Nile virus isolates, 2001-2004: Evidence for the emergence of a dominant genotype". 2005, Virology, vol. 342, pp. 252-265.

Eckels et al., "Formalin-Inactivated Whole Virus and Recombinant Subunit Flavivirus Vaccines". 2003, Advances in Virus Research, vol. 61, pp. 395-418.

International Search Report for PCT/US2009/055564 mailed Dec. 3, 2009.

Konishi et al., "Dengue tetravalet DNA vaccine inducing neutralizing antibody and anamnestic responses to four serotypes in mice". 2006, Vaccine, vol. 24, pp. 2200-2207.

"Scientific Discussion". EMEA, 2008, pp. 1-17.

Anderson et al., "Isolation of West Nile Virus from Mosquitoes, Crows and a Cooper's Hawk in Connecticut". Science, vol. 286, Dec. 1999, pp. 2331-2333.

Arroyo et al., "ChimerVax-West Nile Virus Live-Attenuated Vaccine: Preclinical Evaluation of Safety, Immogenicity, and Efficacy". Journal of Virology, vol. 78, No. 22, Nov. 2004, pp. 12497-12507.

Dauphin et al., "West Nile Virus: Recent Trends in Diagnosis and Vaccine Development". Vaccine, vol. 25, 2007, pp. 5563-5576.

Hall et al., "West Nile Virus Vaccines". Expert Opinion on Biological Therapy, vol. 4, No. 8, 2004, pp. 1295-1305.

Liljeqvist et al., "Production of Recombinant Subunit Vaccines: Protein Immunogens, Live Delivery Systems and Nucleic Acid Vaccines". Journal of Biotechnology, vol. 73, 1999, pp. 1-33.

Lustig et al., "A Live Attenuated West Nile Virus Strain as a Potential Veterinary Vaccine". Viral Immunology, vol. 13, No. 4, 2000, pp. 401-410.

Monath et al., "West Nile Virus Vaccine". Current Drug Targets—Infectious Disorders, vol. 1, No. 1, 2001, pp. 37-50.

Moudy et al., "A Newly Emergent Genotype of West Nile Virus is transmitted Earlier and More Efficiently by Culex Mosquitoes". The American Journal of Tropical Medicine and Hygiene, vol. 77, No. 2, 2007, pp. 365-370.

Malkinson et al., "Use of Live and Inactivated Vaccines in the Control of West Nile Fever in Domestic Geese". Annals of the New York Academy of Sciences, 2001, pp. 255-261.

Wang et al., "Immunization of Mice Again West Nile Virus with Recombinant Envelope Protein". The Journal of Immunology, vol. 167, 2001, pp. 5273-5277.

\* cited by examiner

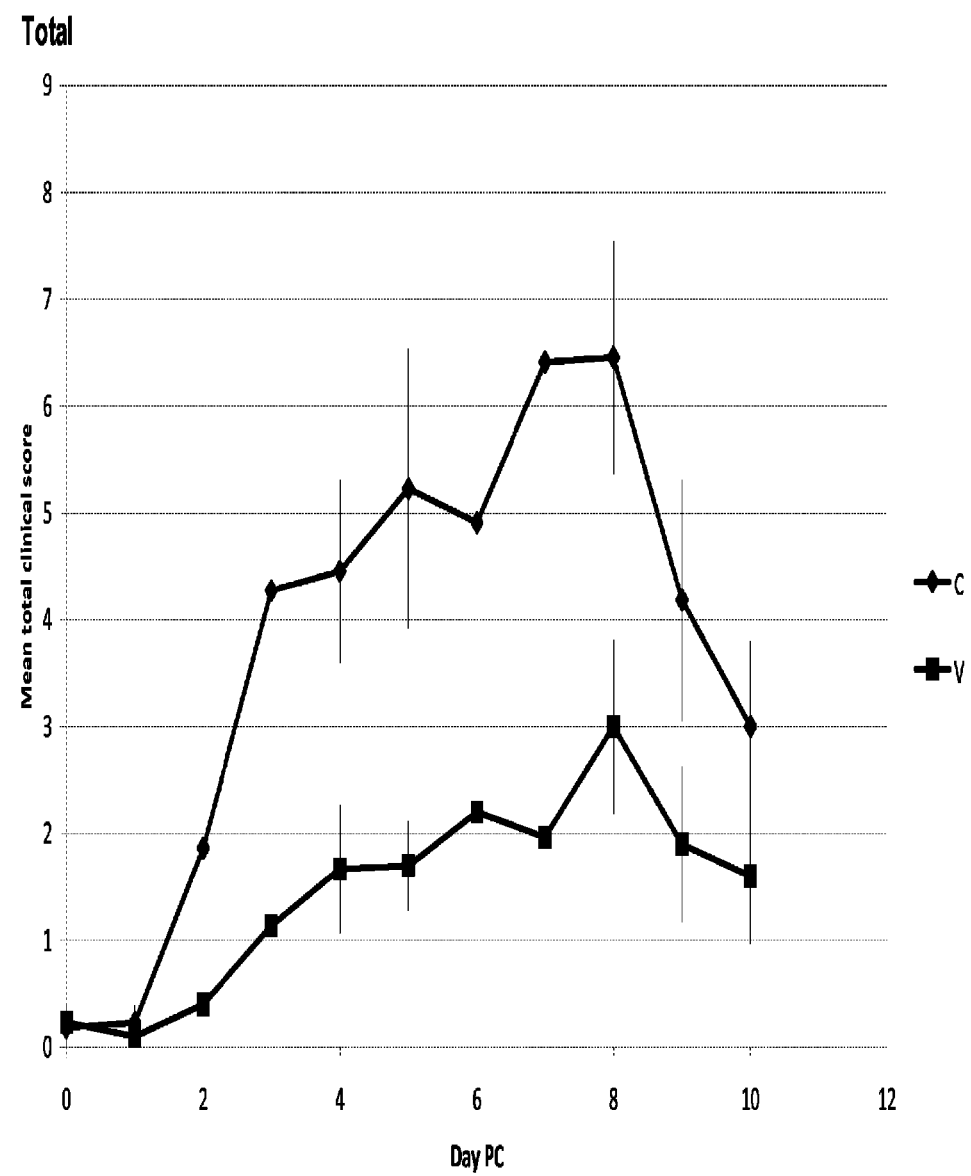

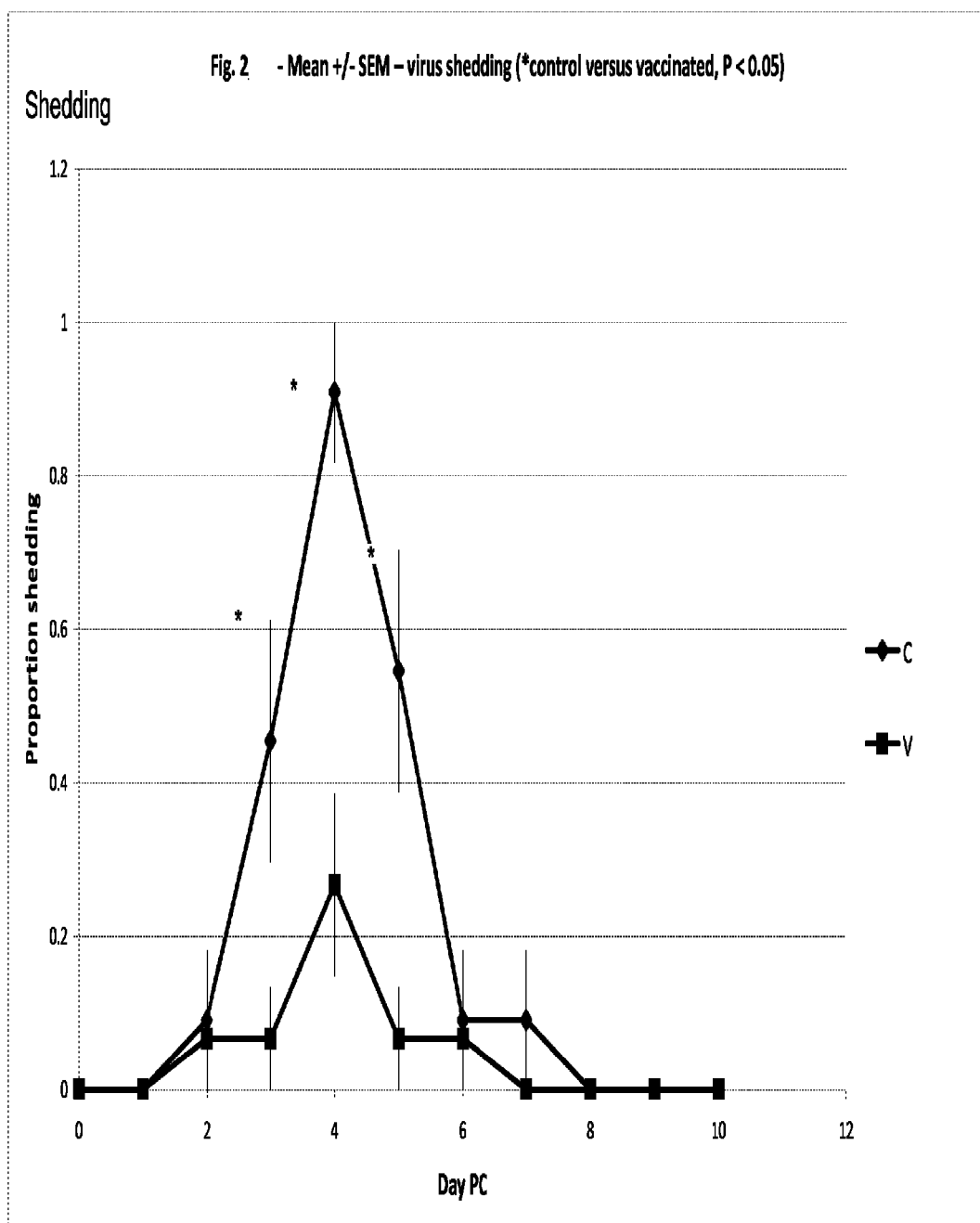

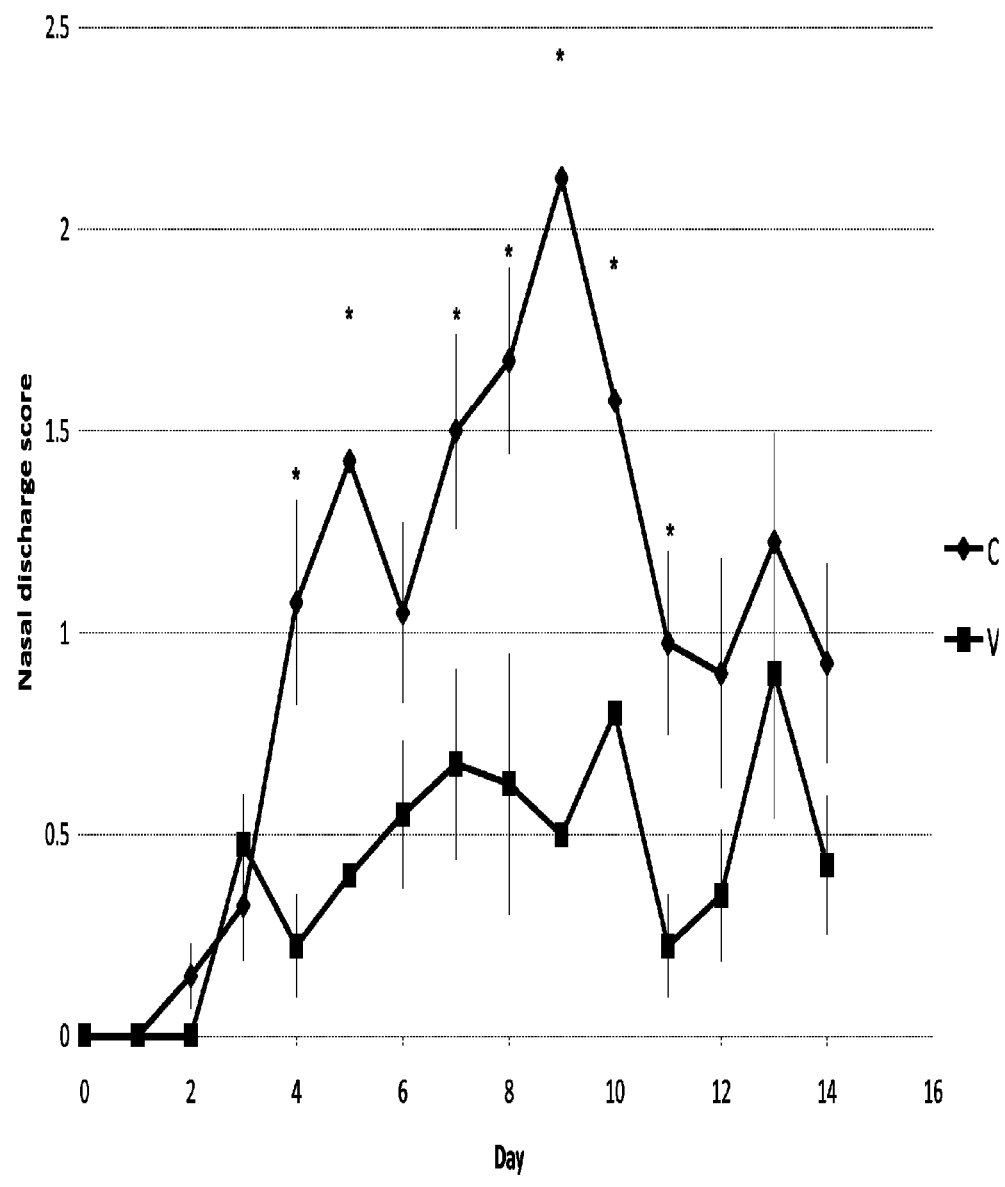

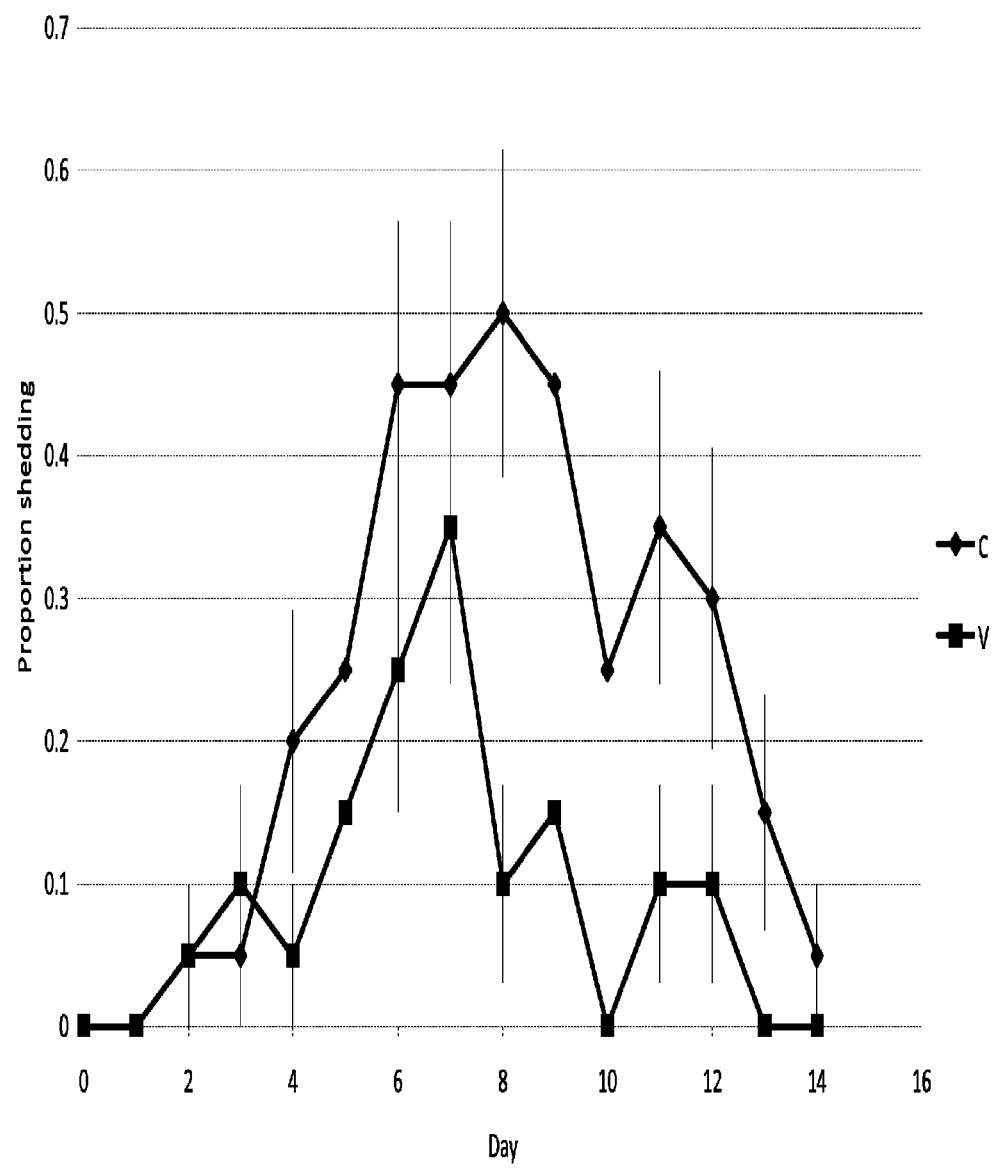

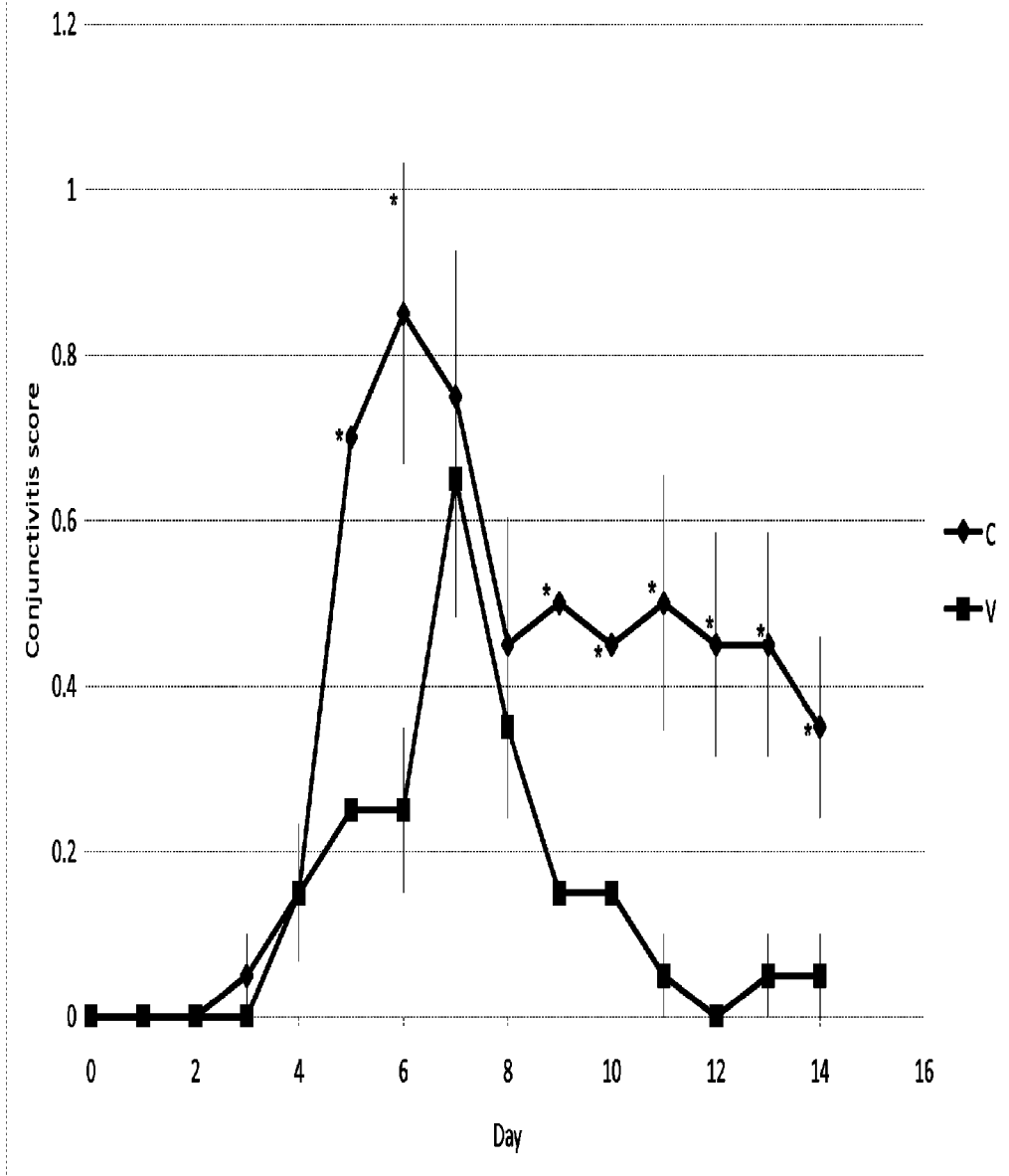

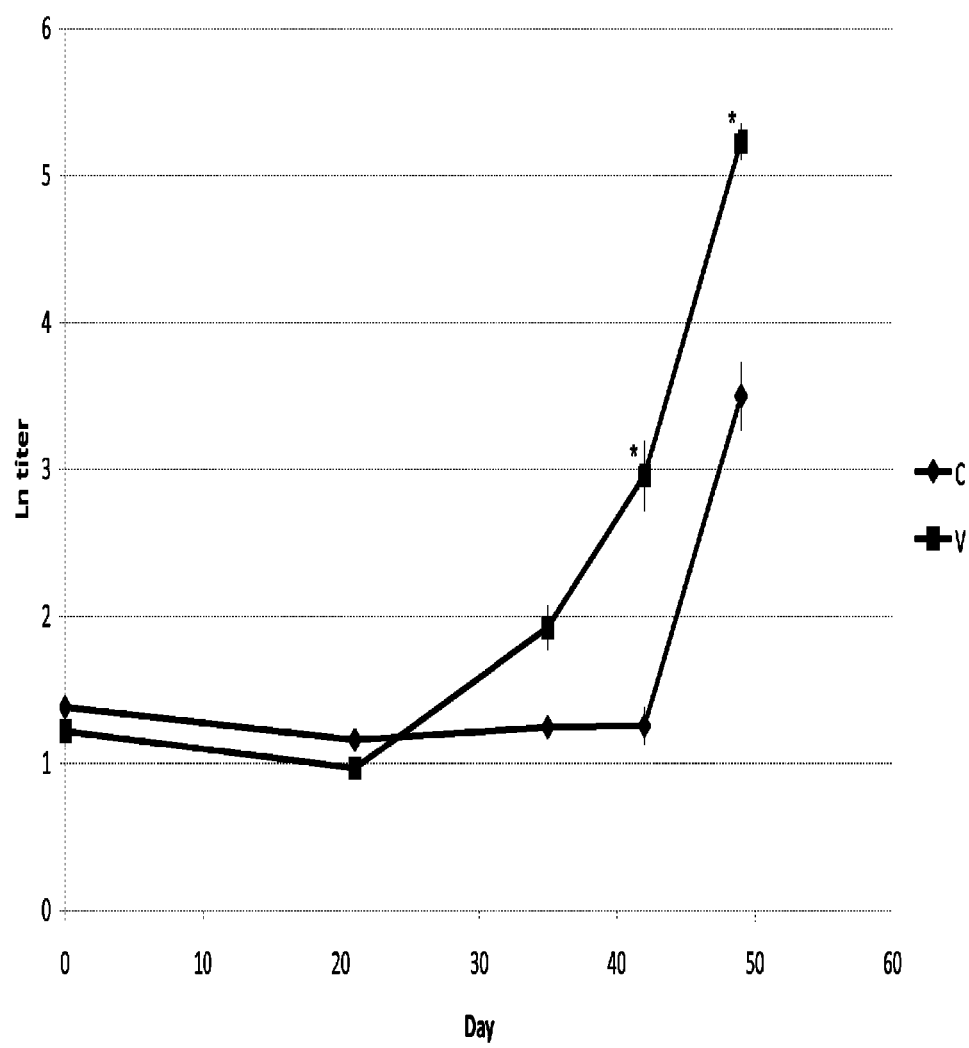

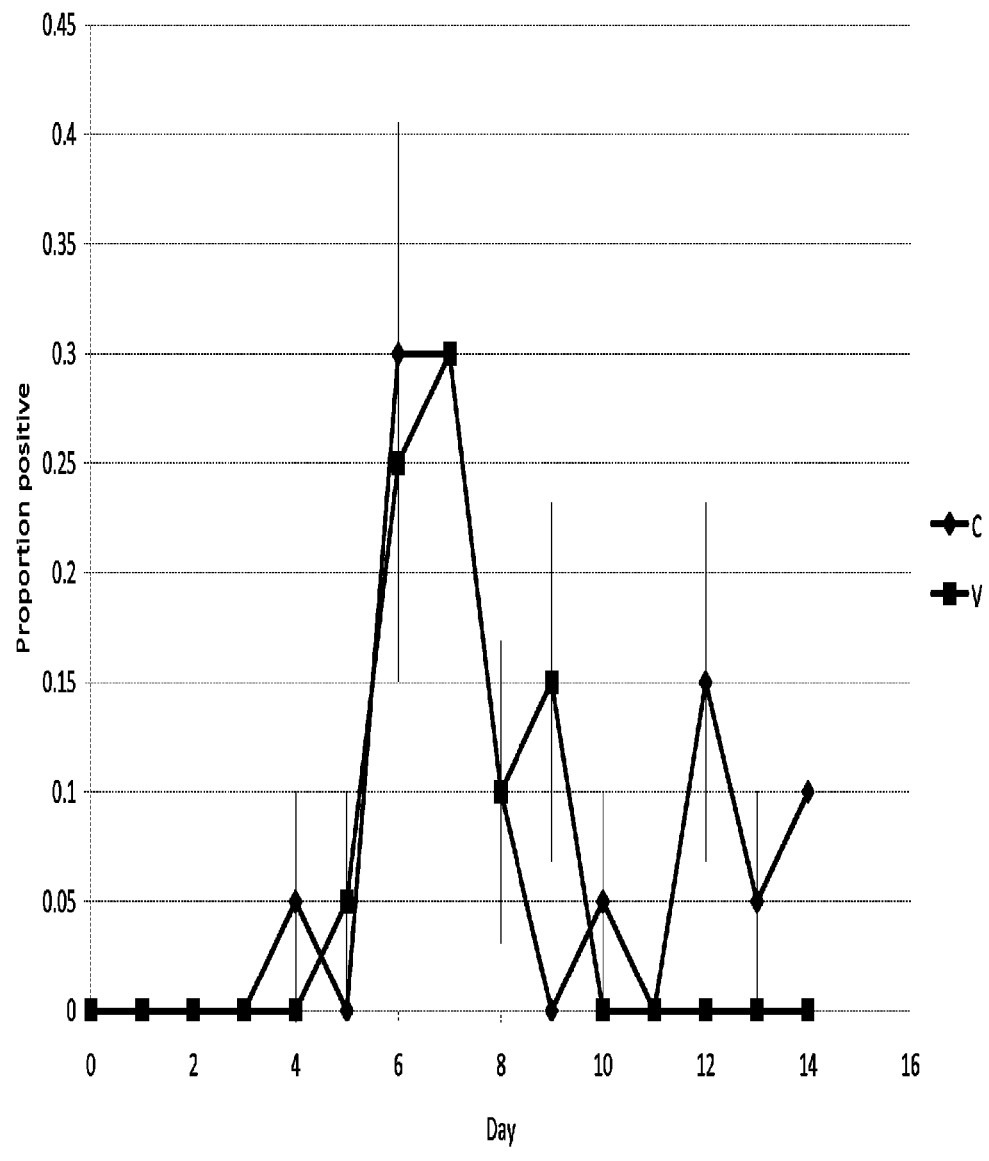

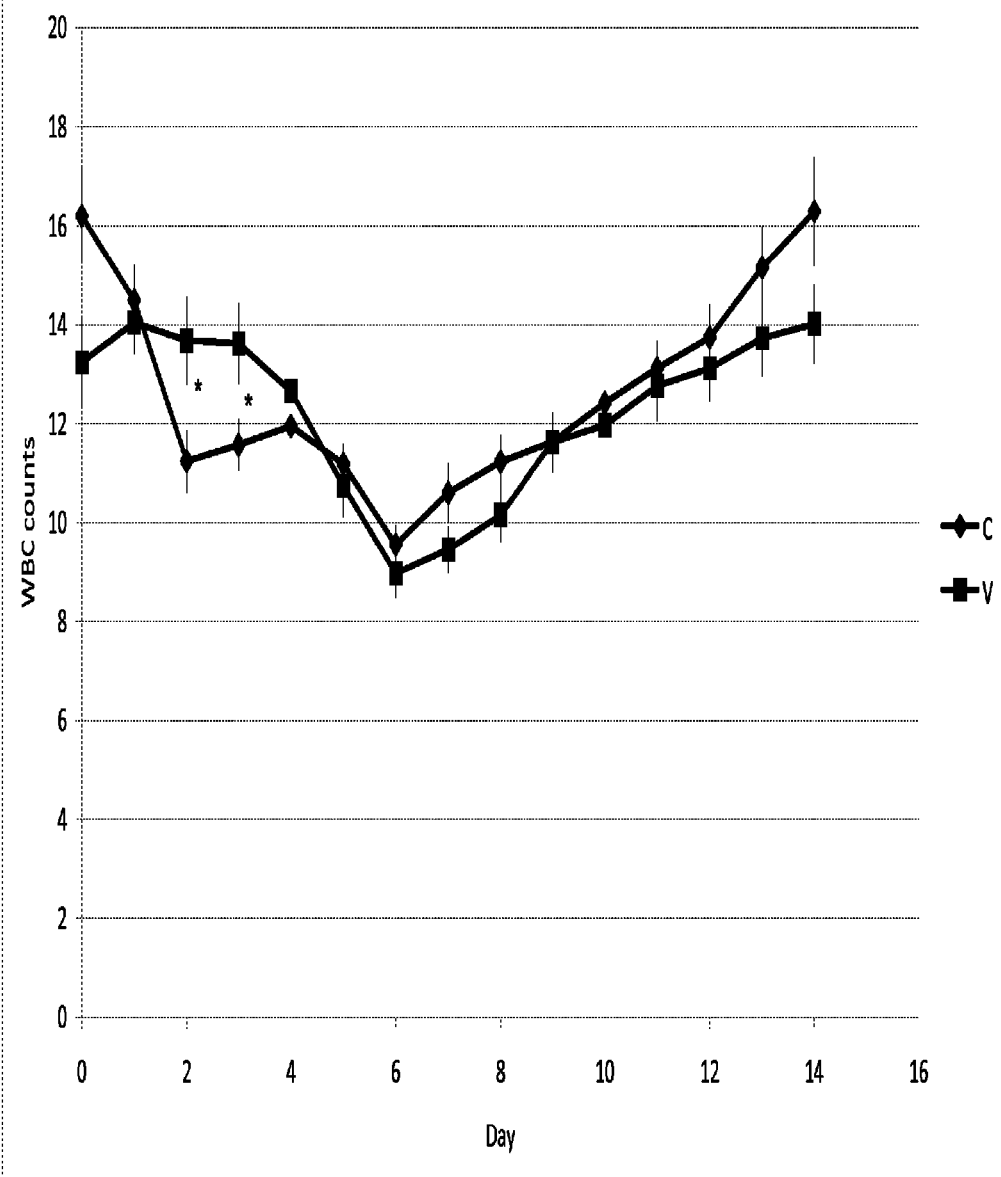

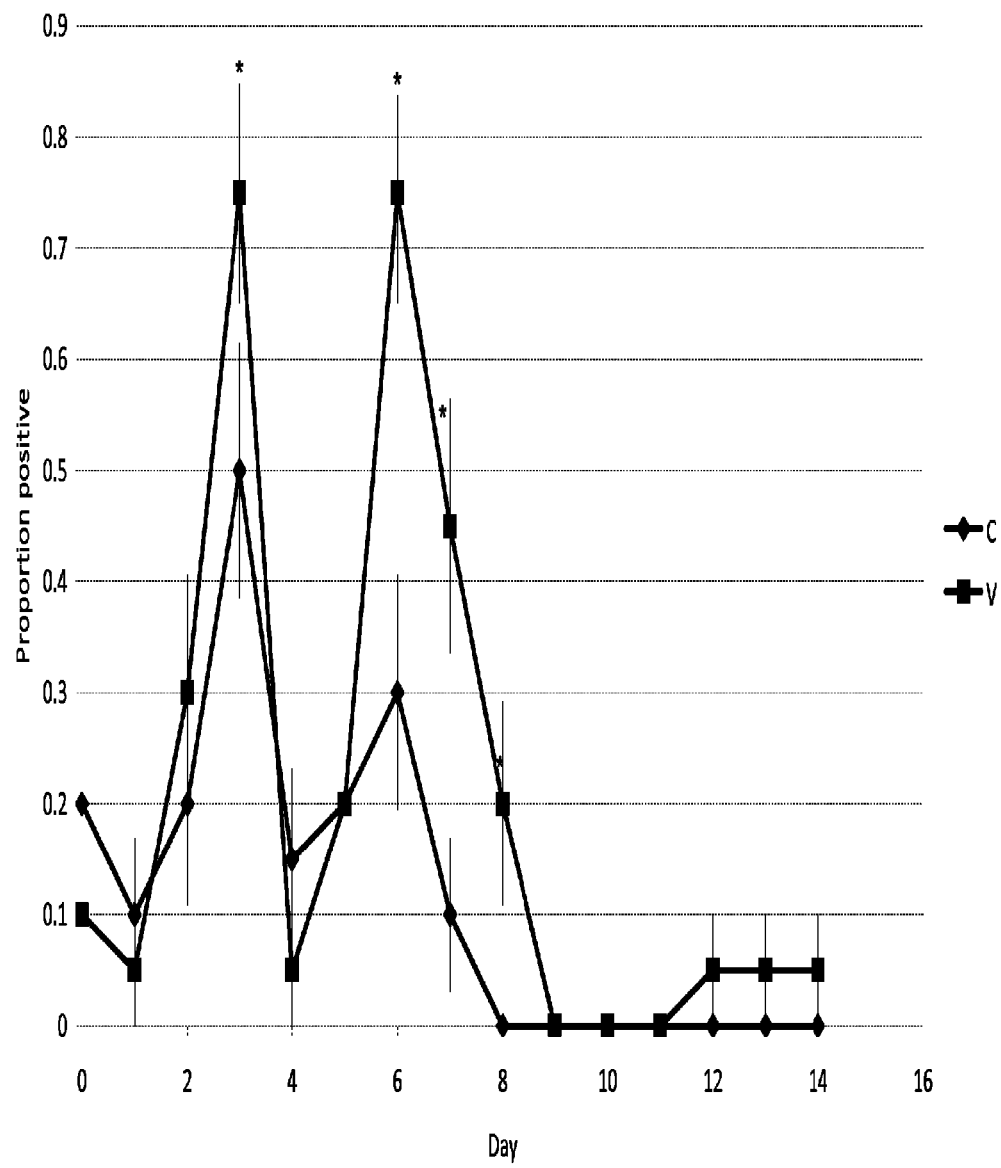

```
NY99 E     TGCTCTACCA  AGGCAATAGG  AAGAACCATC  390
WN02 E     TGCTCTACCA  AGGCAATAGG  AAGAACCATC  390
HEF1       TGCTCTACCA  AGGCAATAGG  AAGAACCATC  267
HEF3       ----------  ----------  ----------  -
HER3 rev   ----------  ----------  ----------  -
HER4 rev   ----------  ----------  ----------  -
Consensus  TGCTCTACCA  AGGCAATAGG  AAGAACCATC
```

100%
Conservation
0%

```
NY99 E     TTGAAAGAGA  ATATCAAGTA  CGAAGTGGCC  420
WN02 E     TTGAAAGAGA  ATATCAAGTA  CGAAGTGGCC  420
HEF1       TTGAAAGAGA  ATATCAAGTA  CGAAGTGGCC  297
HEF3       ----------  ----CAAGTA  CGAAGTGGCC  16
HER3 rev   ----------  ----------  ----------  -
HER4 rev   ----------  ----------  ----------  -
Consensus  TTGAAAGAGA  ATATCAAGTA  CGAAGTGGCC
```

100%
Conservation
0%

```
NY99 E     ATTTTTGTCC  ATGGACCAAC  TACTGTGGAG  450
WN02 E     ATTTTTGTCC  ATGGACCAAC  TACTGTGGAG  450
HEF1       ATTTTTGTCC  ATGGACCAAC  TACTGTGGAG  327
HEF3       ATTTTTGTCC  ATGGACCAAC  TACTGTGGAG  46
HER3 rev   ----------  ----------  ----------  -
HER4 rev   ----------  ----------  ----------  -
Consensus  ATTTTTGTCC  ATGGACCAAC  TACTGTGGAG
```

100%
Conservation
0%

```
NY99 E     TCGCACGGAA  ACTACTCCAC  ACAGGTTGGA  480
WN02 E     TCGCACGGAA  ACTATTCCAC  ACAGGCTGGA  480
HEF1       TCGCACGGAA  ACTACTCCAC  ACAGGTTGGA  357
HEF3       TCGCACGGAA  ACTACTCCAC  ACAGGTTGGA  76
HER3 rev   ----------  ----------  ----------  -
HER4 rev   ----------  ----------  ----------  -
Consensus  TCGCACGGAA  ACTACTCCAC  ACAGGTTGGA
```

100%
Conservation
0%

Fig. 10D

```
    NY99 E  TACTACGTGA  TGACTGTTGG  AACAAAGACG  630
    WN02 E  TACTACGTGA  TGACTGTTGG  AACAAAGACG  630
     HEF1   TACTATGTGA  TGACTGTTGG  AACAAAGACG  507
     HEF3   TACTATGTGA  TGACTGTTGG  AACAAAGACG  226
   HER3 rev -----TNTGA  TGACTGTNGG  AACAAAGACG   25
   HER4 rev ----------  ----------  ----------   -
  Consensus TACTATGTGA  TGACTGTTGG  AACAAAGACG NY99 E  TTCTTGGTCC  ATCGTGAGTG  GTTCATGGAC  660
    WN02 E  TTCTTGGTCC  ATCGTGAGTG  GTTCATGGAC  660
     HEF1   TTCTTGGTCC  ATCGTGAGTG  GTTCATGGAC  537
     HEF3   TTCTTGGTCC  ATCGTGAGTG  GTTCATGGAC  256
   HER3 rev TTCTNNNTCC  ATCGTGAGTN  NTTCATGGAC   55
   HER4 rev ----------  ----------  ----------   -
  Consensus T

```
NY99 E       AGGCTGTCCA TCAAGTGTTC GGAGGAGCAT 1348
WN02 E       AGGCTGTCCA TCAAGTGTTC GGAGGAGCAT 1348
HEF1         ---------- ---------- ---------- 945
HEF3         ---------- ---------- ---------- 855
HER3 rev     AGGCTGTCCA TCAAGTGTTC GGAGGAGCAT 743
HER4 rev     AGGCTGTCCA TCAAGTGTTC GGAGGAGCAT 675
Consensus    AGGCTGTCCA TCAAGTGTTC GGAGGAGCAT
100%
Conservation
0%
NY99 E       TCCGCTCACT GTTCGGAGGC ATGTCCTGGA 1378
WN02 E       TCCGCTCACT GTTCGGAGGC ATGTCCTGGA 1378
HEF1         ---------- ---------- ---------- 945
HEF3         ---------- ---------- ---------- 855
HER3 rev     TCCGCTCACT GTTCGGAGGC ATGTCCTGGA 773
HER4 rev     TCCGCTCACT GTTCGGAGGC ATGTCCTGGA 705
Consensus    TCCGCTCACT GTTCGGAGGC ATGTCCTGGA
100%
Conservation
0%
NY99 E       TAACGCAAGG ATTGCTGGGG GCTCTCCTGT 1408
WN02 E       TAACGCAAGG ATTGCTGGGG GCTCTCCTGT 1408
HEF1         ---------- ---------- ---------- 945
HEF3         ---------- ---------- ---------- 855
HER3 rev     TAACGCAAGG ATTGCTGGGG GCTCTCCTGT 803
HER4 rev     TAACGCAAGG ATTGCTGGGG GCTCTCCTGT 735
Consensus    TAACGCAAGG ATTGCTGGGG GCTCTCCTGT
100%
Conservation
0%
NY99 E       TGTGGATGGG CATCAATGCT CGTGATAGGT 1438
WN02 E       TGTGGATGGG CATCAATGCT CGTGATAGGT 1438
HEF1         ---------- ---------- ---------- 945
HEF3         ---------- ---------- ---------- 855
HER3 rev     TGTGGATGGG CATCAATGCT CGTGATAGGT 833
HER4 rev     TGTGGATGGG CATCAATGCT CGTGATAGGT 765
Consensus    TGTGGATGGG CATCAATGCT CGTGATAGGT
100%
Conservation
0%
```

| | | | | |
|---|---|---|---|---|
| NY99 E | CACAATGACA | AACGTGCTGA | CCCAGCTTTT | 270 |
| WN02 E | CACAATGACA | AACGTGCTGA | CCCAGCTTTT | 270 |
| DEF1 | CACAATGACA | AACGTGCTGA | CCCAGCTTTT | 147 |
| DEF3 | ---------- | ---------- | ---------- | - |
| DER3 rev | ---------- | ---------- | ---------- | - |
| DER4 rev | ---------- | ---------- | ---------- | - |
| Consensus | CACAATGACA | AACGTGCTGA | CCCAGCTTTT | |
| NY99 E | GTGTGCAGAC | AAGGAGTGGT | GGACAGGGGC | 300 |
| WN02 E | GTGTGCAGAC | AAGGAGTGGT | GGACAGGGGC | 300 |
| DEF1 | GTGTGCAGAC | AAGGAGTGGT | GGACAGGGGC | 177 |
| DEF3 | ---------- | ---------- | ---------- | - |
| DER3 rev | ---------- | ---------- | ---------- | - |
| DER4 rev | ---------- | ---------- | ---------- | - |
| Consensus | GTGTGCAGAC | AAGGAGTGGT | GGACAGGGGC | |
| NY99 E | TGGGGCAACG | GCTGCGGACT | ATTTGGCAAA | 330 |
| WN02 E | TGGGGCAACG | GCTGCGGACT | ATTTGGCAAA | 330 |
| DEF1 | TGGGGCAACG | GCTGCGGACT | ATTTGGCAAA | 207 |
| DEF3 | ---------- | ---------- | ---------- | - |
| DER3 rev | ---------- | ---------- | ---------- | - |
| DER4 rev | ---------- | ---------- | ---------- | - |
| Consensus | TGGGGCAACG | GCTGCGGACT | ATTTGGCAAA | |
| NY99 E | GGAAGCATTG | ACACATGCGC | CAAATTTGCC | 360 |
| WN02 E | GGAAGCATTG | ACACATGCGC | CAAATTTGCC | 360 |
| DEF1 | GGAAGCATTG | ACACATGCGC | CAAATTTGCC | 237 |
| DEF3 | ---------- | ---------- | ---------- | - |
| DER3 rev | ---------- | ---------- | ---------- | - |
| DER4 rev | ---------- | ---------- | ---------- | - |
| Consensus | GGAAGCATTG | ACACATGCGC | CAAATTTGCC | |

Fig. 11C

| | | | | |
|---|---|---|---|---|
| NY99 E | GCCACTCAGG | CAGGGAGATT | CAGCATCACT | 510 |
| WN02 E | GCCACTCAGG | CAGGGAGATT | CAGCATCACT | 510 |
| DEF1 | GCCACTCAGG | CAGGGAGATT | CAGCATCACT | 387 |
| DEF3 | GCCACTCAGG | CAGGGAGATT | CAGCATCACT | 106 |
| DER3 rev | ---------- | ---------- | ---------- | - |
| DER4 rev | ---------- | ---------- | ---------- | - |
| Consensus | GCCACTCAGG | CAGGGAGATT | CAGCATCACT | |

100%
Conservation
0%

| | | | | |
|---|---|---|---|---|
| NY99 E | CCTGCGGCGC | CTTCACACAC | ACTAAAGCTT | 540 |
| WN02 E | CCTGCGGCGC | CTTCATACAC | ACTAAAGCTT | 540 |
| DEF1 | CCTGCGGCGC | CTTCATACAC | ACTAAAGCTT | 417 |
| DEF3 | CCTGCGGCGC | CTTCATACAC | ACTAAAGCTT | 136 |
| DER3 rev | ---------- | ---------- | ---------- | - |
| DER4 rev | ---------- | ---------- | ---------- | - |
| Consensus | CCTGCGGCGC | CTTCATACAC | ACTAAAGCTT | |

100%
Conservation
0%

| | | | | |
|---|---|---|---|---|
| NY99 E | GGAGAATATG | GAGAGGTGAC | AGTGGACTGT | 570 |
| WN02 E | GGAGAATATG | GAGAGGTGAC | AGTGGACTGT | 570 |
| DEF1 | GGAGAATATG | GAGAGGTGAC | AGTGGACTGT | 447 |
| DEF3 | GGAGAATATG | GAGAGGTGAC | AGTGGACTGT | 166 |
| DER3 rev | ---------- | ---------- | ---------- | - |
| DER4 rev | ---------- | ---------- | ---------- | - |
| Consensus | GGAGAATATG | GAGAGGTGAC | AGTGGACTGT | |

100%
Conservation
0%

| | | | | |
|---|---|---|---|---|
| NY99 E | GAACCACGGT | CAGGGATTGA | CACCAATGCA | 600 |
| WN02 E | GAACCACGGT | CAGGGATTGA | CACCAATGCA | 600 |
| DEF1 | GAACCACGGT | CAGGGATTGA | CACCAATGCA | 477 |
| DEF3 | GAACCACGGT | CAGGGATTGA | CACCAATGCA | 196 |
| DER3 rev | ---------- | ---------- | -----ATGCN | 5 |
| DER4 rev | ---------- | ---------- | ---------- | - |
| Consensus | GAACCACGGT | CAGGGATTGA | CACCAATGCA | |

100%
Conservation
0%

Fig. 11E

| | | | | |
|---|---|---|---|---|
| NY99 E | TTGACGTCGG | GTCATTTGAA | GTGTAGAGTG | 870 |
| WN02 E | TTGACGTCGG | GTCATTTGAA | GTGTAGAGTG | 870 |
| DEF1 | TTGACGTCGG | GTCATTTGAA | GTGTAGAGTG | 747 |
| DEF3 | TTGACGTCGG | GTCATTTGAA | GTGTAGAGTG | 466 |
| DER3 rev | TNGACGTCGG | NTCATTTGAA | GTGTAGAGTG | 266 |
| DER4 rev | TTGACGTCGG | GTCATTTGAA | GTGTAGAGTG | 121 |
| Consensus | TTGACGTCGG | GTCATTTGAA | GTGTAGAGTG | |

| | | | | |
|---|---|---|---|---|
| NY99 E | AAGATGGAAA | AATTGCAGTT | GAAGGGAACA | 900 |
| WN02 E | AAGATGGAAA | AATTGCAGTT | GAAGGGAACA | 900 |
| DEF1 | AAGATGGAAA | AATTGCAGTT | GAAGGGAACA | 777 |
| DEF3 | AAGATGGAAA | AATTGCAGTT | GAAGGGAACA | 496 |
| DER3 rev | AAGATGGAAA | AATTGCAGTT | GAAGGGAACA | 296 |
| DER4 rev | AAGATGGAAA | AATTGCAGTT | GAAGGGAACA | 151 |
| Consensus | AAGATGGAAA | AATTGCAGTT | GAAGGGAACA | |

| | | | | |
|---|---|---|---|---|
| NY99 E | ACCTATGGCG | TCTGTTCAAA | GGCTTTCAAG | 930 |
| WN02 E | ACCTATGGCG | TCTGTTCAAA | GGCTTTCAAG | 930 |
| DEF1 | ACCTATGGCG | TCTGTTCAAA | GGCTTTCAAG | 807 |
| DEF3 | ACCTATGGCG | TCTGTTCAAA | GGCTTTCAAG | 526 |
| DER3 rev | ACNTATGGCG | TCTGTTCAAA | GGCTTTCAAG | 326 |
| DER4 rev | ACNTATGGCG | TCTGTTCAAA | GGCTTTCAAG | 181 |
| Consensus | ACCTATGGCG | TCTGTTCAAA | GGCTTTCAAG | |

| | | | | |
|---|---|---|---|---|
| NY99 E | TTTCTTGGGA | CTCCGCAGA | CACAGGTCAC | 960 |
| WN02 E | TTTCTTGGGA | CTCCGCAGA | CACAGGTCAC | 960 |
| DEF1 | TTTCTTGGGA | CTCCGCAGA | CACAGGTCAC | 837 |
| DEF3 | TTTCTTGGGA | CTCCGCAGA | CACAGGTCAC | 556 |
| DER3 rev | TTTCTTGGGA | CTCCGCAGA | CACAGGTCAC | 356 |
| DER4 rev | TTTCTTGGGA | CTCCGCAGA | CACAGGTCAC | 211 |
| Consensus | TTTCTTGGGA | CTCCGCAGA | CACAGGTCAC | |

Fig. 11H

```
NY99 E    TTTGTTTCAG  TGGCCACGGC  CAACGCTAAG  1110
WN02 E    TTTGTTTCAG  TGGCCACGGC  CAACGCTAAG  1110
  DEF1    ----------  ----------  ----------   944
  DEF3    TTTGTTTCAG  TGGCCACGGC  CAACGCTAAG   706
DER3 rev  TTTGTTTCAG  TGGCCACGGC  CAACGCTAAG   506
DER4 rev  TTTGTTTCAG  TGGCCACGGC  CAACGCTAAG   361
Consensus TTTGTTTCAG  TGGCCACGGC  CAACGCTAAG NY99 E    GTCCTGATTG  AATTGGAACC  ACCCTTTGGA  1140
WN02 E    GTCCTGATTG  AATTGGAACC  ACCCTTTGGA  1140
  DEF1    ----------  ----------  ----------   944
  DEF3    GTCCTGATTG  AATTGGAACC  ACCCTTTGGA   736
DER3 rev  GTCCTGATTG  AATTGGAACC  ACCCTTTGGA   536
DER4 rev  GTCCTGATTG  AATTGGAACC  ACCCTTTGGA   391
Consensus GTCCTGATTG  AATTGGAACC  ACCCTTTGGA NY99 E    GACTCATACA  TAGTGGTGGG  CAGAGGAGAA  1170
WN02 E    GACTCATACA  TAGTGGTGGG  CAGAGGAGAA  1170
  DEF1    ----------  ----------  ----------   944
  DEF3    GACTCATACA  TAGTGGTGGG  CAGAGGAGAA   766
DER3 rev  GACTCATACA  TAGTGGTGGG  CAGAGGAGAA   566
DER4 rev  GACTCATACA  TAGTGGTGGG  CAGAGGAGAA   421
Consensus GACTCATACA  TAGTGGTGGG  CAGAGGAGAA NY99 E    CAACAGATCA  ATCACCATTG  GCACAAGTCT  1200
WN02 E    CAACAGATCA  ATCACCATTG  GCACAAGTCT  1200
  DEF1    ----------  ----------  ----------   944
  DEF3    CAACAGATCA  ATCACCATTG  GCACAAGTCT   796
DER3 rev  CAACAGATCA  ATCACCATTG  GCACAAGTCT   596
DER4 rev  CAACAGATCA  ATCACCATTG  GCACAAGTCT   451
Consensus CAACAGATCA  ATCACCATTG  GCACAAGTCT
```

Fig. 11J

```
NY99 E    GGAAGCAGCA  TTGGCAAAGC  CTTTACAACC  1230
WN02 E    GGAAGTAGCA  TTGGCAAAGC  CTTTACAACC  1230
DEF1      ----------  ----------  ----------   944
DEF3      GGAAGCAGCA  TTGGCAAAGC  CTTTACAACC   826
DER3 rev  GGAAGCAGCA  TTGGCAAAGC  CTTTACAACC   626
DER4 rev  GGAAGCAGCA  TTGGCAAAGC  CTTTACAACC   481
Consensus GGAAGCAGCA  TTGGCAAAGC  CTTTACAACC NY99 E    ACCCTCAAAG  GAGCGCAGAG  ACTAGCCGCT  1260
WN02 E    ACCCTCAAAG  GAGCGCAGAG  ACTAGCCGCT  1260
DEF1      ----------  ----------  ----------   944
DEF3      ACCCTCAAAG  GANCGCAGAG  ACTAGCCGCT   856
DER3 rev  ACCCTCAAAG  GAGCGCAGAG  ACTAGCCGCT   656
DER4 rev  ACCCTCAAAG  GAGCGCAGAG  ACTAGCCGCT   511
Consensus ACCCTCAAAG  GAGCGCAGAG  ACTAGCCGCT NY99 E    CTAGGAGACA  CAGCTTGGGA  CTTTGGATCA  1290
WN02 E    CTAGGAGACA  CAGCTTGGGA  CTTTGGATCA  1290
DEF1      ----------  ----------  ----------   944
DEF3      CTAGGANACA  CAGCTTNGGA  CTTTGGATCA   886
DER3 rev  CTAGGAGACA  CAGCTTGGGA  CTTTGGATCA   686
DER4 rev  CTAGGAGACA  CAGCTTGGGA  CTTTGGATCA   541
Consensus CTAGGAGACA  CAGCTTGGGA  CTTTGGATCA NY99 E    GTTGGAGGGG  TGTTCACCTC  AGTTGGGAA-  1319
WN02 E    GTTGGAGGGG  TGTTCACCTC  AGTTGGGAA-  1319
DEF1      ----------  ----------  ----------   944
DEF3      GTTGGAGGGG  TGTTCACCTC  AGTTGGGAAN   916
DER3 rev  GTTGGAGGGG  TGTTCACCTC  AGTTGGGAA-   715
DER4 rev  GTTGGAGGGG  TGTTCACCTC  AGTTGGGAA-   570
Consensus GTTGGAGGGG  TGTTCACCTC  AGTTGGGAA-
```

Fig. 11K

```
NY99 E      GGCTGTCCAT  CAAGTGTTCG  GAGGAGCATT  1349
WN02 E      GGCTGTCCAT  CAAGTGTTCG  GAGGAGCATT  1349
DEF1        ----------  ----------  ----------  944
DEF3        GGNTGTCCAT  CAAGTGNTCG  GAGGAGCATT  946
DER3 rev    GGCTGTCCAT  CAAGTGTTCG  GAGGAGCATT  745
DER4 rev    GGCTGTCCAT  CAAGTGTTCG  GAGGAGCATT  600
Consensus   GGCTGTCCAT  CAAGTGTTCG  GAGGAGCATT
```
100% Conservation 0%
```
NY99 E      -CCGCTCACT  GTTCGGAGGC  ATGTCCTGGA  1378
WN02 E      -CCGCTCACT  GTTCGGAGGC  ATGTCCTGGA  1378
DEF1        ----------  ----------  ----------  944
DEF3        NCCGCTCACT  GNTCGGAGGC  ATGTNCGGN   976
DER3 rev    -CCGCTCACT  GTTCGGAGGC  ATGTCCTGGA  774
DER4 rev    -CCGCTCACT  GTTCGGAGGC  ATGTCCTGGA  629
Consensus   -CCGCTCACT  GTTCGGAGGC  ATGTCCTGGA
```
100% Conservation 0%
```
NY99 E      TAACGCAAGG  ATTGCTGGGG  GCTCTCCTGT  1408
WN02 E      TAACGCAAGG  ATTGCTGGGG  GCTCTCCTGT  1408
DEF1        ----------  ----------  ----------  944
DEF3        NNACGCAAGG  NTNGNTGGGG  G---------  997
DER3 rev    TAACGCAAGG  ATTGCTGGGG  GCTCTCCTGT  804
DER4 rev    TAACGCAAGG  ATTGCTGGGG  GCTCTCCTGT  659
Consensus   TAACGCAAGG  ATTGCTGGGG  GCTCTCCTGT
```
100% Conservation 0%
```
NY99 E      TGTGGATGGG  CATCAATGCT  CGTGATAGGT  1438
WN02 E      TGTGGATGGG  CATCAATGCT  CGTGATAGGT  1438
DEF1        ----------  ----------  ----------  944
DEF3        ----------  ----------  ----------  997
DER3 rev    TGTGGATGGG  CATCAATGCT  CGTGATAGGT  834
DER4 rev    TGTGGATGGG  CATCAATGCT  CGTGATAGGT  689
Consensus   TGTGGATGGG  CATCAATGCT  CGTGATAGGT
```
100% Conservation 0%

Fig. 11L

| | | | | |
|---|---|---|---|---|
| NY99 E | - - - - - - - - - - | - - - - - - - - - - | - - - - - - - - - - | 1503 |
| WN02 E | - - - - - - - - - - | - - - - - - - - - - | - - - - - - - - - - | 1503 |
| DEF1 | - - - - - - - - - - | - - - - - - - - - - | - - - - - - - - - - | 944 |
| DEF3 | - - - - - - - - - - | - - - - - - - - - - | - - - - - - - - - - | 997 |
| DER3 rev | - - - - - - - - - - | - - - - - - - - - - | - - - - - - - - - - | 940 |
| DER4 rev | TGTTCATACA | CAATGATGTG | GAGGCTTGGA | 839 |

Consensus
100%
Conservation
0%

| | | | | |
|---|---|---|---|---|
| NY99 E | - - - - - - - - - - | - - - - - - - - - - | - - - - - - - - - - | 1503 |
| WN02 E | - - - - - - - - - - | - - - - - - - - - - | - - - - - - - - - - | 1503 |
| DEF1 | - - - - - - - - - - | - - - - - - - - - - | - - - - - - - - - - | 944 |
| DEF3 | - - - - - - - - - - | - - - - - - - - - - | - - - - - - - - - - | 997 |
| DER3 rev | - - - - - - - - - - | - - - - - - - - - - | - - - - - - - - - - | 940 |
| DER4 rev | TGGACCGGTA | CAAGTATTAC | CCTGAAACGC | 869 |

Consensus
100%
Conservation
0%

| | | | | |
|---|---|---|---|---|
| NY99 E | - - - - - - - - - - | - - - - - - - - - - | - - - - - - - - - - | 1503 |
| WN02 E | - - - - - - - - - - | - - - - - - - - - - | - - - - - - - - - - | 1503 |
| DEF1 | - - - - - - - - - - | - - - - - - - - - - | - - - - - - - - - - | 944 |
| DEF3 | - - - - - - - - - - | - - - - - - - - - - | - - - - - - - - - - | 997 |
| DER3 rev | - - - - - - - - - - | - - - - - - - - - - | - - - - - - - - - - | 940 |
| DER4 rev | CACAAGGCCT | AGCCAAGATC | ATTCAGAAAG | 899 |

Consensus
100%
Conservation
0%

| | | | | |
|---|---|---|---|---|
| NY99 E | - - - - - - - - - - | - - - - - - - - - - | - - - - - - - - - - | 1503 |
| WN02 E | - - - - - - - - - - | - - - - - - - - - - | - - - - - - - - - - | 1503 |
| DEF1 | - - - - - - - - - - | - - - - - - - - - - | - - - - - - - - - - | 944 |
| DEF3 | - - - - - - - - - - | - - - - - - - - - - | - - - - - - - - - - | 997 |
| DER3 rev | - - - - - - - - - - | - - - - - - - - - - | - - - - - - - - - - | 940 |
| DER4 rev | CTCATAAGGA | AGGAGTGTGC | GGTCTACGAT | 929 |

Consensus
100%
Conservation
0%

Fig. 11N

```
NY99 E      - -  1503
WN02 E      - -  1503
  DEF1      - -   944
  DEF3      - -   997
DER3 rev    - A   941
DER4 rev    C A   931
Consensus   - -
     100%
Conservation
      0%
```

Fig. 11O

|           |            |            |            |     |
|-----------|------------|------------|------------|-----|
| NY99 NS5  | ---------- | ---------- | ---------- | -   |
| WN02 NS5  | ---------- | ---------- | ---------- | -   |
| D NS5F2   | ---------- | ---------- | ---------- | 1   |
| D NS5F5   | ACCCCAATAC | GAGGAAGATG | TAAACTTGGG | 150 |
| D NS5R3 rev | ---------- | ---------- | ---------- | -   |
| D NS5R5 rev | ACCCCAATAC | NNG-AAGATG | TAAACTTGGG | 32  |
| Consensus | ---------- | ---------- | ---------- |     |

100% Conservation 0%

|           |            |            |            |     |
|-----------|------------|------------|------------|-----|
| NY99 NS5  | ---------- | ---------- | ---------- | -   |
| WN02 NS5  | ---------- | ---------- | ---------- | -   |
| D NS5F2   | ---------- | ---------- | ---------- | 1   |
| D NS5F5   | AAGTGGAACC | AGGGCGGTGG | GAAAACCCCT | 180 |
| D NS5R3 rev | ---------- | ---------- | ---------- | -   |
| D NS5R5 rev | AAGNN-ANCN | NGGGCGGTGG | GAAA--CCNN | 59  |
| Consensus | ---------- | ---------- | ---------- |     |

100% Conservation 0%

|           |            |            |            |     |
|-----------|------------|------------|------------|-----|
| NY99 NS5  | ---------- | ---------- | ---------- | -   |
| WN02 NS5  | ---------- | ---------- | ---------- | -   |
| D NS5F2   | ---------- | ---------- | ---------- | 1   |
| D NS5F5   | GCTCAACTCA | GACACCAGTA | AAATCAAGAA | 210 |
| D NS5R3 rev | ---------- | ---------- | ---------- | -   |
| D NS5R5 rev | GNTCAACTCA | GACNCCAGTA | AAATCAAGAN | 89  |
| Consensus | ---------- | ---------- | ---------- |     |

100% Conservation 0%

|           |            |            |            |     |
|-----------|------------|------------|------------|-----|
| NY99 NS5  | ---------- | ---------- | ---------- | -   |
| WN02 NS5  | ---------- | ---------- | ---------- | -   |
| D NS5F2   | ---------- | ---------- | ---------- | 1   |
| D NS5F5   | CAGGATTGAA | CGACTCAGGC | GTGAGTACAG | 240 |
| D NS5R3 rev | ---------- | ---------- | ---------- | -   |
| D NS5R5 rev | CAGGATTGAA | CGANTCAGGC | GTGAGTACAG | 119 |
| Consensus | ---------- | ---------- | ---------- |     |

100% Conservation 0%

Fig. 12B

| | | | | |
|---|---|---|---|---|
| NY99 NS5 | ---------- | ---------- | ---------- | - |
| WN02 NS5 | ---------- | ---------- | ---------- | - |
| D NS5F2 | TGGGTGCCNT | GTTTGAAGAG | CAGAATCAAT | 46 |
| D NS5F5 | TGGGTGCCAT | GTTTGAAGAG | CAGAATCAAT | 629 |
| D NS5R3 rev | TGGGTGCCAT | GTTTGAAGAG | CAGAATCAAT | 302 |
| D NS5R5 rev | TGGGTGCCAT | GTTTGAAGAG | CAGAATCAAT | 508 |
| Consensus | TGGGTGCCAT | GTTTGAAGAG | CAGAATCAAT | |

Conservation 100% / 0%

| | | | | |
|---|---|---|---|---|
| NY99 NS5 | ---------- | ---------- | ---------- | - |
| WN02 NS5 | ---------- | ---------- | ---------- | - |
| D NS5F2 | GGAGGAGCGC | CAGAGAAGCA | GTTGAAGATC | 76 |
| D NS5F5 | GGAGGAGCGC | CAGAGAAGCA | GTTGAAGATC | 659 |
| D NS5R3 rev | GGAGGAGCGC | CAGAGAAGCA | GTTGAAGATC | 332 |
| D NS5R5 rev | GGAGGAGCGC | CAGAGAAGCA | GTTGAAGATC | 538 |
| Consensus | GGAGGAGCGC | CAGAGAAGCA | GTTGAAGATC | |

Conservation 100% / 0%

| | | | | |
|---|---|---|---|---|
| NY99 NS5 | ---------- | ---------- | ---------- | - |
| WN02 NS5 | ---------- | ---------- | ---------- | - |
| D NS5F2 | CAAAATTTTG | GGAGATGGTG | GATGAGGAGC | 106 |
| D NS5F5 | CAAAATTTTG | GGAGATGGTG | GATGAGGAGC | 689 |
| D NS5R3 rev | CAAAATTTTG | GGAGATGGTG | GATGAGGAGC | 362 |
| D NS5R5 rev | CAAAATTTTG | GGAGATGGTG | GATGAGGAGC | 568 |
| Consensus | CAAAATTTTG | GGAGATGGTG | GATGAGGAGC | |

Conservation 100% / 0%

| | | | | |
|---|---|---|---|---|
| NY99 NS5 | ---------- | ----CGGGGG | GAATGTCACA | 16 |
| WN02 NS5 | ---------- | ----CGGGGG | GAATGTCACA | 16 |
| D NS5F2 | GCGAGGCACA | TCTGCGGGGG | GAATGTCACA | 136 |
| D NS5F5 | GCGAGGCACA | TCTGCGGGGG | GAATGTCACA | 719 |
| D NS5R3 rev | GCGAGGCACA | TCTGCGGGGG | GAATGTCACA | 392 |
| D NS5R5 rev | GCGAGGCACA | TCTGCGGGGG | GAATGTCACA | 598 |
| Consensus | GCGAGGCACA | TCTGCGGGGG | GAATGTCACA | |

Conservation 100% / 0%

Fig. 12F

```
   NY99 NS5    CTTGCATTTA  CAACATGATG  GGAAAGAGAG  46
   WN02 NS5    CTTGCATTTA  CAACATGATG  GGAAAGAGAG  46
    D NS5F2    CTTGCATTTA  CAACATGATG  GGAAAGAGAG  166
    D NS5F5    CTTGCATTTA  CAACATGATG  GGAAAGAGAG  749
 D NS5R3 rev   CTTGCATTTA  CAACATGATG  GGAAAGAGAG  422
 D NS5R5 rev   CTTGCATTTA  CAACATGATG  GGAAAGAGAG  628
   Consensus   CTTGCATTTA  CAACATGATG  GGAAAGAGAG NY99 NS5    AGAAAAACC   CGGAGAATTC  GGAAAGGCCA  76
   WN02 NS5    AGAAAAACC   CGGAGAGTTC  GGAAAGGCCA  76
    D NS5F2    AGAAAAACC   CGGAGAGTTC  GGAAAGGCCA  196
    D NS5F5    AGAAAAACC   CGGAGAGTTC  GGAAAGGCCA  779
 D NS5R3 rev   AGAAAAACC   CGGAGAGTTC  GGAAAGGCCA  452
 D NS5R5 rev   AGAAAAACC   CGGAGAGTTC  GGAAAGGCCA  658
   Consensus   AGAAAAACC   CGGAGAGTTC  GGAAAGGCCA NY99 NS5    AGGGAAGCAG  AGCCATTTGG  TTCATGTGGC  106
   WN02 NS5    AGGGAAGCAG  AGCCATTTGG  TTCATGTGGC  106
    D NS5F2    AGGGAAGCAG  AGCCATTTGG  TTCATGTGGC  226
    D NS5F5    AGGGAAGCAG  AGCCATTTGG  TTCATGTGGC  809
 D NS5R3 rev   AGGGAAGCAG  AGCCATTTGG  TTCATGTGGC  482
 D NS5R5 rev   AGGGAAGCAG  AGCCATTTGG  TTCATGTGGC  688
   Consensus   AGGGAAGCAG  AGCCATTTGG  TTCATGTGGC NY99 NS5    TCGGAGCTCG  CTTTCTGGAG  TTCGAGGCTC  136
   WN02 NS5    TCGGAGCTCG  CTTTCTGGAG  TTCGAGGCTC  136
    D NS5F2    TCGGAGCTCG  CTTTCTGGAG  TTCGAGGCTC  256
    D NS5F5    TCGGANCTCG  CTTTCTGGAG  TTCGAGGCTC  839
 D NS5R3 rev   TCGGAGCTCG  CTTTCTGGAG  TTCGAGGCTC  512
 D NS5R5 rev   TCGGAGCTCG  CTTTCTGGAG  TTCGAGGCTC  718
   Consensus   TCGGAGCTCG  CTTTCTGGAG  TTCGAGGCTC
```

Fig. 12G

| | | | | |
|---|---|---|---|---|
| NY99 NS5 | AGATCTATGC | TGATGACACA | GCTGGCTGGG | 286 |
| WN02 NS5 | AGATCTATGC | TGATGACACA | GCTGGCTGGG | 286 |
| D NS5F2 | AGATCTATGC | TGATGACACA | GCTGGCTGGG | 406 |
| D NS5F5 | ---------- | ---------- | ---------- | 955 |
| D NS5R3 rev | AGATCTATGC | TGATGACACA | GCTGGCTGGG | 662 |
| D NS5R5 rev | AGATCTATGC | TGATGACACA | GCTGGCTGGG | 868 |
| Consensus | AGATCTATGC | TGATGACACA | GCTGGCTGGG | |
| NY99 NS5 | ACACCCGCAT | CACGAGAGCT | GACTTGGAAA | 316 |
| WN02 NS5 | ACACCCGCAT | CACGAGTGCT | GACTTGGAAA | 316 |
| D NS5F2 | ACACCCGCAT | CACGAGAGCT | GACTTGGAAA | 436 |
| D NS5F5 | ---------- | ---------- | ---------- | 955 |
| D NS5R3 rev | ACACCCGCAT | CACGAGAGCT | GACTTGGAAA | 692 |
| D NS5R5 rev | ACACCCGCAT | CACGAGAGCT | GACTTGGAAA | 898 |
| Consensus | ACACCCGCAT | CACGAGAGCT | GACTTGGAAA | |
| NY99 NS5 | ATGAAGCTAA | GGTGCTTGAG | CTGCTTGATG | 346 |
| WN02 NS5 | ATGAAGCTAA | GGTGCTTGAG | TTGCTTGATG | 346 |
| D NS5F2 | ATGAAGCTAA | GGTGCTTGAG | TTGCTTGATG | 466 |
| D NS5F5 | ---------- | ---------- | ---------- | 955 |
| D NS5R3 rev | ATGAAGCTAA | GGTGCTTGAG | TTGCTTGATG | 722 |
| D NS5R5 rev | ATGAAGCTAA | GGTGCTTGAG | TTGCTTGATG | 928 |
| Consensus | ATGAAGCTAA | GGTGCTTGAG | TTGCTTGATG | |
| NY99 NS5 | GGGAACATCG | GCGTCTTGCC | AGGGCCATCA | 376 |
| WN02 NS5 | GGGAACATCG | GCGTCTTGCC | AGGGCCATCA | 376 |
| D NS5F2 | GGGAACATCG | GCGTCTTGCC | AGGGCCATCA | 496 |
| D NS5F5 | ---------- | ---------- | ---------- | 955 |
| D NS5R3 rev | GGGAACATCG | GCGTCTTGCC | AGGGCCATCA | 752 |
| D NS5R5 rev | GGGAACATCG | GCGTCTTGCC | AGGGCCATCA | 958 |
| Consensus | GGGAACATCG | GCGTCTTGCC | AGGGCCATCA | |

Fig. 12I

| | | | | |
|---|---|---|---|---|
| NY99 NS5 | TTGAGCTCAC | CTATCGTCAC | AAAGTTGTGA | 406 |
| WN02 NS5 | TTGAGCTCAC | CTATCGTCAC | AAAGTTGTGA | 406 |
| D NS5F2 | TTGAGCTCAC | CTATCGTCAC | AAAGTTGTGA | 526 |
| D NS5F5 | ---------- | ---------- | ---------- | 955 |
| D NS5R3 rev | TTGAGCTCAC | CTATCGTCAC | AAAGTTGTGA | 782 |
| D NS5R5 rev | TTGAGCTCAC | CNA------- | ---------- | 971 |
| Consensus | TTGAGCTCAC | CTATCGTCAC | AAAGTTGTGA | |

| | | | | |
|---|---|---|---|---|
| NY99 NS5 | AAGTGATGCG | CCCGGCTGCT | GATGGAAGAA | 436 |
| WN02 NS5 | AAGTGATGCG | CCCGGCTGCT | GATGGAAGAA | 436 |
| D NS5F2 | AAGTGATGCG | CCCGGCTGCT | GATGGAAGAA | 556 |
| D NS5F5 | ---------- | ---------- | ---------- | 955 |
| D NS5R3 rev | AAGTGATGCG | CCCGGCTGCT | GATGGAAGAA | 812 |
| D NS5R5 rev | ---------- | ---------- | ---------- | 971 |
| Consensus | AAGTGATGCG | CCCGGCTGCT | GATGGAAGAA | |

| | | | | |
|---|---|---|---|---|
| NY99 NS5 | CCGTCATGGA | TGTTATCTCC | AGAGAAGATC | 466 |
| WN02 NS5 | CCGTCATGGA | TGTTATCTCC | AGAGAAGATC | 466 |
| D NS5F2 | CCGTCATGGA | TGTTATCTCC | AGAGAAGATC | 586 |
| D NS5F5 | ---------- | ---------- | ---------- | 955 |
| D NS5R3 rev | CCGTCATGGA | TGTTATCTCC | AGAGAAGATC | 842 |
| D NS5R5 rev | ---------- | ---------- | ---------- | 971 |
| Consensus | CCGTCATGGA | TGTTATCTCC | AGAGAAGATC | |

| | | | | |
|---|---|---|---|---|
| NY99 NS5 | AGAGGGGGAG | TGGACAAGTT | GTCACCTACG | 496 |
| WN02 NS5 | AGAGGGGGAG | TGGACAAGTT | GTCACCTACG | 496 |
| D NS5F2 | AGAGGGGGAG | TGGACAAGTT | GTCACCTACG | 616 |
| D NS5F5 | ---------- | ---------- | ---------- | 955 |
| D NS5R3 rev | AGAGGGGGAG | TGGACAAGTT | GTCACCTACG | 872 |
| D NS5R5 rev | ---------- | ---------- | ---------- | 971 |
| Consensus | AGAGGGGGAG | TGGACAAGTT | GTCACCTACG | |

Fig. 12J

```
NY99 NS5      CCCTAAACAC  TTTCACCAAC  CTGGCCGTCC  526
WN02 NS5      CCCTAAACAC  TTTCACCAAC  CTGGCCGTCC  526
D NS5F2       CCCTAAACAC  TTTCACCAAC  CTGGCCGTCC  646
D NS5F5       ----------  ----------  ----------  955
D NS5R3 rev   CCCTAAACAC  TTTCACCAAC  CTGGCCGTCC  902
D NS5R5 rev   ----------  ----------  ----------  971
Consensus     CCCTAAACAC  TTTCACCAAC  CTGGCCGTCC
100%
Conservation
0%

NY99 NS5      AGCTGGTGAG  GATGATGGAA  GGGGAA-GGA  555
WN02 NS5      AGCTGGTGAG  GATGATGGAA  GGGGAA-GGA  555
D NS5F2       AGCTGGTGAG  GATGATGGAA  GGGGAANGGA  676
D NS5F5       ----------  ----------  ----------  955
D NS5R3 rev   AGCTGGTGAG  GATGATGGAA  GGGGAA-GGA  931
D NS5R5 rev   ----------  ----------  ----------  971
Consensus     AGCTGGTGAG  GATGATGGAA  GGGGAA-GGA
100%
Conservation
0%

NY99 NS5      GTGATTGGCC  CAGATGATGT  GGAGAAACTC  585
WN02 NS5      GTGATTGGCC  CAGATGATGT  GGAGAAACTC  585
D NS5F2       GTGATTGGCC  CAGATGATGT  GGAGAAACTC  706
D NS5F5       ----------  ----------  ----------  955
D NS5R3 rev   GTGATTGGCC  CAGATGATGT  GGAGAAACTC  961
D NS5R5 rev   ----------  ----------  ----------  971
Consensus     GTGATTGGCC  CAGATGATGT  GGAGAAACTC
100%
Conservation
0%

NY99 NS5      ACAAAAGGGA  AAGGACCCAA  AGT-------  608
WN02 NS5      ACAAAAGGGA  AAGGACCCAA  AGT-------  608
D NS5F2       ACAAAAGGGA  AAGGACCCAA  AGTCAGGACC  736
D NS5F5       ----------  ----------  ----------  955
D NS5R3 rev   ACAAAAGG--  ----------  ----------  969
D NS5R5 rev   ----------  ----------  ----------  971
Consensus     ACAAAAGGGA  AAGGACCCAA  AGT-------
100%
Conservation
0%
```

Fig. 12K

```
NY99 NS5      - - - - - - - - - -   - - - - - - - - - -   - - - - - - - - - -   608
WN02 NS5      - - - - - - - - - -   - - - - - - - - - -   - - - - - - - - - -   608
  D NS5F2     T G G C T G T T T G   A G A A T G G G G A   A G A A A G A C T C   766
  D NS5F5     - - - - - - - - - -   - - - - - - - - - -   - - - - - - - - - -   955
D NS5R3 rev   - - - - - - - - - -   - - - - - - - - - -   - - - - - - - - - -   969
D NS5R5 rev   - - - - - - - - - -   - - - - - - - - - -   - - - - - - - - - -   971
  Consensus   - - - - - - - - - -   - - - - - - - - - -   - - - - - - - - - -
       100%
Conservation
         0%

NY99 NS5      - - - - - - - - - -   - - - - - - - - - -   - - - - - - - - - -   608
WN02 NS5      - - - - - - - - - -   - - - - - - - - - -   - - - - - - - - - -   608
  D NS5F2     A G C C G C A T G G   C T G T C A G T G G   A G A T G A C T G T   796
  D NS5F5     - - - - - - - - - -   - - - - - - - - - -   - - - - - - - - - -   955
D NS5R3 rev   - - - - - - - - - -   - - - - - - - - - -   - - - - - - - - - -   969
D NS5R5 rev   - - - - - - - - - -   - - - - - - - - - -   - - - - - - - - - -   971
  Consensus   - - - - - - - - - -   - - - - - - - - - -   - - - - - - - - - -
       100%
Conservation
         0%

NY99 NS5      - - - - - - - - - -   - - - - - - - - - -   - - - - - - - - - -   608
WN02 NS5      - - - - - - - - - -   - - - - - - - - - -   - - - - - - - - - -   608
  D NS5F2     G T G G T A A A G C   C C C T G G A C G A   T C G C T T T G C C   826
  D NS5F5     - - - - - - - - - -   - - - - - - - - - -   - - - - - - - - - -   955
D NS5R3 rev   - - - - - - - - - -   - - - - - - - - - -   - - - - - - - - - -   969
D NS5R5 rev   - - - - - - - - - -   - - - - - - - - - -   - - - - - - - - - -   971
  Consensus   - - - - - - - - - -   - - - - - - - - - -   - - - - - - - - - -
       100%
Conservation
         0%

NY99 NS5      - - - - - - - - - -   - - - - - - - - - -   - - - - - - - - - -   608
WN02 NS5      - - - - - - - - - -   - - - - - - - - - -   - - - - - - - - - -   608
  D NS5F2     A C C T C G C T C C   A C T T C C T C A A   T G C T A T G T C A   856
  D NS5F5     - - - - - - - - - -   - - - - - - - - - -   - - - - - - - - - -   955
D NS5R3 rev   - - - - - - - - - -   - - - - - - - - - -   - - - - - - - - - -   969
D NS5R5 rev   - - - - - - - - - -   - - - - - - - - - -   - - - - - - - - - -   971
  Consensus   - - - - - - - - - -   - - - - - - - - - -   - - - - - - - - - -
       100%
Conservation
         0%
```

Fig. 12L

| | | | | |
|---|---|---|---|---|
| NY99 NS5 | - - - - - - - - - - | - - - - - - - - - - | - - - - - - - - - - | |
| WN02 NS5 | - - - - - - - - - - | - - - - - - - - - - | - - - - - - - - - - | |
| H NS5F2 | - - - - - - - - - - | - - - - - - - - - - | - - - - - - - - - - | |
| H NS5F5 | AAAACC-ATG | GGACACCATC | ACGAATGTTA | 389 |
| H NS5R3 rev | AAAACCCNTG | GGACNCCATC | NCGAANNNNC | 109 |
| H NS5R5 rev | AAAACC-ATG | GGACACCATC | ACGAATGTTA | 314 |
| Consensus | AAAACC--TG | GGAC-CCATC | -CGAA----- | |
| 100% Conservation 0% | | | | |
| NY99 NS5 | - - - - - - - - - - | - - - - - - - - - - | - - - - - - - - - - | |
| WN02 NS5 | - - - - - - - - - - | - - - - - - - - - - | - - - - - - - - - - | |
| H NS5F2 | - - - - - - - - - - | - - - - - - - - - - | - - - - - - - - - - | |
| H NS5F5 | CCACCATGGC | CATGACTGAC | ACTACTCCC- | 418 |
| H NS5R3 rev | CACCATNGNC | CATGACTGNC | ACTACTCCCN | 139 |
| H NS5R5 rev | CCACCATGGC | CATGACTGAC | ACTACTCCC- | 343 |
| Consensus | C--C---G-C | CATGACTG-C | ACTACTCCC- | |
| 100% Conservation 0% | | | | |
| NY99 NS5 | - - - - - - - - - - | - - - - - - - - - - | - - - - - - - - - - | |
| WN02 NS5 | - - - - - - - - - - | - - - - - - - - - - | - - - - - - - - - - | |
| H NS5F2 | - - - - - - - - - - | - - - - - - - - - - | - - - - - - - - - - | |
| H NS5F5 | TTCGGGCAGC | AGCGAGTGTT | CAAAGAGAAG | 448 |
| H NS5R3 rev | TTCGGGCAGC | AGCGAGTGTT | CAAAGAGAAG | 169 |
| H NS5R5 rev | TTCGGGCAGC | AGCGAGTGTT | CAAAGAGAAG | 373 |
| Consensus | TTCGGGCAGC | AGCGAGTGTT | CAAAGAGAAG | |
| 100% Conservation 0% | | | | |
| NY99 NS5 | - - - - - - - - - - | - - - - - - - - - - | - - - - - - - - - - | |
| WN02 NS5 | - - - - - - - - - - | - - - - - - - - - - | - - - - - - - - - - | |
| H NS5F2 | - - - - - - - - - - | - - - - - - - - - - | - - - - - - - - - - | |
| H NS5F5 | GTGGACACGA | AAGCTCCTGA | ACCGCCAGAA | 478 |
| H NS5R3 rev | GTGGACACGA | AAGCTCNNGA | ACCGCCAGAA | 199 |
| H NS5R5 rev | GTGGACACGA | AAGCTCCTGA | ACCGCCAGAA | 403 |
| Consensus | GTGGACACGA | AAGCTC--GA | ACCGCCAGAA | |
| 100% Conservation 0% | | | | |

Fig. 13D

| | | | | |
|---|---|---|---|---|
| NY99 NS5 | ---------- | ---------- | ---------- | - |
| WN02 NS5 | ---------- | ---------- | ---------- | - |
| H NS5F2 | ---------- | ---------- | ---------- | - |
| H NS5F5 | GGAGTGAAGT | ACGTGCTCAA | CGAGACCACC | 508 |
| H NS5R3 rev | GGAGTGAAGT | ACGTGCTCAA | CGAGACCACC | 229 |
| H NS5R5 rev | GGAGTGAAGT | ACGTGCTCAA | CGAGACCACC | 433 |
| Consensus | GGAGTGAAGT | ACGTGCTCAA | CGAGACCACC | |
| NY99 NS5 | ---------- | ---------- | ---------- | - |
| WN02 NS5 | ---------- | ---------- | ---------- | - |
| H NS5F2 | ---------- | ---------- | ---------- | - |
| H NS5F5 | AACTGGTTGT | GGGCGTTTTT | GGCCAGAGAA | 538 |
| H NS5R3 rev | AACTGGTTGT | GGGCGTTTTT | GGCCAGAGAA | 259 |
| H NS5R5 rev | AACTGGTTGT | GGGCGTTTTT | GGCCAGAGAA | 463 |
| Consensus | AACTGGTTGT | GGGCGTTTTT | GGCCAGAGAA | |
| NY99 NS5 | ---------- | ---------- | ---------- | - |
| WN02 NS5 | ---------- | ---------- | ---------- | - |
| H NS5F2 | ---------- | ---------- | ---------- | - |
| H NS5F5 | AAACGTCCCA | GAATGTGCTC | TCGAGAGGAA | 568 |
| H NS5R3 rev | AAACGTCCCA | GAATGTGCTC | TCGAGAGGAA | 289 |
| H NS5R5 rev | AAACGTCCCA | GAATGTGCTC | TCGAGAGNNN | 493 |
| Consensus | AAACGTCCCA | GAATGTGCTC | TCGAGAG--- | |
| NY99 NS5 | ---------- | ---------- | ---------- | - |
| WN02 NS5 | ---------- | ---------- | ---------- | - |
| H NS5F2 | ---------- | -----CACAG | CAATGCAGCT | 15 |
| H NS5F5 | TTCATAAGAA | AGGTCAACAG | CAATGCAGCT | 598 |
| H NS5R3 rev | TTCATNAGAA | AGGTCAACAG | CAATGCAGCT | 319 |
| H NS5R5 rev | NNNATAAGAA | AGGTCAACAG | CAATGCAGCT | 523 |
| Consensus | ---AT-AGAA | AGGTCAACAG | CAATGCAGCT | |

Fig. 13E

| | | | | |
|---|---|---|---|---|
| NY99 NS5 | CTGGGTTTTC | TCAATGAAGA | CCACTGGCTT | 165 |
| WN02 NS5 | CTGGGTTTTC | TCAATGAAGA | CCACTGGCTT | 165 |
| H NS5F2 | CTGGGTTTTC | TCAATGAAGA | TCACTGGCTT | 285 |
| H NS5F5 | CTNGGTTTTC | TCAATGAAGA | TCACTGGCTT | 868 |
| H NS5R3 rev | CTGGGTTTTC | TCAATGAAGA | TCACTGGCTT | 589 |
| H NS5R5 rev | CTGGGTTTTC | TCAATGAAGA | TCACTGGCTT | 793 |
| Consensus | CTGGGTTTTC | TCAATGAAGA | TCACTGGCTT | |
| NY99 NS5 | GGAAGAAAGA | ACTCAGGAGG | AGGTGTCGAG | 195 |
| WN02 NS5 | GGAAGAAAGA | ACTCAGGAGG | AGGTGTCGAG | 195 |
| H NS5F2 | GGAAGAAAGA | ACTCAGGAGG | AGGTGTCGAG | 315 |
| H NS5F5 | GGAAGAAAGA | ACTCNNNANG | AGGTGTCGAG | 898 |
| H NS5R3 rev | GGAAGAAAGA | ACTCAGGAGG | AGGTGTCGAG | 619 |
| H NS5R5 rev | GGAAGAAAGA | ACTCAGGAGG | AGGTGTCGAG | 823 |
| Consensus | GGAAGAAAGA | ACTCAGGAGG | AGGTGTCGAG | |
| NY99 NS5 | GGCTTGGGCC | TCCAAAAACT | GGGTTACATC | 225 |
| WN02 NS5 | GGCTTGGGCC | TCCAAAAACT | GGGTTACATC | 225 |
| H NS5F2 | GGCTTGGGCC | TCCAAAAACT | GGGTTACATC | 345 |
| H NS5F5 | GGCTTGGGCC | TCCAAAAACT | GGGTTACATC | 928 |
| H NS5R3 rev | GGCTTGGGCC | TCCAAAAACT | GGGTTACATC | 649 |
| H NS5R5 rev | GGCTTGGGCC | TCCAAAAACT | GGGTTACATC | 853 |
| Consensus | GGCTTGGGCC | TCCAAAAACT | GGGTTACATC | |
| NY99 NS5 | CTGCGTGAAG | TTGGCACCCG | G-CCTGGGGG | 254 |
| WN02 NS5 | CTGCGTGAAG | TTGGCACCCG | G-CCTGGGGG | 254 |
| H NS5F2 | CTGCGTGAAG | TTGGCACCCG | G-CCTGGGGG | 374 |
| H NS5F5 | CTGCGTGAAG | TTGGCACCCN | GNCCTGGGGG | 958 |
| H NS5R3 rev | CTGCGTGAAG | TTGGCACCCG | G-CCTGGGGG | 678 |
| H NS5R5 rev | CTGCGTGAAG | TTGGCACCCG | G-CCTGGGGG | 882 |
| Consensus | CTGCGTGAAG | TTGGCACCCG | G-CCTGGGGG | |

Fig. 13H

| | | | | |
|---|---|---|---|---|
| NY99 NS5 | CGCCCTAAAC | ACTTTCACCA | ACCTGGCCGT | 524 |
| WN02 NS5 | CGCCCTAAAC | ACTTTCACCA | ACCTGGCCGT | 524 |
| H NS5F2 | CGCNCTAAAC | ACTTTCACCA | ACCTGGCCGT | 644 |
| H NS5F5 | - - - - - - - - - - | - - - - - - - - - - | - - - - - - - - - - | 1027 |
| H NS5R3 rev | CNCNCTAAAC | ACTTTCACCA | ACCTGGCCGT | 948 |
| H NS5R5 rev | - - - - - - - - - - | - - - - - - - - - - | - - - - - - - - - - | 1015 |
| Consensus | CGCCCTAAAC | ACTTTCACCA | ACCTGGCCGT | |

| | | | | |
|---|---|---|---|---|
| NY99 NS5 | CCAGCTGGTG | AGGATGATGG | AAGGGGAA - G | 553 |
| WN02 NS5 | CCAGCTGGTG | AGGATGATGG | AAGGGGAA - G | 553 |
| H NS5F2 | CCAGCTGGTG | AGGATGATGG | AAGGGGAANG | 674 |
| H NS5F5 | - - - - - - - - - - | - - - - - - - - - - | - - - - - - - - - - | 1027 |
| H NS5R3 rev | CCAGCTGGTG | AGGATGATGG | AAGGGGAA - G | 977 |
| H NS5R5 rev | - - - - - - - - - - | - - - - - - - - - - | - - - - - - - - - - | 1015 |
| Consensus | CCAGCTGGTG | AGGATGATGG | AAGGGGAA - G | |

| | | | | |
|---|---|---|---|---|
| NY99 NS5 | GAGTGATTGG | CCCAGATGAT | GTGGAGAAAC | 583 |
| WN02 NS5 | GAGTGATTGG | CCCAGATGAT | GTGGAGAAAC | 583 |
| H NS5F2 | GAGTGATTGG | CCCAGATGAT | GTGGAGAAAC | 704 |
| H NS5F5 | - - - - - - - - - - | - - - - - - - - - - | - - - - - - - - - - | 1027 |
| H NS5R3 rev | GAGTGATTGG | CCCAGATGAT | GTGGAGAAAC | 1007 |
| H NS5R5 rev | - - - - - - - - - - | - - - - - - - - - - | - - - - - - - - - - | 1015 |
| Consensus | GAGTGATTGG | CCCAGATGAT | GTGGAGAAAC | |

| | | | | |
|---|---|---|---|---|
| NY99 NS5 | TCACAAAAGG | GAAAGGACCC | AAAGT - - - - - | 608 |
| WN02 NS5 | TCACAAAAGG | GAAAGGACCC | AAAGT - - - - - | 608 |
| H NS5F2 | TCACAAAAGG | GAAAGGACCC | AAAGTCAGGA | 734 |
| H NS5F5 | - - - - - - - - - - | - - - - - - - - - - | - - - - - - - - - - | 1027 |
| H NS5R3 rev | TCACAAAAGG | GA - - - - - - - - | - - - - - - - - - - | 1019 |
| H NS5R5 rev | - - - - - - - - - - | - - - - - - - - - - | - - - - - - - - - - | 1015 |
| Consensus | TCACAAAAGG | GAAAGGACCC | AAAGT - - - - - | |

Fig. 13K

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| NS5F2 | - - - - - - - - - - | - - - - - - - - - - | - - - - - - - - - - | - |
| NS5F5 | TCNCGGATTC | CNCGCACGAG | ATGTATTGGG | 30 |
| NS5R3 rev | - - - - - - - - - - | - - - - - - - - - - | - - - - - - - - - - | - |
| NS5R5 rev | - - - - - - - - - - | - - - - - - - - - - | - - - - - - - - - - | - |
| Consensus | - - - - - - - - - - | - - - - - - - - - - | - - - - - - - - - - | |

100%
Conservation
0%

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| NS5F2 | - - - - - - - - - - | - - - - - - - - - - | - - - - - - - - - - | - |
| NS5F5 | TGAGTCGAGC | TTCAGGCAAT | GTGGTACATT | 60 |
| NS5R3 rev | - - - - - - - - - - | - - - - - - - - - - | - - - - - - - - - - | - |
| NS5R5 rev | - - - - - - - - - - | - - - - - - - - - - | - - - - - - - - - - | - |
| Consensus | - - - - - - - - - - | - - - - - - - - - - | - - - - - - - - - - | |

100%
Conservation
0%

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| NS5F2 | - - - - - - - - - - | - - - - - - - - - - | - - - - - - - - - - | - |
| NS5F5 | CAGTGAATAT | GACCAGCCAG | GTGCTCCTAG | 90 |
| NS5R3 rev | - - - - - - - - - - | - - - - - - - - - - | - - - - - - - - - - | - |
| NS5R5 rev | - - - - - - - - - - | - - - - - - - - - - | - - - - - - - - - - | - |
| Consensus | - - - - - - - - - - | - - - - - - - - - - | - - - - - - - - - - | |

100%
Conservation
0%

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| NS5F2 | - - - - - - - - - - | - - - - - - - - - - | - - - - - - - - - - | - |
| NS5F5 | GAAGAATGGA | AAAAAGGACC | TGGAAGGGAC | 120 |
| NS5R3 rev | - - - - - - - - - - | - - - - - - - - - - | - - - - - - - - - - | - |
| NS5R5 rev | - - - - - - - - - - | - - - - - - - - - - | - - - - - GGGAC | 5 |
| Consensus | - - - - - - - - - - | - - - - - - - - - - | - - - - - - - - - - | |

100%
Conservation
0%

Fig. 14A

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| NS5F2 | - - - - - - - - - - | - - - - - - - - - - | - - - - - - - - - - | - |
| NS5F5 | CCCAATACGA | GGAAGATGTA | AACTTGGGAA | 150 |
| NS5R3 rev | - - - - - - - - - - | - - - - - - - - - - | - - - - - - - - - - | - |
| NS5R5 rev | CCCAATACGA | GGAAGATGTA | AACTNGGGAA | 35 |
| Consensus | - - - - - - - - - - | - - - - - - - - - - | - - - - - - - - - - | |
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| NS5F2 | - - - - - - - - - - | - - - - - - - - - - | - - - - - - - - - - | - |
| NS5F5 | GTGGAACCAG | GGCGGTGGGA | AAACCCCTGC | 180 |
| NS5R3 rev | - - - - - - - - - - | - - - - - - - - - - | - - - - - - - - - - | - |
| NS5R5 rev | GTGGANCCAG | GGCGGTGGGA | AAACCCNNGC | 65 |
| Consensus | - - - - - - - - - - | - - - - - - - - - - | - - - - - - - - - - | |
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| NS5F2 | - - - - - - - - - - | - - - - - - - - - - | - - - - - - - - - - | - |
| NS5F5 | TCAACTCAGA | CACCAGTAAA | ATCAAGAACA | 210 |
| NS5R3 rev | - - - - - - - - - - | - - - - - - - - - - | - - - - - - - - - - | - |
| NS5R5 rev | TCAACTCAGA | CACCAGTAAA | ATCAAGAACA | 95 |
| Consensus | - - - - - - - - - - | - - - - - - - - - - | - - - - - - - - - - | |
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| NS5F2 | - - - - - - - - - - | - - - - - - - - - - | - - - - - - - - - - | - |
| NS5F5 | GGATTGAACG | ACTCAGGCGT | GAGTACAGTT | 240 |
| NS5R3 rev | - - - - - - - - - - | - - - - - - - - - - | - - - - - - - - - - | - |
| NS5R5 rev | GGATTGAACG | ANTCAGGCGT | GAGTACAGTT | 125 |
| Consensus | - - - - - - - - - - | - - - - - - - - - - | - - - - - - - - - - | |

Fig. 14B

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| NS5F2 | - - - - - - - - - - | - - - - - - - - - - | - - - - - - - - - - | - |
| NS5F5 | CGACGTGGCA | CCACGATGAG | AACCACCCAT | 270 |
| NS5R3 rev | - - - - - - - - - - | - - - - - - - - - - | - - - - - - - - - - | - |
| NS5R5 rev | CGACGTGGCA | CCACGATGAG | AACCACCCAT | 155 |
| Consensus | - - - - - - - - - - | - - - - - - - - - - | - - - - - - - - - - | |

100%
Conservation
0%

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| NS5F2 | - - - - - - - - - - | - - - - - - - - - - | - - - - - - - - - - | - |
| NS5F5 | ATAGAACCTG | GAACTATCAC | GGCAGTTATG | 300 |
| NS5R3 rev | - - - - - - - - - - | - - - - - - - - - - | - - - - - - - - - - | - |
| NS5R5 rev | ATAGAACCTG | GAACTATCAC | GGCAGTTATG | 185 |
| Consensus | - - - - - - - - - - | - - - - - - - - - - | - - - - - - - - - - | |

100%
Conservation
0%

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| NS5F2 | - - - - - - - - - - | - - - - - - - - - - | - - - - - - - - - - | - |
| NS5F5 | ATGTGAAGCC | CACAGGCTCC | GCCAGTTCGC | 330 |
| NS5R3 rev | - - - - - - - - - - | - - - - - - - - - - | - - - - - - - - - - | - |
| NS5R5 rev | ATGTGAAGCC | CACAGGCTCC | GCCAGTTCGC | 215 |
| Consensus | - - - - - - - - - - | - - - - - - - - - - | - - - - - - - - - - | |

100%
Conservation
0%

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| NS5F2 | - - - - - - - - - - | - - - - - - - - - - | - - - - - - - - - - | - |
| NS5F5 | TGGTTAATGG | AGTGGTCAGG | CTCCTCTCAA | 360 |
| NS5R3 rev | - - - - - AATGG | AGNGGTCAGG | CTCCTCTCAA | 25 |
| NS5R5 rev | TGGTTAATGG | AGTGGTCAGG | CTCCTCTCAA | 245 |
| Consensus | - - - - - AATGG | AG - GGTCAGG | CTCCTCTCAA | |

100%
Conservation
0%

Fig. 14C

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| NS5F2 | - - - - - - - - - - | - - - - - - - - - - | - - - - - - - - - - | - |
| NS5F5 | AA - CCATGGG | ACACCATCAC | GAATGTTACC | 389 |
| NS5R3 rev | AACCCNTGGG | ACACCATCAC | GAATGNTACC | 55 |
| NS5R5 rev | AA - CCATGGG | ACACCATCAC | GAATGTTACC | 274 |
| Consensus | AA - CC - TGGG | ACACCATCAC | GAATG - TACC | |

Conservation 100% / 0%

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| NS5F2 | - - - - - - - - - - | - - - - - - - - - - | - - - - - - - - - - | - |
| NS5F5 | ACCATGGCCA | TGACTGACAC | TACTCCC - TT | 418 |
| NS5R3 rev | ACCATGGCCA | TGACTGACAC | TACTCCCNTT | 85 |
| NS5R5 rev | ACCATGGCCA | TGACTGACAC | TACTCCC - TT | 303 |
| Consensus | ACCATGGCCA | TGACTGACAC | TACTCCC - TT | |

Conservation 100% / 0%

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| NS5F2 | - - - - - - - - - - | - - - - - - - - - - | - - - - - - - - - - | - |
| NS5F5 | CGGGCAGCAG | CGAGTGTTCA | AAGAGAAGGT | 448 |
| NS5R3 rev | CGGGCAGCAG | CGAGTGTTCA | AAGAGAAGGT | 115 |
| NS5R5 rev | CGGGCAGCAG | CGAGTGTTCA | AAGAGAAGGT | 333 |
| Consensus | CGGGCAGCAG | CGAGTGTTCA | AAGAGAAGGT | |

Conservation 100% / 0%

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| NS5F2 | - - - - - - - - - - | - - - - - - - - - - | - - - - - - - - - - | - |
| NS5F5 | GGACACGAAA | GCTCCTGAAC | CGCCAGAAGG | 478 |
| NS5R3 rev | GGACACGAAA | GCTCNTGAAC | CGCCAGAAGG | 145 |
| NS5R5 rev | GGACACGAAA | GCTCCTGAAC | CGCCAGAAGG | 363 |
| Consensus | GGACACGAAA | GCTC - TGAAC | CGCCAGAAGG | |

Conservation 100% / 0%

Fig. 14D

| | | | | |
|---|---|---|---|---|
| NY99 NS5 | ---------- | ---------- | ---------- | - |
| WN02 NS5 | ---------- | ---------- | ---------- | - |
| NS5F2 | GGGTGCCATG | TTTGAAGAGC | AGAATCAATG | 43 |
| NS5F5 | GGGTGCCATG | TTTGAAGAGC | AGAATCAATG | 628 |
| NS5R3 rev | GGGTGCCATG | TTTGAAGAGC | AGAATCAATG | 295 |
| NS5R5 rev | GGGTGCCATG | TTTGAAGAGC | AGAATCAATG | 513 |
| Consensus | GGGTGCCATG | TTTGAAGAGC | AGAATCAATG | |

| NY99 NS5 | ---------- | ---------- | ---------- | - |
|---|---|---|---|---|
| WN02 NS5 | ---------- | ---------- | ---------- | - |
| NS5F2 | GAGGAGCGCC | AGANAAGCAG | TTGAAGATCC | 73 |
| NS5F5 | GAGGAGCGCC | AGAGAAGCAG | TTGAAGATCC | 658 |
| NS5R3 rev | GAGGAGCGCC | AGAGAAGCAG | TTGAAGATCC | 325 |
| NS5R5 rev | GAGGAGCGCC | AGAGAAGCAG | TTGAAGATCC | 543 |
| Consensus | GAGGAGCGCC | AGAGAAGCAG | TTGAAGATCC | |

| NY99 NS5 | ---------- | ---------- | ---------- | - |
|---|---|---|---|---|
| WN02 NS5 | ---------- | ---------- | ---------- | - |
| NS5F2 | AAAATTTTGG | GAGATGGTGG | ATGAGGAGCG | 103 |
| NS5F5 | AAAATTTTGG | GAGATGGTGG | ATGAGGAGCG | 688 |
| NS5R3 rev | AAAATTTTGG | GAGATGGTGG | ATGAGGAGCG | 355 |
| NS5R5 rev | AAAATTTTGG | GAGATGGTGG | ATGAGGAGCG | 573 |
| Consensus | AAAATTTTGG | GAGATGGTGG | ATGAGGAGCG | |

| NY99 NS5 | ---------- | ---CGGGGGG | AATGTCACAC | 17 |
|---|---|---|---|---|
| WN02 NS5 | ---------- | ---CGGGGGG | AATGTCACAC | 17 |
| NS5F2 | CGAGGCACAT | CTGCGGGGGG | AATGTCACAC | 133 |
| NS5F5 | CGAGGCACAT | CTGCGGGGGG | AATGTCACAC | 718 |
| NS5R3 rev | CGAGGCACAT | CTGCGGGGGG | AATGTCACAC | 385 |
| NS5R5 rev | CGAGGCACAT | CTGCGGGGGG | AATGTCACAC | 603 |
| Consensus | CGAGGCACAT | CTGCGGGGGG | AATGTCACAC | |

Fig. 14F

| | | | | |
|---|---|---|---|---|
| NY99 NS5 | TTGCATTTAC | AACATGATGG | GAAAGAGAGA | 47 |
| WN02 NS5 | TTGCATTTAC | AACATGATGG | GAAAGAGAGA | 47 |
| NS5F2 | TTGCATTTAC | AACATGATGG | GAAAGAGAGA | 163 |
| NS5F5 | TTGCATTTAC | AACATGATGG | GAAAGAGAGA | 748 |
| NS5R3 rev | TTGCATTTAC | AACATGATGG | GAAAGAGAGA | 415 |
| NS5R5 rev | TTGCATTTAC | AACATGATGG | GAAAGAGAGA | 633 |
| Consensus | TTGCATTTAC | AACATGATGG | GAAAGAGAGA | |
| NY99 NS5 | GAAAAAACCC | GGAGAATTCG | GAAAGGCCAA | 77 |
| WN02 NS5 | GAAAAAACCC | GGAGAGTTCG | GAAAGGCCAA | 77 |
| NS5F2 | GAAAAAACCC | GGAGAGTTCG | GAAAGGCTAA | 193 |
| NS5F5 | GAAAAAACCC | GGAGAGTTCG | GAAAGGCTAA | 778 |
| NS5R3 rev | GAAAAAACCC | GGAGAGTTCG | GAAAGGCTAA | 445 |
| NS5R5 rev | GAAAAAACCC | GGAGAGTTCG | GAAAGGCTAA | 663 |
| Consensus | GAAAAAACCC | GGAGAGTTCG | GAAAGGCTAA | |
| NY99 NS5 | GGGAAGCAGA | GCCATTTGGT | TCATGTGGCT | 107 |
| WN02 NS5 | GGGAAGCAGA | GCCATTTGGT | TCATGTGGCT | 107 |
| NS5F2 | GGGAAGCAGA | GCCATTTGGT | TCATGTGGCT | 223 |
| NS5F5 | GGGAAGCAGA | GCCATTTGGT | TCATGTGGCT | 808 |
| NS5R3 rev | GGGAAGCAGA | GCCATTTGGT | TCATGTGGCT | 475 |
| NS5R5 rev | GGGAAGCAGA | GCCATTTGGT | TCATGTGGCT | 693 |
| Consensus | GGGAAGCAGA | GCCATTTGGT | TCATGTGGCT | |
| NY99 NS5 | CGGAGCTCGC | TTTCTGGAGT | TCGAGGCTCT | 137 |
| WN02 NS5 | CGGAGCTCGC | TTTCTGGAGT | TCGAGGCTCT | 137 |
| NS5F2 | CGGAGCTCGC | TTTCTGGAGT | TCGAGGCTCT | 253 |
| NS5F5 | CGGANCTCGC | TTTCTGGAGT | TCGAGGCTCT | 838 |
| NS5R3 rev | CGGAGCTCGC | TTTCTGGAGT | TCGAGGCTCT | 505 |
| NS5R5 rev | CGGAGCTCGC | TTTCTGGAGT | TCGAGGCTCT | 723 |
| Consensus | CGGAGCTCGC | TTTCTGGAGT | TCGAGGCTCT | |

Fig. 14G

| | | | | |
|---|---|---|---|---|
| NY99 NS5 | GGGTTTTCTC | AATGAAGACC | ACTGGCTTGG | 167 |
| WN02 NS5 | GGGTTTTCTC | AATGAAGACC | ACTGGCTTGG | 167 |
| NS5F2 | GGGTTTTCTC | AATGAAGACC | ACTGGCTTGG | 283 |
| NS5F5 | GGGTTTTCTC | AATGAAGACC | ACTGGCTTGG | 868 |
| NS5R3 rev | GGGTTTTCTC | AATGAAGACC | ACTGGCTTGG | 535 |
| NS5R5 rev | GGGTTTTCTC | AATGAAGACC | ACTGGCTTGG | 753 |
| Consensus | GGGTTTTCTC | AATGAAGACC | ACTGGCTTGG | |

| | | | | |
|---|---|---|---|---|
| NY99 NS5 | AAGAAAGAAC | TCAGGAGGAG | GTGTCGAGGG | 197 |
| WN02 NS5 | AAGAAAGAAC | TCAGGAGGAG | GTGTCGAGGG | 197 |
| NS5F2 | AAGAAAGAAC | TCAGGAGGAG | GTGTCGAGGG | 313 |
| NS5F5 | AAGAAAGAAC | TCNNGAGGAG | GTGTCGAGGG | 898 |
| NS5R3 rev | AAGAAAGAAC | TCAGGAGGAG | GTGTCGAGGG | 565 |
| NS5R5 rev | AAGAAAGAAC | TCAGGAGGAG | GTGTCGAGGG | 783 |
| Consensus | AAGAAAGAAC | TCAGGAGGAG | GTGTCGAGGG | |

| | | | | |
|---|---|---|---|---|
| NY99 NS5 | CTTGGGCCTC | CAAAAACTGG | GTTACATCCT | 227 |
| WN02 NS5 | CTTGGGCCTC | CAAAAACTGG | GTTACATCCT | 227 |
| NS5F2 | CTTGGGCCTC | CAAAAACTGG | GTTACATCCT | 343 |
| NS5F5 | CTTGGGCCTC | CAAAAACTGG | GTTACATCCT | 928 |
| NS5R3 rev | CTTGGGCCTC | CAAAAACTGG | GTTACATCCT | 595 |
| NS5R5 rev | CTTGGGCCTC | CAAAAACTGG | GTTACATCCT | 813 |
| Consensus | CTTGGGCCTC | CAAAAACTGG | GTTACATCCT | |

| | | | | |
|---|---|---|---|---|
| NY99 NS5 | GCGTGAAGTT | GGCACCCGGC | CTGGGGGCAA | 257 |
| WN02 NS5 | GCGTGAAGTT | GGCACCCGGC | CTGGGGGCAA | 257 |
| NS5F2 | GCGTGAAGTT | GGCACCCGAC | CTGGGGGCAA | 373 |
| NS5F5 | GCGTGAAGTT | GGCACCCGAC | CTGGGGGCAA | 958 |
| NS5R3 rev | GCGTGAAGTT | GGCACCCGAC | CTGGGGGCAA | 625 |
| NS5R5 rev | GCGTGAAGTT | GGCACCCGAC | CTGGGGGCAA | 843 |
| Consensus | GCGTGAAGTT | GGCACCCGAC | CTGGGGGCAA | |

Fig. 14H

| | | | | |
|---|---|---|---|---|
| NY99 NS5 | GATCTATGCT | GATGACACAG | CTGGCTGGGA | 287 |
| WN02 NS5 | GATCTATGCT | GATGACACAG | CTGGCTGGGA | 287 |
| NS5F2 | GATCTATGCT | GATGACACAG | CCGGCTGGGA | 403 |
| NS5F5 | GATCTATGCT | GATGACA- - - | - - - - - - - - - - | 975 |
| NS5R3 rev | GATCTATGCT | GATGACACAG | CCGGCTGGGA | 655 |
| NS5R5 rev | GATCTATGCT | GATGACACAG | CCGGCTGGGA | 873 |
| Consensus | GATCTATGCT | GATGACACAG | CCGGCTGGGA | |

100% Conservation 0%

| | | | | |
|---|---|---|---|---|
| NY99 NS5 | CACCCGCATC | ACGAGAGCTG | ACTTGGAAAA | 317 |
| WN02 NS5 | CACCCGCATC | ACGAGTGCTG | ACTTGGAAAA | 317 |
| NS5F2 | CACCCGCATC | ACGAGAGCTG | ACTTGGAAAA | 433 |
| NS5F5 | - - - - - - - - - - | - - - - - - - - - - | - - - - - - - - - - | 975 |
| NS5R3 rev | CACCCGCATC | ACGAGAGCTG | ACTTGGAAAA | 685 |
| NS5R5 rev | CACCCGCATC | ACGAGAGCTG | ACTTGGAAAA | 903 |
| Consensus | CACCCGCATC | ACGAGAGCTG | ACTTGGAAAA | |

100% Conservation 0%

| | | | | |
|---|---|---|---|---|
| NY99 NS5 | TGAAGCTAAG | GTGCTTGAGC | TGCTTGATGG | 347 |
| WN02 NS5 | TGAAGCTAAG | GTGCTTGAGT | TGCTTGATGG | 347 |
| NS5F2 | TGAAGCTAAG | GTGCTTGAGT | TGCTTGATGG | 463 |
| NS5F5 | - - - - - - - - - - | - - - - - - - - - - | - - - - - - - - - - | 975 |
| NS5R3 rev | TGAAGCTAAG | GTGCTTGAGT | TGCTTGATGG | 715 |
| NS5R5 rev | TGAAGCTAAG | GTGCTTGAGT | TGCTTGATGG | 933 |
| Consensus | TGAAGCTAAG | GTGCTTGAGT | TGCTTGATGG | |

100% Conservation 0%

| | | | | |
|---|---|---|---|---|
| NY99 NS5 | GGAACATCGG | CGTCTTGCCA | GGGCCATCAT | 377 |
| WN02 NS5 | GGAACATCGG | CGTCTTGCCA | GGGCCATCAT | 377 |
| NS5F2 | GGAACATCGG | CGTCTTGCCA | GGGCCATCAT | 493 |
| NS5F5 | - - - - - - - - - - | - - - - - - - - - - | - - - - - - - - - - | 975 |
| NS5R3 rev | GGAACATCGG | CGTCTTGCCA | GGGCCATCAT | 745 |
| NS5R5 rev | GGAACATCGG | CGTCTTGCCA | GGGCCATC- - | 961 |
| Consensus | GGAACATCGG | CGTCTTGCCA | GGGCCATCAT | |

100% Conservation 0%

Fig. 14I

```
NY99 NS5     - - - - - - - - - -  - - - - - - - - - -  - - - - - - - - - -  608
WN02 NS5     - - - - - - - - - -  - - - - - - - - - -  - - - - - - - - - -  608
   NS5F2     GGTTCGCAAA           GACATCCAAG           AGTGGAAACC           883
   NS5F5     - - - - - - - - - -  - - - - - - - - - -  - - - - - - - - - -  975
 NS5R3 rev   - - - - - - - - - -  - - - - - - - - - -  - - - - - - - - - -  957
 NS5R5 rev   - - - - - - - - - -  - - - - - - - - - -  - - - - - - - - - -  961
Consensus    - - - - - - - - - -  - - - - - - - - - -  - - - - - - - - - -
       100%
Conservation
         0%

NY99 NS5     - - - - - - - - - -  - - - - - - - - - -  - - - - - -  608
WN02 NS5     - - - - - - - - - -  - - - - - - - - - -  - - - - - -  608
   NS5F2     GTCAACTGGA           TGGTATGATT           GGCAGC       909
   NS5F5     - - - - - - - - - -  - - - - - - - - - -  - - - - - -  975
 NS5R3 rev   - - - - - - - - - -  - - - - - - - - - -  - - - - - -  957
 NS5R5 rev   - - - - - - - - - -  - - - - - - - - - -  - - - - - -  961
Consensus    - - - - - - - - - -  - - - - - - - - - -  - - - - - -
       100%
Conservation
         0%
```

Fig. 14M

| | | | | |
|---|---|---|---|---|
| NY99 E | TTCAACTGCC | TTGGAATGAG | CAACAGAGAC | 30 |
| WN02 E | TTCAACTGCC | TTGGAATGAG | CAACAGAGAC | 30 |
| EF1 | ---------- | ---------- | ---------- | - |
| EF3 | ---------- | ---------- | ---------- | - |
| ER3 rev | ---------- | ---------- | ---------- | - |
| ER4 rev | ---------- | ---------- | ---------- | - |
| Consensus | ---------- | ---------- | ---------- | |

| | | | | |
|---|---|---|---|---|
| NY99 E | TTCTTGGAAG | GAGTGTCTGG | AGCAACATGG | 60 |
| WN02 E | TTCTTGGAAG | GAGTGTCTGG | AGCAACATGG | 60 |
| EF1 | ---------- | ---------- | ---------- | - |
| EF3 | ---------- | ---------- | ---------- | - |
| ER3 rev | ---------- | ---------- | ---------- | - |
| ER4 rev | ---------- | ---------- | ---------- | - |
| Consensus | ---------- | ---------- | ---------- | |

| | | | | |
|---|---|---|---|---|
| NY99 E | GTGGATTTGG | TTCTCGAAGG | CGACAGCTGC | 90 |
| WN02 E | GTGGATTTGG | TTCTCGAAGG | CGACAGCTGC | 90 |
| EF1 | ---------- | ---------- | ---------- | - |
| EF3 | ---------- | ---------- | ---------- | - |
| ER3 rev | ---------- | ---------- | ---------- | - |
| ER4 rev | ---------- | ---------- | ---------- | - |
| Consensus | ---------- | ---------- | ---------- | |

| | | | | |
|---|---|---|---|---|
| NY99 E | GTGACTATCA | TGTCTAAGGA | CAAGCCTACC | 120 |
| WN02 E | GTGACTATCA | TGTCTAAGGA | CAAGCCTACC | 120 |
| EF1 | ---------- | ---------- | ---------- | - |
| EF3 | ---------- | ---------- | ---------- | - |
| ER3 rev | ---------- | ---------- | ---------- | - |
| ER4 rev | ---------- | ---------- | ---------- | - |
| Consensus | ---------- | ---------- | ---------- | |

Fig. 15A

| | | | | |
|---|---|---|---|---|
| NY99 E | ATCGATGTGA | AGATGATGAA | TATGGAGGCG | 150 |
| WN02 E | ATCGATGTGA | AGATGATGAA | TATGGAGGCG | 150 |
| EF1 | - - -GATGTGN | -GANGANGAA | TATGGAGGCG | 26 |
| EF3 | - - - - - - - - - - | - - - - - - - - - - | - - - - - - - - - - | - |
| ER3 rev | - - - - - - - - - - | - - - - - - - - - - | - - - - - - - - - - | - |
| ER4 rev | - - - - - - - - - - | - - - - - - - - - - | - - - - - - - - - - | - |
| Consensus | - - -GATGTG- | -GA-GA-GAA | TATGGAGGCG | |
| NY99 E | GCCAACCTGG | CAGAGGTCCG | CAGTTATTGC | 180 |
| WN02 E | GCCAACCTGG | CAGAGGTCCG | CAGTTATTGC | 180 |
| EF1 | GCCAACCTGG | CAGAGGTCCG | CAGTTATTGC | 56 |
| EF3 | - - - - - - - - - - | - - - - - - - - - - | - - - - - - - - - - | - |
| ER3 rev | - - - - - - - - - - | - - - - - - - - - - | - - - - - - - - - - | - |
| ER4 rev | - - - - - - - - - - | - - - - - - - - - - | - - - - - - - - - - | - |
| Consensus | GCCAACCTGG | CAGAGGTCCG | CAGTTATTGC | |
| NY99 E | TATTTGGCTA | CCGTCAGCGA | TCTCTCCACC | 210 |
| WN02 E | TATTTGGCTA | CCGTCAGCGA | TCTCTCCACC | 210 |
| EF1 | TATTTGGCTA | CCGTCAGCGA | TCTCTCCACC | 86 |
| EF3 | - - - - - - - - - - | - - - - - - - - - - | - - - - - - - - - - | - |
| ER3 rev | - - - - - - - - - - | - - - - - - - - - - | - - - - - - - - - - | - |
| ER4 rev | - - - - - - - - - - | - - - - - - - - - - | - - - - - - - - - - | - |
| Consensus | TATTTGGCTA | CCGTCAGCGA | TCTCTCCACC | |
| NY99 E | AAAGCTGCGT | GCCCGACCAT | GGGAGAAGCT | 240 |
| WN02 E | AAAGCTGCGT | GCCCGACCAT | GGGAGAAGCT | 240 |
| EF1 | AAAGCTGCGT | GCCCGACCAT | GGGAGAAGCT | 116 |
| EF3 | - - - - - - - - - - | - - - - - - - - - - | - - - - - - - - - - | - |
| ER3 rev | - - - - - - - - - - | - - - - - - - - - - | - - - - - - - - - - | - |
| ER4 rev | - - - - - - - - - - | - - - - - - - - - - | - - - - - - - - - - | - |
| Consensus | AAAGCTGCGT | GCCCGACCAT | GGGAGAAGCT | |

Fig. 15B

```
NY99 E    TGCTCTACCA  AGGCAATAGG  AAGAACCATC  390
WN02 E    TGCTCTACCA  AGGCAATAGG  AAGAACCATC  390
  EF1     TGCTCTACCA  AGGCAATAGG  AAGAACCATC  266
  EF3     ----------  ----------  ---------C  1
ER3 rev   ----------  ----------  ----------  -
ER4 rev   ----------  ----------  ----------  -
Consensus TGCTCTACCA  AGGCAATAGG  AAGAACCATC
```

```
NY99 E    TTGAAAGAGA  ATATCAAGTA  CGAAGTGGCC  420
WN02 E    TTGAAAGAGA  ATATCAAGTA  CGAAGTGGCC  420
  EF1     TTGAAAGAGA  ATATCAAGTA  CGAAGTGGCC  296
  EF3     TTNANAGANA  ---TCAAGTA  CGAAGTGGCC  28
ER3 rev   ----------  ----------  ----------  -
ER4 rev   ----------  ----------  ----------  -
Consensus TTGAAAGAGA  ATATCAAGTA  CGAAGTGGCC
```

```
NY99 E    ATTTTTGTCC  ATGGACCAAC  TACTGTGGAG  450
WN02 E    ATTTTTGTCC  ATGGACCAAC  TACTGTGGAG  450
  EF1     ATTTTTGTCC  ATGGACCAAC  TACTGTGGAG  326
  EF3     ATTTTTGTCC  ATGGACCAAC  TACTGTGGAG  58
ER3 rev   ----------  ----------  ----------  -
ER4 rev   ----------  ----------  ----------  -
Consensus ATTTTTGTCC  ATGGACCAAC  TACTGTGGAG
```

```
NY99 E    TCGCACGGAA  ACTACTCCAC  ACAGGTTGGA  480
WN02 E    TCGCACGGAA  ACTATTCCAC  ACAGGCTGGA  480
  EF1     TCGCACGGAA  ACTACTCCAC  ACAGGCTGGA  356
  EF3     TCGCACGGAA  ACTACTCCAC  ACAGGCTGGA  88
ER3 rev   ----------  ----------  ----------  -
ER4 rev   ----------  ----------  ----------  -
Consensus TCGCACGGAA  ACTACTCCAC  ACAGGCTGGA
```

Fig. 15D

```
NY99 E    GCCACTCAGG  CAGGGAGATT  CAGCATCACT  510
WN02 E    GCCACTCAGG  CAGGGAGATT  CAGCATCACT  510
  EF1     GCCACTCAGG  CAGGGAGATT  CAGCATCACT  386
  EF3     GCCACTCAGG  CAGGGAGATT  CAGCATCACT  118
ER3 rev   ----------  ----------  ----------  -
ER4 rev   ----------  ----------  ----------  -
Consensus GCCACTCAGG  CAGGGAGATT  CAGCATCACT NY99 E    CCTGCGGCGC  CTTCACACAC  ACTAAAGCTT  540
WN02 E    CCTGCGGCGC  CTTCATACAC  ACTAAAGCTT  540
  EF1     CCTGCGGCGC  CTTCATACAC  ACTAAAGCTT  416
  EF3     CCTGCGGCGC  CTTCATACAC  ACTAAAGCTT  148
ER3 rev   ----------  ----------  ----------  -
ER4 rev   ----------  ----------  ----------  -
Consensus CCTGCGGCGC  CTTCATACAC  ACTAAAGCTT NY99 E    GGAGAATATG  GAGAGGTGAC  AGTGGACTGT  570
WN02 E    GGAGAATATG  GAGAGGTGAC  AGTGGACTGT  570
  EF1     GGAGAATATG  GAGAGGTGAC  AGTGGACTGT  446
  EF3     GGAGAATATG  GAGAGGTGAC  AGTGGACTGT  178
ER3 rev   --AGANTATG  GAGNGNNGNC  AGTGGACTGT   28
ER4 rev   ----------  ----------  ----------  -
Consensus GGAGAATATG  GAGAGGTGAC  AGTGGACTGT NY99 E    GAA-CCACGG  TCAGGGATTG  ACACCAATGC  599
WN02 E    GAA-CCACGG  TCAGGGATTG  ACACCAATGC  599
  EF1     GAA-CCACGG  TCAGGGATTG  ACACCAATGC  475
  EF3     GAA-CCACGG  TCAGGGATTG  ACACCAATGC  207
ER3 rev   GAANCCNCGG  TCAGGGATTG  ACACCAATGC   58
ER4 rev   ----------  ----------  ----------  -
Consensus GAA-CCACGG  TCAGGGATTG  ACACCAATGC
```

Fig. 15E

| | | | | |
|---|---|---|---|---|
| NY99 E | TGGAGTTTGA | GGAACCACAC | GCCACGAAGC | 748 |
| WN02 E | TGGAGTTTGA | GGAACCACAC | GCCACGAAGC | 748 |
| EF1 | TGGAGTTTGA | GGAACCACAC | GCCACGAAGC | 624 |
| EF3 | TGGAGTTTGA | GGAACCACAC | GCCACGAAGC | 356 |
| ER3 rev | TGGAGTTTGA | GGAACCACAC | GCCACGAAGC | 207 |
| ER4 rev | TGGAGTTTGA | GGAACCACAC | GCCACGAAGC | 74 |
| Consensus | TGGAGTTTGA | GGAACCACAC | GCCACGAAGC | |
| NY99 E | AGTCTGTGAT | AGCATTGGGC | TCACAAGAGG | 778 |
| WN02 E | AGTCTGTGAT | AGCATTGGGC | TCACAAGAGG | 778 |
| EF1 | AGTCTGTGAT | AGCATTGGGC | TCACAAGAGG | 654 |
| EF3 | AGTCTGTGAT | AGCATTGGGC | TCACAAGAGG | 386 |
| ER3 rev | AGTCTGTGAT | AGCATTGGGC | TCACAAGAGG | 237 |
| ER4 rev | AGTCTGTGAT | AGCATTGGGC | TCACAAGAGG | 104 |
| Consensus | AGTCTGTGAT | AGCATTGGGC | TCACAAGAGG | |
| NY99 E | GAGCTCTGCA | GCAAGCTTTG | GCTGGAGCCA | 808 |
| WN02 E | GAGCTCTGCA | TCAAGCTTTG | GCTGGAGCCA | 808 |
| EF1 | GAGCTCTGCA | TCAAGCTTTG | GCTGGAGCCA | 684 |
| EF3 | GAGCTCTGCA | TCAAGCTTTG | GCTGGAGCCA | 416 |
| ER3 rev | GAGCTCTGCA | TCAAGCTTTG | GCTGGAGCCA | 267 |
| ER4 rev | GAGCTCTGCA | TCAAGCTTTG | GCTGGAGCCA | 134 |
| Consensus | GAGCTCTGCA | TCAAGCTTTG | GCTGGAGCCA | |
| NY99 E | TTCCTGTGGA | ATTTTCAAGC | AACACTGTCA | 838 |
| WN02 E | TTCCTGTGGA | ATTTTCAAGC | AACACTGTCA | 838 |
| EF1 | TTCCTGTGGA | ATTTTCAAGC | AACACTGTCA | 714 |
| EF3 | TTCCTGTGGA | ATTTTCAAGC | AACACTGTCA | 446 |
| ER3 rev | TTCCTGTGGA | ATTTTCAAGC | AACACTGTCA | 297 |
| ER4 rev | TTCCTGTGGA | ATTTTCAAGC | AACACTGTCA | 164 |
| Consensus | TTCCTGTGGA | ATTTTCAAGC | AACACTGTCA | |

Fig. 15G

| | | | | |
|---|---|---|---|---|
| NY99 E | AGTTGACGTC | GGGTCATTTG | AAGTGTAGAG | 868 |
| WN02 E | AGTTGACGTC | GGGTCATTTG | AAGTGTAGAG | 868 |
| EF1 | AGTTGACGTC | GGGTCATTTG | AAGTGTAGAG | 744 |
| EF3 | AGTTGACGTC | GGGTCATTTG | AAGTGTAGAG | 476 |
| ER3 rev | AGTTGACGTC | GGGTCATTTG | AAGTGTAGAG | 327 |
| ER4 rev | AGTTGACGTC | GGGTCATTTG | AAGTGTAGAG | 194 |
| Consensus | AGTTGACGTC | GGGTCATTTG | AAGTGTAGAG | |
| NY99 E | TGAAGATGGA | AAAATTGCAG | TTGAAGGGAA | 898 |
| WN02 E | TGAAGATGGA | AAAATTGCAG | TTGAAGGGAA | 898 |
| EF1 | TGAAGATGGA | AAAATTGCAG | TTGAAGGGAA | 774 |
| EF3 | TGAAGATGGA | AAAATTGCAG | TTGAAGGGAA | 506 |
| ER3 rev | TGAAGATGGA | AAAATTGCAG | TTGAAGGGAA | 357 |
| ER4 rev | TGAAGATGGA | AAAATTGCAG | TTGAAGGGAA | 224 |
| Consensus | TGAAGATGGA | AAAATTGCAG | TTGAAGGGAA | |
| NY99 E | CAACCTATGG | CGTCTGTTCA | AAGGCTTTCA | 928 |
| WN02 E | CAACCTATGG | CGTCTGTTCA | AAGGCTTTCA | 928 |
| EF1 | CAACCTATGG | CGTCTGTTCA | AAGGCTTTCA | 804 |
| EF3 | CAACCTATGG | CGTCTGTTCA | AAGGCTTTCA | 536 |
| ER3 rev | CAACCTATGG | CGTCTGTTCA | AAGGCTTTCA | 387 |
| ER4 rev | CAACCTATGG | CGTCTGTTCA | AAGGCTTTCA | 254 |
| Consensus | CAACCTATGG | CGTCTGTTCA | AAGGCTTTCA | |
| NY99 E | AGTTTCTTGG | GACTCCCGCA | GACACAGGTC | 958 |
| WN02 E | AGTTTCTTGG | GACTCCCGCA | GACACAGGTC | 958 |
| EF1 | AGTTTCTTGG | GACTCCCGCA | GACACAGGTC | 834 |
| EF3 | AGTTTCTTGG | GACTCCCGCA | GACACAGGTC | 566 |
| ER3 rev | AGTTTCTTGG | GACTCCCGCA | GACACAGGTC | 417 |
| ER4 rev | AGTTTCTTGG | GACTCCCGCA | GACACAGGTC | 284 |
| Consensus | AGTTTCTTGG | GACTCCCGCA | GACACAGGTC | |

Fig. 15H

| | | | | |
|---|---|---|---|---|
| NY99 E | ACGGCACTGT | GGTGTTGGAA | TTGCAGTACA | 988 |
| WN02 E | ACGGCACTGT | GGTGTTGGAA | TTGCAGTACA | 988 |
| EF1 | ACGGCACTGT | GGTGTTGGAA | TTGCAGTACA | 864 |
| EF3 | ACGGCACTGT | GGTGTTGGAA | TTGCAGTACA | 596 |
| ER3 rev | ACGGCACTGT | GGTGTTGGAA | TTGCAGTACA | 447 |
| ER4 rev | ACGGCACTGT | GGTGTTGGAA | TTGCAGTACA | 314 |
| Consensus | ACGGCACTGT | GGTGTTGGAA | TTGCAGTACA | |
| NY99 E | CTGGCACGGA | TGGACCTTGC | AAAGTTCCTA | 1018 |
| WN02 E | CTGGCACGGA | TGGACCTTGC | AAAGTTCCTA | 1018 |
| EF1 | CTGGCACGGA | TGGACCTTGC | AAAGTTCCTA | 894 |
| EF3 | CTGGCACGGA | TGGACCTTGC | AAAGTTCCTA | 626 |
| ER3 rev | CTGGCACGGA | TGGACCTTGC | AAAGTTCCTA | 477 |
| ER4 rev | CTGGCACGGA | TGGACCTTGC | AAAGTTCCTA | 344 |
| Consensus | CTGGCACGGA | TGGACCTTGC | AAAGTTCCTA | |
| NY99 E | TCTCGTCAGT | GGCTTCATTG | AACGACCTAA | 1048 |
| WN02 E | TCTCGTCAGT | GGCTTCATTG | AACGACCTAA | 1048 |
| EF1 | TCTCGTCAGT | GGCTTCATTG | AACGATCTAA | 924 |
| EF3 | TCTCGTCAGT | GGCTTCATTG | AACGATCTAA | 656 |
| ER3 rev | TCTCGTCAGT | GGCTTCATTG | AACGATCTAA | 507 |
| ER4 rev | TCTCGTCAGT | GGCTTCATTG | AACGATCTAA | 374 |
| Consensus | TCTCGTCAGT | GGCTTCATTG | AACGATCTAA | |
| NY99 E | CGCCAGTGGG | CAGATTGGTC | ACTGTCAACC | 1078 |
| WN02 E | CGCCAGTGGG | CAGATTGGTC | ACTGTCAACC | 1078 |
| EF1 | CGCCAGTGGG | CAGATTNNTC | ACTGTCAACC | 954 |
| EF3 | CGCCAGTGGG | CAGATTGGTC | ACTGTCAACC | 686 |
| ER3 rev | CGCCAGTGGG | CAGATTGGTC | ACTGTCAACC | 537 |
| ER4 rev | CGCCAGTGGG | CAGATTGGTC | ACTGTCAACC | 404 |
| Consensus | CGCCAGTGGG | CAGATTGGTC | ACTGTCAACC | |

Fig. 15I

| | | | | |
|---|---|---|---|---|
| NY99 E | CTTTTGTTTC | AGTGGCCACG | GCCAACGCTA | 1108 |
| WN02 E | CTTTTGTTTC | AGTGGCCACG | GCCAACGCTA | 1108 |
| EF1 | CTTTTGTTTC | AGTG------ | ---------- | 968 |
| EF3 | CTTTTGTTTC | AGTGGCCACG | GCCAACGCTA | 716 |
| ER3 rev | CTTTTGTTTC | AGTGGCCACG | GCCAACGCTA | 567 |
| ER4 rev | CTTTTGTTTC | AGTGGCCACG | GCCAACGCTA | 434 |
| Consensus | CTTTTGTTTC | AGTGGCCACG | GCCAACGCTA | |

100% / Conservation / 0%

| | | | | |
|---|---|---|---|---|
| NY99 E | AGGTCCTGAT | TGAATTGGAA | CCACCCTTTG | 1138 |
| WN02 E | AGGTCCTGAT | TGAATTGGAA | CCACCCTTTG | 1138 |
| EF1 | ---------- | ---------- | ---------- | 968 |
| EF3 | AGGTCCTGAT | TGAATTGGAA | CCACCCTTTG | 746 |
| ER3 rev | AGGTCCTGAT | TGAATTGGAA | CCACCCTTTG | 597 |
| ER4 rev | AGGTCCTGAT | TGAATTGGAA | CCACCCTTTG | 464 |
| Consensus | AGGTCCTGAT | TGAATTGGAA | CCACCCTTTG | |

100% / Conservation / 0%

| | | | | |
|---|---|---|---|---|
| NY99 E | GAGACTCATA | CATAGTGGTG | GGCAGAGGAG | 1168 |
| WN02 E | GAGACTCATA | CATAGTGGTG | GGCAGAGGAG | 1168 |
| EF1 | ---------- | ---------- | ---------- | 968 |
| EF3 | GAGACTCATA | CATAGTGGTG | GGCAGAGGAG | 776 |
| ER3 rev | GAGACTCATA | CATAGTGGTG | GGCAGAGGAG | 627 |
| ER4 rev | GAGACTCATA | CATAGTGGTG | GGCAGAGGAG | 494 |
| Consensus | GAGACTCATA | CATAGTGGTG | GGCAGAGGAG | |

100% / Conservation / 0%

| | | | | |
|---|---|---|---|---|
| NY99 E | AACAACAGAT | CAATCACCAT | TGGCACAAGT | 1198 |
| WN02 E | AACAACAGAT | CAATCACCAT | TGGCACAAGT | 1198 |
| EF1 | ---------- | ---------- | ---------- | 968 |
| EF3 | AACAACAGAT | CAATCACCAT | TGGCACAAGT | 806 |
| ER3 rev | AACAACAGAT | CAATCACCAT | TGGCACAAGT | 657 |
| ER4 rev | AACAACAGAT | CAATCACCAT | TGGCACAAGT | 524 |
| Consensus | AACAACAGAT | CAATCACCAT | TGGCACAAGT | |

100% / Conservation / 0%

Fig. 15J

| | | | | |
|---|---|---|---|---|
| NY99 E | CTGGAAGCAG | CATTGGCAAA | GCCTTTACAA | 1228 |
| WN02 E | CTGGAAGTAG | CATTGGCAAA | GCCTTTACAA | 1228 |
| EF1 | - - - - - - - - - - | - - - - - - - - - - | - - - - - - - - - - | 968 |
| EF3 | CTGGAAGCAG | CATTGGCAAA | GCCTTTACAA | 836 |
| ER3 rev | CTGGAAGCAG | CATTGGCAAA | GCCTTTACAA | 687 |
| ER4 rev | CTGGAAGCAG | CATTGGCAAA | GCCTTTACAA | 554 |
| Consensus | CTGGAAGCAG | CATTGGCAAA | GCCTTTACAA | |

| | | | | |
|---|---|---|---|---|
| NY99 E | CCACCCTCAA | AGGAGCGCAG | AGACTAGCCG | 1258 |
| WN02 E | CCACCCTCAA | AGGAGCGCAG | AGACTAGCCG | 1258 |
| EF1 | - - - - - - - - - - | - - - - - - - - - - | - - - - - - - - - - | 968 |
| EF3 | CCACCCTCAA | AGGAGCGCAG | AGACTAGCCG | 866 |
| ER3 rev | CCACCCTCAA | AGGAGCGCAG | AGACTAGCCG | 717 |
| ER4 rev | CCACCCTCAA | AGGAGCGCAG | AGACTAGCCG | 584 |
| Consensus | CCACCCTCAA | AGGAGCGCAG | AGACTAGCCG | |

| | | | | |
|---|---|---|---|---|
| NY99 E | CTCTAGGAGA | CACAGCTTGG | GACTTTGGAT | 1288 |
| WN02 E | CTCTAGGAGA | CACAGCTTGG | GACTTTGGAT | 1288 |
| EF1 | - - - - - - - - - - | - - - - - - - - - - | - - - - - - - - - - | 968 |
| EF3 | CTCTAGGAGA | CACAGCTTGG | GACTTTGGAT | 896 |
| ER3 rev | CTCTAGGAGA | CACAGCTTGG | GACTTTGGAT | 747 |
| ER4 rev | CTCTAGGAGA | CACAGCTTGG | GACTTTGGAT | 614 |
| Consensus | CTCTAGGAGA | CACAGCTTGG | GACTTTGGAT | |

| | | | | |
|---|---|---|---|---|
| NY99 E | CAGTTGGAGG | GGTGTTCACC | TCAGTTGGGA | 1318 |
| WN02 E | CAGTTGGAGG | GGTGTTCACC | TCAGTTGGGA | 1318 |
| EF1 | - - - - - - - - - - | - - - - - - - - - - | - - - - - - - - - - | 968 |
| EF3 | CAGTTGGAGG | GGTGTTCACC | TCAGTTGGGA | 926 |
| ER3 rev | CAGTTGGAGG | GGTGTTCACC | TCAGTTGGGA | 777 |
| ER4 rev | CAGTTGGAGG | GGTGTTCACC | TCAGTTGGGA | 644 |
| Consensus | CAGTTGGAGG | GGTGTTCACC | TCAGTTGGGA | |

Fig. 15K

| | | | | |
|---|---|---|---|---|
| NY99 E | AGGCTGTCCA | TCAAGTGTTC | GGAGGAGCAT | 1348 |
| WN02 E | AGGCTGTCCA | TCAAGTGTTC | GGAGGAGCAT | 1348 |
| EF1 | ---------- | ---------- | ---------- | 968 |
| EF3 | AGGCTGTCCA | TCAAGTGTTC | GGAGGAGCAT | 956 |
| ER3 rev | AGGCTGTCCA | TCAAGTGTTC | GGAGGAGCAT | 807 |
| ER4 rev | AGGCTGTCCA | TCAAGTGTTC | GGAGGAGCAT | 674 |
| Consensus | AGGCTGTCCA | TCAAGTGTTC | GGAGGAGCAT | |

| | | | | |
|---|---|---|---|---|
| NY99 E | TCCGCTCACT | GTTCGGAGGC | ATGTCCTGGA | 1378 |
| WN02 E | TCCGCTCACT | GTTCGGAGGC | ATGTCCTGGA | 1378 |
| EF1 | ---------- | ---------- | ---------- | 968 |
| EF3 | TCCGCACACT | GTTCGGANGC | ATG------- | 979 |
| ER3 rev | TCCGCACACT | GTTCGGAGGC | ATGTCCTGGA | 837 |
| ER4 rev | TCCGCACACT | GTTCGGAGGC | ATGTCCTGGA | 704 |
| Consensus | TCCGCACACT | GTTCGGAGGC | ATGTCCTGGA | |

| | | | | |
|---|---|---|---|---|
| NY99 E | TAACGCAAGG | ATTGCTGGGG | GCTCTCCTGT | 1408 |
| WN02 E | TAACGCAAGG | ATTGCTGGGG | GCTCTCCTGT | 1408 |
| EF1 | ---------- | ---------- | ---------- | 968 |
| EF3 | ---------- | ---------- | ---------- | 979 |
| ER3 rev | TAACGCAAGG | ATTGCTGGGG | GCTCTCCTGT | 867 |
| ER4 rev | TAACGCAAGG | ATTGCTGGGG | GCTCTCCTGT | 734 |
| Consensus | TAACGCAAGG | ATTGCTGGGG | GCTCTCCTGT | |

| | | | | |
|---|---|---|---|---|
| NY99 E | TGTGGATGGG | CATCAATGCT | CGTGATAGGT | 1438 |
| WN02 E | TGTGGATGGG | CATCAATGCT | CGTGATAGGT | 1438 |
| EF1 | ---------- | ---------- | ---------- | 968 |
| EF3 | ---------- | ---------- | ---------- | 979 |
| ER3 rev | TGTGGATGGG | CATCAATGCT | CGTGATAGGT | 897 |
| ER4 rev | TGTGGATGGG | CATCAATGCT | CGTGATAGGT | 764 |
| Consensus | TGTGGATGGG | CATCAATGCT | CGTGATAGGT | |

Fig. 15L

| | | | | |
|---|---|---|---|---|
| NY99 E | - - - - - - - - - - | - - - - - - - - - - | - - - - - - - - - - | 1503 |
| WN02 E | - - - - - - - - - - | - - - - - - - - - - | - - - - - - - - - - | 1503 |
| EF1 | - - - - - - - - - - | - - - - - - - - - - | - - - - - - - - - - | 968 |
| EF3 | - - - - - - - - - - | - - - - - - - - - - | - - - - - - - - - - | 979 |
| ER3 rev | - - - - - - - - - - | - - - - - - - - - - | - - - - - - - - - - | 1003 |
| ER4 rev | TGTTCATACA | CAATGATGTG | GAGGCTTGGA | 914 |
| Consensus | - - - - - - - - - - | - - - - - - - - - - | - - - - - - - - - - | |

| | | | | |
|---|---|---|---|---|
| NY99 E | - - - - - - - - - - | - - - - - - - - - - | - - - - - - - - - - | 1503 |
| WN02 E | - - - - - - - - - - | - - - - - - - - - - | - - - - - - - - - - | 1503 |
| EF1 | - - - - - - - - - - | - - - - - - - - - - | - - - - - - - - - - | 968 |
| EF3 | - - - - - - - - - - | - - - - - - - - - - | - - - - - - - - - - | 979 |
| ER3 rev | - - - - - - - - - - | - - - - - - - - - - | - - - - - - - - - - | 1003 |
| ER4 rev | TGGACCGGTA | CAAGTATTAC | CCTGAAACGC | 944 |
| Consensus | - - - - - - - - - - | - - - - - - - - - - | - - - - - - - - - - | |

| | | | | |
|---|---|---|---|---|
| NY99 E | - - - - - - - - - - | - - - - - - - - - - | - - - - - - - - - - | 1503 |
| WN02 E | - - - - - - - - - - | - - - - - - - - - - | - - - - - - - - - - | 1503 |
| EF1 | - - - - - - - - - - | - - - - - - - - - - | - - - - - - - - - - | 968 |
| EF3 | - - - - - - - - - - | - - - - - - - - - - | - - - - - - - - - - | 979 |
| ER3 rev | - - - - - - - - - - | - - - - - - - - - - | - - - - - - - - - - | 1003 |
| ER4 rev | CACAAGGCCT | AGCCAAGATC | ATTCAGAAAG | 974 |
| Consensus | - - - - - - - - - - | - - - - - - - - - - | - - - - - - - - - - | |

| | | | | |
|---|---|---|---|---|
| NY99 E | - - - - - - - - - - | - - - - - - - - - - | - - - - - - - - - - | 1503 |
| WN02 E | - - - - - - - - - - | - - - - - - - - - - | - - - - - - - - - - | 1503 |
| EF1 | - - - - - - - - - - | - - - - - - - - - - | - - - - - - - - - - | 968 |
| EF3 | - - - - - - - - - - | - - - - - - - - - - | - - - - - - - - - - | 979 |
| ER3 rev | - - - - - - - - - - | - - - - - - - - - - | - - - - - - - - - - | 1003 |
| ER4 rev | CTCATAAGGA | AGGAGTGTGC | GNTCTACGAN | 1004 |
| Consensus | - - - - - - - - - - | - - - - - - - - - - | - - - - - - - - - - | |

Fig. 15N

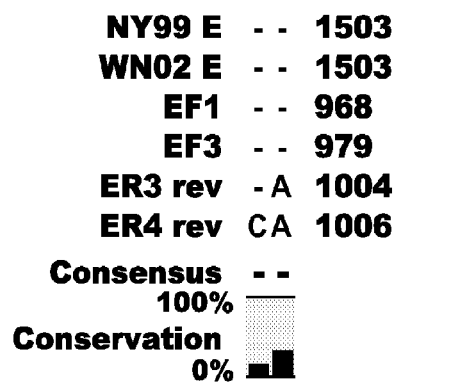
Fig. 15O/17

```
         AY369442.1  · · · · · · · · · ·   · · · · · · · · · ·   · · · · · · · · · ·  ·
         AY369440.1  · · · · · · · · · ·   · · · · · · · · · ·   · · · · · · · · · ·  ·
      H NS5 consensus GGAACTATCC           GGAGTATGAT           GTGAAGCTCG           30
      D NS5 consensus TTCGCTGTC-           - -AATGGAGT           GTCAGGCTC-           26
   H WN05 NS5 consensus - - - - - - - - - -   - -AATGGAGG           GTCAGGCTC-           17
         Consensus   - - - - - - - - - -   - -AATGGAGT           GTCAGGCTC-
```
Conservation 100% – 0%

```
         AY369442.1  · · · · · · · · · ·   · · · · · · · · · ·   · · · · · · · · · ·  ·
         AY369440.1  · · · · · · · · · ·   · · · · · · · · · ·   · · · · · · · · · ·  ·
      H NS5 consensus CTGTCAATGA           GTGTCAGGCT           CTTCAAAACC           60
      D NS5 consensus CTCTCAA-AA           CCATGGGACA           CC- - - - -ATC           50
   H WN05 NS5 consensus CTCTCAA-AA           CC-TGGGACA           CC- - - - -ATC           40
         Consensus   CTCTCAA-AA           CC-TGGGACA           CC- - - - -ATC
```
Conservation 100% – 0%

```
         AY369442.1  · · · · · · · · · ·   · · · · · · · · · ·   · · · · · · · · · ·  ·
         AY369440.1  · · · · · · · · · ·   · · · · · · · · · ·   · · · · · · · · · ·  ·
      H NS5 consensus TGGGACCCAT           CCGAACCGCC           ATGACTG-CA           89
      D NS5 consensus ACGAAT- - -C           CACCATGGCC           ATGACTGACA           77
   H WN05 NS5 consensus ACGAATGTAC           CACCATGGCC           ATGACTGACA           70
         Consensus   ACGAAT- - -C           CACCATGGCC           ATGACTG-CA
```
Conservation 100% – 0%

Fig. 16A

```
         AY369442.1  · · · · · · · · · ·  · · · · · · · · · ·  · · · · · · · · · ·  ·
         AY369440.1  · · · · · · · · · ·  · · · · · · · · · ·  · · · · · · · · · ·  ·
    H NS5 consensus  GACCACCAAC TGGTTGTGGG CGTTTTTGGC 208
    D NS5 consensus  GACCACCAAC TGGTTGTGGG CGTTTTTGGC 195
H WN05 NS5 consensus GACCACCAAC TGGTTGTGGG CGTTTTTGGC 190
          Consensus  GACCACCAAC TGGTTGTGGG CGTTTTTGGC
               100%
       Conservation
                 0%

AY369442.1  · · · · · · · · · ·  · · · · · · · · · ·  · · · · · · · · · ·  ·
         AY369440.1  · · · · · · · · · ·  · · · · · · · · · ·  · · · · · · · · · ·  ·
    H NS5 consensus  CAGAGAAAAA CGTCCCAGAA TGTGCTCTCG 238
    D NS5 consensus  CAGAGAAAAA CGTCCCAGAA TGTGCTCTCG 225
H WN05 NS5 consensus CAGAGAAAAA CGTCCCAGAA TGTGCTCTCG 220
          Consensus  CAGAGAAAAA CGTCCCAGAA TGTGCTCTCG
               100%
       Conservation
                 0%

AY369442.1  · · · · · · · · · ·  · · · · · · · · · ·  · · · · · · · · · ·  ·
         AY369440.1  · · · · · · · · · ·  · · · · · · · · · ·  · · · · · · · · · ·  ·
    H NS5 consensus  AGAGATA· · ·  · · · ·GAAAGG TCAACAGCAA 261
    D NS5 consensus  AGAGGAATTC ATA·GAAAGG TCAACAGCAA 254
H WN05 NS5 consensus AGAGGAATTC ATAAGAAAGG TCAACAGCAA 250
          Consensus  AGAGGAA· · ·  · · · ·GAAAGG TCAACAGCAA
               100%
       Conservation
                 0%
```

Fig. 16C

```
         AY369442.1  ..........  ..........  ..........  .
         AY369440.1  ..........  ..........  ..........  .
     H NS5 consensus  TGCAGCTTTG  GGTGCCATGT  TTGAAGAGCA  291
     D NS5 consensus  TGCAGCTTTG  GGTGCCATGT  TTGAAGAGCA  284
  H WN05 NS5 consensus  TGCAGCTTTG  GGTGCCATGT  TTGAAGAGCA  280
          Consensus  TGCAGCTTTG  GGTGCCATGT  TTGAAGAGCA
              100%
        Conservation
                0%

AY369442.1  ..........  ..........  ..........  .
         AY369440.1  ..........  ..........  ..........  .
     H NS5 consensus  GAATCAATGG  AGGAGCGCCA  GAGAAGCAGT  321
     D NS5 consensus  GAATCAATGG  AGGAGCGCCA  GAGAAGCAGT  314
  H WN05 NS5 consensus  GAATCAATGG  AGGAGCGCCA  GAGAAGCAGT  310
          Consensus  GAATCAATGG  AGGAGCGCCA  GAGAAGCAGT
              100%
        Conservation
                0%

AY369442.1  ..........  ..........  ..........  .
         AY369440.1  ..........  ..........  ..........  .
     H NS5 consensus  TGAAGATCCA  AAATTTTGGG  AGATGGTGGA  351
     D NS5 consensus  TGAAGATCCA  AAATTTTGGG  AGATGGTGGA  344
  H WN05 NS5 consensus  TGAAGATCCA  AAATTTTGGG  AGATGGTGGA  340
          Consensus  TGAAGATCCA  AAATTTTGGG  AGATGGTGGA
              100%
        Conservation
                0%
```

Fig. 16D

```
AY369442.1         ----------  ----------  --CGGGGGGA    8
AY369440.1         ----------  ----------  --CGGGGGGA    8
H NS5 consensus    TGAGGAGCGC  GAGGCACATC  TGCGGGGGGA  381
D NS5 consensus    TGAGGAGCGC  GAGGCACATC  TGCGGGGGGA  374
H WN05 NS5 consensus TGAGGAGCGC GAGGCACATC TGCGGGGGGA  370
Consensus          TGAGGAGCGC  GAGGCACATC  TGCGGGGGGA
```

```
AY369442.1         ATGTCACACT  TGCATTTACA  ACATGATGGG   38
AY369440.1         ATGTCACACT  TGCATTTACA  ACATGATGGG   38
H NS5 consensus    ATGTCACACT  TGCATTTACA  ACATGATGGG  411
D NS5 consensus    ATGTCACACT  TGCATTTACA  ACATGATGGG  404
H WN05 NS5 consensus ATGTCACACT TGCATTTACA ACATGATGGG  400
Consensus          ATGTCACACT  TGCATTTACA  ACATGATGGG
```

```
AY369442.1         AAAGAGAGAG  AAAAAACCCG  GAGAATTCGG   68
AY369440.1         AAAGAGAGAG  AAAAAACCCG  GAGAGTTCGG   68
H NS5 consensus    AAAGAGAGAG  AAAAAACCCG  GAGAGTTCGG  441
D NS5 consensus    AAAGAGAGAG  AAAAAACCCG  GAGAGTTCGG  434
H WN05 NS5 consensus AAAGAGAGAG AAAAAACCCG GAGAGTTCGG  430
Consensus          AAAGAGAGAG  AAAAAACCCG  GAGAGTTCGG
```

Fig. 16E

| | | | | |
|---|---|---|---|---|
| AY369442.1 | CTGGCTTGGA | AGAAAGAACT | CAGGAGGAGG | 188 |
| AY369440.1 | CTGGCTTGGA | AGAAAGAACT | CAGGAGGAGG | 188 |
| H NS5 consensus | CTGGCTTGGA | AGAAAGAACT | CAGGAGGAGG | 561 |
| D NS5 consensus | CTGGCTTGGA | AGAAAGAACT | CAGGAGGAGG | 554 |
| H WN05 NS5 consensus | CTGGCTTGGA | AGAAAGAACT | CAGGAGGAGG | 550 |
| Consensus | CTGGCTTGGA | AGAAAGAACT | CAGGAGGAGG | |

| | | | | |
|---|---|---|---|---|
| AY369442.1 | TGTCGAGGGC | TTGGGCCTCC | AAAAACTGGG | 218 |
| AY369440.1 | TGTCGAGGGC | TTGGGCCTCC | AAAAACTGGG | 218 |
| H NS5 consensus | TGTCGAGGGC | TTGGGCCTCC | AAAAACTGGG | 591 |
| D NS5 consensus | TGTCGAGGGC | TTGGGCCTCC | AAAAACTGGG | 584 |
| H WN05 NS5 consensus | TGTCGAGGGC | TTGGGCCTCC | AAAAACTGGG | 580 |
| Consensus | TGTCGAGGGC | TTGGGCCTCC | AAAAACTGGG | |

| | | | | |
|---|---|---|---|---|
| AY369442.1 | TTACATCCTG | CGTGAAGTTG | GCACCCGGCC | 248 |
| AY369440.1 | TTACATCCTG | CGTGAAGTTG | GCACCCGGCC | 248 |
| H NS5 consensus | TTACATCCTG | CGTGAAGTTG | GCACCCGGCC | 621 |
| D NS5 consensus | TTACATCCTG | CGTGAAGTTG | GCACCCGGCC | 614 |
| H WN05 NS5 consensus | TTACATCCTG | CGTGAAGTTG | GCACCCGACC | 610 |
| Consensus | TTACATCCTG | CGTGAAGTTG | GCACCCGGCC | |

Fig. 16G

```
         AY369442.1  TGGAAGAACC GTCATGGATG TTATCTCCAG 458
         AY369440.1  TGGAAGAACC GTCATGGATG TTATCTCCAG 458
     H NS5 consensus TGGAAGAACC GTCATGGATG TTATCTCCAG 831
     D NS5 consensus TGGAAGAACC GTCATGGATG TTATCTCCAG 824
H WN05 NS5 consensus TGGAAGAACC GTCATGGATG TTATCTCCAG 820
           Consensus TGGAAGAACC GTCATGGATG TTATCTCCAG
                100%
        Conservation
                 0%

AY369442.1  AGAAGATCAG AGGGGGAGTG GACAAGTTGT 488
         AY369440.1  AGAAGATCAG AGGGGGAGTG GACAAGTTGT 488
     H NS5 consensus AGAAGATCAG AGGGGGAGTG GACAAGTTGT 861
     D NS5 consensus AGAAGATCAG AGGGGGAGTG GACAAGTTGT 854
H WN05 NS5 consensus AGAAGATCAG AGGGGGAGTG GACAAGTTGT 850
           Consensus AGAAGATCAG AGGGGGAGTG GACAAGTTGT
                100%
        Conservation
                 0%

AY369442.1  CACCTACGCC CTAAACACTT TCACCAACCT 518
         AY369440.1  CACCTACGCC CTAAACACTT TCACCAACCT 518
     H NS5 consensus CACCTACGCC CTAAACACTT TCACCAACCT 891
     D NS5 consensus CACCTACGCC CTAAACACTT TCACCAACCT 884
H WN05 NS5 consensus CACCTACGCC CTAAACACTT TCACCAACCT 880
           Consensus CACCTACGCC CTAAACACTT TCACCAACCT
                100%
        Conservation
                 0%
```

Fig. 16J

```
         AY369442.1  GGCCGTCCAG CTGGTGAGGA TGATGGAAGG  548
         AY369440.1  GGCCGTCCAG CTGGTGAGGA TGATGGAAGG  548
     H NS5 consensus  GGCCGTCCAG CTGGTGAGGA TGATGGAAGG  921
     D NS5 consensus  GGCCGTCCAG CTGGTGAGGA TGATGGAAGG  914
H WN05 NS5 consensus  GGCCGTCCAG CTGGTGAGGA TGATGGAAGG  910
           Consensus  GGCCGTCCAG CTGGTGAGGA TGATGGAAGG
```

100%
Conservation
0%

```
         AY369442.1  GGAAGGAGTG ATTGGCCCAG ATGATGTGGA  578
         AY369440.1  GGAAGGAGTG ATTGGCCCAG ATGATGTGGA  578
     H NS5 consensus  GGAAGGAGTG ATTGGCCCAG ATGATGTGGA  951
     D NS5 consensus  GGAAGGAGTG ATTGGCCCAG ATGATGTGGA  944
H WN05 NS5 consensus  GGAAGGAGTG ATTGGCCCAG ATGATGTGGA  940
           Consensus  GGAAGGAGTG ATTGGCCCAG ATGATGTGGA
```

100%
Conservation
0%

```
         AY369442.1  GAAACTCACA AAAGGGAAAG GACCCAAAGT  608
         AY369440.1  GAAACTCACA AAAGGGAAAG GACCCAAAGT  608
     H NS5 consensus  GAAACTCACA AAAGGGAAAG GACCCAAAGT  981
     D NS5 consensus  GAAACTCACA AAAGGGAAAG GACCCAAAGT  974
H WN05 NS5 consensus  GAAACTCACA AAAGGGAAAG GACCCAAAGT  970
           Consensus  GAAACTCACA AAAGGGAAAG GACCCAAAGT
```

100%
Conservation
0%

Fig. 16K

```
AY590210.1    TTCAACTGCC  TTGGAATGAG  CAACAGAGAC  30
AY590223.1    TTCAACTGCC  TTGGAATGAG  CAACAGAGAC  30
H E consensus   . . . . . . . . . .    . . . . . . . . . .    . . . . . . . . . .
D E consensus   . . . . . . . . . .    . . . . . . . . . .    . . . . . . . . . .
H WN05 E consensus  . . . . . . . . . .    . . . . . . . . . .    . . . . . . . . . .
Consensus     . . . . . . . . . .    . . . . . . . . . .    . . . . . . . . . .

AY590210.1    TTCTTGGAAG  GAGTGTCTGG  AGCAACATGG  60
AY590223.1    TTCTTGGAAG  GAGTGTCTGG  AGCAACATGG  60
H E consensus   . . . . . . . . . .    . . . . . . . . . .    . . . . . . . . . .
D E consensus   . . . . . . . . . .    . . . . . . . . . .    . . . . . . . . . .
H WN05 E consensus  . . . . . . . . . .    . . . . . . . . . .    . . . . . . . . . .
Consensus     . . . . . . . . . .    . . . . . . . . . .    . . . . . . . . . .

AY590210.1    GTGGATTTGG  TTCTCGAAGG  CGACAGCTGC  90
AY590223.1    GTGGATTTGG  TTCTCGAAGG  CGACAGCTGC  90
H E consensus   . . . . . . . . . .    . . . . . . . . . .    . . . . . . . . . .
D E consensus   . . . . . . . . . .    . . . . . . . . . .    . . . . . . . . . .
H WN05 E consensus  . . . . . . . . . .    . . . . . . . . . .    . . . . . . . . . .
Consensus     . . . . . . . . . .    . . . . . . . . . .    . . . . . . . . . .
```

Fig. 17A

```
       AY590210.1  GTGACTATCA  TGTCTAAGGA  CAAGCCTACC  120
       AY590223.1  GTGACTATCA  TGTCTAAGGA  CAAGCCTACC  120
      H E consensus  ..........  ..........  ..........
      D E consensus  ..........  ..........  ..........
   H WN05 E consensus  ..........  ..........  ..........
         Consensus  ..........  ..........  ..........

AY590210.1  ATCGATGTGA  AGATGATGAA  TATGGAGGCG  150
       AY590223.1  ATCGATGTGA  AGATGATGAA  TATGGAGGCG  150
      H E consensus  ---GATGTGG  AGA----GAA  TATGGAGGCG   23
      D E consensus  ---GATGTGG  AGA----GAA  TATGGAGGCG   23
   H WN05 E consensus  ---GATGTGG  AGA----GAA  TATGGAGGCG   23
         Consensus  ---GATGTGG  AGA----GAA  TATGGAGGCG AY590210.1  GCCAACCTGG  CAGAGGTCCG  CAGTTATTGC  180
       AY590223.1  GCCAACCTGG  CAGAGGTCCG  CAGTTATTGC  180
      H E consensus  GCCAACCTGG  CAGAGGTCCG  CAGTTATTGC   53
      D E consensus  GCCAACCTGG  CAGAGGTCCG  CAGTTATTGC   53
   H WN05 E consensus  GCCAACCTGG  CAGAGGTCCG  CAGTTATTGC   53
         Consensus  GCCAACCTGG  CAGAGGTCCG  CAGTTATTGC
```

Fig. 17B

```
      AY590210.1 TGCTCTACCA AGGCAATAGG AAGAACCATC 390
      AY590223.1 TGCTCTACCA AGGCAATAGG AAGAACCATC 390
     H E consensus TGCTCTACCA AGGCAATAGG AAGAACCATC 263
     D E consensus TGCTCTACCA AGGCAATAGG AAGAACCATC 263
H WN05 E consensus TGCTCTACCA AGGCAATAGG AAGAACCATC 263
        Consensus TGCTCTACCA AGGCAATAGG AAGAACCATC
             100%
     Conservation
              0%

AY590210.1 TTGAAAGAGA ATATCAAGTA CGAAGTGGCC 420
      AY590223.1 TTGAAAGAGA ATATCAAGTA CGAAGTGGCC 420
     H E consensus TTGAAAGAGA ATATCAAGTA CGAAGTGGCC 293
     D E consensus TTGAAAGAGA ATATCAAGTA CGAAGTGGCC 293
H WN05 E consensus TTGAAAGAGA ATATCAAGTA CGAAGTGGCC 293
        Consensus TTGAAAGAGA ATATCAAGTA CGAAGTGGCC
             100%
     Conservation
              0%

AY590210.1 ATTTTTGTCC ATGGACCAAC TACTGTGGAG 450
      AY590223.1 ATTTTTGTCC ATGGACCAAC TACTGTGGAG 450
     H E consensus ATTTTTGTCC ATGGACCAAC TACTGTGGAG 323
     D E consensus ATTTTTGTCC ATGGACCAAC TACTGTGGAG 323
H WN05 E consensus ATTTTTGTCC ATGGACCAAC TACTGTGGAG 323
        Consensus ATTTTTGTCC ATGGACCAAC TACTGTGGAG
             100%
     Conservation
              0%
```

Fig. 17E

```
AY590210.1      TTTGTTTCAG  TGGCCACGGC  CAACGCTAAG  1110
AY590223.1      TTTGTTTCAG  TGGCCACGGC  CAACGCTAAG  1110
H E consensus   TTTGTTTCAG  TGGCCACGGC  CAACGCTAAG   983
D E consensus   TTTGTTTCAG  TGGCCACGGC  CAACGCTAAG   983
H WN05 E consensus TTTGTTTCAG TGGCCACGGC CAACGCTAAG   983
Consensus       TTTGTTTCAG  TGGCCACGGC  CAACGCTAAG
```

100% Conservation 0%

```
AY590210.1      GTCCTGATTG  AATTGGAACC  ACCCTTTGGA  1140
AY590223.1      GTCCTGATTG  AATTGGAACC  ACCCTTTGGA  1140
H E consensus   GTCCTGATTG  AATTGGAACC  ACCCTTTGGA  1013
D E consensus   GTCCTGATTG  AATTGGAACC  ACCCTTTGGA  1013
H WN05 E consensus GTCCTGATTG AATTGGAACC ACCCTTTGGA  1013
Consensus       GTCCTGATTG  AATTGGAACC  ACCCTTTGGA
```

100% Conservation 0%

```
AY590210.1      GACTCATACA  TAGTGGTGGG  CAGAGGAGAA  1170
AY590223.1      GACTCATACA  TAGTGGTGGG  CAGAGGAGAA  1170
H E consensus   GACTCATACA  TAGTGGTGGG  CAGAGGAGAA  1043
D E consensus   GACTCATACA  TAGTGGTGGG  CAGAGGAGAA  1043
H WN05 E consensus GACTCATACA TAGTGGTGGG CAGAGGAGAA  1043
Consensus       GACTCATACA  TAGTGGTGGG  CAGAGGAGAA
```

100% Conservation 0%

Fig. 17M

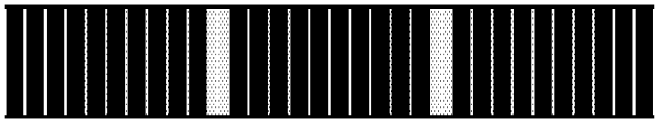
Fig. 17N

| | | | | |
|---|---|---|---|---|
| AY590210.1 | ATAGCTCTCA | CGTTTCTCGC | AGTTGGAGGA | 1470 |
| AY590223.1 | ATAGCTCTCA | CGTTTCTCGC | AGTTGGAGGA | 1470 |
| H E consensus | ATAGCTCTCA | CGTTTCTCGC | AGTTGGAGGA | 1343 |
| D E consensus | ATAGCTCTCA | CGTTTCTCGC | AGTTGGAGGA | 1343 |
| H WN05 E consensus | ATAGCTCTCA | CGTTTCTCGC | AGTTGGAGGA | 1343 |
| Consensus | ATAGCTCTCA | CGTTTCTCGC | AGTTGGAGGA | |

| | | | | |
|---|---|---|---|---|
| AY590210.1 | GTTCTGCTCT | TCCTCTCCGT | GAACGTGCAC | 1500 |
| AY590223.1 | GTTCTGCTCT | TCCTCTCCGT | GAACGTGCAT | 1500 |
| H E consensus | GTTCTGCTCT | TCCTNCCGT | GAACGTGCAC | 1373 |
| D E consensus | GTTCTGCTCT | TCCTCTCCGT | GAACGTGCAT | 1373 |
| H WN05 E consensus | GTTCTGCTCT | TCCTCTCCGT | GAACGTGCAT | 1373 |
| Consensus | GTTCTGCTCT | TCCTCTCCGT | GAACGTGCAT | |

| | | |
|---|---|---|
| AY590210.1 | GCT - | 1503 |
| AY590223.1 | GCT - | 1503 |
| H E consensus | GCT - | 1376 |
| D E consensus | GCT - | 1376 |
| H WN05 E consensus | GCT - | 1376 |
| Consensus | GCT - | |

Fig. 17Q

WEST NILE VIRUS VACCINE

BACKGROUND

West Nile Virus ("WNV") is in the family Flavivirade. Infection is usually contracted through a mosquito vector transferred through the insect's bite. West Nile infects all types of animals and birds across the globe. This virus was first discovered in the North American region in 1999 with the first diagnosis occurring in Canadian horses. Presently, West Nile Virus has become endemic in the United States affecting birds, humans, and animals of all types. In 2002, over 14,700 confirmed cases of West Nile Virus were reported in 43 states.

The spread of WNV has been influenced by several factors. Since the mosquito is the vector for the virus and perpetuates WNV, the ecological conditions conducive to growth and development of mosquito populations have had an impact of the spread of the WNV. There are several tactics that have been utilized to control populations of mosquitoes in an effort to prevent the spread of WNV. These tactics include the use of pesticides, repellants, physical barriers preventing contact between mosquitoes and animals, eliminating environments that perpetuate breeding of mosquitoes, and the use of immunizations. Typical signs of WNV include various symptoms affecting the central nervous system. Symptoms of encephalitis are often seen and include viremia, histopathologic lesions of the central nervous system, anorexia, depression, fever, weakness, abnormal gait, paralysis of hind limbs, impaired vision, ataxia, aimless wandering, convulsions, inability to swallow, coma, and death.

A few vaccines directed towards WNV have been introduced which are undesirable for various reasons. For example, one vaccine was produced from a canarypox-vectored West Nile Virus. Another set of vaccines were produced from a recombinant chimeric protein of West Nile Virus, wherein the chimeric protein vaccine was designed by fusing a modified version of bacterial flagellin (STF2 Delta) to the EIII domain of the WNV envelope protein. Another vaccine included an inactivated early North American West Nile strain that required a metabolizable oil as an adjuvant. Finally, a live, attenuated chimeric vaccine was produced from an infectious clone of yellow fever 17D virus in which the pre-membrane and envelope proteins have been replaced by the corresponding genes of WN(4).

There are several problems inherent in vaccines described above. Vaccines containing live viral organisms have the risk of infecting an animal with the virus through vaccination leading to sickness and even death. Chimeric protein vaccines, recombinantly expressed vaccines, and some subunit vaccines have the problem of limited immunological activity and effect related to the number of proteins included in the vaccine composition. The efficacy of these types of vaccines is usually limited and the risk of infection by the virus or reversion to wild type virus is prevalent. In addition, some of the adjuvants utilized in common vaccines are comprised of metabolizable oils which are removed relatively rapidly from the body and limit the duration during which the immune system of the vaccinated animal may respond to the immunogenically active composition. Other adjuvants can cause allergic reactions and unfavorable effects in the vaccinated animals. Additionally, these vaccines do not include antigens for stimulating immunity to other pathogens besides WNV, so they fail to protect animals against several diseases with both convenience and safety. Also, all previous vaccines were derived from an early isolate of WNV that is no longer present in the environment, and hence, can no longer infect animals and cause disease.

Accordingly, what is needed in the art is a vaccine that is safe for administration to animals of all ages, including pregnant animals, that includes adjuvants suitable for aiding the immunogenic effect and duration of the vaccine, and that is prepared from contemporary or dominant isolates of WNV that remain present in the natural environment and cause disease against which such vaccines would afford protection. What is further needed is a vaccine that reduces the incidence and/or severity of up to and including the elimination or prevention of clinical signs associated with the disease or infection by West Nile Virus. Additionally what is needed is a vaccine against West Nile virus, which includes West Nile Virus antigens in combination with antigens from other equine pathogens, thereby providing further protection by reducing the incidence of or severity of clinical signs of disease from both West Nile Virus and the other pathogen(s).

SUMMARY OF INVENTION

The present invention overcomes the problems inherent in the prior art and provides a distinct advance in the state of the art. More particularly, the present invention provides for a vaccine or immunogenic composition comprising an immunogenically active antigenic component comprised of one or more strains or isolates of West Nile Virus. In some preferred embodiments, the composition further comprises an adjuvant, preferably a carbomer, and a pharmaceutically acceptable carrier. Preferably, the West Nile Virus antigen is killed or inactivated. This composition induces an immunogenic response in animals susceptible to contraction of West Nile Virus and provides for a safe vaccine for animals of any age.

The present invention additionally provides for a vaccine composition, which is immunogenically active, and which overcomes the limitations of those previously described. The present invention provides an inactivated vaccine thereby providing unique safety for the vaccinated animals, including pregnant females. Additionally, the immunogenic composition of the present invention overcomes interference from passively acquired maternal immunity and stimulates active immunity in vaccinated animals. Advantageously, the present invention provides a broad and effective immunogenically active composition containing many or all relevant antigenic components and proteins of pathogenic WNV. The immunogenic composition of the present invention is unique in that it includes antigens of contemporary isolates or epidemiologically dominant isolates of WNV in the composition, providing protective immunogenic responses by reducing the incidence of and/or severity of clinical signs of WNV infection up to and including immunity against the most prevalent isolates seen in animals, including horses, today. In a preferred embodiment, those contemporary isolates of WNV include those isolates that are part of the North American West Nile Virus isolates or North American Dominant West Nile Virus isolates For purposes of the present invention, WN02 is a representative example of a WNV strain that can be referred to as a North American Dominant West Nile Virus strain or isolate. Specifically, North American Dominant strains and isolates are those having at least 1 nucleotide change resulting in an amino acid change from the WN99 isolates. Strain NY99 (GenBank accession no. AF196835) serves as a reference strain for determining if a strain or isolate is North American Dominant. In addition, these strains or isolates may have one or more silent amino acid changes. In a preferred embodiment, the nucleotide change results in an amino acid change in an envelope protein of the strain or isolate and, more preferably, the nucleotide change results in an amino acid change from valine to alanine. Preferably, this amino acid change is associated with a greater ability to replicate in the intermediate host, namely, the mosquito. More preferably, North American Dominant strains include either (and preferably both) a U to C mutation and a C to U mutation at positions 1442 and 2466 (in comparison to a North American strain, e.g. NY 99 and SEQ ID NO.23), respectively. Still more preferably, North American Dominant strains or isolates further include a mutation in the nucleotide sequence encoding the E protein and the C to U mutation at position 9352 in the sequence encoding the NS5 protein (again in comparison to a North American strain, e.g. NY 99 and SEQ ID NO. 23). These preferred mutations are shown in Example 10 and in Phylogenetic Analysis of North American West Nile Virus Isolates, 2001-2004: Evidence For the Emergence of a Dominant Genotype, C. Todd Davis, et. al, Virology 342, p. 252-265 (2005), the teaching and content of which is hereby incorporated by reference herein.

The present invention also provides for a method of making the immunogenic composition of the present invention. The method generally comprises the steps of combining a West Nile Virus antigen and an excipient or pharmaceutically or veterinary acceptable carrier. A preferred embodiment further comprises the step of adding one or more additional equine antigens. In another embodiment, the method further comprises the step of adding a suitable adjuvant to the composition.

In one preferred embodiment, the present invention includes WNV antigens and a non-metabolizable oil adjuvant, preferably mineral oil, to extend the duration during which the immune system of the vaccinated animal may respond to the immunogenically active composition. The non-metabolizable oil is understood to be an oil that, when administered with an antigen, does not metabolize in the body after administration. A preferred non-metabolizable oil is mineral oil. In other preferred forms, both a carbomer adjuvant and non-metabolizable oil (preferably mineral oil) are present in addition to the WNV antigens. The adjuvant(s) can be used in any of the compositions described herein.

In an additional embodiment, the composition of the present invention contains WNV antigens, preferably an inactivated or killed WNV from a North American dominant strain, and essentially no oil or oil-based adjuvants. In such an embodiment, other adjuvants, preferably carbomer, can be included.

In another embodiment, a vaccine composition comprised of WNV antigens in combination with other antigens from equine microbial pathogens is provided in order to confer a broad scope of protection to the animal. In such embodiments, the WNV antigens are in any form as described above.

In one preferred embodiment, the present invention provides a vaccine composition comprising WNV antigens as described above in combination with one or more immunologically effective amounts of antigenic components selected from the group consisting of Venezuelan Equine Encephalomyelitis (VEE), Eastern Equine Encephalomyelitis (EEE), Western Equine Encephalomyelitis (WEE), Tetanus toxoid (T), Equine herpes viruses (EHV) including types 1 and 4, Equine influenza viruses (EIV), and combinations thereof, along with a pharmaceutically acceptable carrier. Preferably such embodiments will include an adjuvant, preferably carbomer, and a pharmaceutically acceptable carrier. Additionally, a non-metabolizable oil, preferably mineral oil, may be present, however, such an oil is not required.

Preferred embodiments also include WNV antigens, as described above, in combination with: Eastern Equine Encephalomyelitis; Western Equine Encephalomyelitis; Venezuelan Equine Encephalomyelitis; Tetanus Toxoid; Eastern Equine Encephalomyelitis and Western Equine Encephalomyelitis; Eastern Equine Encephalomyelitis and Venezuelan Equine Encephalomyelitis; Eastern Equine Encephalomyelitis and Tetanus Toxoid; Eastern Equine Encephalomyelitis, Western Equine Encephalomyelitis, and Venezuelan Equine Encephalomyelitis; Eastern Equine Encephalomyelitis, Western Equine Encephalomyelitis, and Tetanus Toxoid; Eastern Equine Encephalomyelitis, Western Equine Encephalomyelitis, Venezuelan Equine Encephalomyelitis and Tetanus Toxoid; Western Equine Encephalomyelitis and Venezuelan Equine Encephalomyelitis; Western Equine Encephalomyelitis and Tetanus Toxoid; Western Equine Encephalomyelitis, Venezuelan Equine Encephalomyelitis, and Tetanus Toxoid; Venezuelan Equine Encephalomyelitis and Tetanus Toxoid; and Eastern Equine Encephalomyelitis, Venezuelan Equine Encephalomyelitis and Tetanus Toxoid. The most preferred combination of these specified combinations includes WNV antigens in combination with antigens or antigenic components of Eastern Equine Encephalomyelitis, Western Equine Encephalomyelitis, Venezuelan Equine Encephalomyelitis, and Tetanus Toxoid. In each such specified combination, an adjuvant or combination of adjuvants can be used, with carbomer, and even more preferably carbopol, being particularly preferred. In the most preferred forms of the combination of WNV and Eastern Equine Encephalomyelitis, Western Equine Encephalomyelitis, Venezuelan Equine Encephalomyelitis and Tetanus Toxoid, no oil (metabolizable or non-metabolizable) is present. The NJO strain of Eastern Equine Encephalomyelitis, the Fleming strain of Western Equine Encephalomyelitis strain, and the TC-83 strain of Venezuelan Equine Encephalomyelitis strain are all representative strains of these vaccine components.

Further preferred embodiments of the present invention can be made using each of the specified combination vaccines listed above and adding in antigens from Equine Herpesvirus, preferably type 1, type 4, (EHV1 and/or EHV4) or combinations thereof.

Still further variations of each of the specified combination vaccines listed above, including those that include EHV1 and/or EHV4 can be made by adding in antigens from Equine influenza virus (EIV). Preferred embodiments incorporating Equine influenza virus include: West Nile Virus, at least one strain of Equine Influenza Virus, and Tetanus Toxoid; West Nile Virus, at least one strain of Equine Influenza Virus, Tetanus Toxoid, and Eastern Equine Encephalomyelitis; West Nile Virus, at least one strain of Equine Influenza Virus, Tetanus Toxoid, Eastern Equine Encephalomyelitis, and Western Equine Encephalomyelitis; West Nile Virus, at least one strain of Equine Influenza Virus, Tetanus Toxoid, Eastern Equine Encephalomyelitis, Western Equine Encephalomyelitis; and Venezuelan Equine Encephalomyelitis; West Nile Virus, at least one strain of Equine Influenza Virus, and Eastern Equine Encephalomyelitis; West Nile Virus, at least one strain of Equine Influenza Virus, and Western Equine Encephalomyelitis; West Nile Virus, at least one strain of Equine Influenza Virus, and Venezuelan Equine Encephalomyelitis; West Nile Virus, at least one strain of Equine Influenza Virus, Eastern Equine Encephalomyelitis, and Western Equine Encephalomyelitis; West Nile Virus, at least one strain of Equine Influenza Virus, Eastern Equine Encephalomyelitis, and Venezuelan Equine Encephalomyelitis; West Nile Virus, at least one strain of Equine Influenza Virus, Western Equine Encephalomyelitis, and Venezuelan Equine Encephalomyelitis; West Nile Virus, at least one strain of Equine Influenza Virus, Western Equine Encephalomyelitis, and tetanus toxoid; West Nile Virus, at least one strain of Equine Influenza Virus, Venezuelan Equine Encephalomyelitis, and tetanus toxoid; West Nile Virus, at least one strain of Equine Influenza Virus, Venezuelan Equine Encephalomyelitis, Western Equine Encephalomyelitis, and tetanus toxoid; and West Nile Virus, at least one strain of Equine Influenza Virus, Venezuelan Equine Encephalomyelitis, Eastern Equine Encephalomyelitis, and tetanus toxoid. In each specified embodiment any one or more strains or isolates of Equine Influenza may be present. Preferred strains of Equine Influenza virus include Influenza A/equine-2/Ohio/03, Influenza A/equine-2/New Market/2/93, Influenza A/equine-2/Kentucky/95, and combinations thereof. In all of the combinations listed above, it is preferred to use at least two strains of Equine Influenza and still more preferred to use at least 3 strains of Equine Influenza. Preferred embodiments incorporating Equine Herpes Virus include: West Nile Virus, at least one strain of Equine Influenza Virus, Tetanus Toxoid, and Equine Herpes Virus; West Nile Virus, at least one strain of Equine Influenza Virus, Tetanus Toxoid, Eastern Equine Encephalomyelitis, and Equine Herpes Virus; West Nile Virus, at least one strain of Equine Influenza Virus, Tetanus Toxoid, Eastern Equine Encephalomyelitis, Western Equine Encephalomyelitis, and Equine Herpes Virus; West Nile Virus, at least one strain of Equine Influenza Virus, Tetanus Toxoid, Eastern Equine Encephalomyelitis, Western Equine Encephalomyelitis; Venezuelan Equine Encephalomyelitis, and Equine Herpes Virus; West Nile Virus, at least one strain of Equine Influenza Virus, and Eastern Equine Encephalomyelitis; West Nile Virus, at least one strain of Equine Influenza Virus, Western Equine Encephalomyelitis and Equine Herpes Virus; West Nile Virus, at least one strain of Equine Influenza Virus, Venezuelan Equine Encephalomyelitis, and Equine Herpes Virus; West Nile Virus, at least one strain of Equine Influenza Virus, Eastern Equine Encephalomyelitis, Western Equine Encephalomyelitis, and Equine Herpes Virus; West Nile Virus, at least one strain of Equine Influenza Virus, Eastern Equine Encephalomyelitis, Venezuelan Equine Encephalomyelitis, and Equine Herpes Virus; West Nile Virus, at least one strain of Equine Influenza Virus, Western Equine Encephalomyelitis, Venezuelan Equine Encephalomyelitis, and Equine Herpes Virus; West Nile Virus, at least one strain of Equine Influenza Virus, Western Equine Encephalomyelitis, Tetanus Toxoid, and Equine Herpes Virus; West Nile Virus, at least one strain of Equine Influenza Virus, Venezuelan Equine Encephalomyelitis, tetanus toxoid, and Equine Herpes Virus; West Nile Virus, at least one strain of Equine Influenza Virus, Venezuelan Equine Encephalomyelitis, Western Equine Encephalomyelitis, Tetanus Toxoid, and Equine Herpes Virus; and West Nile Virus, at least one strain of Equine Influenza Virus, Venezuelan Equine Encephalomyelitis, Eastern Equine Encephalomyelitis, Tetanus Toxoid, and Equine Herpes Virus. In all of the combinations listed above, it is preferred to use at least two strains of Equine Influenza and still more preferred to use at least 3 strains of Equine Influenza. Additionally, in all combinations above, the "at least one" strain of Equine Herpesvirus is preferred to be selected from the group consisting of EHV-1 and EHV-4. In some preferred forms, both strains, EHV-1 and EHV-4, will be included in the immunogenic composition. In other preferred forms, just EHV-1 will be included. The WNV component of the combination will preferably be an inactivated or killed North American dominant strain as described herein.

The vaccine composition can be administered in any immunogenically effective dose. In a preferred embodiment, the vaccine composition is administered as a single dose. Preferably, the dose has a total volume between about 0.5 ml and 2.5 ml, more preferably between about 0.6 ml and 2.0 ml, even more preferably between about 0.7 ml and 1.75 ml, still more preferably between about 0.8 ml and 1.5 ml, even more preferably between about 0.9 ml and 1.25 ml, with a single 1.0 ml dose being the most preferred.

In another embodiment, the vaccine is administered with a first dose being administered prior to the administration of a second (booster) dose. Preferably, the second dose is administered at least 15 days after the first dose. More preferably, the second dose is administered between 15 and 28 days after the first dose. Even more preferably, the second dose is administered at least 17 days after the first dose. Still more preferably, the second dose is administered between 17 and 25 days after the first dose. Even more preferably, the second dose is administered at least 19 days after the first dose. Still more preferably, the second dose is administered between 19 and 23 days after the first dose. Most preferably the second dose is administered at least 21 days after the first dose. In a preferred embodiment, both the first and second doses of the vaccine are in the same amount. Preferably, each dose is in the preferred amounts specified above, with a dose of 1 ml for the first and second dose being most preferred. In addition to the first and second dose regimen, an alternate embodiment comprises further subsequent doses. For example, a third, fourth, or fifth dose could be administered in these embodiments. Preferably, subsequent third, fourth, and fifth dose regimens are administered in the same amount as the first dose, with the time frame between the doses being consistent with the timing between the first and second doses mentioned above.

In an additional preferred embodiment, in each dose of the composition of the present invention, the WNV antigen comprises at least $10^{2.0}$ $TCID_{50}$/dose. More preferably, the WNV antigen comprises between about $10^{2.0}$ $TCID_{50}$/dose to $10^{10.0}$ $TCID_{50}$/dose. Still more preferably, the WNV antigen comprises at least $10^{2.5}$ $TCID_{50}$/dose. Even more preferably, the WNV antigen comprises between about $10^{2.5}$ $TCID_{50}$/dose to about $10^{9.5}$ $TCID_{50}$/dose. Still more preferably, the WNV antigen comprises at least $10^{3.0}$ $TCID_{50}$/dose. Even more preferably, the WNV antigen comprises between about $10^{3.0}$ $TCID_{50}$/dose to about $10^{9.0}$ $TCID_{50}$/dose. Still more preferably, the WNV antigen comprises at least $10^{3.5}$ $TCID_{50}$/dose. Even more preferably, the WNV antigen comprises between about $10^{3.5}$ $TCID_{50}$/dose to about $10^{9.0}$ $TCID_{50}$/dose. Most preferably, the WNV antigen comprises between $10^{7.0}$ $TCID_{50}$/dose and $10^{9.0}$ $TCID_{50}$/dose. The $TCID_{50}$ values of an inactivated WNV vaccine or any other inactivated vaccine refer in general to the antigen content in the final vaccine that however is equivalent to the antigen content calculated for the vaccine composition prior to the inactivation of its antigen. Preferably, the immunogenic composition of the present invention stimulates serum neutralizing antibodies to WNV at a titer of 1:4 or higher when determined in a commercial available detection assay or using the procedures known to those of skill in the art with a representative example provided herein. In a preferred embodiment, in each dose of an embodiment of the present invention that comprises additional equine antigen, the amount of Eastern Equine Encephalomyelitis or Venezuelan Equine Encephalomyelitis in any dose is preferably at least $10^{5.5}$ $TCID_{50}$/dose. Even more preferably, the dose is between about $10^{5.5}$ $TCID_{50}$/dose and $10^{9.5}$ $TCID_{50}$/dose. Still more preferably, the dose is at least $10^{6.0}$ $TCID_{50}$/dose. Still more preferably, the dose is between about $10^{6.0}$ $TCID_{50}$/dose and $10^{9.0}$ $TCID_{50}$/dose. Even more preferably, the dose is at least $10^{6.5}$ $TCID_{50}$/dose. Still more preferably, the dose is between about $10^{6.5}$ $TCID_{50}$/dose and $10^{9.5}$ $TCID_{50}$/dose. Even more preferably, the dose is at least $10^{7.0}$ $TCID_{50}$/dose. Most preferably, the dose is between $10^{6.7}$ $TCID_{50}$ and $10^{9.2}$ $TCID_{50}$/dose.

Preferably, the Western Equine Encephalomyelitis antigen, when present in the composition of the present invention, is in an amount of at least $10^{6.2}$ PFU/ml. Even more preferably, the amount is between $10^{6.2}$ PFU/ml and $10^{10.2}$ PFU/ml. Still more preferably, the amount is at least $10^{6.7}$ PFU/ml. Even more preferably, the amount is between $10^{6.5}$ PFU/ml and $10^{9.7}$ PFU/ml. Still more preferably, the amount is at least $10^{7.2}$ PFU/ml. Even more preferably, the amount is between about $10^{7.2}$ PFU/ml and $10^{9.2}$ PFU/ml. Still more preferably, the amount is at least $10^{7.7}$ PFU/ml with at between $10^{6.5}$ PFU/dose and $10^{9.0}$ PFU/ml being the most preferred.

In another preferred embodiment, the amount of tetanus toxoid, if present in the composition of the present invention, is in an amount of at least 3 CPU, more preferably, between about 3 CPU and 20 CPU, still more preferably, at least 4 CPU, and most preferably, at least 5 CPU but not more than 20 CPU.

In an alternate embodiment, where one or more strains of Equine Influenza Virus is present, the amount of Equine Influenza present in the composition is in an amount of at least $10^{5.0}$ TCID$_{50}$/mL. More preferably, the Equine Influenza is in an amount of between about $10^{5.0}$ TCID$_{50}$/mL to $10^{9.0}$ TCID$_{50}$/mL, and, more preferably, at least $10^{6.0}$ TCID$_{50}$/mL. Still more preferably, the amount is between about $10^{6.0}$ TCID$_{50}$/mL to $10^{8.0}$ TCID$_{50}$/mL and, more preferably, the amount is at least $10^{6.5}$ TCID$_{50}$/mL. Still more preferably, the amount is between about $10^{6.5}$ TCID$_{50}$/mL to $10^{7.0}$ TCID$_{50}$/mL, with the most preferred amount being between about $10^{6.7}$ TCID$_{50}$/mL to $10^{7.0}$.

In an embodiment that comprises Equine Herpes Virus, the amount of Equine Herpes Virus in each dose is at least $10^{6.0}$ TCID$_{50}$/mL. More preferably, Equine Herpes Virus is present in the composition in an amount of between $10^{6.0}$ TCID$_{50}$/mL to $10^{9.5}$ TCID$_{50}$/mL and, more preferably, in an amount of about $10^{7.0}$ TCID$_{50}$/mL. Still more preferably, Equine Herpes Virus is present in an amount between $10^{7.5}$ TCID$_{50}$/mL to $10^{9.0}$ TCID$_{50}$/mL and, more preferably, in an amount of about $10^{8.0}$ TCID$_{50}$/mL. Still more preferably, Equine Herpes Virus is present in an amount of between $10^{8.0}$ TCID$_{50}$/mL to $10^{9.0}$ TCID$_{50}$/mL and, most preferably, in an amount of about $10^{8.50}$ TCID$_{50}$/mL.

In yet another preferred embodiment, a vaccine composition comprising the chronologically contemporary and epidemiologically prevalent strains of WNV is provided. Such a composition will generally improve the efficacy of the composition. Preferably, such a prevalent strain is isolated from the tissues of a horse. Such a source is a preferred source of WNV for preparing vaccine seed virus for an immunological composition for a species for which a comprehensively safe and effective WNV vaccine is particularly needed, namely, the horse. Further, the present invention discloses a vaccine composition comprising an inactivated low passage strain of WNV from the tissues of a horse, thereby overcoming the limitations of previous vaccines with the inappropriate limited repertoire of protein antigens found in either high passage attenuated vaccines, subunit vaccines, or other compositions produced by recombinant technology that express less than the full complement of proteins. This inactivated low passage WNV strain, isolated from horse tissues, overcomes deficiencies inherent in previous vaccines and provides a broad number of immunogenic proteins of most relevance by virtue of being produced from a highly virulent equine strain of low passage, thereby comprising a uniquely and comprehensively effective, yet safe, immunogenic composition not previously available for vaccination of the horse. Additionally, preferred chronologically contemporary and epidemiologically prevalent strains of WNV are North American dominant WNV strains, as defined herein.

The present invention provides for a broader scope of protection than traditional immunogenic or vaccine compositions, as the present invention provides protection against a broad range of isolates of a particular antigen. The challenge model used to evaluate the efficacy of the composition of the present invention utilized a heterologous challenge strain, evidencing the composition's ability to provide protection to isolates and strains outside of the particular strain or isolate used to vaccinate the animal. This is a unique feature of the present invention.

The present invention additionally provides for a method of reduction of the incidence and/or severity of clinical signs associated with West Nile Virus infection in an animal, preferably a horse, when compared to wild type infection. Such methods generally comprise the step of administering a vaccine composition comprising a killed or inactivated isolate of West Nile virus, preferably a North American dominant WNV strain, and a pharmaceutically acceptable carrier. In some preferred embodiments of the present application, an adjuvant is added to the composition, and in other preferred forms, no adjuvant is provided. In an alternate preferred embodiment, the method comprises administering a vaccine composition comprising one or more killed or inactivated isolate(s) of West Nile virus in combination with immunologically effective amounts of antigenic components from other equine pathogens. Preferably those isolates are selected from the group consisting of Eastern Equine Encephalomyelitis antigen, Western Equine Encephalomyelitis antigen, Venezuelan Equine Encephalomyelitis antigen, tetanus toxoid, and combinations thereof, and more preferably being those combinations described above. In another preferred embodiment, the vaccine of the present invention is combined with a suitable adjuvant, diluent, or pharmaceutically acceptable carrier.

The present invention provides for reduction of the incidence and/or severity of clinical symptoms associated with West Nile Virus infection in a herd, when compared to wild type infection. Preferably, the severity and/or incidence of clinical symptoms in animals receiving the immunogenic composition of the present invention are reduced at least 10% in comparison to animals not receiving such an administration when both groups (animals receiving and animals not receiving the composition) are challenged with or exposed to wild type infection by WNV. More preferably, the incidence or severity is reduced at least 20%, even more preferably, at least 30%, still more preferably, at least 40%, even more preferably, at least 50%, still more preferably, at least 60%, even more preferably, at least 70%, still more preferably, at least 80%, even more preferably, at least 90%, still more preferably, at least 95%, and most preferably, at least 100%, wherein the animals receiving the composition of the present invention exhibit no clinical symptoms. Preferably, the WNV strain is a North American dominant strain of WNV. Advantageously, the present invention also provides protection from heterologous strains (relative to the strain used in the composition) of pathogens.

The present invention further provides a method of stimulating serum neutralizing or serum hemagglutination antibodies to a pathogen selected from the group consisting of WNV, WEE, VEE, EEE, EHV, EIV, and combinations thereof by administering a composition in accordance with the present invention described herein. Preferably the compositions of the present invention stimulate serum neutralizing antibodies to WNV at a titer of 1:4 or higher, thereby preventing or reducing WNV viremia.

The immunogenic composition of the present invention provides an extended duration of immunity against all antigens present in the vaccine. Preferably, the duration of immunity against West Nile is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against EIV is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against EHV is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against Western Equine Encephalomyelitis is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against Eastern Equine Encephalomyelitis is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against Venezuelan Equine Encephalomyelitis is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against Tetanus Toxoid is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity of at least 12 months further relates to any combination of antigens forming the immunogenic composition of the present invention.

In another preferred embodiment comprising EIV and/or EHV antigen, as described above, the immunogenic composition ameliorates shedding of infectious EIV or EHV to prevent spread of the virus to other susceptible animals.

In yet another preferred embodiment, compositions in accordance with the present invention described herein overcome interference from passively acquired maternal immunity and stimulates active immunity and a reduction in the incidence of or severity of clinical signs of EIV infection in vaccinated animals against EIV.

In another preferred embodiment of the present invention, an immunogenic composition comprising VEE, WEE, EEE, tetanus, WNV, equine rhinopneumonitis and equine influenza, all as described herein, demonstrates efficacy against VEE, WEE, EEE, tetanus, WNV, equine rhinopneumonitis and equine influenza after administration in accordance with the present invention. Preferably, such a composition will further include an adjuvant, preferably mineral oil and/or a carbomer, and a veterinary acceptable carrier. In preferred forms, the composition will be administered in a single, 1 ml dose.

Each of the immunogenic compositions described herein that include WNV antigen can be administered as described such that they reduce the incidence of or lessen the severity of clinical symptoms associated with West Nile Virus.

Each of the immunogenic compositions described herein that include EIV antigen can be administered as described such that they reduce the incidence of or lessen the severity of clinical symptoms associated with Equine Influenza.

The present invention also provides a method for reducing the incidence of or lessening the severity of clinical symptoms associated with Equine Herpes virus comprising the step of administering any one of the immunogenic compositions described above, that includes an Equine Herpes virus antigen, to an animal.

The present invention also provides a method for reducing the incidence of clinical symptoms associated with West Nile Virus comprising the step of administering any one of the immunogenic compositions that includes West Nile Virus antigen, as described herein, to an animal.

The present invention also provides a method for reducing the incidence of clinical symptoms associated with Equine Influenza Virus comprising the step of administering any one of the immunogenic compositions described above, that includes an Equine Influenza antigen, to an animal.

The present invention further provides a method for reducing the incidence of clinical symptoms associated with Equine Herpes Virus comprising the step of administering any one of the immunogenic compositions described above that includes an Equine Herpes virus antigen, to an animal.

The present invention also provides a method of reducing the incidence of clinical symptoms associated with Equine Influenza Virus comprising the step of administering any one of the immunogenic compositions described above to an animal, wherein the reduction in clinical signs, compared to animals not receiving the immunogenic composition, is at least a 10% reduction in clinical signs.

The present invention provides a method of reducing the incidence of infection in a herd comprising the step of administering any one of the immunogenic compositions described above to an animal.

The present invention provides a method of reducing the incidence of infection in a herd comprising the step of administering any one of the immunogenic compositions described above to an animal, wherein the reduction of incidence of infection, compared to herds not receiving the immunogenic composition, is from about 10%-50% reduction.

The present invention provides a method of reducing the incidence and severity of clinical symptoms of EHV in a herd, wherein the clinical symptoms are selected from the group consisting of respiratory disease, abortion, reproductive complications, neurological disease, central nervous system disease, and combinations thereof.

The present invention provides a method for reducing the incidence of or lessening the severity of clinical symptoms associated with Equine Herpes Virus comprising the step of administering any one of the immunogenic compositions described above, that includes an Equine Herpes Virus antigen, to an animal.

The present invention provides a method for reducing the severity of or lessening the severity of clinical symptoms associated with Equine Influenza in a herd, comprising the step of administering any one of the immunogenic compositions described above, that includes an Equine Influenza antigen, to an animal.

The present invention provides a method for reducing the incidence of or lessening the severity of clinical symptoms associated with West Nile Virus in a herd, comprising the step of administering any one of the immunogenic compositions described above, that includes a West Nile Virus antigen, to an animal.

The present invention provides a method for reducing the incidence of or lessening the severity of clinical symptoms associated with Eastern Equine Encephalomyelitis in a herd, comprising the step of administering any one of the immunogenic compositions described above that includes an Eastern Equine Encephalomyelitis antigen to an animal.

The present invention further provides a method for reducing the incidence of or lessening the severity of clinical symptoms associated with Western Equine Encephalomyelitis in a herd, comprising the step of administering any one of the immunogenic compositions described above, that includes an Western Equine Encephalomyelitis antigen, to an animal.

The present invention further provides a method for reducing the incidence of or lessening the severity of clinical symptoms associated with Venezuelan Equine Encephalomyelitis in a herd, comprising the step of administering any one of the immunogenic compositions described above, that includes a Venezuelan Equine Encephalomyelitis antigen, to an animal.

The present invention also provides a method of making any one of the immunogenic composition of the present invention as described above and herein, comprising the steps of combining a West Nile Virus antigen with a suitable excipient or pharmaceutical carrier. In preferred forms, this method further comprises the step of adding one or more equine antigens. A preferred group of equine antigens are selected from the group consisting of Western Equine Encephalomyelitis, Eastern Equine Encephalomyelitis, Venezuelan Equine Encephalomyelitis, Tetanus Toxoid, EHV, EIV, and combinations thereof. In some preferred forms, the methods described herein can further comprise a filtration step, wherein the final product is in a purified form.

"Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), non-metabolizable oil, mineral and/or plant/vegetable and/or animal oils, polymers, carbomers, surfactants, natural organic compounds, plant extracts, carbohydrates, cholesterol, lipids, water-in-oil emulsion, oil-in-water emulsion, water-in-oil-in-water emulsion. The emulsion can be based in particular on light liquid paraffin oil (European Pharmacopeia type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997). In a preferred embodiment the adjuvant is at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product. Of the possible adjuvants used in combination with the present invention, it is preferred to not use a metabolizable oil. In a preferred embodiment, the adjuvant is at least a non-metabolizable oil, preferably mineral oil. In an alternate preferred embodiment, the vaccine composition contains essentially no oil-based adjuvants. In a most preferred embodiment the vaccine composition contains both a non-metabolizable oil, preferably mineral oil, and carbomer as adjuvants.

In addition, the immunogenic and vaccine compositions of the present invention can include one or more veterinary-acceptable carriers. As used herein, "a veterinary-acceptable carrier" includes any and all solvents, dispersion media, coatings, adjuvants, stabilizing agents, diluents, preservatives, excipients, antibacterial and antifungal agents, antimicrobic agents, isotonic agents, adsorption delaying agents, and the like. In some preferred embodiments, and especially those that include lyophilized immunogenic compositions, stabilizing agents for use in the present invention include stabilizers for lyophilization or freeze-drying.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

In a preferred embodiment, the immunogenic composition of the present invention is prepared comprising a preservative and a stabilizer; and, more preferably, the immunogenic composition of the present invention is prepared comprising gentamycin, EDTA, Glycerol, and combinations thereof.

An "immunogenic or immunological composition" refers to a composition of matter that comprises at least one antigen, which elicits an immunological response in the host of a cellular and/or antibody-mediated immune response to the composition or vaccine of interest. Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of clinical signs normally displayed by an infected host, a quicker recovery time and/or a lowered duration or bacterial titer in the tissues or body fluids or excretions of the infected host.

The term "in need of such administration" or "in need of such administration treatment", as used herein means that the administration/treatment is associated with the boosting or improvement in health or any other positive medicinal effect on health of the animals which receive the immunogenic composition in accordance with the present invention.

The term "West Nile Virus" antigen means, but is not limited to the components of the WNV virion that are immunogenic when present in an animal, and most particularly protein components, such as envelope and non-structural proteins, of the WNV that provoke humoral or cellular immune responses when present in an animal. Such antigens can include DNA, protein subunits, modified live virus, and killed or inactivated virus. In preferred forms of the invention, the WNV antigen or antigens comprise inactivated or killed, and even more preferably, North American dominant, WNV strains.

The term "North American West Nile Virus (strains)" refers to, but is not limited to any West Nile Virus strain or isolate that has ever been discovered on the North American continent. Preferably, a North American West Nile Virus strain has a sequence identity to the NY99 strain (GenBank accession no. AF196835 or NCBI reference sequence NC_00942.1 (SEQ ID No. 23) of at least 97%, even more preferably, at least 98%, still more preferably, at least 98.5%, more preferably, at least 99%, even more preferably, at least 99.2%, and, most preferably of at least 99.4%.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The term "North American Dominant West Nile Virus" strains and isolates refers to those strains or isolates defined as such in *Phylogenetic Analysis of North American West Nile Virus Isolates, 2001-2004: Evidence For the Emergence of a Dominant Genotype*, C. Todd Davis, et. al, Virology 342, p. 252-265 (2005), the teaching and content of which is hereby incorporated by reference herein. As noted therein, North American Dominant WNV strains or isolates have at least 1 nucleotide change resulting in an amino acid change from the WN99 isolates. Strain NY99 (GenBank accession no. AF196835), an example of which is provided in SEQ ID. NO. 23, serves as a reference strain for determining if a strain or isolate is North American Dominant. In a preferred embodiment, the nucleotide change results in an amino acid change in an envelope protein of the strain or isolate and, more preferably, the nucleotide change results in an amino acid change from valine to alanine at position 159 in the critical envelope protein or "E159". Preferably, this amino acid change is associated with a greater ability to replicate in the intermediate host, namely, the mosquito. In addition, these strains or isolates may have one or more silent amino acid changes. Preferably, North American Dominant strains also include either (and preferably both) a U to C mutation and a C to U mutation at positions 1442 and 2466 (in comparison to a North American strain, e.g. NY 99 and SEQ ID NO.23), respectively. Still more preferably, North American Dominant strains or isolates further include a mutation in the nucleotide sequence encoding the E protein and the C to U mutation at position 9352 in the sequence encoding the NS5 protein (again in comparison to a North American strain, e.g. NY 99 and SEQ ID NO. 23). These preferred mutations are shown in detail for specific regions in Example 10 and FIGS. 10-17. Representative North American Dominant WNV strains are listed in this application. Additionally, for purposes of the present invention North American Dominant and WN02 are used interchangeably.

For purposes of the present invention, Horse Origin 2005 strain North American Equine E159, E159 (Horse Origin), NAEE159, United States Department of Agriculture Isolate 405330 (USDA 2005) Horse Origin, and E159 strain are used interchangeably. For purposes of the present invention, Donkey Origin 2004 strain, United States Department of Agricultures Isolate 292206 (USDA 2004) Donkey Origin, E159 (Donkey Origin), and North American Donkey E159 (NADE159) are used interchangeably. E159 indicates that the amino acid change in the envelope protein from valine to alanine occurs at position 159, as described above.

West Nile Virus strains or isolates, for purposes of the present invention, are not limited to horse and equine West Nile Virus strains but encompass, while not being limited to, those West Nile Virus strains of bird origin, donkey origin, pig origin, human origin, mammal origin, and equine origin.

For purposes of the present invention the terms "strain" and "isolate" have the same meaning and are used interchangeably.

As used herein, "a pharmaceutically" or "veterinary acceptable carrier" or "pharmaceutical carrier" includes any and all solvents, growth media, dispersion media, coatings, adjuvants, stabilizing agents, diluents, preservatives, antibacterial and antifungal agents, isotonic agents, adsorption delaying agents, and the like.

An "immunogenic or immunological composition" refers to a composition of matter that comprises at least one antigen which elicits an immunological response in the host of a cellular and/or antibody-mediated immune response to the composition or vaccine of interest. Usually, an "immunological response" includes but is not limited to one or more of the following effects: the production or activation of antibodies, B cells, helper T cells, suppressor T cells, and/or cytotoxic T cells and/or gamma-delta T cells, and/or virus neutralizing antibodies directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of clinical signs normally displayed by an infected host, a quicker recovery time and/or a lowered duration of clinical disease or higher viral antibody titer in the tissues or body fluids or excretions of the infected host, or lessened viremia in the blood, or lessened gross or histopathological lesions due to infection.

In addition, the immunogenic and vaccine compositions of the present invention can include one or more veterinary-acceptable carriers. As used herein, "a veterinary-acceptable carrier" includes any and all solvents, dispersion media, cell culture media and cell culture constituents, coatings, adjuvants, stabilizing agents, diluents, preservatives, antibacterial and antifungal agents, isotonic agents, adsorption delaying agents, and the like. "Diluents" can include water, saline, buffered saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Clinical signs" of West Nile Virus, for purposes of this invention, include, but are not limited to, symptoms or lesions associated with encephalitis, viremia, anorexia, depression, fever, weakness, abnormal gait, paralysis of hind limbs, impaired vision, ataxia, aimless wandering, convulsions, inability to swallow, coma, posterior weakness, paralysis, poor coordination, depression and related behavior, tremors, convulsions, paddling of the limbs, neurological problems, swelling of the central nervous system, death, and combinations thereof. The clinical signs exhibited by an infected animal vary depending on the severity of infection "Clinical Signs" of Equine Herpes virus, for purposes of this invention include, but are not limited to, abortion, neurological deficiencies, respiratory disease, reproductive system deficiencies and failure, and symptoms relating to the central nervous system. Additionally, clinical symptoms of EHV 1 include, but are not limited to, the phenomenon of foals infected with EHV1, exhibiting respiratory complications, passing the virus to the older members of the herd who then exhibit reproductive deficiencies, including abortion, and neurological deficiencies, normally exhibited in the central nervous system.

"Clinical Signs" of Eastern Equine Encephalomyelitis, Western Equine Encephalomyelitis, and Venezuelan Equine Encephalomyelitis, for purposes of the present invention are those symptoms normally known to be associated with encephalomyelitis, including, but are not limited to fever, nervous signs such as sensitivity to sound, periods of excitement, and restlessness, brain lesions, drowsiness, drooping ears, circling, abnormal gait, paralysis, loss of appetite, depression, head pressing, lack of coordination, long-term disability, brain damage, death, and combinations thereof. "Safety" as used herein, refers to the absence of adverse consequences in the vaccinated animal following vaccination, including but not limited to, potential reversion of vaccine virus to virulence and clinically significant side effects, such as persistent systemic illness or unacceptable inflammation at the site of vaccine administration.

"Reduction of the incidence and/or severity of clinical signs" or "reduction in the incidence and/or severity of clinical symptoms", as referred to herein, means reducing the number of infected animals in a group, reducing or eliminating the number of animals exhibiting clinical signs of infection, or reducing the severity of any clinical signs that are present in the animals, in comparison to wild-type infection. For example, in the experiments herein, such clinical signs included viremia, fever, antibody response, and histopathology. Preferably, these are reduced in animals receiving the composition of the present invention by at least 10% in comparison to animals not receiving the vaccination which may become infected. More preferably, clinical signs are reduced in animals receiving the composition of the present invention by at least 20%, more preferably by at least 30%, even more preferably by at least 40%, and even more preferably by at least 50%.

"Duration of Immunity," as used herein, refers to the minimum number of days during which an animal produces an immunogenic response such that the animal will be relatively immune from contracting a virus and/or benefit from reduction of incidence and/or severity of clinical signs, as described herein.

The terms "strain" and "isolate", when used herein, are meant to be used interchangeably.

The terms "vaccine" and "immunogenic composition", when used herein, are meant to be used interchangeably.

Any West Nile Virus strain(s) or isolate(s) can be used in accordance with the present invention. In a preferred embodiment, the isolate is selected from one or more of the following: New York (Northeastern North American) Isolate (WN-NY 99), Horse Origin, 1999, New York (Northeastern North American) Isolate (WN-NY 99), Crow Origin, 1999, United States Department of Agricultures Isolate 292206 (USDA 2004), Donkey Origin, United States Department of Agriculture Isolate 405330 (USDA 2005), Horse Origin, North American Isolate (WN-Texas-2002/2003), Southeast Texas Coastal Isolate 2002, Mexico (Tabasco) Isolate 2003, and combinations thereof, and in a more preferred embodiment the isolate is selected from one or more of the following: United States Department of Agricultures Isolate 292206 (USDA 2004), Donkey Origin, United States Department of Agriculture Isolate 405330 (USDA 2005), Horse Origin, North American Isolate (WN-Texas-2002/2003), Southeast Texas Coastal Isolate 2002, Mexico (Tabasco) Isolate 2003, and combinations thereof. In a most preferred embodiment, the isolate is United States Department of Agriculture Isolate 405330 (USDA 2005), Horse Origin singularly or in combination with one or more isolates as listed above. In an additionally preferred embodiment, those isolates which are part of the North American West Nile Virus isolates are included. In yet another preferred embodiment North American Dominant West Nile Virus isolates are included. In addition to those listed above, specific isolates include, but are not limited to, WN02 and isolates which have at least 1, preferably at least 2, and even more preferably at least 3 nucleotide changes resulting in at least one amino acid change from the WN NY99 isolates, and most preferred are strains with the amino acid change from valine to alanine at position 159 of the envelope protein. Most preferred North American Dominant strains include, but are not limited to: NY2002Nassau, NY2002Clinton, NY2002Queens, GA20021, GA20022, TX20021, TX20022, IN2002, NY2003Albany, NY2003Suffolk, NY2003Chatauqua, CO20031, CO20032, TX2003, TX2003Harris4, TX2003Harris6, TX2003Harris7, TX2003Harris10, AZ2004, and TX2004Harris4, and combinations thereof. The strains of West Nile Virus useful in the vaccine or immunogenic composition of the present invention can be any strain or isolate. In a preferred embodiment, the North American Dominant West Nile Virus strain used is either E-159 (Horse Origin) or E-159 (Donkey Origin). A representative strain of such a North American Dominant WNV strain includes the Horse Origin 2005 strain deposited with the ATCC (ATCC Accession No. PTA-9409), located at 10801 University Boulevard, Manassas, Va., 20110-2209, on Aug. 14, 2008, under the provisions of the Budapest Treaty. Equine Influenza strains useful in the vaccine or immunogenic composition of the present invention can be any strain or isolate. Representative strains include Equi-2/Ohio/03, deposited as ATCC Accession No. PTA-9522, Equi-2/Kentucky/95, deposited as ATCC Accession No. PTA-9523, and Equi-2/New Market/2/93, deposited as ATCC Accession No. PTA-9524. Representative strains ATCC Accession Nos. PTA-9522, PTA-9523, and PTA-9524 were each deposited with the ATCC at 10801 University Boulevard, Manassas, Va., 20110-2209 on Sep. 23, 2008, under the provisions of the Budapest Treaty.

Equine Herpes Virus ("EHV") strains useful in the vaccine or immunogenic composition of the present invention can be any strain or isolate. Representative strains include EHV Subtype 1, deposited as ATCC Accession No. PTA-9525, and EHV Subtype 4, deposited as ATCC Accession No. PTA-9526. Representative strains ATCC Accession Nos. PTA-9525 and PTA-9526 were each deposited with the ATCC at 10801 University Boulevard, Manassas, Va., 20110-2209 on Sep. 23, 2008, under the provisions of the Budapest Treaty.

Western Equine Encephalomyelitis strains useful in the vaccine or immunogenic composition of the present invention can be any strain or isolate. A representative strain includes the Fleming Strain, deposited with the ATCC (ATCC Accession No. PTA-9410), located at 10801 University Boulevard, Manassas, Va., 20110-2209, on Aug. 14, 2008, under the provisions of the Budapest Treaty.

Venezuelan Equine Encephalomyelitis strains useful in the vaccine or immunogenic composition of the present invention can be any strain or isolate. A representative strain includes the TC-83 strain, deposited with the ATCC (ATCC Accession No. PTA-9411), located at 10801 University Boulevard, Manassas, Va., 20110-2209, on Aug. 14, 2008, under the provisions of the Budapest Treaty.

Eastern Equine Encephalomyelitis strains useful in the vaccine or immunogenic composition of the present invention can be any strain or isolate. A representative strain includes the NJO strain, deposited with the ATCC (ATCC Accession No. PTA-9412), located at 10801 University Boulevard, Manassas, Va., 20110-2209, on Aug. 14, 2008, under the provisions of the Budapest Treaty.

Tetanus toxoid strains useful in the vaccine or immunogenic composition of the present invention can be any strain or isolate. A representative strain is that taken from a master seed of *Clostridium tetani* from The Massachusetts Department of Public Health Institute of Laboratories in Boston, Mass.

The vaccine of the present invention is safe for administration in WNV susceptible species, particularly equidae, at any age and at any stage of reproduction, including pregnant females. In a preferred embodiment, the present invention is safe for administration to foals 12 months of age or older, more preferably, it is safe for administration to foals 10 months of age or older, more preferably, it is safe for administration to foals 8 months or older, more preferably, it is safe for administration to foals 6 months of age or older, more preferably, is safe for administration to foals 4 months of age or older, more preferably, it is safe for administration to foals 2 months of age or older, more preferably, it is safe for administration to foals 1 month of age or older, even more preferably, it is safe for administration to foals between 1 day and 1 month of age, and, most preferably, it is safe for administration to foals 1 day of age or older.

The composition of the present invention can be administered in any conventional manner. Examples of administration methods include any that afford access by cells of the immune system to the immunogenic composition including oral, transdermal/intradermal, intravenous, subcutaneous, intramuscular, intraocular, intraperitoneal, intrarectal, intravaginal, intranasal, intragastrical, intratracheal, intrapulmonarial, or any combination thereof. In a preferred embodiment, the vaccine is administered parenterally, preferably intranasally, subcutaneously, or intramuscularly, and in the most preferred embodiment the vaccine is administered intramuscularly.

BRIEF DESCRIPTION OF THE DRAWINGS

FIG. 1 is a graphical representation of the Mean Total Clinical Scores;

FIG. 2 is a graphical representation of the Proportion Shedding;

FIG. 3 is a graphical representation of the Nasal Discharge Score;

FIG. 4 is a graphical representation of Proportion Virus Shedding;

FIG. 5 is a graphical representation of Conjunctivitis Score;

FIG. 6 is a graphical representation of Serum Neutralization Titers;

FIG. 7 is a graphical representation of Proportion Positive for EHV-1;

FIG. 8 is a graphical representation of Mean White Blood Cell Count;

FIG. 9 is a graphical representation of Proportion Positive (pyrexic);

DETAILED DESCRIPTION

Examples

Figure 10A:
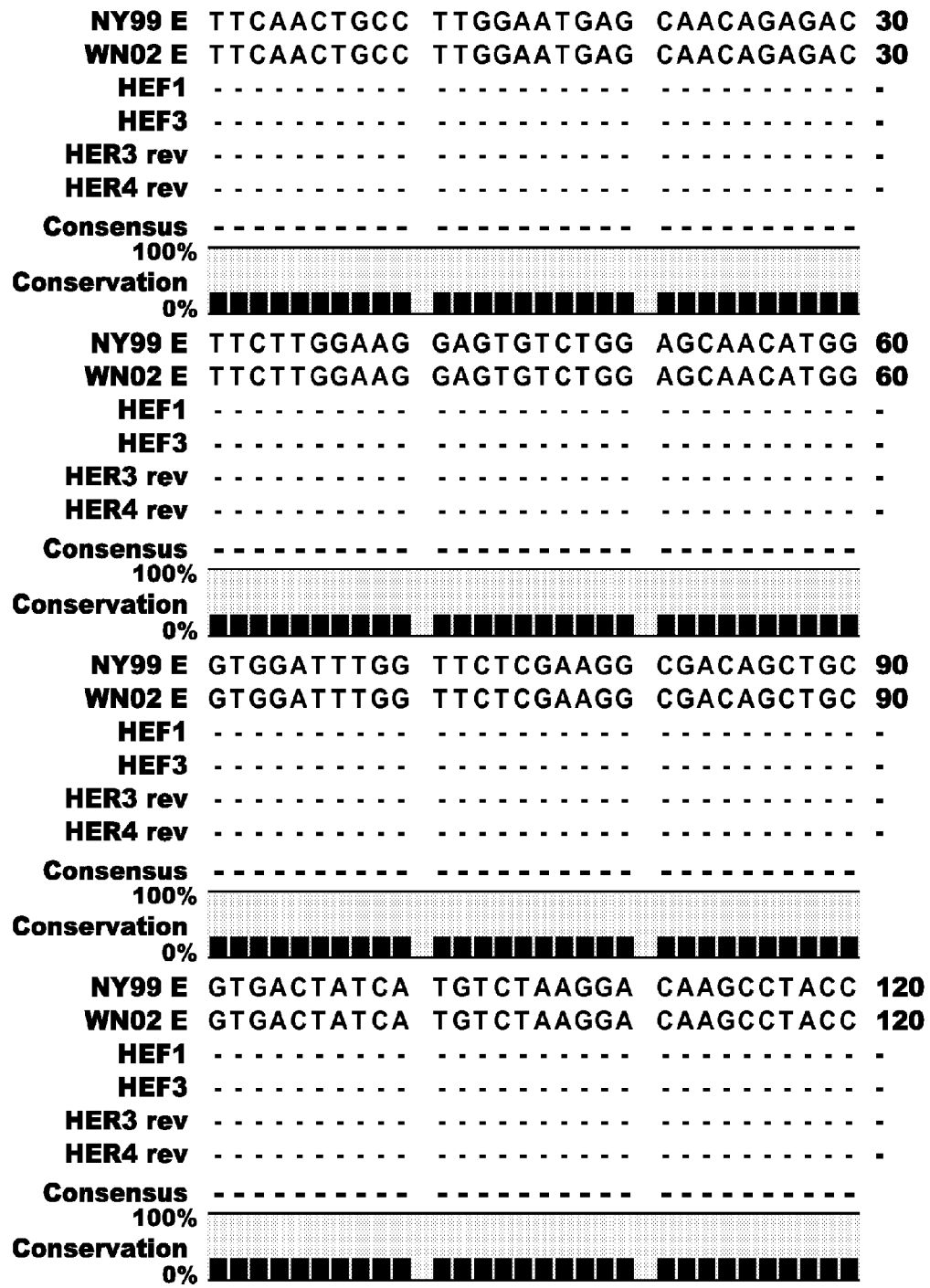
FIG. 10 is a nucleotide alignment of the HE region of WNV isolates.

The following examples are set forth below to illustrate specific embodiments of the present invention. These examples are merely illustrative and are understood not to limit the scope or the underlying principles of the present invention.

Example 1

This example illustrates a preferred vaccine composition in accordance with the present invention.

Materials and Methods

For preparation of working cell stock, the Master Cell Stock (MCS), consisting of the Vero Cell Line known to propagate West Nile Virus, which was tested for purity, identity, and karyology, was thawed and used to inoculate a range of T25 up to T150 $cm^2$ vessels or 1050 $cm^2$ roller bottles, or bioreactors or other suitable sterile vessels. Thawed cells were suspended in growth medium at a rate of 0.0015 mL to 5.0 L per vessel, depending on vessel volume. Cells were then incubated at 36-38° C. for up to seven days. Cultures planted from frozen stock were re-fed with medium, if needed, within thirty-six hours after planting to remove residual DMSO. Cultures were re-fed with medium, if needed, during the growth period to remove excessive debris, or to stimulate the growth of cultures which have not reached confluence, or to maintain viability of confluent cultures.

Cells were passaged 1-20 times by decanting the spent medium and then by adding 5-500 mL of 0.25% Trypsin-EDTA Solution to each vessel, depending upon vessel volume. The vessels were agitated gently until the cells slough from the surface. The cells were then removed from the vessels by rinsing with growth medium and pooled together. Prior to inoculation, cell growth medium was decanted from Vero Working Cells that are at least 55% confluent. Virus growth medium described was added to each vessel at 0.15 to 0.4 mL per $cm^2$ surface area. A Multiplicity of Infection (MOI) of 0.000001-0.0002 was used for infection as determined by performing a cell count of at least two representative vessels. Roller bottle cultures infected were incubated at 36-38° C. for two to five days at 0.1-0.8 rpm.

During the growth period, cultures were checked for typical CPE microscopically and for gross contamination macroscopically. Unsuitable cultures were discarded after sterilization. Cultures may be attenuated using standard techniques or may be used without attenuation.

The microorganisms were then harvested for production purposes. Virus fluids were harvested when CPE reached 85% or greater. Roller bottles were swirled to remove loose cells, and fluids and then pooled into sterile 2-20 L glass, plastic, or PETG bottles, 20 L sterile polypropylene containers or 2-500 L sterile stainless steel tanks containers appropriate for clarification.

Next, the product was prepared. Clarified fluids were inactivated with Formaldehyde Solution, USP, 0.2% by volume, or another effective inactivating agent, transferred to a secondary container, and held at 20-25° C. (room temperature) with agitation for forty-eight hours. A sample of at least 12 mL of the inactivated fluids was taken for inactivation assurance testing (described below) prior to concentration. After inactivation was completed, inactivated lot material was held at 2-7° C. for up to sixty days prior to concentration. A number of suitable adjuvants may be added to the vaccine formulation, most preferably a non-metabolizable oil, preferably mineral oil, and/or a carbomer. Typical processing steps may be employed such as mixing, blending, microfluidization, and emulsification, of the adjuvant and/or the harvested virus antigens with other ingredients.

The product was then standardized. Sufficient volumes of clarified, inactivated, concentrated (optional) lots were combined to provide a calculated titer of at least $10^{4.0}$ TCID$_{50}$ per dose of each strain in the final product. Multiple lots may be blended to achieve the titer requirements per dose.

The product was then assembled to final formulation. Based on the desired final serial volume, the amounts of antigenic components, adjuvant, stabilizer and diluent were calculated as follows:

a. West Nile Virus, Horse Origin 2005 (ATCC No. PTA-9409): minimum $10^{4.0}$ TCID$_{50}$/dose b. Adjuvant: The total adjuvant concentration, preferably a non metabolizable oil, and more preferably mineral oil and/or a carbomer, in a serial is at least 10% v/v and is added at time of serial batching/assembly.

c. Diluent: An appropriate volume of phosphate buffered saline (PBS) is added to bring the final volume to the desired volume.

d. Additional Formalin: An appropriate volume of 37% Formalin is added to maintain an appropriate level.

e. Gentamicin Sulfate

The required amounts of adjuvant and PBS were combined in a sterile vessel. The pH of this mixture was adjusted to approximately 4.9-5.1 with 10N NaOH or 5N HCl if necessary. Clarified, killed, concentrated West Nile Virus, as well as Gentamicin, and Formalin were added and the pH adjusted to 6.9 to 7.1. This was mixed at 2-6° C. for at least 8 hours, not to exceed 48 hours.

The vaccine was given by typical hypodermic injection, with booster vaccinations if desired. Most preferably, the initial dose and the booster doses were 1 mL volume administered intramuscularly at 21-day intervals. The vaccination regimen of initial and booster dose was given at the most preferred 1 mL dose volume to horses, other equidae, and other WNV susceptible species to reduce the incidence of and or severity of clinical signs of WNV infection, and preferably to prevent infection by WNV as well as to prevent disease due to West Nile Virus infection for a sustained period following vaccination.

Results and Discussion

The vaccine was given by various appropriate parenteral routes, dose volumes, and dosing regimens to animals of varying immunological status for WNV, including naive and those with passive antibody, and provided for long duration of immunity up to and exceeding at least 2 years following vaccination. The vaccine was safe for administration in WNV susceptible species, particularly equidae, at any age and at any stage of reproduction, including pregnant females.

Example 2

This investigation was carried out to obtain an efficacy evaluation of a vaccine to protect horses from challenge with West Nile Virus (WNV).

Materials and Methods

A total of 30 horses were randomly divided into groups of 15 horses each. A total of 20 horses received 2 doses of vaccine at 21-day intervals and 10 horses were used for control. Each group of horses, Block 1 and Block 2, contained 10 vaccinated horses and 5 control horses. The vaccine was a combination including WNV antigen, specifically an inactivated or killed North American Dominant Strain of WNV, Horse Origin 2005 (ATCC Deposit No. PTA-9409) as well as antigenic components of Venezuelan Equine Encephalomyelitis, TC-83 strain (ATCC Deposit No. PTA-9411) Eastern Equine Encephalomyelitis, NJO strain (ATCC Deposit No. PTA-9412) Western Equine Encephalomyelitis, Fleming strain (ATCC Deposit No. PTA-9410) and Tetanus toxoid formulated approximately as follows:

| | |
|---|---|
| Eastern Equine Encephalomyelitis | $10^{6.7}$-$10^{9.2}$ TCID$_{50}$/mL |
| Western Equine Encephalomyelitis | $10^{6.7}$-$10^{9.2}$ PFU/mL |
| Venezuelan Equine Encephalomyelitis | $10^{6.7}$-$10^{9.2}$ TCID$_{50}$/mL |
| West Nile Virus | $10^{7.0}$-$10^{9.}$ TCID$_{50}$/mL |
| Tetanus Toxoid | 5-10 CPU/mL |
| Adjuvant | 100-200 µl/mL |
| Diluent - DMEM containing | q.s. |
| Gentamycin (30 µg/mL of diluent volume) | |
| Formaldehyde (0.1% of diluent volume) | |

All groups were challenged with intrathecal inoculation of 1 ml PBS containing approximately $10^5$ pfu of a heterologous strain of WNV (NY99, 4132, crow isolate). The challenge was conducted under ketamine-xylazine anesthesia.

Horses were monitored for a maximum of 14 days, then humanely euthanized. Those that developed severe disease prior to 14 days were euthanized prematurely.

The following data were collected to assess the effectiveness of the vaccine:
Basic clinical evaluation
Body temperature
Assay for viremia
Histopathology: two sections of brainstem were evaluated by a board-certified veterinary pathologist.

Sera collected on appropriate days were evaluated for characterization of serologic responses to challenge.

Results and Discussion

Viremia after challenge and serum neutralization titers were considered the primary outcome variables in this study. The first block of horses that had been vaccinated were 100% protected from viremia after challenge in this study. In comparison, 4 of the 5 control horses demonstrated viremia for 4-5 days post-challenge and 1 of 5 control horses demonstrated viremia for 1 timepoint. In addition, serum neutralization titers of vaccinated horses were statistically significantly higher than those of control horses at each time point examined after vaccination. Furthermore, the data establish that a WNV vaccine that provides a serum neutralization titer of 1:4 or higher is effective in preventing WNV viremia. The serum titers and viremia after challenge for Block 1 is summarized in Table 1 below:

TABLE 1

Serum Titers and Viremia for Block 1

| Horse Number | Treatment | Serum Titer Day of Challenge | Viremia After Challenge Highest Titer |
|---|---|---|---|
| 1 | Control | <2 | 390 |
| 2 | Vaccinate | 12 | <5 |
| 3 | Vaccinate | 12 | <5 |
| 4 | Control | <2 | 65 |
| 5 | Control | <2 | 1475 |
| 6 | Vaccinate | 6 | <5 |
| 7 | Vaccinate | 97 | <5 |
| 8 | Vaccinate | 10 | <5 |
| 9 | Vaccinate | 21 | <5 |
| 10 | Vaccinate | 35 | <5 |

TABLE 1-continued

Serum Titers and Viremia for Block 1

| Horse Number | Treatment | Serum Titer Day of Challenge | Viremia After Challenge Highest Titer |
|---|---|---|---|
| 11 | Vaccinate | 10 | <5 |
| 12 | Vaccinate | 24 | <5 |
| 13 | Vaccinate | 4 | <5 |
| 14 | Control | <2 | 235 |
| 15 | Control | <2 | 165 |

Viremia after challenge and serum neutralization titers were also considered the primary outcome variables in the second block of horses in this study. In the second block of horses only one vaccinate group horse displayed any timepoints of viremia throughout the challenge period. That horse had 3 separate timepoints on 3 mornings (not those same evenings) with minimal value readings of 5 (where <5 is negative). All control horses in the study (with the exception of one horse which exited the study prematurely but displayed definitive WNV histopathology and was excluded from evaluation) showed high levels of viremia for 1-8 timepoints after challenge.

Since viremia is a prerequisite before virus can cross the blood-brain barrier to cause WNV encephalitis, viremia is well justified as the primary parameter for evaluation of protection in an experimental study of this type.

This study demonstrated that 2 doses of the experimental combination vaccine administered to foals 4 to 5 months of age reliably and effectively stimulated protective serological serum neutralization titers. In addition the data confirm that post vaccination SN titers as low as 1:4 resulting from vaccination using an effectively batched antigen amount of West Nile Virus in this experimental combination vaccine protected vaccinated horses from viremia, clinical disease, and histopathology after a severe intrathecal challenge with a heterologous strain of West Nile Virus.

Histopathology also was different between the two groups with the likelihood of lesions in vaccinates being 40% less in Block 2 and 100% less in Block 1 than the likelihood of lesions in control animals challenged with virulent West Nile virus.

In addition a Control Group horse became weak on his hind legs on Day 9 post-challenge and got progressively worse until he was no longer able to stand. Histopathology of the pons and medulla from this horse showed severe encephalitis and myelitis consistent with WNV pathology that was more prevalent than signs of disease from any other horse in this study.

Two Block 2 control horses in this study displayed 3 days each of clinical signs relating to infection with West Nile Virus. One other control horse had a single timepoint of weakness due to disease. Another control horse did not display any timepoints of clinical signs, although it had multiple days of viremia. Although several vaccinated Block 2 horses in the study had mild to moderate histopathological changes in tissue as a result of the intrathecal challenge of WNV, only very mild clinical disease (mild head tremors) was noted for one vaccinate on one day of the study as compared to multiple days of clinical disease in 2 control horses and a single day of clinical disease in a third control horse.

The results demonstrated that the vaccine is effective and that an immunogenic reaction is induced in the animals that were administered the vaccine. The effectiveness of the vaccine was evidenced in this example by reduction in WNV viremia, by stimulation of high serum neutralization titers to WNV, and by prevention of WNV related clinical signs and histopathology in the brain and meninges. Because this vaccine is comprised of unique constituents, including a long lasting non-metabolizable adjuvant, it was formulated in a low 1 mL dose volume to provide a high degree of safety as a highly immunogenic low passage whole inactivated virus WNV isolate of recent origin and high epidemiological prevalence, and a WNV isolated from the tissues of an infected horse, it provides more comprehensive safety and effectiveness than other vaccines currently available. Additionally, it has the effect of providing a safe vaccine when administered to animals.

Example 3

This example illustrates the efficacy of the immunogenic composition of the present invention against infection by EHV-4

Materials and Methods

Thirty-seven (37) horses, 4-5 months of age, were used in this study. Horses were randomly assigned to either vaccinate or control groups by random number generator and then vaccinated. Twenty-four (24) horses served as vaccinates and thirteen (13) horses were mock-vaccinated control horses. All horses had low (≤1:14, avg.=1:7) EHV-4 serum neutralization (SN) titers prior to initiation of the study, indicative of horses susceptible to infection. The vaccine used was an experimental vaccine and had the following components:

The final formulated vaccine contains the following ingredients per 1 mL dose:

| | |
|---|---|
| EHV-1 (PTA-9525) | $10^{7.0-9.0}$ $TCID_{50}$/mL |
| Influenza A2/Ohio/03 (PTA-9522) | $10^{6.0-9.5}$ $TCID_{50}$/mL |
| Influenza A2/KY/95 (PTA-9523 | $10^{6.0-9.5}$ $TCID_{50}$/mL |
| Influenza A2/NewMarket/2/93 (PTA-9524) | $10^{6.0-9.5}$ $TCID_{50}$/mL |
| Tetanus Toxoid | 5-10 CPU |
| Eastern Equine Encephalomyelitis, (ATCC Deposit No. PTA-9412) | $10^{6.7-9.2}$ $TCID_{50}$/mL |
| Western Equine Encephalomyelitis, (ATCC Deposit No. PTA-9410) | $10^{6.7-9.2}$ PFU/mL |
| Venezuelan Equine Encephalomyelitis, (ATCC Deposit No. PTA-9411) | $10^{6.7-9.2}$ $TCID_{50}$/mL |
| West Nile Virus, Horse Origin 2005 (ATCC Deposit No. PTA-9409) | $10^{7.0-9.0}$ $TCID_{50}$/mL |
| Adjuvant | 100-200 μl |
| Glycerol | 100-200 μl |
| EDTA 240 mM solution | 10-20 μl |
| Diluent - DMEM containing Gentamicin (30 μg/mL of diluent volume) Formaldehyde (0.1-0.2% of diluent volume) | q.s. |

The Experimental Vaccine was administered intramuscularly in a 1 mL dose volume to each of 24 horses in the vaccinate group. Thirteen horses in the control group received a 1 mL dose of adjuvanted DMEM (Lot 004) containing excipients used in the 9-way vaccine (Gentamicin and formaldehyde) but no antigens. Challenge inoculation of virulent EHV-4 HRA005 strain virus was performed 15 days post-booster vaccination.

Each of the vaccinated and control horses was challenged with an EHV-4 strain of virus (HRA005). The titer of the dilute challenge virus was sufficient to provoke disease due to EHV infection in the non-vaccinated horses.

Sedivet® (romifidine hydrochloride), a sedative and analgesic, was administered intravenously to each horse prior to challenge at a dosage of 50 μg/kg of body weight. Each horse was then challenged with the EHV-4 strain HRA005 virus. The challenge virus was administered intranasally as an aerosol produced by a nebulizer into an Equine AeroMask (Trudell Medical International, Ontario, Canada).

Daily morning rectal temperatures were recorded for each of the 37 vaccinated and control horses on Day of Challenge and for 14 days post challenge by means of a calibrated, electronic thermometer (GSA Electronics) probe. The daily rectal temperatures were recorded in degrees Fahrenheit (° F.).

Complete Blood Cell Counts

Venous blood from each of the 37 vaccinated and control horses was collected daily on the Day of Challenge and for 14 days post-challenge directly into a Vacutainer Disodium EDTA tube for Complete Blood Counts.

Nasal Exudate Evaluation

All nasal exudate observations were made prior to collection of nasopharyngeal swabs. On the Day of Challenge and for 14 days post challenge, the nasal passages and muzzle of each of the 37 vaccinated and control horses were examined and graded using the grading and scoring description listed below.

The scoring grades of 0 through 6 were assigned on the basis of the severity of the disease indicated by each of the following classifications:

TABLE 2

Scores for Clinical Symptoms

| Score | Description of symptoms | Score sheet designation |
|---|---|---|
| 0 | Essentially normal indicates the horse was clean and essentially free of nasal exudate | EN |
| 1 | Slight clear serous discharge that may be frequently observed in both diseased and normal horses | C-1 |
| 2 | Moderate clear serous discharge is indicative of a definite increase in volume over that normally observed | C-2 |
| 3 | Copious clear serous discharge that is generally observed only in diseased horses | C-3 |
| 1.5 | Very slight mucopurulent discharge indicates that mucus was definitely present in small amounts in either one or both nostrils | VSM |
| 2 | Slightly mucopurulent is a discharge easily observed in one or both nostrils | SM |
| 4 | Moderately mucopurulent indicates that mucoid discharges were present in large quantities in both nostrils | MM |
| 6 | Heavy mucopurulent indicates that copious amounts of a mucoid discharge filled both nostrils | HM |

Nasopharyngeal Viral Isolation Methods

On each observation test day each nasal passage of each vaccinated and control was sampled deeply by means of sterile swabs. On collection, each of two swabs were immediately placed in a single tube containing 4 mL of chilled transport medium (Dulbecco's Minimal Essential Medium (DMEM) supplemented with 2% FBS, 2× Pen/Strep, 2× Gentamicin, and 2× Amphotericin B).

For isolation of virus, the tubes were mixed, the swabs aseptically removed, and the medium centrifuged at 1500 rpm for 10 minutes to remove particulates. Medium was filtered through a 0.2µ syringe filter prior to inoculation on tissue culture cells. One mL of the clarified transport medium was used to inoculate a 2 cm² one day old monolayer of ED cells grown in a 24 well tissue culture plate from which the growth medium had been aseptically removed. Following inoculation, the inoculum was allowed to adsorb on the cell monolayer for one hour at 37° C. in a humidified incubator containing a 5% $CO_2$ atmosphere. After the adsorption period, an additional 1 mL of re-feed medium (DMEM containing 2-5% fetal bovine serum (FBS), 2 mM L-glutamine and 3× Gentamicin and 2× Amphotericin B) was added to each well. Following addition of re-feed media the plates were then incubated at 37° C. in a $CO_2$ incubator. Each test and control tissue culture well was examined microscopically for 7 days for signs of cytopathic effect (CPE) typical of the EHV-4 challenge virus. Wells that were negative at the end of the 7 day observation period were subcultured onto fresh cells and observed for an additional 7 days.

Serum Neutralization Testing Procedure

A standard microtiter serum neutralization test was employed in this study. All sera were tested in sterile flat bottom microtiter plates using 5 wells per dilution and an 8 well dilution series for each of the 5 test wells. Each of the 5 test wells contained 25 µl of serum dilution mixed with 25 µl of the indicator virus and 150 µl of a freshly planted ED cell suspension containing approximately $5 \times 10^4$ cells. The test indicator virus used was EHV-4 HRA005 Lot 033106 SN Stock Virus. In all tests the indicator virus back titration titers ranged between 68-149 $TCID_{50}/25$ µl. Serum neutralizing antibody titers are expressed as Reed-Muench $ID_{50}$ titers.

For performance of the test, two-fold dilutions of each test serum was made in a sterile flat bottom microtiter plate using five replicate wells per test serum and an 8 well dilution series. Dilutions were made with an adjustable volume single or multi-channel pipetting instrument using sterile microtiter tips. The volume of serum added each of 5 wells of the first row was 50 µl. All other wells contained 25 µl of DMEM (no FBS). Following serial dilution down the plate, 25 µl was discarded from the last row. 25 µl of a pre-determined dilution of the indicator virus was added to each test well. Plates were then mixed and incubated for one hour at 37° C. in 5% $CO_2$. On conclusion of the incubation period, 150 µl of a suspension containing $5 \times 10^4$ ED cells was added to each test and cell control well. The plates were incubated at 37° C. in a $CO_2$ incubator for 5-7 days, at which time plates were microscopically examined for CPE typical of EHV-4. However, any other commercial available test or any test described in the prior art could be used for this purpose.

Results and Conclusion

Nasal Exudate Evaluation

The vaccination group by day interaction was statistically significant for the nasal discharge scores (P<0.05, Table 1). Statistically significant group effects were seen on Days 6-10 and Day 14 post-challenge (lower nasal scores in the vaccinated group).

When the daily scores were summed over the post-challenge period, horses in the vaccinated group had lower total scores than those in the control group (P<0.05, Table 1). The mitigated fraction was estimated to be 0.824 (95% ASE CI: 0.629, 1.000).

TABLE 3

Nasal Discharge Score

|  | Control | Vaccinate | P-value | Mitigated fraction (95% ASE CI) |
|---|---|---|---|---|
| Cumulative nasal discharge score | 28.9 | 13.6 | <0.0001 | 0.824 (0.629, 1.000) |

Conjunctivitis

The vaccination group by day interaction was statistically significant for the conjunctivitis scores. Statistically significant group effects were seen on Days 6, 7, 9, 10, 13 and 14 post-challenge (lower scores in the vaccinated group on 5 of the 6 days, P<0.05, FIG. 2).

Serological Studies

Titers were log transformed prior to the statistical analysis. The vaccination group by day interaction was statistically significant for SN titers. Statistically significant group effects were seen on Day 0 (pre-vaccination; control group titers>vaccinated group titers), Days 35 (the day of challenge) and 7 and 14 days post-challenge (study days 42 and 49). Horses in the vaccinated group had higher titers on Days 35, 42 and 49 than those in the control group (P<0.05, Table 4).

TABLE 4

Titers

| Study day | Control | Vaccinated | P-value |
|---|---|---|---|
| 0 | 8.31 | 5.74 | 0.0303 |
| 21 | 8.25 | 6.51 | 0.1639 |
| 35 (day of challenge) | 6.12 | 8.56 | 0.0495 |
| 42 | 4.57 | 7.27 | 0.0069 |
| 49 | 4.87 | 13.12 | <0.0001 |

White Blood Cell Counts (WBC) and Lymphocyte Counts

The vaccination group by day interaction was statistically significant for WBC and lymphocyte counts. Statistically significant group effects were seen on Days 4-6 (WBC) and Days 4 and 5 (lymphocytes) post-challenge. Horses in the vaccinated group were protected from leucopenia due to EHV4 disease and had higher WBC and lymphocyte counts than those in the control group (P<0.05).

Discussion and Conclusions

In this study, moderate and adequate clinical signs of EHV-4 infection were seen after challenge. Significantly fewer clinical signs of nasal exudate were seen in vaccinated horses on Days 6-10 and Day 14 post-challenge. Conjunctivitis scores were significantly lower in vaccinated horses on Days 7, 9, 10, 13, and 14 post-challenge. Despite the adequate display of clinical signs following challenge, virus shedding in nasal swab samples was infrequent following this EHV-4 challenge. Nasal swabs were examined by virus isolation in cell culture.

Significant group effects for WBCs and lymphocytes were seen on Days 4-6 (WBC) and Days 4-5 (lymphocytes) with vaccinated animals showing higher WBC and lymphocyte counts than control horses. These values establish that control horses did succumb to the immunosuppression brought on by infection with Herpesvirus, and also demonstrate that vaccination with a cross-protective strain of EHV-1 allowed vaccinated horses to be more refractive to the immunosuppressive properties of Herpesvirus infection. Additionally, horses in the vaccinated group had higher serum neutralization titers on Days 35, 42 and 49 than those in the control group Data from this study confirm that horses vaccinated with a multi-component vaccine containing EHV-1 demonstrate cross-protective immunity when challenged with a heterologous EHV-4 challenge organism.

Example 4

This example is to illustrate the efficacy of the combination vaccine of the present invention as well as duration of immunity.

Materials and Methods

The influenza viral antigen used in the vaccine evaluated in this study was produced on Madin Darby Canine Kidney (MDCK) cells. Following growth, viral fluids were filtered, formalin inactivated, and concentrated. The inactivated viral fluids were tested for residual live virus after inactivation. On completion of satisfactory residual live virus testing the inactivated viral fluids were then used to formulate a vaccine which also contained inactivated Venezuelan, TC-83 strain (ATCC Accession No. PTA-9411), Eastern, NJO strain (ATCC Accession No. PTA-9412), and Western, Fleming strain (ATCC Accession No. PTA-9410), equine encephalomyelitis viruses, inactivated EHV-1 (ATCC Accession No. PTA-9525), inactivated influenza A/equine-2/Kentucky/95 (ATCC Accession No. PTA-9523) and influenza A/equine-2/NewMarket/2/93 (ATCC Accession No. PTA-9524) viruses, inactivated West Nile Virus, Horse Origin 2005 (ATCC Accession No. PTA-9409), and tetanus toxoid.

Vaccine was formulated to appropriate specifications for all antigens included in the product. Influenza A/equi-2/Ohio/03 (ATCC Accession No. PTA-9522) antigen was added to the vaccine at a pre-inactivation titer of $10^{6.7}$ $TCID_{50}$/mL.

The final formulated vaccine contains the following ingredients per 1 mL dose:

| | |
|---|---|
| EHV-1 | $10^{7.0-9.0}$ $TCID_{50}$/mL |
| Influenza A2/Ohio/03 | $10^{6.7-9.5}$ $TCID_{50}$/mL |
| Influenza A2/KY/95 | $10^{6.7-9.5}$ $TCID_{50}$/mL |
| Influenza A2/NewMarket/2/93 | $10^{6.7-9.5}$ $TCID_{50}$/mL |
| Tetanus Toxoid | 5-10 CPU |
| Eastern Equine Encephalomyelitis | $10^{6.7-9.2}$ $TCID_{50}$/mL |
| Western Equine Encephalomyelitis | $10^{6.7-9.2}$ PFU/mL |
| Venezuelan Equine Encephalomyelitis | $10^{6.7-9.2}$ $TCID_{50}$/mL |
| West Nile Virus | $10^{7.0-9.0}$ $TCID_{50}$/mL |
| Adjuvant (preferably mineral oil) | 100-200 μl |
| Glycerol | 100-200 μl |
| EDTA 240 mM solution | 10-20 μl |
| Diluent - DMEM containing | q.s. |
| Gentamicin (30 μg/mL of diluent volume) | |
| Formaldehyde (0.1-0.2% of diluent volume) | |

Twenty-six (26) horses, 4-5 months of age, were used in this study. Fifteen horses served as vaccinates and eleven horses were mock-vaccinated control horses.

Vaccine was administered intramuscularly in a 1 mL dose volume to each of 15 horses in the vaccinate group. Eleven horses in the control group received a 1 mL dose of adjuvanted DMEM (Lot 004) containing excipients used in the 9-way vaccine (Gentamicin and formaldehyde) but no antigens. Challenge inoculation of virulent influenza A/equi-2/Ohio/03 strain virus was performed 4 months post-booster vaccination.

Serum samples for serological evaluation were collected from the vaccinated and control horses prior to initial vaccination, at 21 days post first dose vaccination (day of booster vaccination), on the day of challenge, and at 7 and 14 days post challenge. Body temperature, whole blood samples, and nasal swabs were obtained from each horse on the day of challenge, and daily throughout the 10 day post-challenge observation period for a total of 11 observation days. Clinical data was also recorded daily for each horse for the 11-day observation period.

for 10 days post challenge, the nasal passages and muzzle of each of the 26 vaccinated and control horses were examined and graded using the grading and scoring description listed below.

The scoring grades of 0 through 6 were assigned on the basis of the severity of the disease indicated by each of the following classification:

TABLE 5

Scoring Grades

| Score | Description of symptoms | Score sheet designation |
|---|---|---|
| 0 | Essentially normal indicates the horse was clean and essentially free of nasal exudate | EN |
| 1 | Slight clear serous discharge that may be frequently observed in both diseased and normal horses | C-1 |
| 2 | Moderate clear serous discharge is indicative of a definite increase in volume over that normally observed | C-2 |
| 3 | Copious clear serous discharge that is generally observed only in diseased horses | C-3 |
| 1.5 | Very slight mucopurulent discharge indicates that mucus was definitely present in small amounts in either one or both nostrils | VSM |
| 2 | Slightly mucopurulent is a discharge easily observed in one or both nostrils | SM |
| 4 | Moderately mucopurulent indicates that mucoid discharges were present in large quantities in both nostrils | MM |
| 6 | Heavy mucopurulent indicates that copious amounts of a mucoid discharge filled both nostrils | HM |

Challenge

The challenge virus seed of Influenza A/equi-2/Ohio/03 was produced in eggs. Challenge virus was diluted on the morning of challenge 1:20 with tissue culture media to affect a titer sufficient to cause clinical influenza in the non-vaccinated challenged horses.

Sedivet® (romifidine hydrochloride), a sedative and analgesic, was administered intravenously to each horse prior to challenge at a dosage of 50 µg/kg of body weight. Each horse was then challenged with influenza A/equi-2/Ohio/03 virus. The challenge virus was administered intranasally as an aerosol produced by a nebulizer into an Equine AeroMask (Trudell Medical International, Ontario, Canada) by the following method:

Four milliliters of challenge virus were placed into the nebulizer cup in the AeroMask device. A pressure hose was fitted from an air compressor to the inlet port of the nebulizer. The outlet tube was then inserted into the AeroMask attached to the head of the horse being challenged and air pressure was applied to the inlet port. During this time approximately two milliliters of challenge virus fluid was aerosolized directly into the nostrils of the horse being challenged.

Temperature

Daily rectal temperatures were recorded for each of the 26 vaccinated and control horses on Day of Challenge and for 10 days post challenge by means of a calibrated, electronic thermometer (GSA Electronics) probe. The daily rectal temperatures were recorded in degrees Fahrenheit (° F.).

White Blood Cell Counts

Venous blood from each of the 26 vaccinated and control horses was collected daily on the Day of Challenge and for 10 days post-challenge directly into a vacutainer Disodium EDTA tube for WBC counts.

Nasal Exudate Evaluation

All nasal exudate observations were made prior to collection of nasopharyngeal swabs. On the Day of Challenge and Coughing Episodes of coughing on each observation day were counted for each horse during the entirety of the observation period, whether or not the individual animal was being examined by the investigator at that time. Observers other than the investigator recorded the number of episodes of coughing of each individual horse during the observation period. Scoring of coughing episodes was actual counts of coughing episodes per horse.

Conjunctivitis

Conjunctivitis was evaluated daily at the time of nasal exudate evaluation. Conjunctivitis scores were recorded as 0=normal; 1=mild to moderate conjunctivitis and 2=severe conjunctivitis.

Nasopharyngeal Viral Isolation/Hemagglutination (HA) Methods

On each observation test day each nasal passage of each vaccinated and control was sampled deeply by means of sterile swabs. On collection, each of two swabs was immediately placed in a single tube containing 4 mL of chilled transport medium (Dulbecco's Minimal Essential Medium (DMEM) supplemented with 2% FBS, 2× Pen/Strep, 2× Amphotericin B).

For isolation of virus, the tubes were mixed, the swabs aseptically removed, and the medium centrifuged at 1500 rpm for 10 to 15 minutes to remove particulates. Medium was filtered through a 0.2µ syringe filter prior to inoculation on tissue culture cells. After filtration, 4-6% of sterile 85% sucrose solution was added to each sample for freezing at −80° C. in order for all samples to be tested concurrently.

All samples were tested in sterile flat bottom microtiter plates using five wells per dilution and a 4 well dilution series for each of the 5 test wells. Upon thawing, 22 µL of the clarified sample medium was used to inoculate one day old monolayer of MDCK-S cells from which the growth medium had been aseptically removed and replaced with 200 µl of influenza growth medium (DMEM containing 5-10 units/mL of 10,000 U stock solution Porcine Trypsin, 2 mM L-glutamine, 1× Pen-Strep and 1× Amphotericin B). The plates were then incubated at 35° C. in a $CO_2$ incubator for 5-7 days. After the 5-7 day incubation period, 50 µl from a of the titration plates were transferred directly into a labeled 96 well vinyl HA plate. Chicken red blood cells were added to each well and allowed to settle for 30-90 minutes at room temperature. Wells were read for positive agglutination as evidence of presence of equine influenza virus.

Hemagglutination Inhibition (HI) Testing Procedure

Serum samples were prepared by dispensing 0.15 ml of each sample into a test tube and extracting with 0.3 mL of 0.01M Sodium Periodate Solution at room temperature for 15 minutes. Glycerol Solution 3% (0.125 mL) was added to each tube, mixed and incubated at room temperature for 15 minutes. All samples were then heat-inactivated at 56° C. for 30 minutes.

A 0.5% solution of chicken red blood cells was prepared in PBS (SAFC catalog number 59321C) and standardized to an optical density of 0.5 at 550 nm.

Extracted serum samples were tested in duplicate in U bottom polystyrene plates using a 2-fold dilution scheme in PBS ranging from 1:4 to 1:256, 25 ul per well. Influenza A/Equi2/Ohio03 stock virus (25 µL) was added to serum sample dilution. Plates were gently tapped to mix, and incubated at room temperature for 30 minutes. After incubation, chicken red blood cells were added to each well and incubated undisturbed at room temperature for 1 to 1.5 hours. Results were read by observing plates for presence or absence of agglutinated red blood cells in each well. Antibody titer was determined as the highest dilution of serum at which agglutination did not occur.

Results and Conclusions

When pooled across all timepoints post-challenge, vaccinated animals had lower total clinical scores than the control animals. When the total daily scores were summed over the post-challenge period, horses in the vaccinated group had lower total scores than those in the control group (P<0.05). The mitigated fraction was estimated to be 0.6485 (95% ASE CI: 0.3258, 0.9712).

TABLE 6

Total Clinical Score

| Outcome variable | Vaccination group | Day | Group by day interaction |
|---|---|---|---|
| Total clinical score[1] | <0.0001 | <0.0001 | 0.1321 |

[1]The GLIMMIX procedure would not converge, thus an ANOVA approach was used to evaluate the effect of vaccination over time after challenge. Results were interpreted through the bolded values.

TABLE 7

Mitigated fraction - total cumulative clinical score

| | Control | Vaccinate | P-value[1] | Mitigated fraction[2] (95% ASE CI) |
|---|---|---|---|---|
| Total cumulative clinical score[2] | 18.36[3] | 9.93 | 0.0055 | 0.6485 (0.3258, 0.9712) |

[1]P-value from Wilcoxon's rank sum test
[2]Nasal discharge score, conjunctivitis score and coughing score were summed with day and across all time points for each animal then ranked for the estimation of the mitigated fraction.
[3]Mean rank Nasal Discharge The main effect of vaccination was statistically significant and reduced nasal discharge due to the influenza challenge. When pooled across all time points post-challenge, vaccinated animals had lower nasal discharge scores than the control animals.

TABLE 8

Nasal Discharge Score

| Outcome variable | Vaccination group | Day | Group by day interaction |
|---|---|---|---|
| Nasal discharge score[1] | 0.0012 | <0.0001 | 0.4627 |

[1]The GLIMMIX procedure would not converge, thus an ANOVA approach was used to evaluate the effect of vaccination over time after challenge. Results were interpreted through the bolded values.

Conjunctivitis

For conjunctivitis, the main effect of vaccination was statistically significant. When pooled across all time points post-challenge, vaccinated animals had reduced conjunctivitis due to influenza infection as demonstrated by lower conjunctivitis scores than the control animals.

TABLE 9

Conjunctivitis Score

| Outcome variable | Vaccination group | Day | Group by day interaction |
|---|---|---|---|
| Conjunctivitis score[1] | 0.0187 | 0.0001 | 0.2498 |

[1]The GLIMMIX procedure would not converge, thus an ANOVA approach was used to evaluate the effect of vaccination over time after challenge. Results were interpreted through the bolded values.

Coughing

Vaccine also protected against the cough resulting from equine influenza infection. Vaccinated animals had lower scores (P<0.05) on Days 3, 5, 7, 8, and 9 post-challenge than control animals.

TABLE 10

Coughing Score

| Outcome variable | Vaccination group | Day | Group by day interaction |
|---|---|---|---|
| Coughing score[1] | 0.0004 | 0.0009 | 0.0275 |

[1]The GLIMMIX procedure would not converge, thus an ANOVA approach was used to evaluate the effect of vaccination over time after challenge. Results were interpreted through the bolded values.

Virus Shedding (Nasal Swabs)

The vaccination also reduced the percent of horses shedding virus (P<0.05). The figure below represents that the percentage of vaccinated animals shedding virus was lower (P<0.05) on Days 3, 4, and 5 post-challenge than control animals.

TABLE 11

Mitigated fraction - days virus shedding

| | Control | Vaccinate | P-value[1] | Mitigated fraction[2] (95% ASE CI) |
|---|---|---|---|---|
| Days virus positive[2,3] | 2[3] | 0 | 0.0004 | 0.7939 (0.5343, 1.0000) |

[1]P-value from Wilcoxon's rank sum test
[2]The number of days of viral shedding was calculated then ranked for the estimation of the mitigated fraction. Asymptotic standard errors (ASE) were used to estimate the 95% confidence intervals (CI).
[3]The median number of days positive results was obtained from the virus isolation assay.

HI Titers

The vaccine was also effective in eliciting protective antibody titers to equine influenza virus. Statistically significant higher titers in the vaccinated horses were seen on Day 36 (relative to vaccination), Day 154 (the day of challenge), 159 and 164. Horses in the vaccinated group had higher titers on each of these days than those in the control group (P<0.05).

WBC and Lymphocyte Counts

The vaccination also protected horses from reduction in white blood cell counts seen following influenza virus challenge. (P<0.05). Vaccination with the combination vaccine provided statistically significant protection that was seen on Days 2 and 7 for WBC counts, and Days 2, 6, 7, and 8 post-challenge. Horses in the vaccinated group had higher WBC and lymphocyte counts than those in the control group (P<0.05). A four month Duration of Immunity challenge was performed to demonstrate efficacy of the influenza virus fractions of a multi-component vaccine that included West Nile Virus vaccine (Encephalomyelitis-Rhinopneumonitis-Influenza-West Nile Virus Vaccine, Eastern, Western & Venezuelan, Killed Virus, Tetanus Toxoid) containing 3 Equine influenza A/equi-2 virus strains, ATCC Accession Nos. PTA-9522, PTA-9523, and PTA-9524, each of which is currently relevant in the equine population of the Americas, Europe and Asia. Twenty-six horses (15 vaccinates and 11 controls) were vaccinated twice in 3 week intervals with a 1 mL dose of vaccine, or were mock vaccinated with adjuvanted media components of the vaccine without viral antigen. Four months post-booster vaccination, horses were challenged with a virulent live Equine Influenza A/equi-2/Ohio03 virus. This virulent virus is the current Equine Influenza A/equi-2 strain recommended for inclusion into vaccines by OIE and is currently recognized as the most pertinent strain involved in outbreaks in the United States.

Results from this 4-month DOI challenge study show significant protective effects from challenge by vaccination with the test vaccine, a combination West Nile Virus vaccine with flu and other pertinent equine antigens. Importantly, vaccinated horses displayed statistically lower total clinical signs of influenza virus (nasal discharge, conjunctivitis, and coughing, P=0.0055) with a mitigated fraction estimated to be 0.6485 (95% ASE CI: 0.3258, 0.9712). Additionally, viral shedding was statistically lower in vaccinated horses than control horses (P=0.0004) with a mitigated fraction estimated to be 0.7939 (95% ASE CI: 0.5343, 1.0000). Hemagglutination inhibition titers were significantly higher in vaccinated horses than control horses, and white blood cell and lymphocyte counts remained significantly higher in vaccinated horses on multiple days of the study over those of control horses. No differences in rectal temperature were determined between the two groups.

In conclusion, the data from this study demonstrate that administration of 2×1 mL intramuscular doses of this West Nile Virus combination vaccine administered at a 21 day interval to foals 4 to 5 months of age protected against virulent challenge with the Equine Influenza A/equi-2/Ohio03 virus and provided a duration of immunity of at least 4 months for this product.

Example 5

This example illustrates the efficacy of an immunogenic composition of the present invention when challenged with (Equine Herpes Virus Type 1) EHV-1.

Materials and Methods

The EHV-1 viral antigen used in the vaccine evaluated in this study was produced on Madin Darby Bovine Kidney (MDBK) cells. Following growth, viral fluids were filtered, BPL inactivated, and concentrated. The inactivated viral fluids were tested for residual live virus after inactivation. On completion of satisfactory residual live virus testing, the inactivated viral fluids were then used to formulate a vaccine which also contained inactivated Venezuelan Equine Encephalomyelitis, TC-83 strain (ATCC Accession No. PTA-9411) Eastern Equine Encephalomyelitis, NJO strain (ATCC Accession No. PTA-9412) and Western Equine Encephalomyelitis, Fleming strain (ATCC Accession No. PTA-9410) viruses, inactivated influenza A/equine-2/Kentucky/95 (ATCC Accession No. PTA-9523), influenza A/equine-2/NewMarket/2/93 (ATCC Accession No. PTA-9524) and influenza A/equine-2/Ohio/03 (ATCC Accession No. PTA-9522) viruses, inactivated West Nile Virus (ATCC Accession No. PTA-9409) and tetanus toxoid.

Vaccine was formulated to minimum specifications for all antigens included in the product. EHV-1 antigen was added to the vaccine at a pre-inactivation titer of $10^{7.0}$ $TCID_{50}$/mL.

The final formulated vaccine contains the following ingredients per 1 mL dose:

| | |
|---|---|
| EHV-1 | $10^{7.0-9.0}$ $TCID_{50}$/mL |
| Influenza A2/Ohio/03 | $10^{6.7-9.5}$ $TCID_{50}$/mL |
| Influenza A2/KY/95 | $10^{6.7-9.5}$ $TCID_{50}$/mL |
| Influenza A2/NewMarket/2/93 | $10^{6.7-9.5}$ $TCID_{50}$/mL |
| Tetanus Toxoid | 5-10 CPU |
| Eastern Equine Encephalomyelitis | $10^{6.7-9.2}$ $TCID_{50}$/mL |
| Western Equine Encephalomyelitis | $10^{6.7-9.2}$ PFU/mL |
| Venezuelan Equine Encephalomyelitis | $10^{6.7-9.2}$ $TCID_{50}$/mL |
| West Nile Virus | $10^{7.0-9.0}$ $TCID_{50}$/mL |
| Adjuvant (preferably mineral oil) | 100-200 µl |
| Glycerol | 100-200 µl |
| EDTA 240 mM solution | 10-20 µl |
| Diluent - DMEM containing | q.s. |
| Gentamicin (30 µg/mL of diluent volume) | |
| Formaldehyde (0.1-0.2% of diluent volume) | |

Forty (40) horses, 4-5 months of age, were used in this study. Horses were randomly assigned to either vaccinate or control groups and were micro-chipped and then vaccinated. Twenty horses served as vaccinates and twenty horses were mock-vaccinated control horses. All horses had negative to low (<1:6) EHV-1 serum neutralization (SN) titers prior to initiation of the study, indicative of horses susceptible to infection.

Vaccine was administered intramuscularly in a 1 mL dose volume to each of 20 horses in the vaccinate group. Twenty horses in the control group received a 1 mL dose of adjuvanted DMEM (Lot 004) containing excipients used in the 9-way vaccine (Gentamycin and formaldehyde) but no antigens. Challenge inoculation of virulent EHV-1 A183 strain virus was performed 15 days post-booster vaccination.

Serum samples for serological evaluation were collected from the vaccinated and control horses prior to initial vaccination, at 21 days post first dose vaccination (day of booster vaccination), on the day of challenge, and at 7 and 14 days post challenge. Body temperature, whole blood samples, and nasal swabs were obtained from each horse on the day of challenge, and daily throughout the 14 day post-challenge observation period for a total of 15 observation days. Clinical data was also recorded daily for each horse for the 15-day observation period.

Challenge Procedure

Challenge Virus

The original challenge virus seed used in this challenge study was the first passage of the original seed virus on Equine Dermal (ED) cells. This challenge virus was harvested and frozen at a titer of $10^{6.2}$ $TCID_{50}$/mL.

Intranasal Challenge Method

Sedivet® (romifidine hydrochloride), a sedative and analgesic, was administered intravenously to each horse prior to challenge at a dosage of 50 μg/kg of body weight. Each horse was then challenged with approximately $10^{6.5}$ $TCID_{50}$ of EHV-1 strain. The challenge virus was administered intranasally as an aerosol produced by a nebulizer into an Equine AeroMask (Trudell Medical International, Ontario, Canada) by the following method:

A pressure hose was fitted from an air compressor to the inlet port of the nebulizer. The outlet tube was then inserted into the AeroMask attached to the head of the horse being challenged and approximately 10 psi of air pressure was applied to the inlet port for four minutes. During this time approximately two milliliters of a $10^{6.2}$ $TCID_{50}$/mL challenge virus fluid was aerosolized directly into the nostrils of the horse being challenged.

Pre and Post Challenge Evaluation Parameters

Temperature

Daily morning rectal temperatures were recorded for each of the 40 vaccinated and control horses on Day of Challenge and for 14 days post challenge by means of a calibrated, electronic thermometer (GSA Electronics) probe. The daily rectal temperatures were recorded in degrees Fahrenheit (° F.).

White Blood Cell Counts

Venous blood from each of the 40 vaccinated and control horses was collected daily on the Day of Challenge and for 14 days post-challenge directly into a vacutainer Disodium EDTA tube for WBC counts.

Nasal Exudate Evaluation

All nasal exudate observations were made prior to collection of nasopharyngeal swabs. On the Day of Challenge and for 14 days post challenge, the nasal passages and muzzle of each of the 40 vaccinated and control horses were examined and graded using the grading and scoring description listed below.

The scoring grades of 0 through 6 were assigned on the basis of the severity of the disease indicated by each of the following classification:

(EN) Essentially normal indicates the horse was clean and essentially free of nasal exudate, score, 0;

(C-1) Slight clear serous discharge that may be frequently observed in both diseased and normal horses, score 1;

(C-2) Moderate clear serous discharge is indicative of a definite increase in volume over that normally observed, score 2;

(C-3) Copious clear serous discharge that is generally observed only in diseased horses, score 3;

(VSM) Very slight mucopurulent discharge indicates that mucus was definitely present in small amounts in either one or both nostrils, score 1.5;

(SM) Slightly mucopurulent is a discharge easily observed in one or both nostrils, score 2;

(MM) Moderately mucopurulent indicates that mucoid discharges were present in large quantities in both nostrils, score 4; and (HM) Heavy mucopurulent indicates that copious amounts of a mucoid discharge filled both nostrils, score 6.

Nasopharyngeal Viral Isolation Methods

On each observation test day each nasal passage of each vaccinated and control was sampled deeply by means of a sterile swabs. On collection, each of two swabs were immediately placed in a single tube containing 4 mL of chilled transport medium (Dulbecco's Minimal Essential Medium (DMEM) supplemented with 2% FBS, 2× Pen/Strep, 2× Gentamicin, and 2× Amphotericin B).

For isolation of virus, the tubes were mixed, the swabs aseptically removed, and the medium centrifuged at 1500 rpm for 10 minutes to remove particulates. Medium was filtered through a 0.2μ syringe filter prior to inoculation on tissue culture cells. One mL of the clarified transport medium was used to inoculate a 2 $cm^2$ one day old monolayer of ED cells grown in a 24 well tissue culture plate from which the growth medium had been aseptically removed. Following inoculation, the inoculum was allowed to adsorb on the cell monolayer for one hour at 37° C. in a humidified incubator containing a 5% $CO_2$ atmosphere. After the absorption period, an additional 1 mL of re-feed medium (DMEM containing 2-5% fetal bovine serum (FBS), 2 mM L-glutamine and 3× Gentamicin and 2× Amphotericin B) was added to each well. Following addition of re-feed media the plates were then incubated at 37° C. in a $CO_2$ incubator. Each test and control tissue culture well was examined microscopically for 7 days for signs of cytopathic effect (CPE) typical of the EHV-1 A183 challenge virus. Wells that were negative at the end of the 7 day observation period were subcultured onto fresh cells and observed for an additional 7 days.

WBC Buffy Coat Virus Isolation

Venous blood from each of the 40 vaccinated and control horses was collected on the Day of Challenge and daily for 14 days post-challenge by vacutainer into a Disodium EDTA tube. After permitting gravity sedimentation of the erythrocytes in the tube of EDTA anti-coagulated blood, the plasma and white blood cells were pipetted off and placed in a sterile 5 mL snap-cap tube. The plasma and white blood cell mixture was centrifuged at 1500 RPM for 10-15 minutes to pellet the white blood cells. The pellet was washed twice with 3 mL of phosphate buffered saline (PBS) containing 2× Pen/Strep, 2× Gentamicin, and 2× Amphotericin B. Cells were then suspended in 4 mL of DMEM supplemented with 2% fetal bovine serum (FBS) and 2× Pen/Strep, 2× Gentamicin, and 2× Amphotericin B. One mL buffy coat suspension was used to inoculate a 2 $cm^2$ one day old monolayer of ED cells grown in a 24 well tissue culture plate from which the growth medium had been aseptically removed. Following inoculation, the inoculum was allowed to adsorb on the cell monolayer for one hour at 37° C. in a humidified incubator containing a 5% $CO_2$ atmosphere. After the adsorption period, an additional 1 mL of re-feed medium (DMEM containing 5-7% fetal bovine serum (FBS), 2 mM L-glutamine and 1× Gentamicin was added to each well. Following addition of re-feed media the plates were then incubated at 37° C. in a $CO_2$ incubator. Wells could not be observed microscopically due to large volume of white blood cells settled on the monolayer. Therefore, at the end of 7 days, all wells were subcultured onto fresh ED cells using 0.5 ml of the $1^{st}$ passage as inoculum. The subculture was observed for 7 days for CPE typical of challenge virus infection.

Serum Neutralization Testing Procedure

A standard microtiter serum neutralization test was employed in this study. All sera were tested in sterile flat bottom microtiter plates using five wells per dilution and an 8 well dilution series for each of the 5 test wells. Each of the 5 test wells contained 25 μl of serum dilution mixed with 25 μl of the indicator virus and 150 μl of a freshly planted ED cell suspension containing approximately $5 \times 10^4$ cells. The test indicator virus used was EHV-1 subtype 1 strain A183. In all tests the indicator virus back titration titers ranged between 109 to 263 $TCID_{50}$/25 μl. Serum neutralizing antibody titers are expressed as Reed-Muench $ID_{50}$ titers.

For performance of the test, two-fold dilutions of each test serum was made in a sterile flat bottom microtiter plate using five replicate wells per test serum and an 8 well dilution series. Dilutions were made with an adjustable volume single or multi-channel pipetting instrument using sterile microtiter tips. The volume of serum added each of 5 wells of the first row was 50 μl. All other wells contained 25 μl of DMEM (no FBS). Following serial dilution down the plate, 25 μl was discarded from the last row. 25 μl of a pre-determined dilution of the indicator virus was added to each test well. Plates were then mixed and incubated for one hour at 37° C. in 5% $CO_2$. On conclusion of the incubation period, 150 μl of a suspension containing $5 \times 10^4$ ED cells was added to each test and cell control well. The plates were incubated at 37° C. in a $CO_2$ incubator for 3 days, at which time plates were microscopically examined for CPE typical of EHV-1. Alternatively, any conventional or commercial available assay can be used or those of skill in the art would be able to follow the guidance herein.

Results and Conclusion

Nasal discharge scores, nasal shedding of EHV-1 and conjunctivitis scores were considered the primary outcome variables. All other outcomes were considered secondary.

TABLE 12

Summary of the statistical analysis (P-values)

| Outcome variable | Vaccination group | Day | Group by day interaction |
| --- | --- | --- | --- |
| Nasal discharge score[1] | 0.0001 | <.0001 | <0.0001 |
| Virus shedding[1] | 0.0028 | <0.0001 | 0.0863 |
| Conjunctivitis score[1] | 0.0020 | <0.0001 | 0.0017 |
| SN Titers | <0.0001 | <0.0001 | <0.0001 |
| WBC | 0.3064 | <0.0001 | <0.0001 |

[1]The GLIMMIX procedure would not converge, thus an ANOVA approach was used to evaluate the effect of vaccination over time after challenge. Results were interpreted through the bolded values.

Nasal Exudate Evaluation

The vaccination group by day interaction was statistically significant for the nasal discharge scores (P<0.05). Statistically significant group effects were seen on Days 4, 5 and on Days 7-11 post-challenge (lower nasal scores in the vaccinated group, P<0.05). When the daily scores were summed over the post-challenge period, horses in the vaccinated group had lower total scores than those in the control group (P<0.05). The mitigated fraction was estimated to be 0.7250 (95% ASE CI: 0.4886, 0.9614).

TABLE 13

Mitigated fraction - nasal discharge and conjunctivitis scores, nasal virus shedding (mean ranks)

| | Control | Vaccinate | P-value[1] | Mitigated fraction[2] (95% ASE CI) |
| --- | --- | --- | --- | --- |
| Nasal discharge | 27.75 | 13.25 | <0.0001 | 0.7250 (0.4886, 0.9614) |
| Days shedding virus[2] | 24.43 | 15.78 | 0.0068 | 0.4925 (0.1896, 0.7954) |
| Conjunctivitis | 25.80 | 15.20 | 0.0038 | 0.5300 (0.2463, 0.8137) |

[1]P-value from Wilcoxon's rank sum test
[2]Nasal discharge and conjunctivitis scores were summed across all time points then ranked for the estimation of the mitigated fraction. The number of days of viral shedding was calculated then ranked for the estimation of the mitigated fraction. Asymptotic standard errors (ASE) were used to estimate the 95% confidence intervals (CI).

TABLE 14

Mean nasal discharge score (N = 20 horses per group)

| Days post-challenge | Control | Vaccinated | P-value[1] |
| --- | --- | --- | --- |
| 0 | 0.00 | 0.00 | 1.0000 |
| 1 | 0.00 | 0.00 | 1.0000 |
| 2 | 0.15 | 0.00 | 0.6029 |
| 3 | 0.33 | 0.48 | 0.6029 |
| 4 | 1.08 | 0.23 | 0.0033 |
| 5 | 1.43 | 0.40 | 0.0004 |
| 6 | 1.05 | 0.55 | 0.0833 |
| 7 | 1.50 | 0.68 | 0.0044 |
| 8 | 1.68 | 0.63 | 0.0003 |
| 9 | 2.13 | 0.50 | <.0001 |
| 10 | 1.58 | 0.80 | 0.0074 |
| 11 | 0.98 | 0.23 | 0.0095 |
| 12 | 0.90 | 0.35 | 0.0568 |
| 13 | 1.23 | 0.90 | 0.2599 |
| 14 | 0.93 | 0.43 | 0.0833 |

[1]The GLIMMIX procedure would not converge, thus an ANOVA approach was used to evaluate the effect of vaccination over time on the nasal discharge score.

Conjunctivitis

The vaccination group, by day interaction, was statistically significant for the conjunctivitis scores (P<0.05). Statistically significant group effects were seen on Days 5 and 6, and on Days 9-14 post-challenge (lower scores in the vaccinated group, P<0.05). When the daily scores were summed over the post-challenge period, horses in the vaccinated group had lower total scores than those in the control group (P<0.05). The mitigated fraction was estimated to be 0.5300 (95% ASE CI: 0.2463, 0.8137).

TABLE 15

Mean conjunctivitis score (N = 20 horses per group)

| Days post-challenge | Control | Vaccinated | P-value[1] |
| --- | --- | --- | --- |
| 0 | 0.00 | 0.00 | 1.0000 |
| 1 | 0.00 | 0.00 | 1.0000 |
| 2 | 0.00 | 0.00 | 1.0000 |
| 3 | 0.05 | 0.00 | 0.7321 |
| 4 | 0.15 | 0.15 | 1.0000 |
| 5 | 0.70 | 0.25 | 0.0022 |
| 6 | 0.85 | 0.25 | <.0001 |
| 7 | 0.75 | 0.65 | 0.4936 |
| 8 | 0.45 | 0.35 | 0.4936 |
| 9 | 0.50 | 0.15 | 0.0168 |
| 10 | 0.45 | 0.15 | 0.0403 |
| 11 | 0.50 | 0.05 | 0.0022 |
| 12 | 0.45 | 0.00 | 0.0022 |
| 13 | 0.45 | 0.05 | 0.0063 |
| 14 | 0.35 | 0.05 | 0.0403 |

[1]The GLIMMIX procedure would not converge, thus an ANOVA approach was used to evaluate the effect of vaccination over time.

Virus Isolatin from Nasopharylngeal Swabs

The main effect of vaccination group was statistically significant (fewer animals shedding in the vaccinated group, P<0.05). When the number of days shedding was evaluated, horses in the vaccinated group had fewer days of virus shedding than those in the control group (P<0.05, Table 2). The mitigated fraction was estimated to be 0.4925 (95% ASE CI: 0.1896, 0.7954).

TABLE 16

Proportion virus shedding (nasal swab, N = 20 horses per group)

| Days post-challenge | Control | Vaccinated |
| --- | --- | --- |
| 0 | 0.00 | 0.00 |
| 1 | 0.00 | 0.00 |

TABLE 16-continued

Proportion virus shedding (nasal swab, N = 20 horses per group)

| Days post-challenge | Control | Vaccinated |
|---|---|---|
| 2 | 0.05 | 0.05 |
| 3 | 0.05 | 0.10 |
| 4 | 0.20 | 0.05 |
| 5 | 0.25 | 0.15 |
| 6 | 0.45 | 0.25 |
| 7 | 0.45 | 0.35 |
| 8 | 0.50 | 0.10 |
| 9 | 0.45 | 0.15 |
| 10 | 0.25 | 0.00 |
| 11 | 0.35 | 0.10 |
| 12 | 0.30 | 0.10 |
| 13 | 0.15 | 0.00 |
| 14 | 0.05 | 0.00 |

White Blood Cell Counts

The vaccination group by day interaction was statistically significant for WBC counts (P<0.05, Table 1). Statistically significant group effects were seen on Days 2 and 3 post-challenge. Horses in the vaccinated group had higher WBC counts than those in the control group, indicating the vaccine prevented the horses from suffering the leucopenia caused by infection with EHV 1 (P<0.05).

TABLE 17

Mean WBC counts (N = 20 horses per group)

| Days post-challenge | Control | Vaccinated | P-value[1] |
|---|---|---|---|
| 1 | 14.0413 | 14.4887 | 0.6081 |
| 2 | 10.7963 | 14.1287 | 0.0001 |
| 3 | 11.1263 | 14.0687 | 0.0008 |
| 4 | 11.5013 | 13.1037 | 0.0667 |
| 5 | 10.7413 | 11.1987 | 0.6001 |
| 6 | 9.1063 | 9.4187 | 0.7203 |
| 7 | 10.1563 | 9.9037 | 0.7721 |
| 8 | 10.7813 | 10.6037 | 0.8386 |
| 9 | 11.1813 | 12.0737 | 0.3065 |
| 10 | 11.9713 | 12.4187 | 0.6081 |
| 11 | 12.6713 | 13.2137 | 0.5341 |
| 12 | 13.2913 | 13.5637 | 0.7549 |
| 13 | 14.7063 | 14.1737 | 0.5415 |
| 14 | 15.8463 | 14.4587 | 0.1121 |

[1]P-values from the ANOVA

Serological Studies

Titers were log transformed prior to the statistical analysis. The vaccination group by day interaction was statistically significant for SN titers (P<0.05). Statistically significant group effects were seen on Days 35 (the day of challenge) and 7 and 14 days post-challenge (study days 42 and 49). Horses in the vaccinated group had higher titers than those in the control group (P<0.05).

TABLE 18

Geometric mean - serum neutralization titers (N = 20 horses per group)

| Study day | Control | Vaccinated | P-value[1] |
|---|---|---|---|
| 0 | 3.987 | 3.384 | 0.4005 |
| 21 | 3.190 | 2.624 | 0.3168 |
| 35 (day of challenge) | 3.480 | 6.863 | 0.0006 |
| 42 | 3.519 | 19.252 | <0.0001 |
| 49 | 33.153 | 187.417 | <0.0001 |

[1]P-values from the ANOVA. Serum neutralization titers were log (natural) transformed prior to the statistical analysis.

Results and Discussion

Respiratory disease caused by equine herpesvirus type 1 is usually an epidemic disease of naïve weanling and yearling horses that occurs in the first year of life, usually in the fall and winter months. Signs of acute infection include fever up to 106° F., viremia and leucopenia and/or neutropenia. Nasal discharge is usually evident during febrile periods of this first exposure. Natural infection by EHV-1 does not result in permanent immunity of the respiratory tract. Indeed, horses may be re-infected naturally every 3 to 6 months throughout life. After the first experience with this virus, re-infection results in production of virus, but usually without clinical signs of disease, resulting in carrier animals that act as natural reservoirs of the virus.

The equine herpesvirus-1 multi-component vaccine described in this report has been shown to be efficacious in reducing the respiratory manifestations, clinical symptoms and virus shedding from nasal exudate of horses challenged with a virulent heterologous strain of Equine Herpesvirus type 1. Reduction in shedding of virus from the respiratory route is important epidemiologically due to this being the natural route of exposure to naive animals as well as for re-infection of herd mates from those experiencing a natural infection. It was also a safe vaccine with no adverse reactions, either systemic or at the site of vaccine administration, observed following vaccine use in the study horses.

In this study, vaccination group by day interaction showed statistical significance for the primary outcome variables nasal discharge scores and conjunctivitis. Statistically significant group effects were seen in the vaccinate group for nasal discharge on Days 4, 5 and on Days 7-11 post-challenge. Group effects for conjunctivitis were also statistically significant on Days 5 and 6 and 9-14 with lower scores in the vaccinate group (P<0.05). This is significant epidemiologically because the EHV-1 virus is delicate and does not survive in the environment readily. Close contact is important for transmission of disease through nasal secretions containing virulent EHV-1 virus (Campbell and Studdert, 1983).

Importantly, another primary outcome variable in this study, virus shedding in nasal exudates, showed a main effect of vaccination as statistically significant (P<0.05). Horses in the vaccinated group also had statistically fewer days of virus shedding than those in the control group (P<0.05).

Serum neutralization titers were statistically significant after vaccination and throughout the challenge period in vaccinates versus control horses (P<0.05). Humoral immunity and mucosal antibodies may be important in determining whether an EHV-1 infection becomes a productive or limited infection event (Kidd, Smith, Hannant, et. al, 1994).

Example 6

This example illustrates the efficacy and 6 month duration of immunity of an immunogenic composition of the present invention when challenged with West Nile Virus.

Materials and Methods

The WNV viral antigen used in the vaccine evaluated in this study was produced on E vero cells as described in Example 1. A total of 15 horses were randomly divided into groups, one being a control group of 5 horses. The vaccinated group of 10 horses received 2 doses of vaccine at 21-day intervals cells. On completion of satisfactory residual live virus testing the inactivated viral fluids were then used to formulate a vaccine which also contained inactivated Venezuelan Equine Encephalomyelitis, TC-83 strain (ATCC Accession No. PTA-9411), Eastern Equine Encephalomyelitis, NJO strain (ATCC Accession No. PTA-9412), and Western Equine Encephalomyelitis, Fleming strain (ATCC Accession No. PTA-9410) viruses, inactivated influenza A/equine-2/Kentucky/95 (ATCC Accession No. PTA-9523), influenza A/equine-2/NewMarket/2/93 (ATCC Accession No. PTA-9524) and influenza A/equine-2/Ohio/03 (ATCC Accession No. PTA-9522) viruses, inactivated West Nile Virus (ATCC Accession No. 9409) and tetanus toxoid. Vaccine was formulated to minimum specifications for all antigens included in the product.

The final formulated vaccine contains the following ingredients per 1 mL dose:

| | |
|---|---|
| EHV-1 | $10^{7.0-9.0}$ TCID$_{50}$/mL |
| Influenza A2/Ohio/03 | $10^{6.7-9.5}$ TCID$_{50}$/mL |
| Influenza A2/KY/95 | $10^{6.7-9.5}$ TCID$_{50}$/mL |
| Influenza A2/NewMarket/2/93 | $10^{6.7-9.5}$ TCID$_{50}$/mL |
| Tetanus Toxoid | 5-10 CPU |
| Eastern Equine Encephalomyelitis | $10^{6.7-9.2}$ TCID$_{50}$/mL |
| Western Equine Encephalomyelitis | $10^{6.7-9.2}$ PFU/mL |
| Venezuelan Equine Encephalomyelitis | $10^{6.7-9.2}$ TCID$_{50}$/mL |
| West Nile Virus | $10^{7.0-9.0}$ TCID$_{50}$/mL |
| Adjuvant (preferably mineral oil) | 100-200 µl |
| Glycerol | 100-200 µl |
| EDTA 240 mM solution | 10-20 µl |
| Diluent - DMEM containing | q.s. |
| Gentamicin (30 µg/mL of diluent volume) | |
| Formaldehyde (0.1-0.2% of diluent volume) | |

Fifteen horses were used in this study. Horses were randomly assigned to either vaccinate or control groups and then vaccinated. Ten horses served as vaccinates and five horses were mock-vaccinated control horses.

The vaccine was administered intramuscularly in a 1 mL dose volume to each of the horses in the vaccinate group. Each control received a 1 mL dose of adjuvanted DMEM containing excipients used in the 9-way vaccine (gentamycin and formaldehyde) but no antigens.

All groups were challenged approximately 6 months following vaccination with intrathecal inoculation of 1 ml PBS containing approximately $10^5$ pfu of a heterologous strain of WNV (NY99, 4132, crow isolate). The challenge was conducted under ketamine-xylazine anesthesia.

Horses were monitored for a maximum of 14 days.
Results and Discussion

Viremia after challenge was considered the primary outcome variable in this study. The horses that had been vaccinated were 90% protected from viremia after challenge in this study. In comparison, all of the 5 control horses demonstrated viremia for 3-5 days post-challenge.

In addition, serum neutralization titers of vaccinated horses were significantly higher than those of control horses after vaccination. All the vaccinated horses developed measurable serum neutralization titers following vaccination, whereas none of the controls displayed any titer to WNV. This study demonstrated that 2 doses of the experimental combination vaccine reliably and effectively stimulated protective serological serum neutralization titers.

Since viremia is a prerequisite before virus can cross the blood-brain barrier to cause WNV encephalitis, viremia is well justified as the primary parameter for evaluation of protection in an experimental study of this type.

The results demonstrated that an immunogenic reaction is induced in the animals that were administered the vaccine, and that the vaccine is effective at providing protection for at least 6 months following vaccination. The effectiveness of the vaccine was evidenced in this example by reduction in WNV viremia and by stimulation of high serum neutralization titers to WNV. Because this vaccine is comprised of unique constituents including a long lasting non-metabolizable adjuvant, is formulated in a low 1 mL dose volume to provide a high degree of safety as a highly immunogenic low passage whole inactivated virus WNV isolate of recent origin and high epidemiological prevalence (a North American Dominant WNV strain), and a WNV isolated from the tissues of an infected horse, it provides more comprehensive safety and long lasting effectiveness of at least 6 months duration than other vaccines currently available. Additionally, it has the effect of providing a safe vaccine when administered to animals, and in particular to horses.

Example 7

This example illustrates the efficacy of one embodiment of the immunogenic composition of the present invention including encephalomyelitis antigens with tetanus toxoid antigen.
Materials and Methods Host animal and laboratory animal immunization/serology were evaluated to demonstrate efficacy of encephalomyelitis antigens and the tetanus toxoid antigen fraction in an Encephalomyelitis-Rhinopneumonitis-Influenza-West Nile Virus Vaccine, including Eastern, Western, and Venezuelan Encephalomyelitis, Killed Virus, and Tetanus Toxoid. The efficacy and lack of interference on equine encephalitis virus vaccines and tetanus toxoid fractions can be unequivocally demonstrated by laboratory animal potency testing of the combination vaccine. Demonstration of serological response following vaccination of horses is also indicative of vaccine-toxoid efficacy. Hence, both lab animal potency and host animal serology were used in this study to confirm the efficacy of the experimental vaccine. The vaccine was also evaluated for safety in animals including horses.

Horses 4-5 months of age, from non-vaccinated mares, were vaccinated with an efficacy serial of WNV combination vaccine containing inactivated Venezuelan Equine Encephalomyelitis Virus, TC-83 strain (ATCC Accession No. PTA-9411) Eastern Equine Encephalomyelitis Virus, NJO strain (ATCC Accession No. PTA-9412) Western Equine Encephalomyelitis Virus, Fleming strain (ATCC Accession No. PTA-9410) West Nile Virus (WNV), Horse Origin 2005 (ATCC Accession No. PTA-9409) Equine Herpesvirus Type 1 (ATCC Accession No. PTA-9525) (EHV-1), Influenza A/equine-2/Ohio/03 (ATCC Accession No. PTA-9522), Influenza A/equine-2/Kentucky/95 (ATCC Accession No. PTA-9523), Influenza A/equine-2/NewMarket/2/93 (ATCC Accession No. PTA-9524) and Tetanus Toxoid. Horses were vaccinated on Day 0 and Day 21 of the study. Blood samples were collected at Day 0, Day 21 and Day 35. Day 0 and Day 35 serological results are reported herein.

In addition, the same WNV combination vaccine used to vaccinate horses was tested for potency in guinea pigs. Data presented in this report collectively and definitively establish the efficacy of each antigen tested (EEE, VEE, WEE, tetanus) in this study and also confirm the safety of a WNV combination vaccine.

Bulk lots of EEE, WEE, and VEE viruses and tetanus toxoid were produced. Following growth, viral fluids were filtered, formalin inactivated, and concentrated. The inactivated viral fluids were tested for residual live virus after inactivation.

Inactivated viral and toxoid fluids described above were used to formulate a vaccine that also contained inactivated Equine Herpesvirus Type 1, inactivated influenza A/equine-2/Kentucky/95, influenza A/equine-2/NewMarket/2/93 and influenza A/equine-2/Ohio/03 viruses.

The vaccine was formulated to specifications for all antigens included in the product.

The final formulated vaccine contained the following ingredients per 1 mL dose:

| | |
|---|---|
| EHV-1 | $10^{7.0-9.0}$ TCID$_{50}$/mL |
| Influenza A2/Ohio/03 | $10^{6.7-9.5}$ TCID$_{50}$/mL |
| Influenza A2/KY/95 | $10^{6.7-9.5}$ TCID$_{50}$/mL |
| Influenza A2/NewMarket/2/93 | $10^{6.7-9.5}$ TCID$_{50}$/mL |
| Tetanus Toxoid | 5-10 CPU |
| Eastern Equine Encephalomyelitis | $10^{6.7-9.2}$ TCID$_{50}$/mL |
| Western Equine Encephalomyelitis | $10^{6.7-9.2}$ PFU/mL |
| Venezuelan Equine Encephalomyelitis | $10^{6.7-9.2}$ TCID$_{50}$/mL |
| West Nile Virus | $10^{7.0-9.0}$ TCID$_{50}$/mL |
| Adjuvant (preferably mineral oil) | 100-200 µl |
| Glycerol | 100-200 µl |
| EDTA 240 mM solution | 10-20 µl |
| Diluent - DMEM containing | q.s. |
| Gentamicin (30 µg/mL of diluent volume) | |
| Formaldehyde (0.1-0.2% of diluent volume) | |

Forty horses, four to 5 months of age, were used in this study. Horses remained with their dams on pasture throughout the vaccination period and were weaned from their dams when the 2-week post-booster sera were collected. Horses were assigned to either one of the two treatment groups randomly as they were vaccinated intramuscularly (IM) with a 1.0 ml dose. The primary immunization was followed three weeks later by a 1.0 ml IM booster vaccination. Twenty horses received vaccine. Twenty horses received placebo.

Guinea pigs were also vaccinated with the same combination WNV vaccine.

Horses were vaccinated and serum samples collected using the following schedule:

TABLE 19

Vaccination and Serum Sampling Schedule

| Day of Test | Activity |
|---|---|
| 0 | Collect pre-vaccination blood and give primary vaccination |
| 21 | Collect blood and give booster vaccination |
| 35 | Collect blood for final serology |

Guinea pigs were vaccinated and serum collected using the schedule outlined by 9 CFR, 113.207(b) and 113.114(c.).

Sera from horses in this study were tested following general guidelines. The assay was modified to determine titers by testing at 1:2 and 1:10 dilutions for Day 0 samples and at 1:10 and 1:40 dilutions for the 2-week post-booster serum samples. Sera were tested for EEE, WEE and VEE antibody and were tested for Tetanus toxoid antibody.

Results and Discussion

Horse Serological Evaluation for EEE, WEE and VEE

At Day 0 of the Study, not all foals were sero-negative to encephalomyelitis viruses. Five of the vaccinated foals had significant (>1:10) residual maternal antibody to EEE virus. In addition, two of the vaccinated foals had residual maternal antibody (>1:10) to WEE virus. Despite existing and potentially interfering passively acquired, maternal antibody at the time of administration of the first dose of the WNV combination vaccine, titers for all three fractions increased substantially (>4 fold in 80% of horses tested for EEE, >4 fold in 90% of horses tested for WEE and >4 fold in 100% of horses tested for VEE) following vaccination, yet remained negative or low for the non-vaccinated foals. Individual foal data are presented below.

EEE, WEE and VEE Equine Serological Titers

TABLE 20

Plaque Reduction Neutralization Titration

| Horse ID | Test Article | Day 0 EEE | Day 35 EEE | Day 0 WEE | Day 35 WEE | Day 0 VEE | Day 35 VEE |
|---|---|---|---|---|---|---|---|
| 1 | V | >10 | >40 | 2 | >40 | <2 | >40 |
| 2 | V | <2 | >40 | <2 | 10 | <2 | 40 |
| 3 | V | <2 | >40 | <2 | <10 | <2 | >40 |
| 4 | V | <2 | >40 | <2 | 10 | <2 | >40 |
| 5 | V | >10 | >40 | >10 | >40 | <2 | >40 |
| 6 | V | >10 | >40 | <2 | >40 | NS | 10 |
| 7 | V | <2 | >40 | <2 | >40 | <2 | >40 |
| 8 | V | >10 | >40 | 2 | >40 | <2 | >40 |
| 9 | V | <2 | >40 | <2 | >40 | <2 | >40 |
| 10 | V | <2 | >40 | <2 | >40 | <2 | 10 |
| 11 | V | <2 | >40 | <2 | >40 | <2 | >40 |
| 12 | V | <2 | >40 | <2 | >40 | <2 | 40 |
| 13 | V | <2 | >40 | <2 | >40 | <2 | >40 |
| 14 | V | <2 | >40 | <2 | 10 | <2 | >40 |
| 15 | V | >10 | >40 | >10 | >40 | 2 | >40 |
| 16 | V | 2 | >40 | <2 | 10 | <2 | >40 |
| 17 | V | <2 | >40 | <2 | 10 | <2 | >40 |
| 18 | V | <2 | >40 | <2 | >40 | <2 | 40 |
| 19 | V | <2 | 10 | <2 | >40 | <2 | >40 |
| 20 | V | 2 | >40 | <2 | >40 | <2 | 10 |
| 21 | C | <2 | <10 | <2 | <10 | <2 | 10 |
| 22 | C | <2 | <10 | <2 | <10 | <2 | <10 |
| 23 | C | <2 | <10 | <2 | 10 | <2 | <10 |
| 24 | C | <2 | <10 | NS | <10 | <2 | <10 |
| 25 | C | <2 | <10 | <2 | <10 | <2 | <10 |
| 26 | C | <2 | <10 | <2 | 10 | <2 | <10 |
| 27 | C | <2 | <10 | <2 | <10 | <2 | <10 |
| 28 | C | 2 | <10 | <2 | <10 | <2 | 10 |
| 29 | C | 2 | <10 | <2 | 10 | <2 | <10 |
| 30 | C | <2 | <10 | <2 | <10 | <2 | <10 |
| 31 | C | <2 | <10 | <2 | <10 | <2 | <10 |
| 32 | C | <2 | <10 | <2 | <10 | <2 | <10 |
| 33 | C | >10 | >40 | <2 | 10 | <2 | <10 |
| 34 | C | <2 | <10 | <2 | <10 | <2 | <10 |
| 35 | C | >10 | 10 | 2 | <10 | <2 | 10 |
| 36 | C | 2 | <10 | <2 | <10 | <2 | <10 |
| 37 | C | <2 | <10 | <2 | <10 | <2 | <10 |
| 38 | C | <2 | <10 | 2 | <10 | <2 | <10 |
| 39 | C | <2 | 10 | <2 | <10 | <2 | <10 |
| 40 | C | <2 | >40 | <2 | <10 | <2 | <10 |

Guinea Pig Serological Evaluation for EEE, WEE, VEE and Tetanus Toxoid

Nine of ten guinea pigs vaccinated with the combination vaccine seroconverted satisfactorily at (≥1:40) to EEE virus. Ten of ten guinea pigs had satisfactory titers for VEE virus (≥1:4) and ten of ten guinea pigs seroconverted satisfactorily to WEE virus (≥1:40). Also a serum pool from 10 vaccinated guinea pigs was tested for tetanus antibody and was shown to be satisfactory with a value of 4.3 anti-toxin units/ml (AU/ml).

Guinea pig potency tests were completed and found to be satisfactory for all four antigens including tetanus toxoid, EEE, VEE, and WEE.

The vaccine was also administered to horses (20 vaccinates and 20 controls) via primary immunization followed by booster immunization 3 weeks later. Fourteen days post-booster vaccination, horses were bled and serum collected for all serological testing. Equine response to encephalomyelitis antigens was tested utilizing 2 dilutions (1:2 and 1:10 for Day 0 samples and 1:10 and 1:40 for Day 35 samples) in 24-well plates to determine antibody titers.

The satisfactory guinea pig potency testing conclusively establishes the efficacy of 4 antigens (VEE, EEE, WEE and tetanus toxoid) in the West Nile Virus combination vaccine as a 9-antigen-containing vaccine-toxoid. Furthermore, satisfactory potency results are substantiated and confirmed by host animal horse serology data in which vaccinated horses demonstrated a substantial rise in titer to each encephalitis virus fraction following vaccination. Additionally, the absence of observation of any adverse reactions in any of the vaccinated horses or guinea pigs confirms the safety of the WNV combination vaccine in animals.

Example 8

This example illustrates that a vaccine or immunogenic composition in accordance with the present invention has a duration of immunity of at least one year.

Materials and Methods

Host animal vaccination and challenge at least 1 year post-booster vaccination was used to confirm duration of immunity for the West Nile Virus antigen fraction in an Encephalomyelitis-Rhinopneumonitis-Influenza-West Nile Virus Vaccine, Eastern, Western & Venezuelan, Killed Virus, Tetanus Toxoid prepared from a North American Dominant isolate of WNV designated North American Equine E159 (NAEE159).

TABLE 21

The final formulated vaccine contains the following ingredients per 1 mL dose:

| Ingredients | 1 mL Dose |
| --- | --- |
| Eastern Equine Encephalomyelitis | $10^{7.5-9.2}$ $TCID_{50}$/mL |
| Western Equine Encephalomyelitis | $10^{8.2-9.2}$ PFU/mL |
| Venezuelan Equine Encephalomyelitis | $10^{7.7-9.2}$ $TCID_{50}$/mL |
| West Nile Virus (North American Dominant prepared from NAEE159) | $10^{8.0-9.2}$ $TCID_{50}$/mL |
| EHV-1 | $10^{7.0-9.0}$ $TCID_{50}$/mL |
| Equine Influenza A2/Ohio/2003 | $10^{7.3-9.5}$ $TCID_{50}$/mL |
| Equine Influenza A2/Kentucky/95 | $10^{7.3-9.5}$ $TCID_{50}$/mL |
| Equine Influenza A2/NewMarket/2/93 | $10^{7.3-9.5}$ $TCID_{50}$/mL |
| Tetanus Toxoid | 5-10 CPU |
| Non-metabolizable Oil Adjuvant | 100-200 µl |
| Diluent - DMEM containing | q.s. |
| Gentamicin | 30 µg/mL of diluent volume |
| Formaldehyde | 0.1% of diluent volume |

Thirty horses (20 vaccinates and 10 controls), 4-5 months of age were used in this study. Horses were randomly assigned to one of two treatments and vaccinated intramuscularly (IM) with a 1.0 mL dose of the assigned vaccine or control product. The primary immunization was followed three weeks later by a 1.0 mL IM booster vaccination.

Horses were vaccinated once and then again about 30 days later. Horses were randomly assigned to either vaccine or control groups. Twenty horses received the vaccine group receiving VEWT/WNV/EHV-1/Influenza vaccine. Ten horses received adjuvanted DMEM containing excipients used in the vaccine (Gentamicin and formaldehyde) but no antigens. The non-metabolizable oil adjuvant used for all administrations was preferably mineral oil.

Challenge inoculation of the virulent heterologous WNV NY99 strain virus was performed 380 days post-booster vaccination. The second cohort of horses were challenged 408 days post-booster inoculation in a similar manner.

Serum samples for serological evaluation were collected from the vaccinated and control horses prior to initial vaccination, at 21 days post first dose vaccination (day of booster vaccination), monthly post-booster, on the day of challenge, and at 7 and 14 days post-challenge. Body temperature and serum samples were obtained from each horse on the day of challenge, twice daily on Days 1 through 6 post-challenge, and daily on Days 7-10 and Day 14 post-challenge. Clinical data was also recorded during those same time periods for the 15-day observation period.

The heterologous challenge virus, designated WNV NY99, was originally isolated from the brain of an infected crow (CDC, Ft. Collins, Colo.). On the day of challenge, the stock virus was thawed on ice and virus was diluted to the desired concentration in phosphate-buffered saline immediately prior to inoculation of horses.

Rectal temperatures were recorded for each of the vaccinated and control horses on the day before challenge, day of challenge and twice daily on days 1-14, then daily on Days 14-21 post challenge by means of a calibrated, electronic thermometer (GSA Electronics) probe. The daily rectal temperatures were recorded in degrees Fahrenheit (° F.).

Venous blood from each of the vaccinated and control horses was collected on the Day of Challenge, twice daily on Days 1-6, and daily on Days 7-10 and Day 14 days post-challenge by Vacutainer into an SST tube. After centrifugation, serum was aliquotted and frozen immediately.

Vero Cells were grown in 6-well plates to confluency. To perform the plaque assay, serial 10-fold dilutions of serum were prepared in 96-well plates in BA-1 medium (MEM salts containing 1% BSA, 250 mg/L sodium bicarbonate, 50 µl gentamicin and 2.5 µg amphotericin B/mL in 50 mM Tris, pH 7.6). Serum dilutions (0.1 mL) were inoculated into each well of the 6-well plate and incubated for 45-60 minutes with rocking every 15 minutes. After the incubation period, 2 mL of overlay (2× medium containing MEM without phenol red prepared at twice the normal concentration and supplemented with 4% FBS, 200 IU penicillin G/mL and 100 µg streptomycin/mL—warmed to 45° C.) was added to each well. Plates were incubated at 37° C.

Two days after inoculation, 2 mL of a second overlay containing 2× agarose prepared by mixing equal volumes of 2× medium and 2× agarose was added to each well. Plates were examined and plaque numbers recorded in each well on days 3, 4 and 5 following inoculation. The virus titer per mL of original material is calculated as the number of plaques in a well (or average of multiple wells inoculated with the same dilution) times the dilution for the well being counted multiplied by 10.

A standard microtiter serum neutralization test was employed in this study. All sera were tested in sterile flat bottom 96 well microtiter plates using five wells per dilution and an 8 well dilution series for each of the 5 test wells. Each of the 5 test wells contained 25 µL of serum dilution mixed with 25 µL of the indicator virus and 150 µL of a freshly planted Vero cell suspension containing approximately $4 \times 10^4$ cells. The test indicator virus used was WNV NY99. Serum neutralizing antibody titers are expressed as Reed-Muench $ID_{50}$ titers.

For performance of the test, two-fold dilutions of each test serum were made in a sterile flat bottom microtiter plate using five replicate wells per test serum and an 8 well dilution series. Dilutions were made with an adjustable volume single or multi-channel pipetting instrument using sterile microtiter tips. The volume of serum added to each of 5 wells of the first row was 50 µL. All other wells contained 25 µL of DMEM (no FBS). Following serial dilution down the plate, 25 µL was discarded from the last row. 25 µL of a pre-determined dilution of the indicator virus was added to each test well. Plates were then mixed and incubated for one hour at 37° C. in 5% $CO_2$. On conclusion of the incubation period, 150 µL of a suspension containing 4×104 Vero cells were added to each test and cell control well. The plates were incubated at 37° C.

in a $CO_2$ incubator for 5-7 days, at which time plates were microscopically examined for CPE typical of WNV.

Histopathology was evaluated by a Board Certified Veterinary Pathologist. The scoring system used to describe defects in the pons or medulla was as follows:
Score:
0=no significant lesions in section
0.5=rare, small, multifocal glial nodules scattered throughout the parenchyma
1=mild, nonsuppurative encephalitis. This is characterized by mild multifocal perivascular cuffs with lymphocytes and plasma cells and a rare neutrophil and scattered multifocal glial nodules composed of glial cells with a few mononuclear inflammatory cells. Occasionally within this grade, there may be minimal perivascular cuffing and more moderate scattered glial nodules.
2=moderate nonsuppurative encephalitis characterized by moderate lymphoplasmacytic perivascular cuffs around many vessels and multifocal accumulations of glial nodules scattered throughout the parenchyma
3=severe nonsuppurative encephalitis characterized by severe and thick lymphoplasmacytic perivascular cuffing with multiple scattered glial nodules throughout the parenchyma Results and Discussion There were no adverse reactions to vaccine administration at either dosing time point. All 4 to 5 month old foals receiving the experimental vaccine were free of either systemic or injection site adverse reactions in the study. This confirms the excellent safety of the vaccine of the present invention against WNV containing North American Dominant WNV antigen prepared from isolate NAEE159.

Horse Challenge with Heterologous West Nile Virus

Viremia

Each of the 10 control horses (100%) were viremic for at least 1 day post-challenge, while only 2 of 20 horses (10%) in the WNV vaccine group were viremic.

Clinical Signs

Seven of the 10 horses (70%) in the control group developed signs of encephalomyelitis consistent with West Nile Virus infection. Each of these animals was viremic for at least one day during the challenge period. In the WNV vaccine group, 1 of the 20 horses (5%) developed signs consistent with West Nile Virus infection. Notably clinical signs progressed to death or euthanasia in 70% of the controls and only 5% of the vaccinates. All control mortalities were viremic, confirming fatal encephalitis due to WNV, whereas only one of two vaccinated animals that died was viremic during the challenge period.

Serum Neutralization Titers

All vaccinated horses responded favorably to the WNV vaccine by developing protective levels of serum neutralizing (SN) antibody following vaccination. Over one year following vaccination, 17 of 20 (85%) of vaccinated horses maintained protective SN titers. By contrast, none of the control horses developed rising SN titers prior to virulent WNV challenge. Also, all vaccinated horses displayed an anamnestic rise in SN titers following virulent WNV challenge Histopathology Severity scores were provided for both the medulla and pons. Also with regard to this efficacy parameter, WNV vaccine containing North American Dominant WNV antigen prepared from isolate NAEE159 proved highly effective. Among the control horses, 50% displayed severe lesions of WNV encephalitis whereas only 10% of vaccinates were similarly affected.

Discussion and Conclusions

The WNV vaccine was prepared from a viral isolate (North American Equine E159) obtained from a horse in 2005 during the North American pandemic when a specific dominant WNV genotype emerged. This genotype is characterized by a specific valine to alanine amino acid change at the $159^{th}$ amino acid in the envelope (E) protein of the virus (when compared to the publicly available sequence for the WNV-NY99 isolate having the ATCC Accession No. AF196835), which has made all such isolates more robust and prolific, thereby displacing other WNV isolates, and making this genotype dominant among disease-causing WNV isolates in North America. Because it was prepared from the dominant genotype, the vaccine used in this study is indicative of the unique safety and efficacy achievable with vaccine prepared from all such North American Dominant isolates with this E protein profile and resulting prolificacy. Notably, all previously tested WNV vaccines have been prepared from a less prolific isolate of differing genotype and E protein amino acid sequence, namely WNV NY99. Based on this difference in nucleic acid sequence, E protein amino acid sequence, viral prolificacy, and unique ability to cause a pandemic, the North American Dominant isolates are displacing or have displaced NY99 from the environment. The unique genotype and phenotype (prolificacy), and, most importantly, the overwhelming environmental presence of North American Dominant WNV isolates and the absence of WNV NY99 is compelling evidence for the superiority of the North American Dominant West Nile Virus vaccine. Such superiority is confirmed by the safety and efficacy of the vaccine as demonstrated in this challenge study using vaccine prepared from North American Dominant isolate North American Equine E159 (NAEE159) (ATCC Accession No PTA-9409).

In this study, 4 to 5 month old horses were safely and effectively vaccinated with a multi-component VEWT/WNV/EHV-1/Equine Influenza vaccine batched at an appropriate antigen amount with the WNV component being North American Dominant WNV antigen prepared from isolate NAEE159c (ATCC Accession No. PTA-9409).

Study horses were intrathecally challenged at least 380 days post-booster vaccination with $10^5$ PFU of a virulent heterologous West Nile Virus strain. Horses were evaluated for 14 days post-challenge for clinical signs (including temperature and mortality), viremia, serum neutralization titers, and histopathology scores from sections of the pons and medulla taken after euthanasia and necropsy.

Viremia after challenge and serum neutralization titers were key outcome variables in this study that were highly indicative of vaccine efficacy. Horses that had been vaccinated more than one year earlier with VEWT/WNV/EHV-1/Influenza Lot 916 were 90% protected from viremia after challenge in this study. In comparison, 100% of control horses demonstrated viremia post-challenge. Additionally, serum neutralization titers of vaccinated horses were significantly higher than those of control horses at 14 days post-challenge, and displayed an anamnestic response typical of an effective vaccine following heterologous, virulent WNV challenge.

In addition the vaccine containing North American Dominant WNV antigen prepared from isolate NAEE159 reduced clinical signs and mortality resulting from encephalomyelitis following heterologous challenge with virulent WNV. Vaccine efficacy at least one year following vaccination was also confirmed by reduction in lesions typical of WNV infection.

This study demonstrated for the first time that 2 doses of the experimental combination vaccine prepared at appropriate doses of antigen including North American Dominant WNV antigen prepared from isolate NAEE159 administered to foals 4 to 5 months of age safely, reliably and effectively stimulated protective serological serum neutralization titers that resulted in duration of immunity of at least one year with protection from viremia, clinical signs, mortality, and encephalitic lesions after virulent heterologous challenge with West Nile Virus.

Example 9

In this study, a combination vaccine was prepared using a North American Dominant isolate of WNV, North American Equine E159(NAEE159) (ATCC Accession No. PTA-9409). The 14-day post second-vaccination sera samples from the guinea pigs vaccinated with this Encephalomyelitis-Rhinopneumonitis-Influenza-West Nile Virus Vaccine, Eastern, Western & Venezuelan, Killed Virus, Tetanus Toxoid were collected and tested for West Nile Virus plaque reduction neutralization (PRN). The sera from the vaccinated guinea pigs were tested for neutralizing antibody to both a North American Dominant isolate of WNV and to WNV isolate NY99. Notably, the vaccine displayed superior activity in stimulating neutralizing antibodies to North American Dominant WNV, as opposed to NY99 WNV. These data support the conclusion of the superior efficacy of WNV vaccines prepared from North American Dominant WNV isolates as contrasted with earlier less effective vaccines prepared from or based on the NY99 WNV isolate.

Furthermore, a vaccine prepared from an additional North American Dominant isolate of WNV, North American Donkey E159 (NADE159) will similarly demonstrate, as described above, the superior efficacy of such vaccines over the former NY99 based vaccines. Hence, data from multiple North American Dominant isolates cultivated from different host species, originating from unique North American locations, and obtained at different times in North America will confirm the unexpected but superior efficacy of North American Dominant isolates of WNV for vaccine preparation.

The data from the plaque reduction neutralization assay also established that a vaccine prepared from a North American Dominant isolate of WNV that stimulates a titer of 1:12 or higher in vaccinated guinea pigs that provides 50% viral plaque reduction in at least 90% of vaccinated guinea pigs, correlates to vaccine protection against WNV challenge in the horse and provides for a duration of immunity of at least one year. West Nile Virus vaccination/challenge data in the horse at an antigen inclusion level of $10^{7.6-9.0}$ $TCID_{50}$ or higher per dose correlated with these guinea pig PRN titer results and confirmed the WNV immunizing dose that provides 1 year or longer duration of immunity in the horse. The corresponding dose in guinea pigs also stimulates serum neutralizing antibodies to a titer of at least 1:12 against North American Dominant WNV in guinea pigs.

Data presented in this report collectively demonstrate the unexpected efficacy of vaccines prepared from North American Dominant isolates of WNV, define the correlation between vaccine efficacy in the horse and guinea pig serum levels of neutralizing antibody, confirm that a 1:12 titer or higher in guinea pigs identifies an effective equine vaccine providing at least one year duration of immunity, and quite notably, demonstrate the superior efficacy of vaccines prepared from North American Dominant WNV as contrasted with NY99 WNV.

Materials and Methods

In order to demonstrate efficacy of the West Nile Virus antigen, prepared using a North American Dominant isolate of WNV, North American Equine E159(NAEE159) (ATCC Accession No. PTA-9409), in an Encephalomyelitis-Rhinopneumonitis-Influenza-West Nile Virus Vaccine, Eastern, Western & Venezuelan, Killed Virus, Tetanus Toxoid and to establish an effective dose measurable in horses or guinea pigs, host animal vaccination/challenge studies were performed in conjunction with guinea pig vaccination/serology studies. In this study, 14-day post second-vaccination sera samples from guinea pigs vaccinated with Encephalomyelitis-Rhinopneumonitis-Influenza-West Nile Virus Vaccine, Eastern, Western & Venezuelan, Killed Virus, Tetanus Toxoid were collected and tested. Additionally, a plaque reduction neutralization assay was developed to measure the titer correlated to protection against challenge in the host animal. This titer was determined to be 1:12 or higher in the guinea pig.

Vaccine Formulations
Experimental Serials (Protective Dose Vaccine)

Experimental Serials were formulated to confirm protective antigen specifications for all antigens in the vaccine.

TABLE 22

The final formulated vaccines contained the following ingredients per 1 mL dose:

| Ingredients | 1 mL Dose |
|---|---|
| Eastern Equine Encephalomyelitis | $10^{7.5-9.2}$ $TCID_{50}$/mL |
| Western Equine Encephalomyelitis | $10^{8.2-9.2}$ PFU/mL |
| Venezuelan Equine Encephalomyelitis | $10^{7.7-9.2}$ $TCID_{50}$/mL |
| West Nile Virus (North American Dominant prepared from NAEE159) | $10^{7.3-9-2}$ $TCID_{50}$/mL |
| EHV-1 | $10^{7.0-9.0}$ $TCID_{50}$/mL |
| Equine Influenza A2/Ohio/2003 | $10^{7.3-9.5}$ $TCID_{50}$/mL |
| Equine Influenza A2/Kentucky/95 | $10^{7.3-9.5}$ $TCID_{50}$/mL |
| Equine Influenza A2/NewMarket/2/93 | $10^{7.3-9.5}$ $TCID_{50}$/mL |
| Tetanus Toxoid | 5-10 CPU |
| Non-metabolizable Oil Adjuvant | 100-200 µl |
| Diluent - DMEM containing | q.s. |
| Gentamicin | 30 µg/mL of diluent volume |
| Formaldehyde | 0.1% of diluent volume |

Experimental serial 916 was formulated for host animal vaccination studies. Experimental serial 916 is a multi-component vaccine containing VEWT-WNV-EHV-1 and 3 strains of equine influenza type A2 virus. Experimental serial 916 is batched at $10^{7.6-9.2}$ $TCID_{50}$/mL of West Nile Virus antigen North American Equine E159(NAEE159). It is a 1 mL dose vaccine in the horse.

This vaccine was also tested in guinea pigs at the time of host animal vaccinations to confirm the WNV efficacy and laboratory animal potency. Four replicate guinea pig sera dilution experiments were performed for experimental serial 916 to validate a guinea pig assay criterion for this one-year duration of immunity (DOI) vaccine.

Experimental Serial 507 (Comparative Efficacy Serial)

Data from Experimental Serial 507 is included in this report to demonstrate that serials formulated with a North American Dominant isolate of WNV antigen show superior efficacy, measured as guinea pig titers, of the relevant North American Dominant isolates of WNV as compared to the earlier NY99 isolate.

Guinea Pig Serological Evaluation

Sera were tested for WNV antibody as follows:
1) West Nile Virus Indicator Strain: North American Equine E159(NAEE159) (ATCC Accession No. PTA-9409) & North American Donkey E159 (NADE159)
2) Growth medium for Vero Cells is DMEM+5% FBS, 2 mM L-glutamine and 30 µg/mL gentamycin
3) Diluent for Test Serum is DMEM plus 30 µg/mL gentamycin 4) Diluent for indicator virus working solution is DMEM+ 10% normal guinea pig serum (specific to WNV assay)
5) Guinea pig test sera is diluted 1:12
7) Use 4 mL overlay instead of 3 mL (specific to WNV assay)
8) Titers are calculated using 50% plaque reduction
9) Nine of ten vaccinated guinea pigs must have an antibody titer of ≥1:12 to demonstrate efficacy, and negative guinea pigs must be <1:4 (same criteria as VEE assay in SAM).

Results and Discussion
Serological Evaluation for West Nile Virus
Experimental Serial 916 Replicate I West Nile Guinea Pig Plaque Reduction Neutralization Results Using North American Equine E159(NAEE159) as Indicator Virus The study was initiated and the guinea pigs were bled 25 days later.

TABLE 23

| 916 (I) | Number of Plaques/Sera Dilution | | | | | | | | |
|---|---|---|---|---|---|---|---|---|---|
| | 2 | 3 | 4 | 6 | 8 | 12 | 16 | 32 | 64 |
| GP1 | 0 | 2 | 2 | 4 | 5.5 | 2.5 | 17 | 14 | 11 |
| GP2 | 6.5 | 9.5 | 11 | 14 | 9 | 11.5 | 13 | 20 | 22.5 |
| GP3 | 7 | 5 | 6 | 9.5 | 10 | 9.5 | 11 | 10 | 16.5 |
| GP4 | 7 | 5 | 4 | 4 | 1 | 6 | 15.5 | 9.5 | 12.5 |
| GP5 | 6 | 4.5 | 9 | 7 | 17.5 | 13.5 | 12 | 16 | 17 |
| GP6 | 1 | 1 | 2.5 | 7.5 | 3 | 8 | 19.5 | 19.5 | 20.5 |
| GP7 | 9.5 | 8 | 8 | 15.5 | 17.5 | 21.5 | 36 | 17.5 | 20.5 |
| GP8 | 5 | 3.5 | 7.5 | 7.5 | 14.5 | 11 | 26.5 | 26.5 | 27.5 |
| GP9 | 0 | 2 | 7 | 6 | 7 | 12 | 9 | 10.5 | 11.5 |
| GP10 | 4.5 | 4.5 | 5.5 | 11 | 22 | 8.5 | 23 | 29 | 30.5 |
| # Passed | 10/10 | 10/10 | 10/10 | 10/10 | 10/10 | 10/10 | 10/10 | 10/10 | 10/10 |
| Neg. Control 1 | 68.5 | 64.5 | 72.5 | 93.5 | 68 | 82 | 89.5 | 78.5 | 71 |
| Neg. Control 2 | 72 | 61 | 87 | 69.5 | 70.5 | 85.5 | 77.5 | 69.5 | 88 |

Virus Control Values: 99. 70, 68, 88, 77, 64
Virus Control Average Plaques: 79
Virus Control 50% Reduction: 39.5

TABLE 24

Experimental Serial 916 Replicate II West Nile Guinea Pig
Plaque Reduction Neutralization
Results Using North American Equine
E159(NAEE159)as Indicator Virus
Guinea Pigs were bled 35 days after
the initiation of the study
Number of Plaques/Sera Dilution

| 916 (II) | 2 | 3 | 4 | 6 | 8 | 12 | 16 | 32 | 64 |
|---|---|---|---|---|---|---|---|---|---|
| GP1 | 1 | 3 | 6 | 6 | 14.5 | 6.5 | 13.5 | 18 | 17.5 |
| GP2 | 1.5 | 3.5 | 6.5 | 6.5 | 8.5 | 9.5 | 10.5 | 12.5 | 19 |
| GP3 | 12 | 5.5 | 22 | 21 | 41.5 | 34 | 41 | 41 | 43.5 |
| GP4 | 4 | 8.5 | 17.5 | 16.5 | 21 | 36.5 | 28 | 41.5 | 42.5 |
| GP5 | 3.5 | 4.5 | 9.5 | 15 | 26.5 | 25.5 | 13.5 | 23 | 40 |
| GP6 | 1 | 3 | 7 | 13.5 | 17.5 | 14 | 24.5 | 26 | 23 |
| GP7 | 8 | 5.5 | 14.5 | 11.5 | 21.5 | 15.5 | 34 | 26.5 | 28 |
| GP8 | 1 | 1.5 | 2.5 | 3.5 | 4 | 11 | 9 | 20 | 17.5 |
| GP9 | 13.5 | 18 | 25.5 | 29.5 | 29.5 | 35.5 | 28 | 37.5 | 43 |
| GP10 | 9 | 8 | 10.5 | 21.5 | 21 | 20.5 | 27 | 31.5 | 27.5 |
| # Passed | 10/10 | 10/10 | 10/10 | 10/10 | 9/10 | 10/10 | 9/10 | 8/10 | 6/10 |
| Neg. Control 1 | 69.5 | 67 | 71.5 | 69.5 | 72.5 | 73 | 83 | 68 | 78 |
| Neg. Control 2 | 68 | 70.5 | 69 | 72.5 | 82.5 | 66 | 75 | 76 | 74 |

Virus Control Values: 99. 70, 68, 88, 77, 64
Virus Control Average Plaques: 79
Virus Control 50% Reduction: 39.5

TABLE 25

Experimental Serial 916 Replicate III West Nile Guinea Pig
Plaque Reduction Neutralization
Results Using North American Equine
E159(NAEE159)as Indicator Virus
Guinea Pigs were bled 35 days after initiation
Number of Plaques/Sera Dilution

| 916 (III) | 2 | 3 | 4 | 6 | 8 | 12 | 16 | 32 | 64 |
|---|---|---|---|---|---|---|---|---|---|
| GP1 | 0.5 | 1.5 | 0 | 0 | 0 | 1 | 4 | 6 | 3.5 |
| GP2 | 0 | 0 | 1 | 0.5 | 0 | 0 | 0 | 0 | 0 |
| GP3 | 7.5 | 9 | 9 | 16 | 17 | 13.5 | 12 | 18.5 | 23 |
| GP4 | 2.5 | 0 | 0 | 3 | 2 | 2 | 3.5 | 1 | 2.5 |
| GP5 | 13.5 | 15.5 | 18 | 18 | 19.5 | 24 | 16.5 | 21.5 | 33.5 |
| GP6 | 6.5 | 15.5 | 31.5 | 10 | 29.5 | 26.5 | 28.5 | 31.5 | 32 |
| GP7 | 14.5 | 12 | 17.5 | 20.5 | 19.5 | 29.5 | 21.5 | 16 | 22.5 |
| GP8 | 21 | 24.5 | 36 | 28 | 34.5 | 30.5 | 27.5 | 29 | 26 |
| GP9 | 0.5 | 0.5 | 3 | 4 | 6.5 | 5 | 10 | 9.5 | 18 |
| GP10 | 2.5 | 7.5 | 11 | 8 | 12.5 | 9 | 20 | 10.5 | 17 |
| # Passed | 10/10 | 10/10 | 8/10 | 10/10 | 9/10 | 10/10 | 10/10 | 9/10 | 8/10 |
| Neg. Control 1 | 73 | 61.5 | 79.5 | 53.5 | 58.5 | 78 | 57 | 70 | 63 |
| Neg. Control 2 | 55 | 54.5 | 64 | 52.5 | 58 | 68.5 | 66 | 67.5 | 79 |

Virus Control Values: 51, 58, 61, 66, 78
Virus Control Average Plaques: 62
Virus Control 50% Reduction: 31

TABLE 26

Experimental Serial 916 Replicate IV West Nile Guinea Pig
Plaque Reduction Neutralization
Results Using North American Equine
E159(NAEE159)as Indicator Virus
Guinea Pigs were bled 30 days after the initiation of the study
Number of Plaques/Sera Dilution

| 916 (IV) | 2 | 3 | 4 | 6 | 8 | 12 | 16 | 32 | 64 |
|---|---|---|---|---|---|---|---|---|---|
| GP1 | 11.5 | 7 | 5.5 | 20.5 | 12 | 17.5 | 22.5 | 20 | 25 |
| GP2 | 31 | 21.5 | 20.5 | 36.5 | 32 | 30 | 27 | 15 | 28.5 |
| GP3 | 16 | 20.5 | 18 | 23.5 | 21.5 | 16 | 35.5 | 16.5 | 15 |
| GP4 | 1 | 2 | 6.5 | 7 | 11 | 15 | 19 | 14 | 18.5 |
| GP5 | 4 | 1 | 9.5 | 12 | 20 | 17 | 24.5 | 19.5 | 23.5 |
| GP6 | 0 | 0 | 0 | 1.5 | 2.5 | 2.5 | 0.5 | 3 | 3 |
| GP7 | 5.5 | 6.5 | 5.5 | 10 | 7 | 13 | 5.5 | 9.5 | 13 |
| GP8 | 1 | 4.5 | 0.5 | 3 | 7.5 | 4.5 | 13.5 | 17.5 | 11.5 |
| # Passed | 8/8 | 8/8 | 8/8 | 7/8 | 8/8 | 8/8 | 7/8 | 8/8 | 8/8 |
| Neg. Control 1 | 48 | 39 | 46.5 | 39 | 48 | 54 | 39.5 | 54 | 67.5 |
| Neg. Control 2 | 40.5 | 53 | 44 | 44.5 | 54 | 48.5 | 59.5 | 61.5 | 45.5 |

Virus Control Values: 93, 53, 56, 92, 67, 44
Virus Control Average Plaques: 67.5
Virus Control 50% Reduction: 33.8

EXPERIMENTAL SERIAL 507(Demonstrating Superior Efficacy of North American Equine E159(NAEE159) Vaccines, and that other North American Dominant Vaccines, such as North American Donkey E159(NADE159 will provide superior efficacy to NY99 vaccines)
Guinea Pig Serological Evaluation for West Nile Virus

TABLE 27

Experimental Serial 507 West Nile Guinea Pig Plaque Reduction
Neutralization Results using WNV NY 1999 Isolate as Indicator Virus
Number of Plaques/Sera Dilution

| Guinea Pig Number | 4 | 8 | 16 | 32 | 64 |
|---|---|---|---|---|---|
| GP1 | >10 | >15 | >15 | >14.5 | >10.5 |
| GP2 | 4.5 | 5 | 7.5 | 9.5 | 13 |
| GP3 | 1 | 3.5 | 3.5 | 6 | 6.5 |

TABLE 27-continued

Experimental Serial 507 West Nile Guinea Pig Plaque Reduction
Neutralization Results using WNV NY 1999 Isolate as Indicator Virus
Number of Plaques/Sera Dilution

| Guinea Pig Number | 4 | 8 | 16 | 32 | 64 |
|---|---|---|---|---|---|
| GP4 | 8 | 11.5 | >13.5 | >14.5 | >14.5 |
| GP5 | 6 | 7.5 | 7.5 | 8.5 | 9 |
| GP6 | 8.5 | 9.5 | 9.5 | 12 | 14 |
| GP7 | 7 | 8.5 | 9 | >10.5 | >14.5 |
| GP8 | 5 | 10.5 | 10.5 | 14 | 14 |
| GP9 | 5.5 | 7 | 7.5 | 10 | 10 |
| GP10 | 5.5 | 6.5 | 8.5 | >12.5 | 14 |
| # Passed | 9/10 | 6/10 | 5/10 | 2/10 | 1/10 |
| Neg. Control 1 | ≥13.5 | ≥13.5 | ≥13 | ≥13 | ≥14.5 |
| Neg. Control 2 | ≥15.5 | ≥14.5 | ≥16 | ≥17 | ≥16.5 |

Virus Control Values: ≥24, ≥15, ≥14, ≥16, ≥18, ≥20
Virus Control Average Plaques: ≥17.8
Virus Control 50% Reduction: ≥8.9

TABLE 28

Experimental Serial 507 West Nile Guinea
Pig Plaque Reduction Neutralization
Results Using North American Equine
E159(NAEE159)as Indicator Virus
Number of Plaques/Sera Dilution

| Guinea Pig Number | 2 | 4 | 8 | 16 | 32 | 64 |
|---|---|---|---|---|---|---|
| GP1 | 17 | 14 | 18.5 | 14.5 | 19.5 | 26 |
| GP2 | 2.5 | 3.5 | 2 | 6 | 17 | 15 |
| GP3 | 5.5 | 10 | 4.5 | 9 | 5 | 11.5 |
| GP4 | 11.5 | 10 | 15 | 15.5 | 19 | 19.5 |
| GP5 | 13 | 23 | 23.5 | 19.5 | 32.5 | 13 |
| GP6 | 5.5 | 8.5 | 12 | 11 | 13 | 14 |
| GP7 | 8.5 | 12 | 14 | 15 | 16 | 12 |
| GP8 | 14.5 | 14 | 18 | 19.5 | 25.5 | 27.5 |
| GP9 | 1.5 | 3 | 3 | 8.5 | 15.5 | 7 |
| GP10 | 12.5 | 12 | 7 | 18.5 | 14 | 13 |
| # Passed | 9/10 | 9/10 | 7/10 | 7/10 | 5/10 | 7/10 |
| Neg. Control 1 | 24.5 | 21 | 22 | 23.5 | 22 | 25 |
| Neg. Control 2 | 24 | 33 | 29 | 29 | 24.5 | 34.5 |

Virus Control Values: 40, 38, 34, 35, 28, 23
Virus Control Average: 33
Virus Control 50% Reduction: 16.5

Discussion and Conclusions

Guinea pigs were vaccinated and sera tested for West Nile Virus antibody. This assay established that a titer of 1:12 in vaccinated guinea pigs correlates to protection in a horse vaccination/challenge study that provides at least one year duration of immunity for WNV vaccine prepared using a North American Dominant isolate of WNV, such as North American Equine E159(NAEE159).

Concurrently with guinea pig vaccinations, WNV vaccine prepared using a North American Dominant isolate of WNV, North American Equine E159(NAEE159), was also administered to horses (20 vaccinates and 10 controls) via primary immunization followed by booster immunization 3 weeks later. More than one year post-booster vaccination, horses were subjected to virulent West Nile Virus challenge, and were protected when compared to non-vaccinated controls. Vaccinated horses were protected from viremia, clinical signs, mortality, and encephalitic lesions after virulent heterologous challenge with West Nile Virus.

In addition the data substantiate the superior efficacy of WNV vaccines prepared using North American Dominant WNV, as opposed to previously developed vaccines derived from WNV NY99. The sera from the vaccinated guinea pigs were tested for neutralizing antibody to both a North American Dominant isolate of WNV and to WNV isolate NY99. Titers to the isolate frequently occurring in North America, namely North American Dominant (NAEE159), were consistently higher in vaccinated guinea pigs as compared to titers to the isolate that is no longer reported to be present in nor causing disease in North America, WNV NY99. Hence, the vaccine displayed superior activity in stimulating neutralizing antibodies to North American Dominant WNV, as opposed to NY99 WNV. These data support the conclusion of the superior efficacy of WNV vaccines prepared from North American Dominant WNV isolates as contrasted with earlier less effective vaccines prepared from or based on the NY99 WNV isolate.

Example 10

This Example illustrates the genetic differences between North American WNV strains and North American Dominant WNV strains, as used in the present invention.

Materials and Methods

Relevant areas of the genome of WNV NY99 and the North American Dominant WNV isolates suitable for preparation of a novel, superior vaccine were sequenced and compared to confirm the key genetic differences. Examples of North American Dominant isolates used in vaccine preparation include North American Equine E159(NAEE159) (ATCC Accession No. PTA-9409) and North American Donkey E159(NADE159).

Results and Conclusions

Figure 10B:
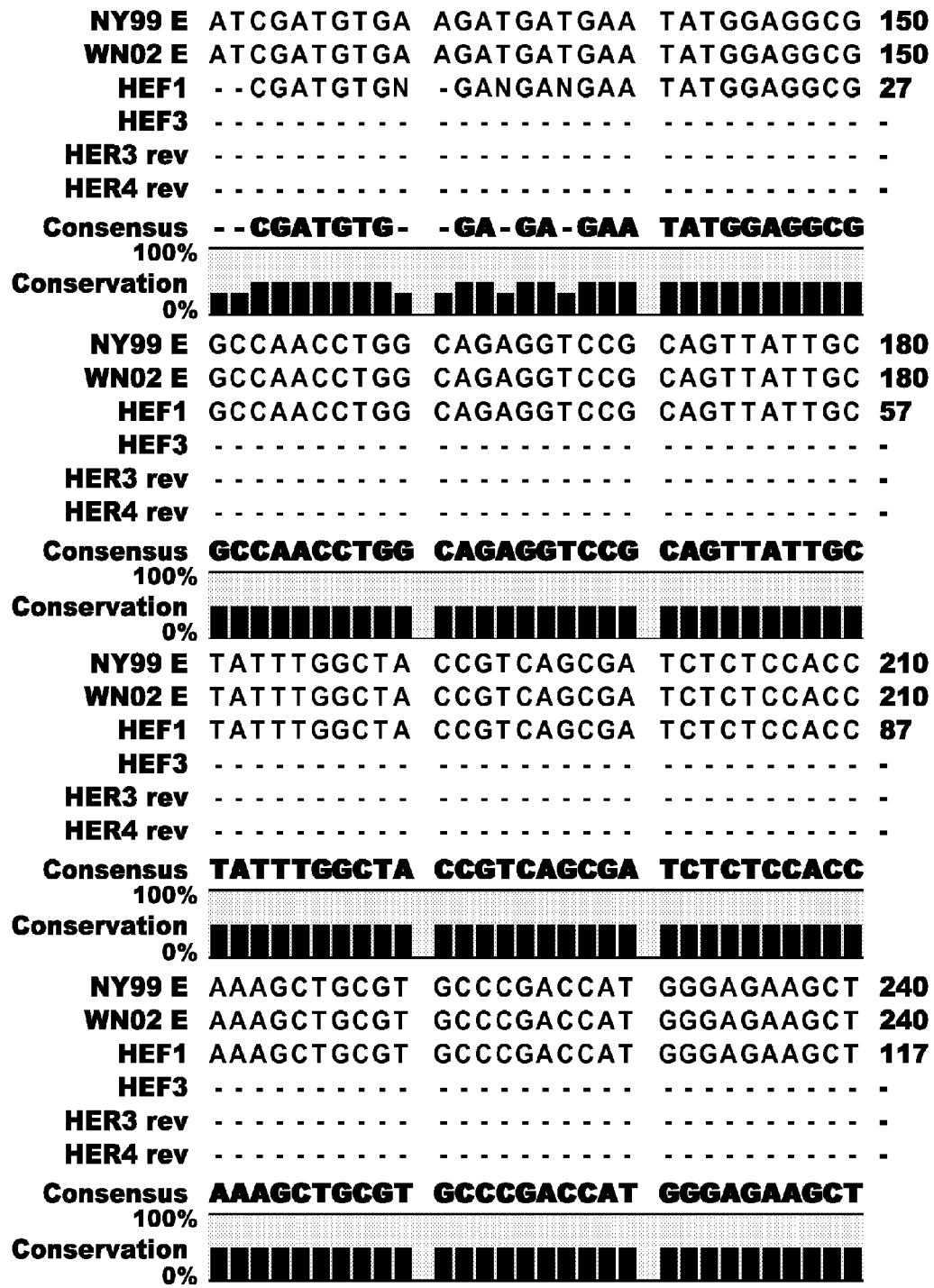
Figure 10C:
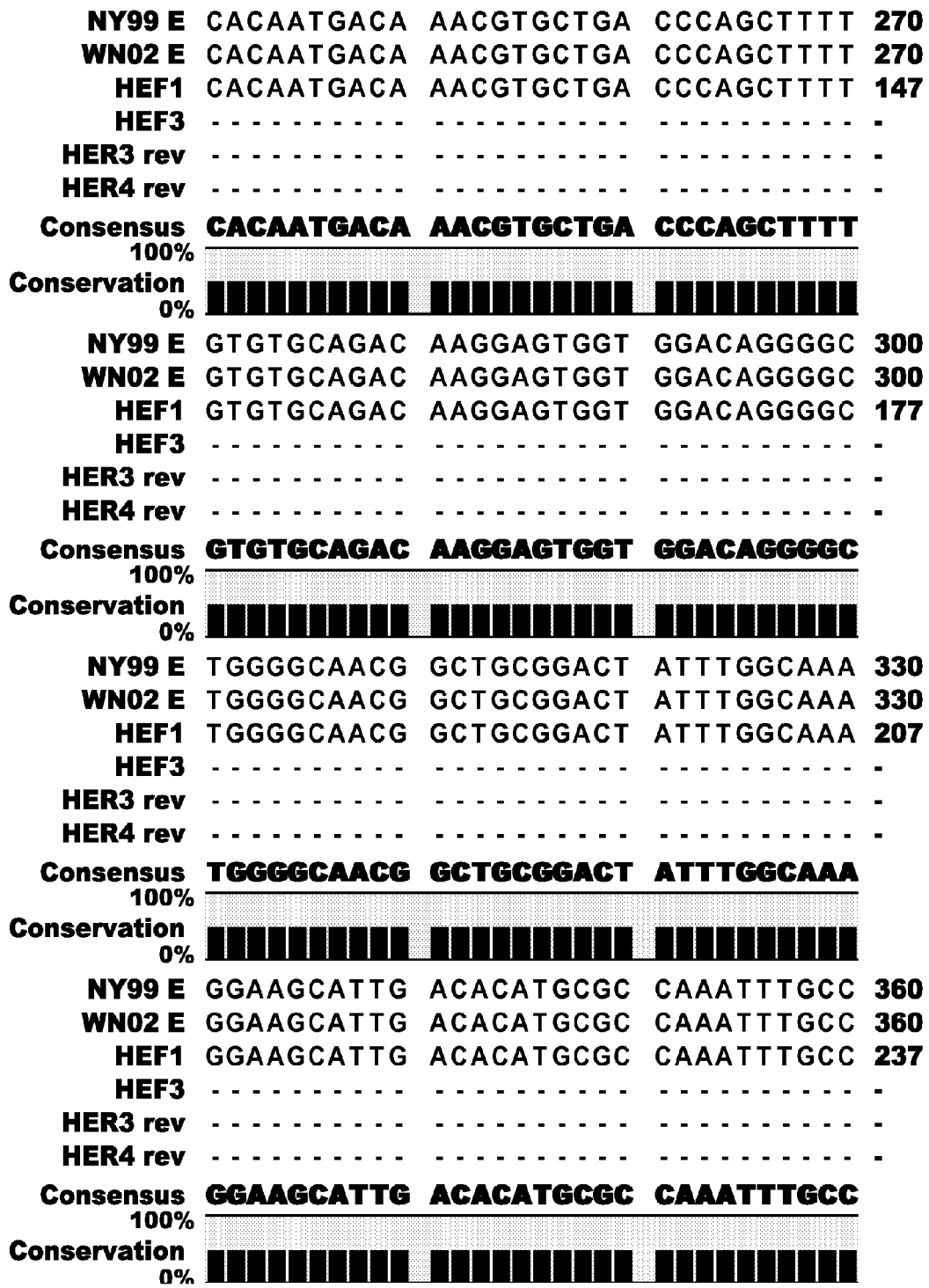
Figure 10E:
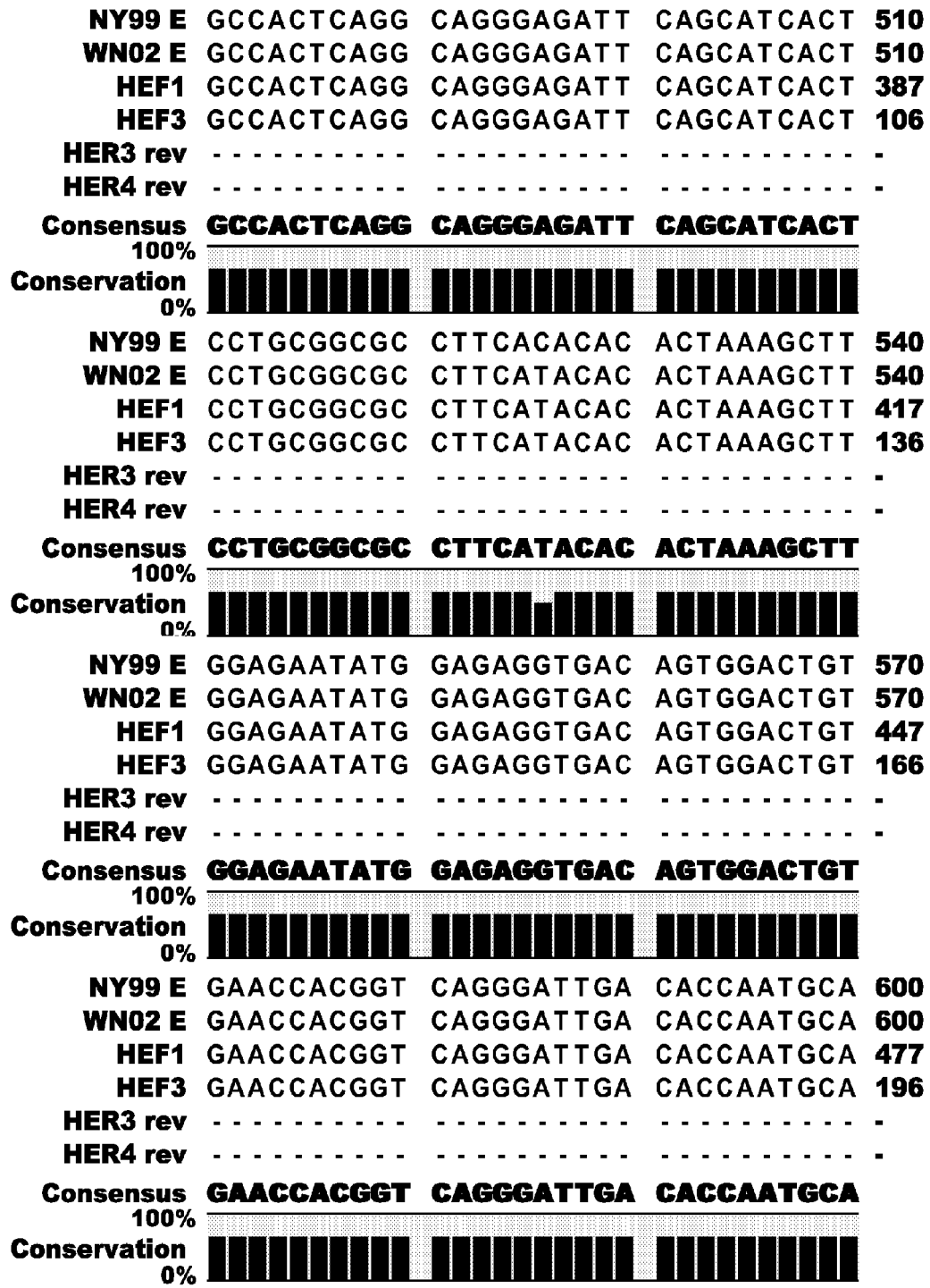
Figure 10G:
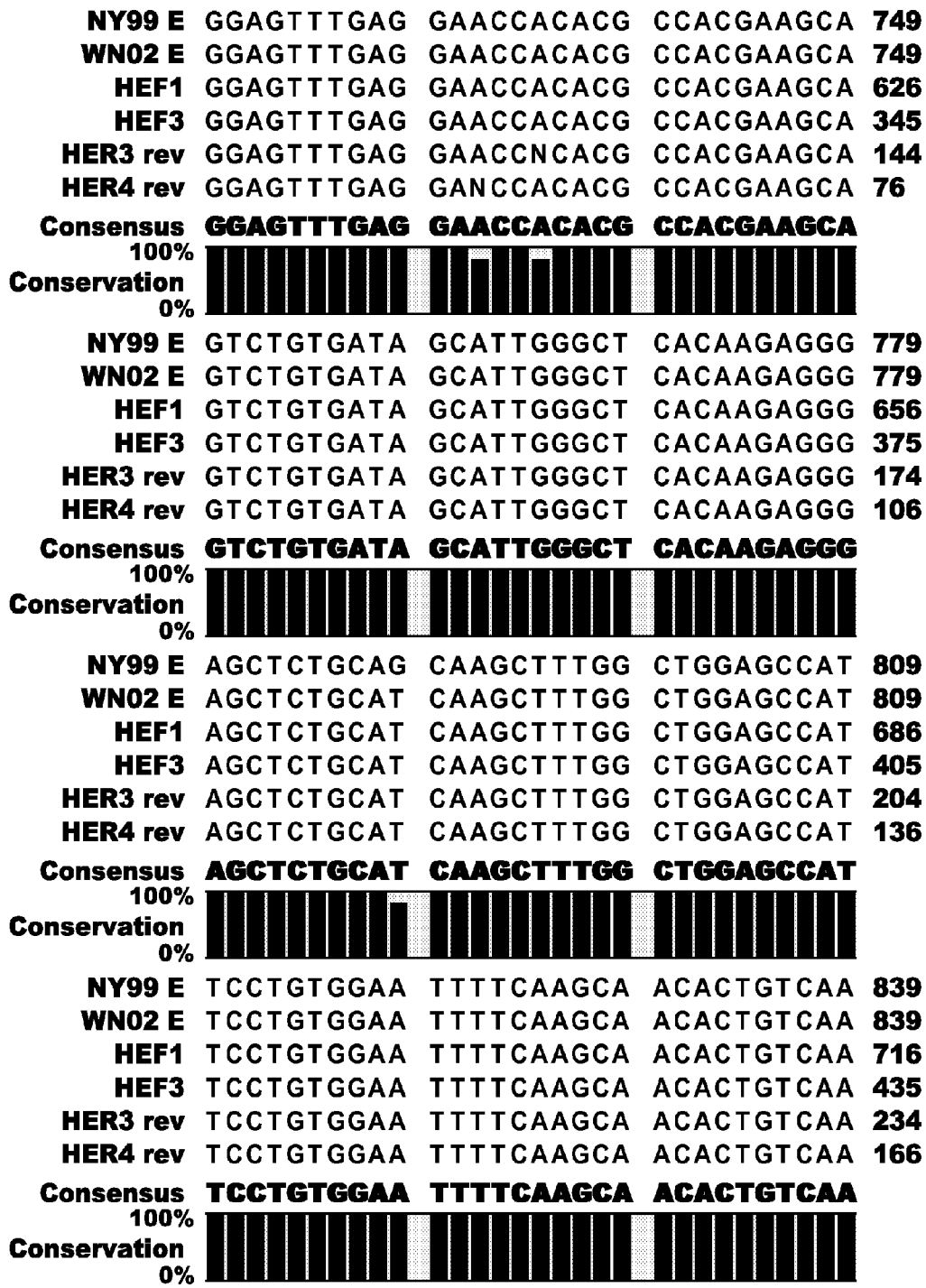
Figure 10H:
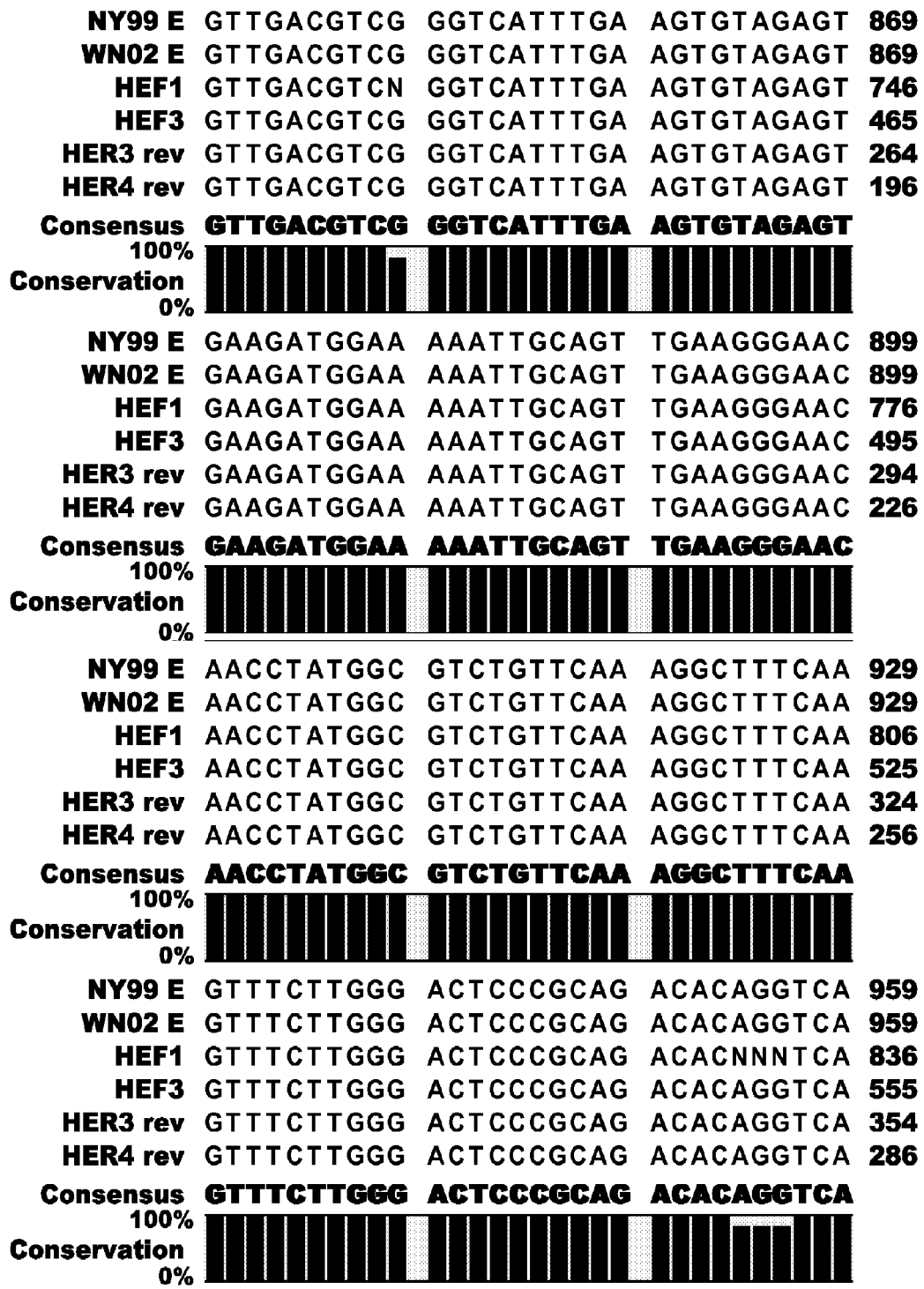
Figure 10I:
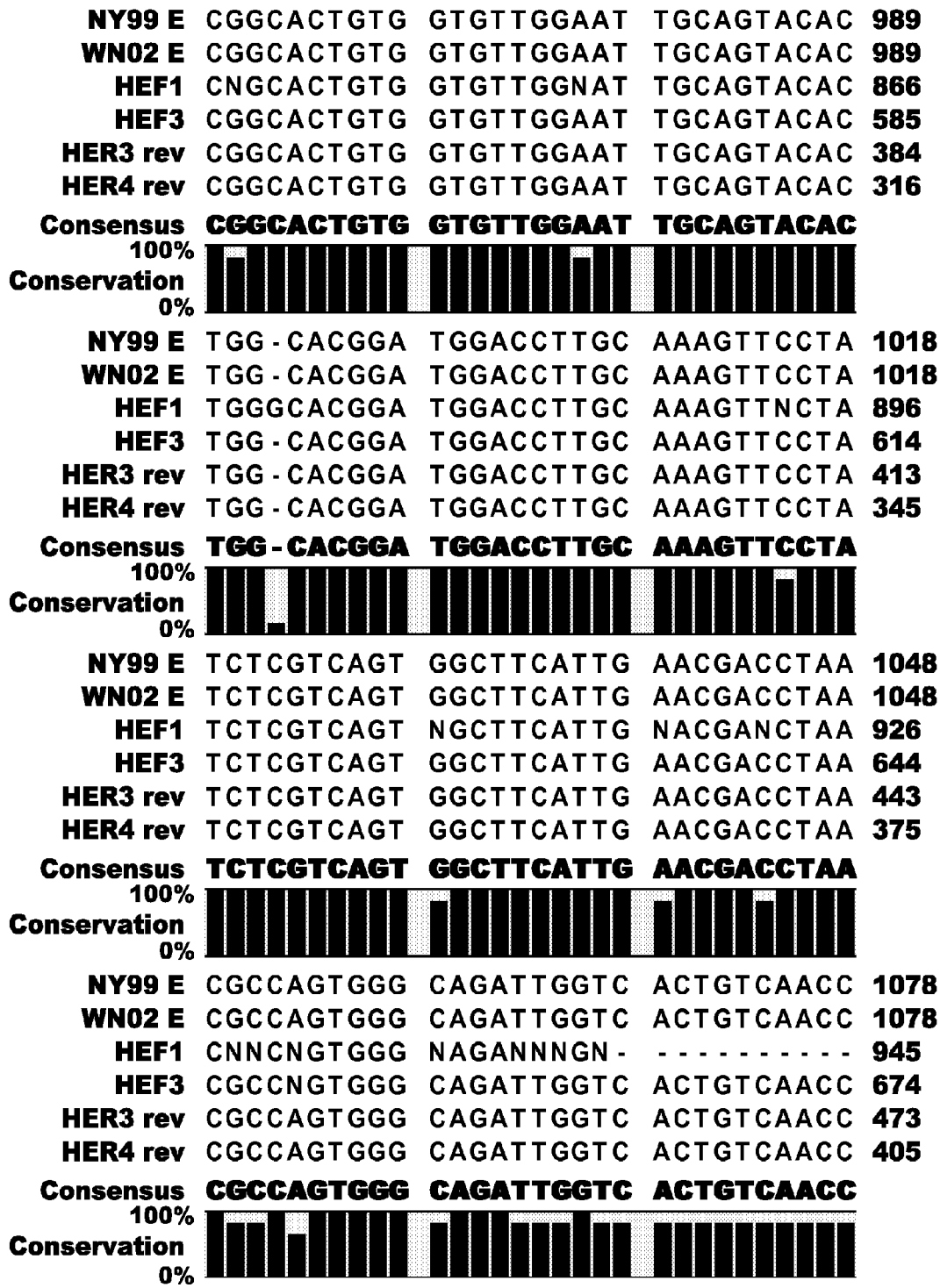
Figure 10J:
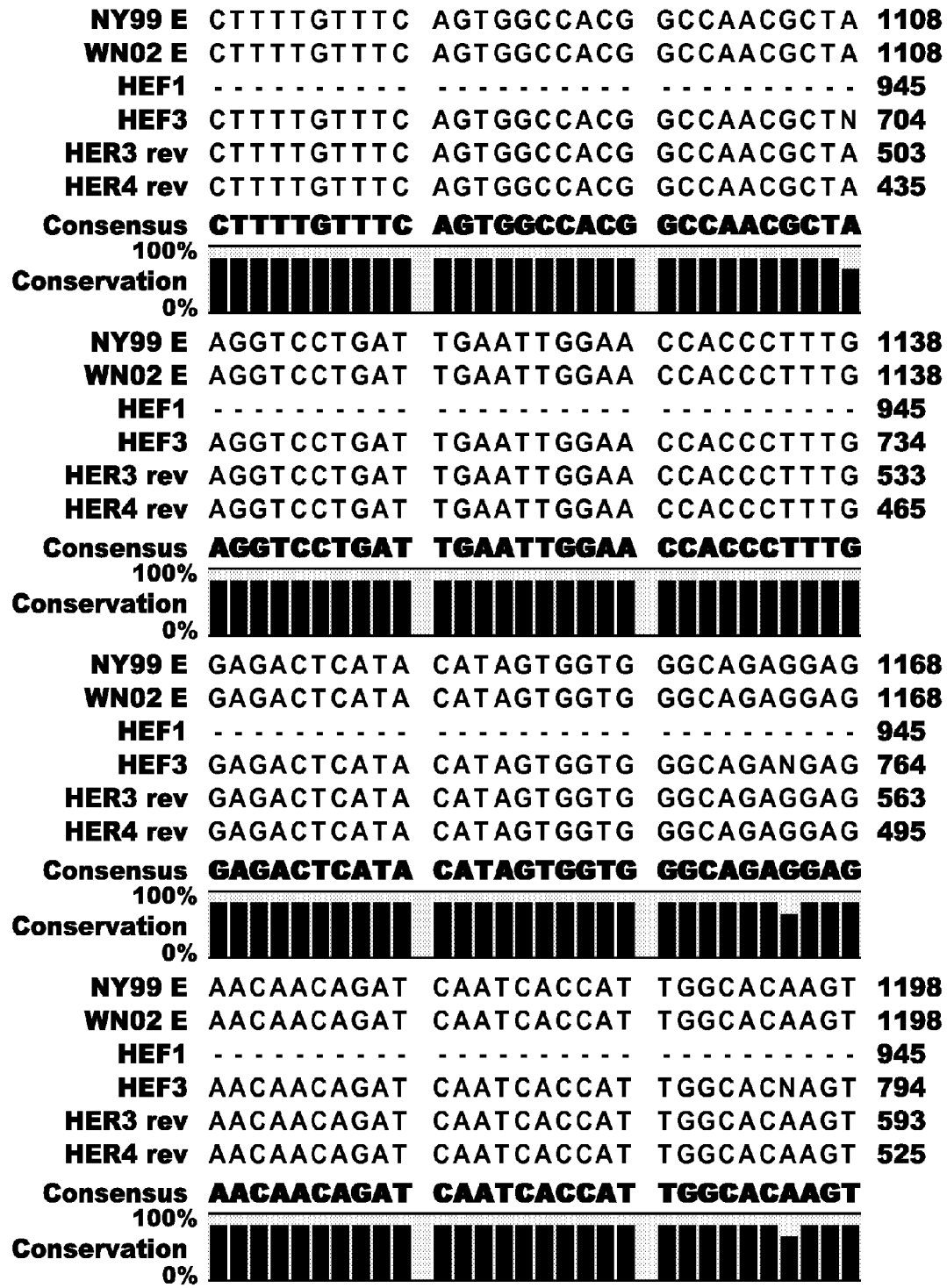
Figure 10K:
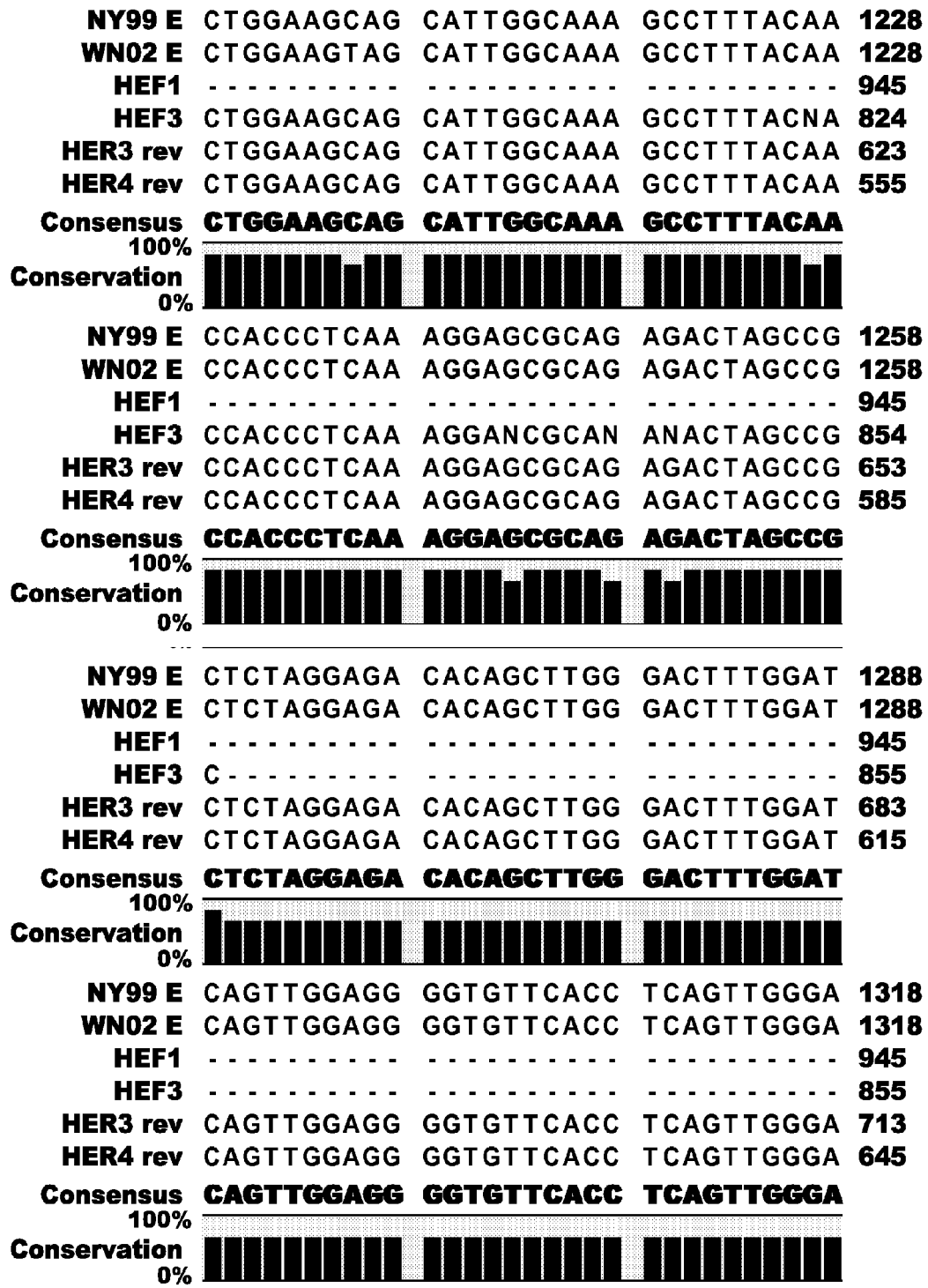
Figure 10M:
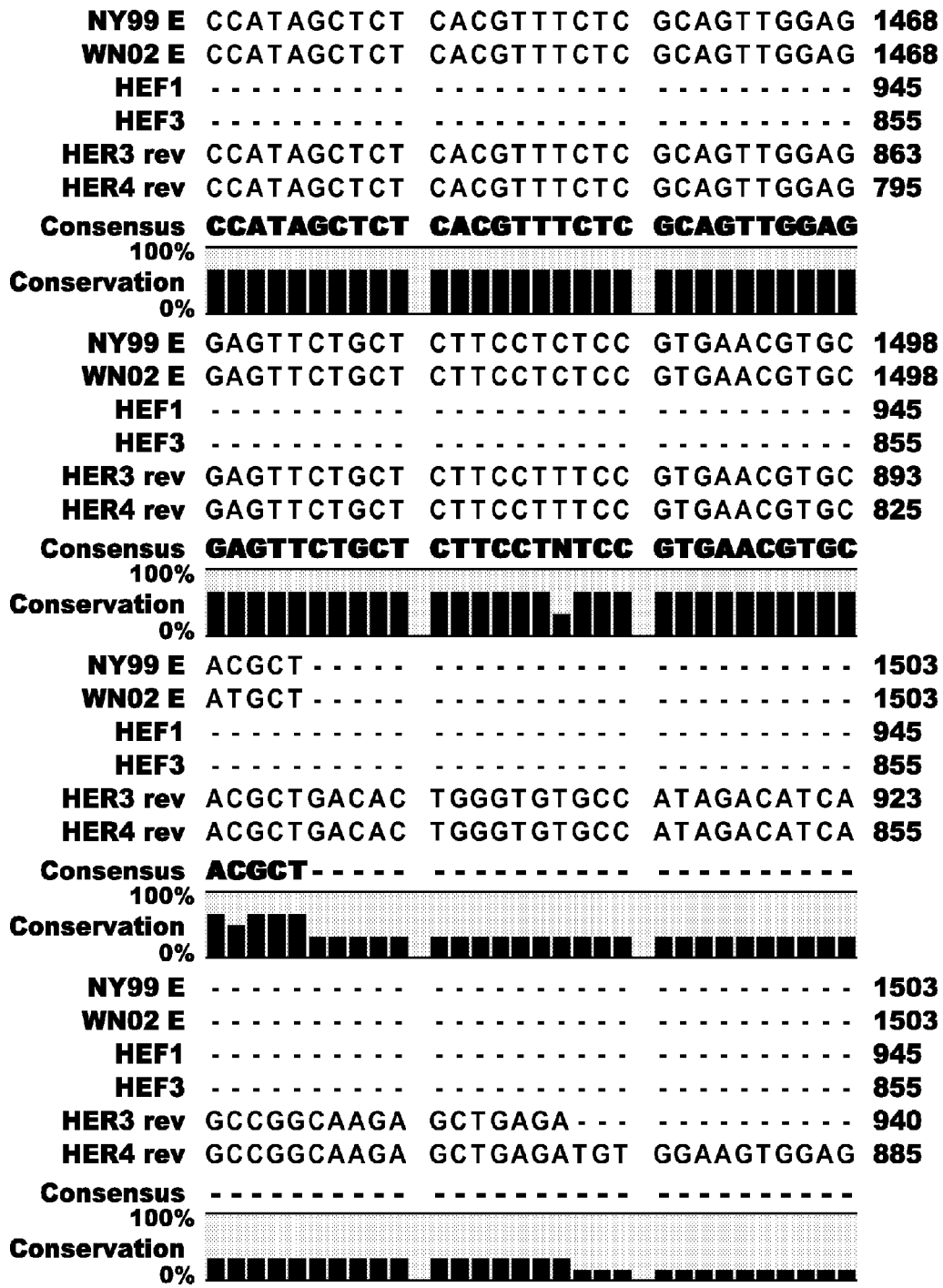
Figure 10N:
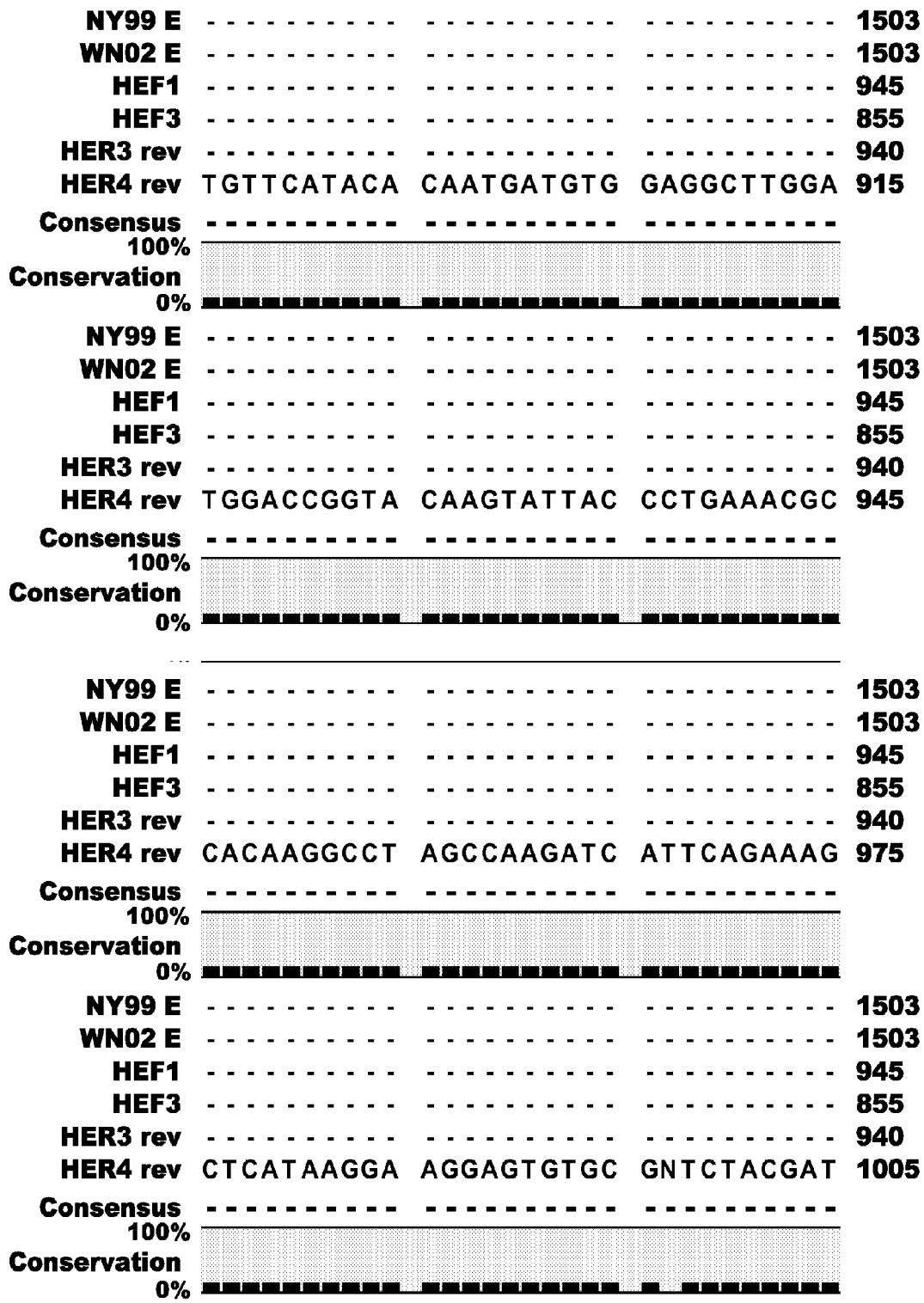
Figure 11A:
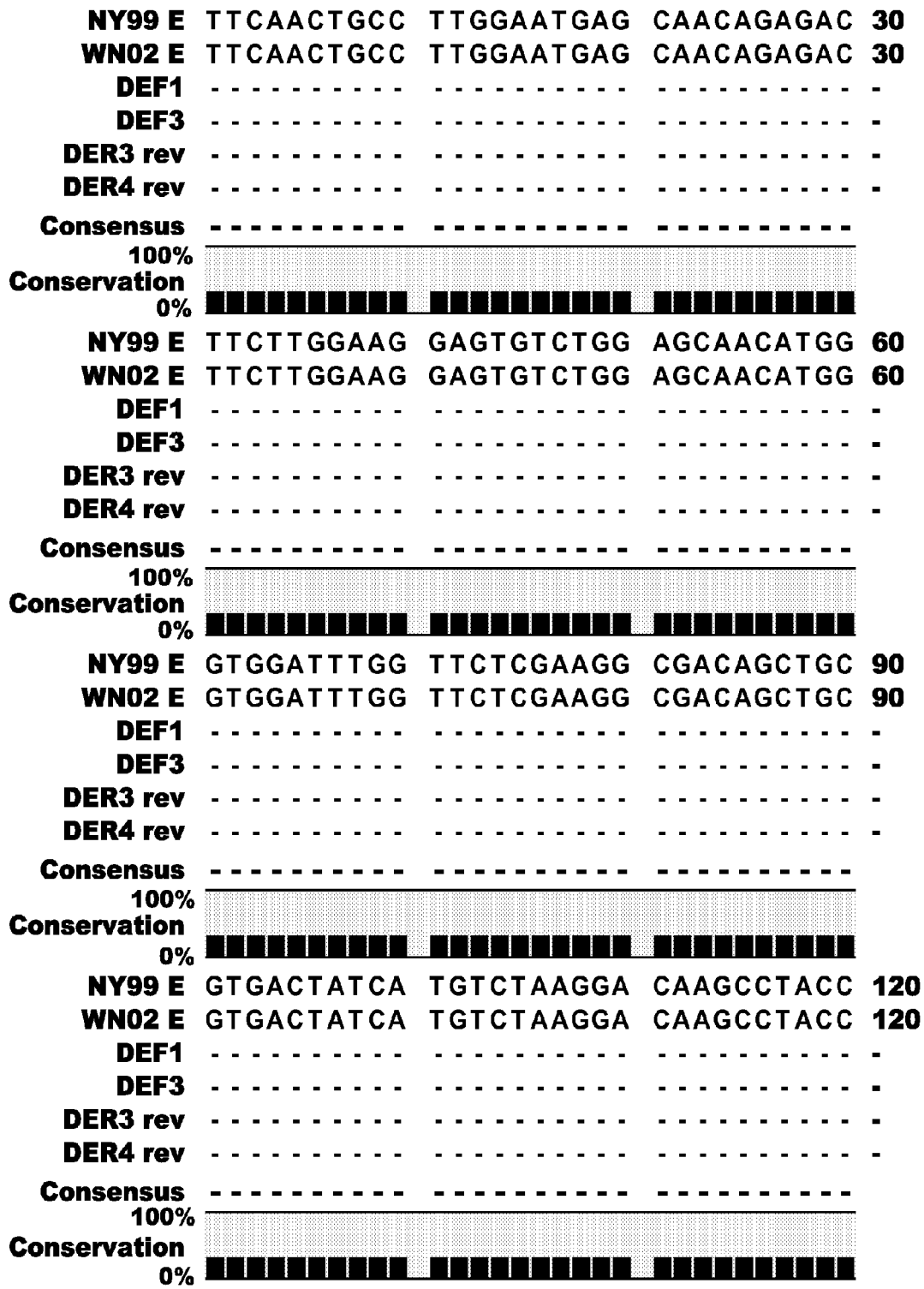
FIG. 11 is a nucleotide alignment of the DE region of WNV isolates.
Figure 11B:
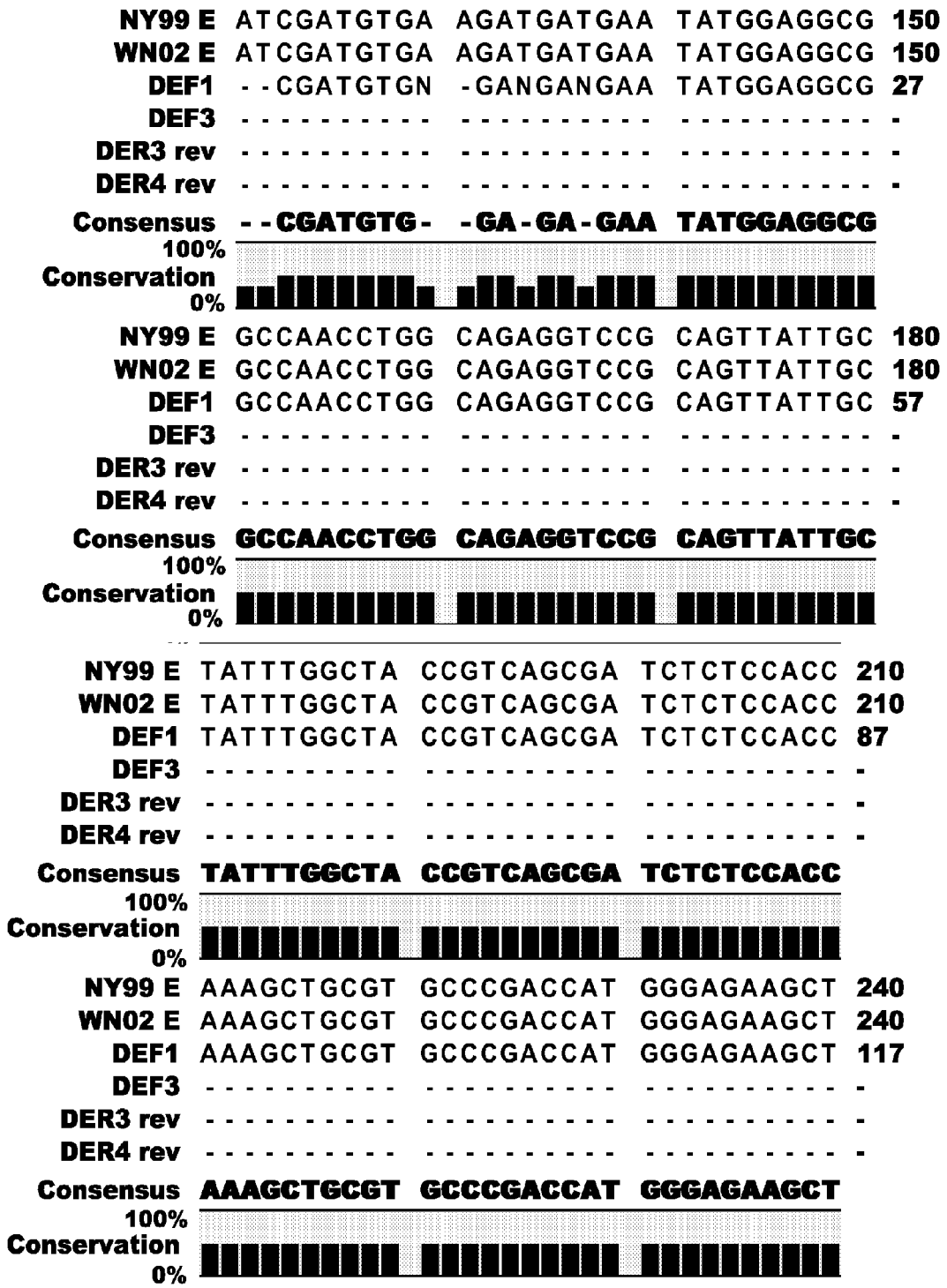
Figure 11D:
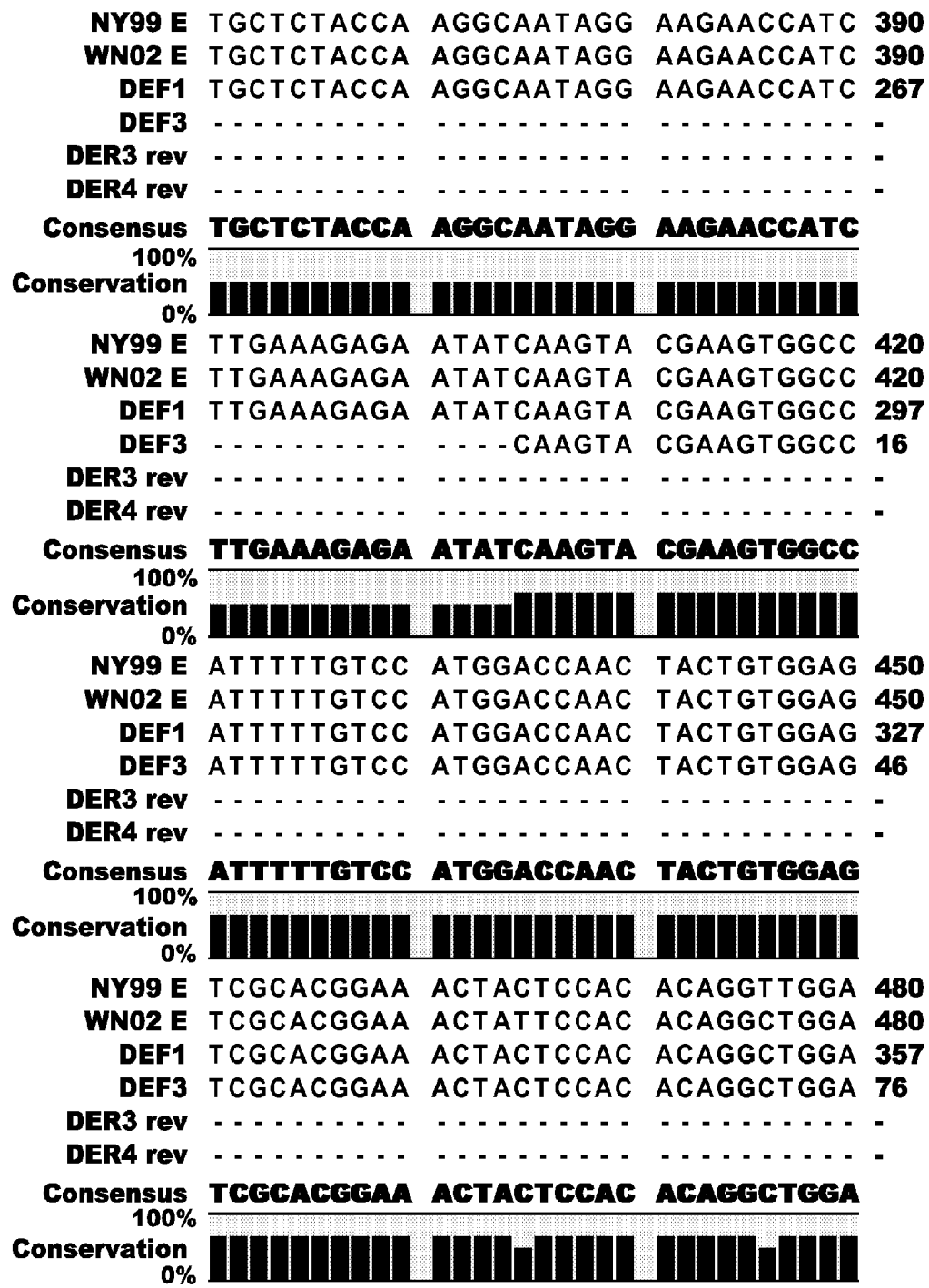
Figure 11F:
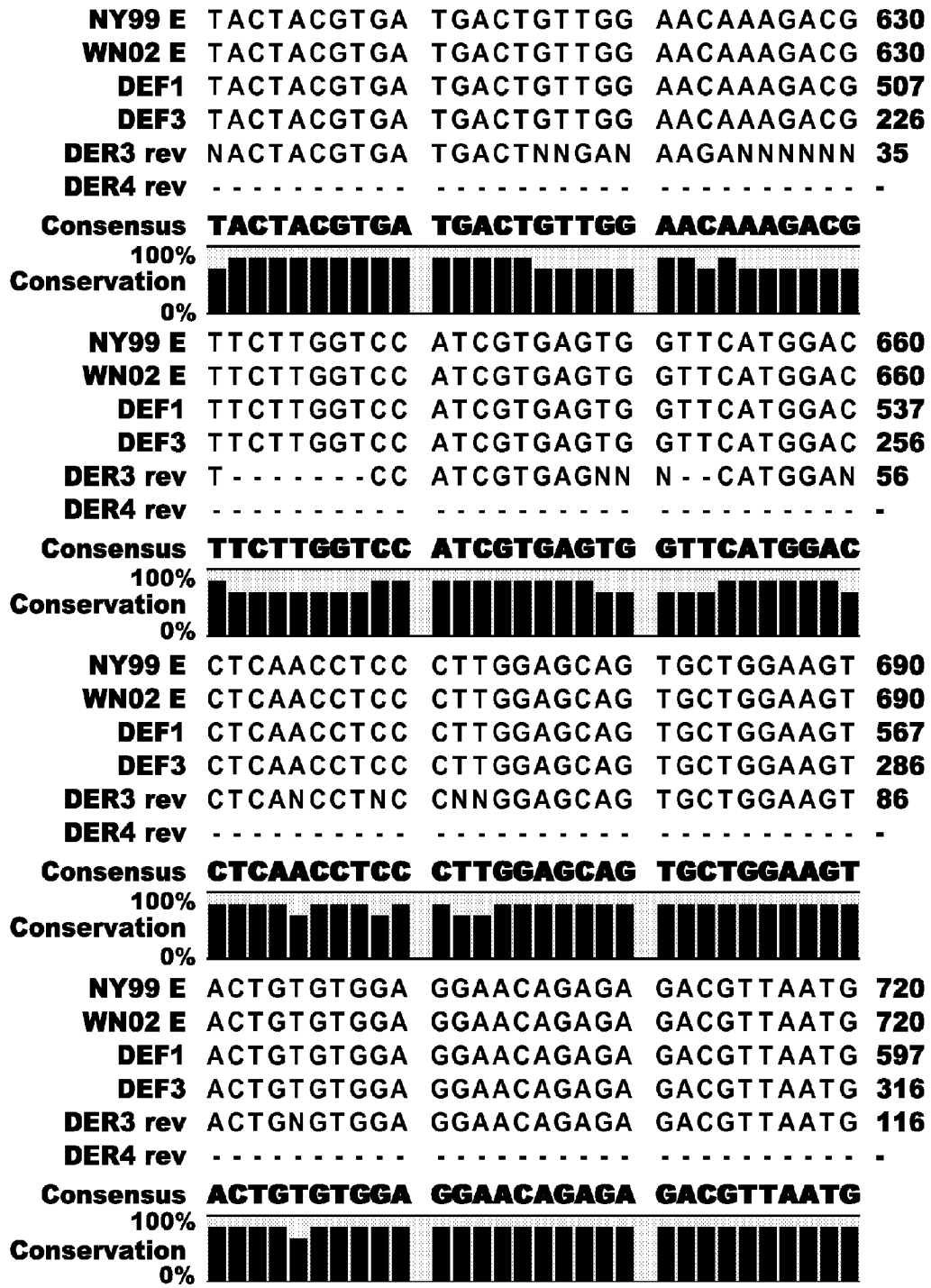
Figure 11G:
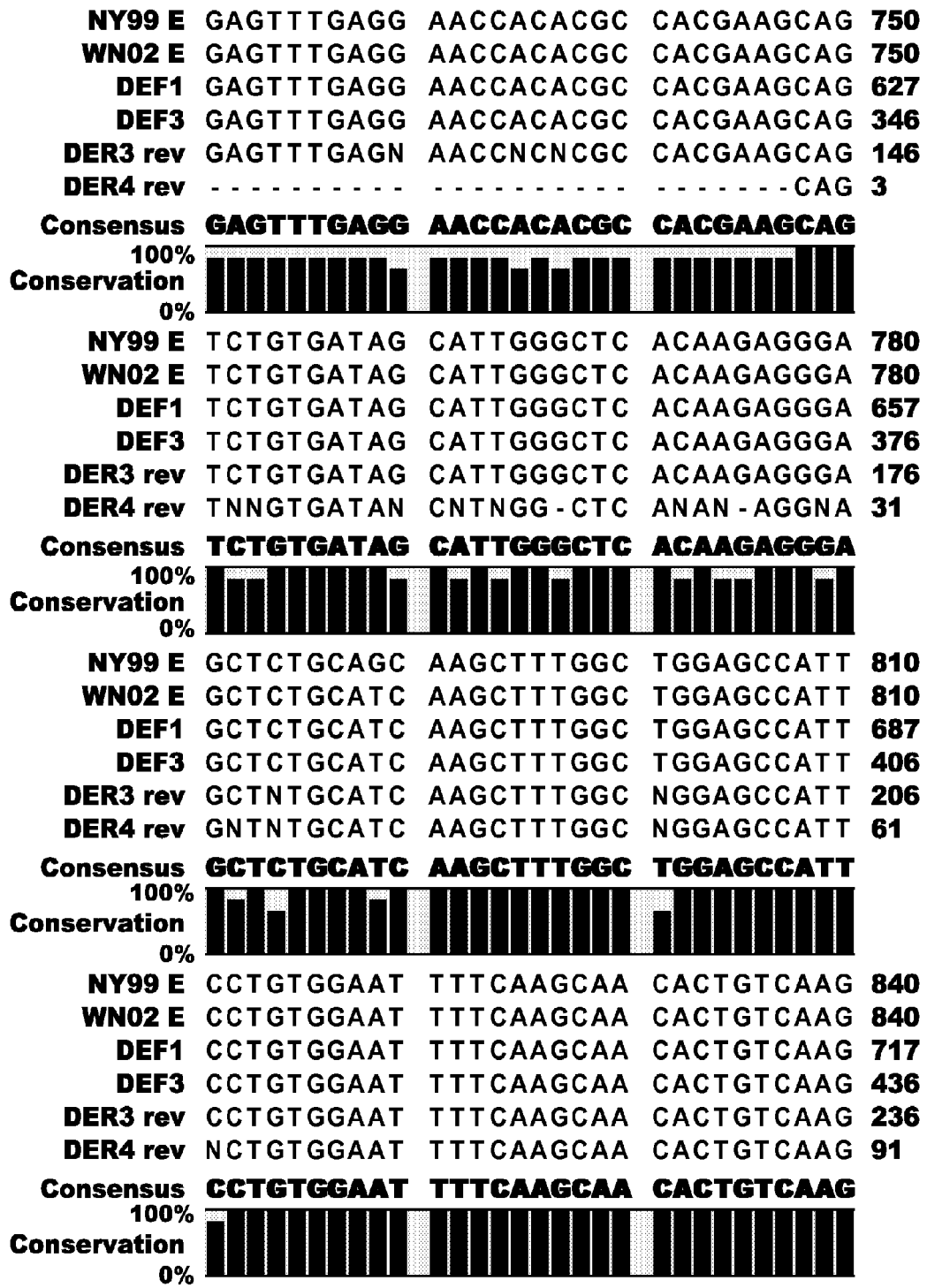
Figure 11I:
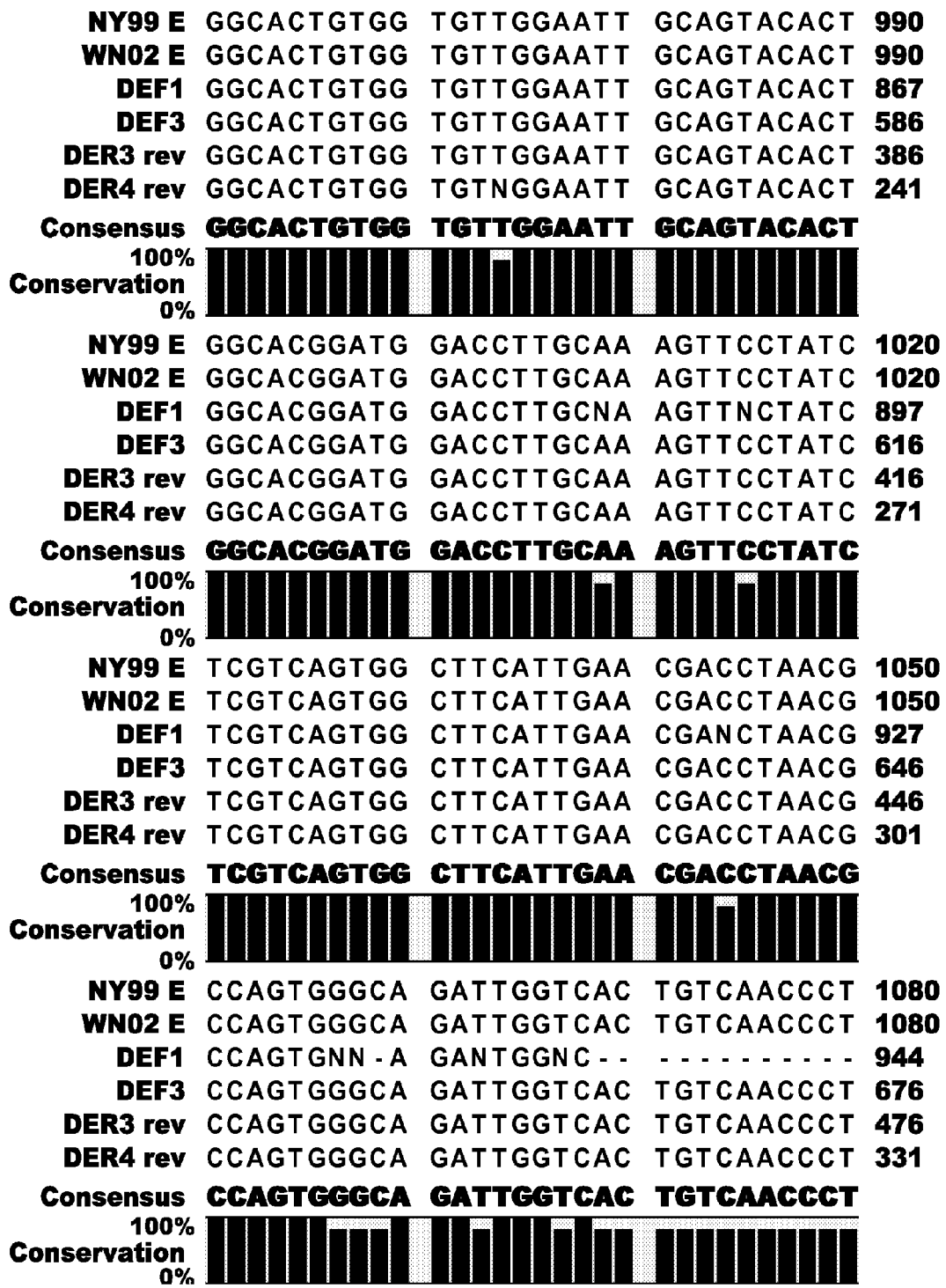
Figure 11M:
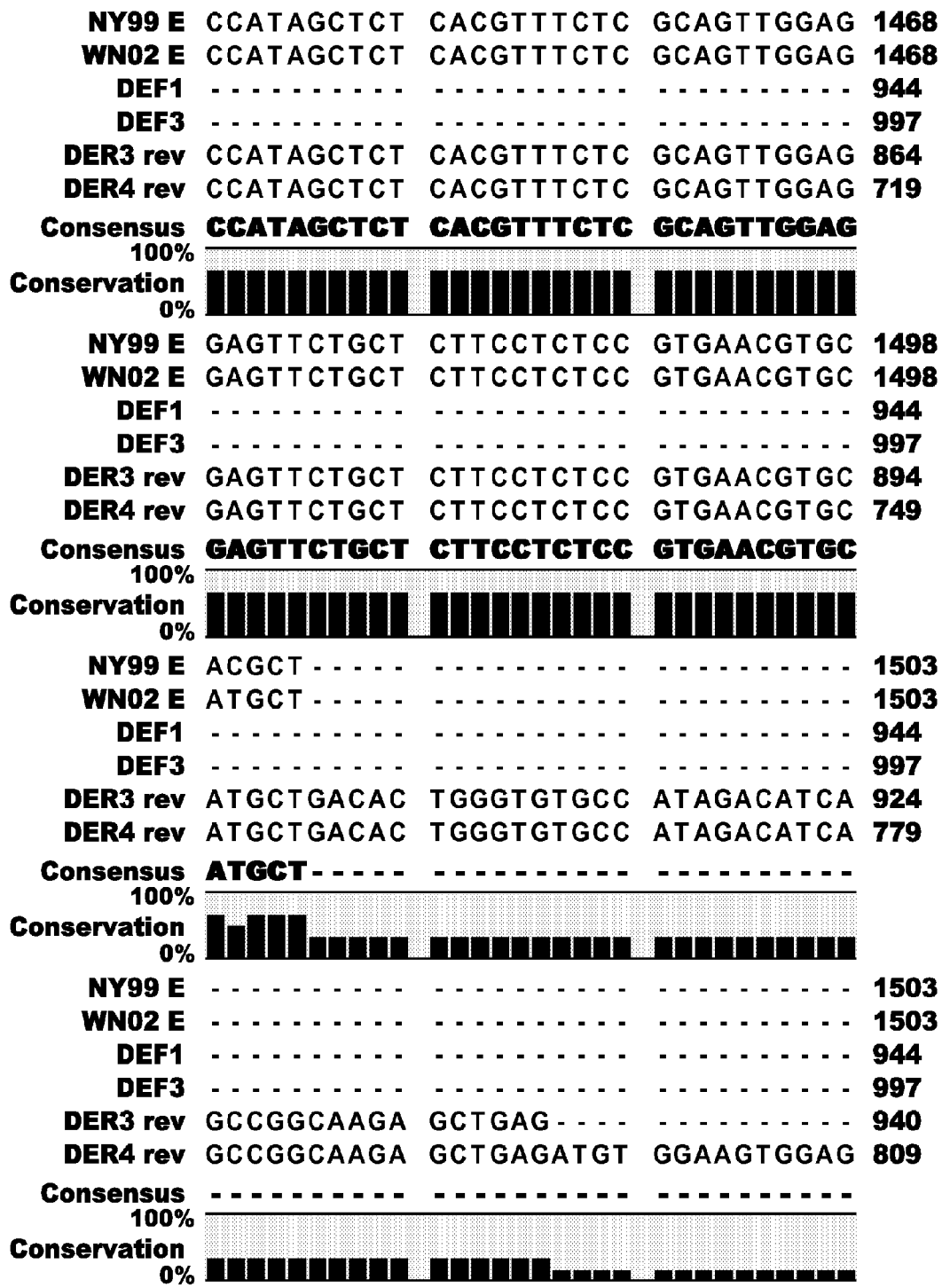
Figure 12A:
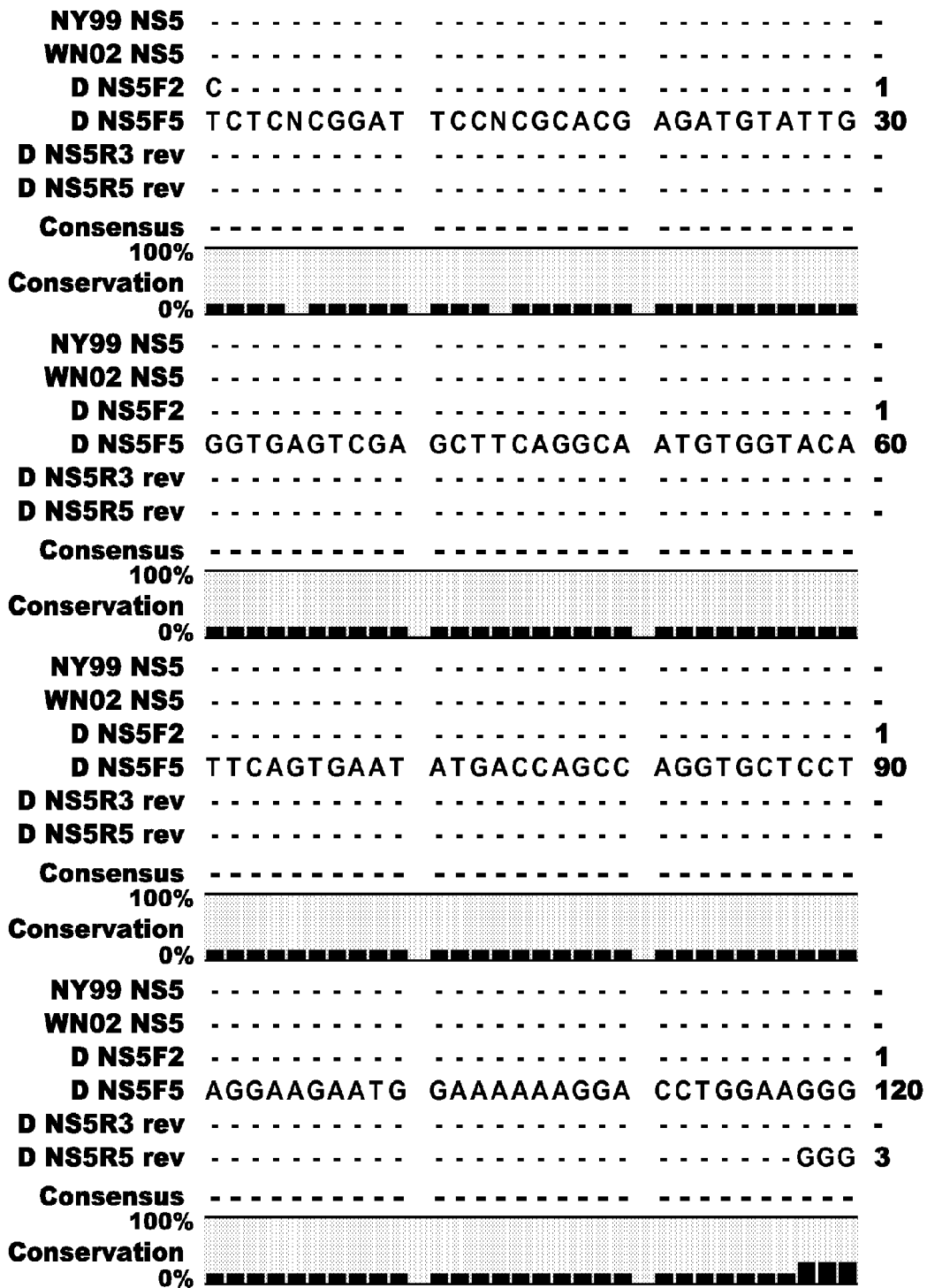
FIG. 12 is a nucleotide alignment of the D NS5 region of WNV isolates.
Figure 12C:
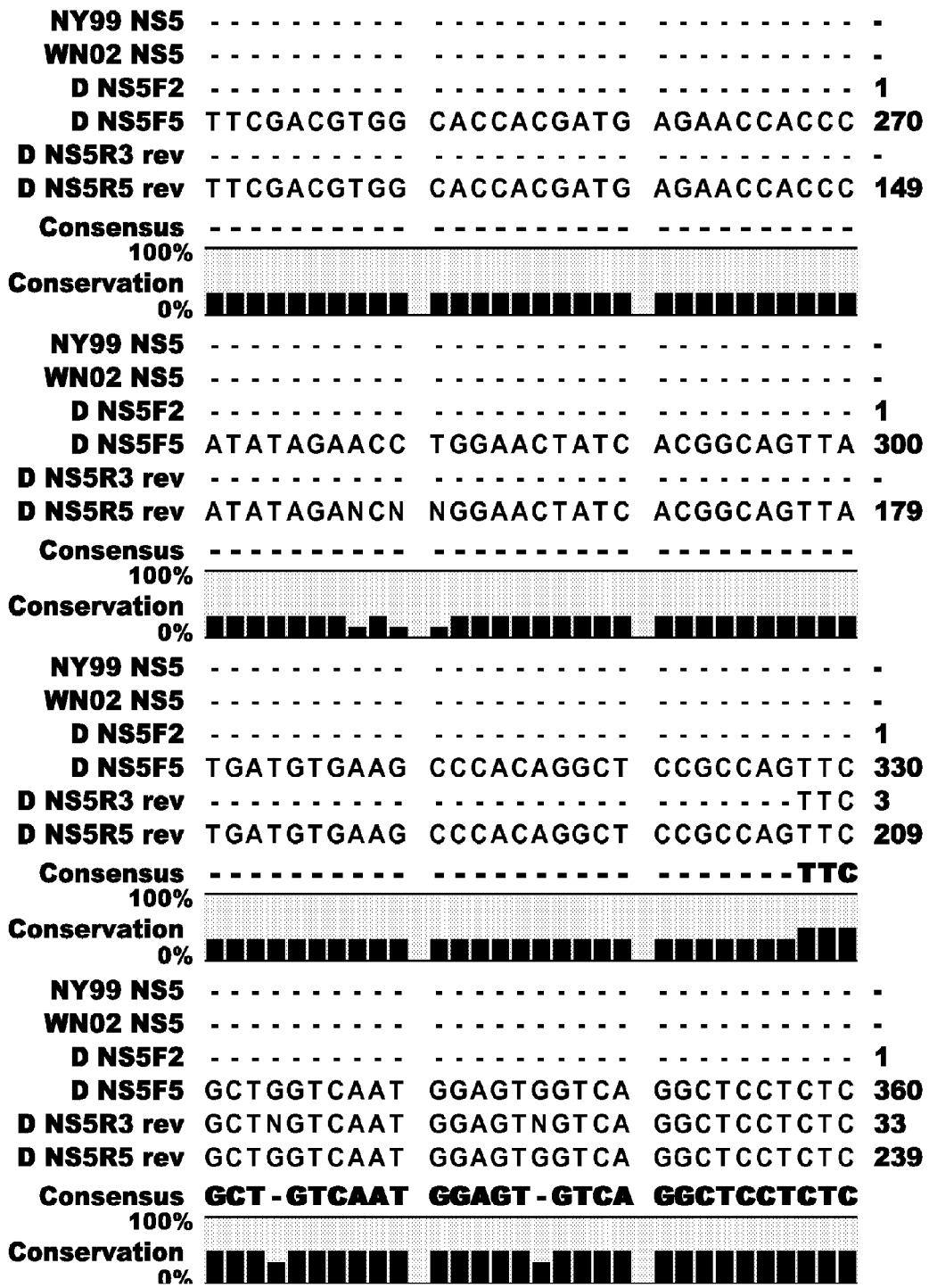
Figure 12D:
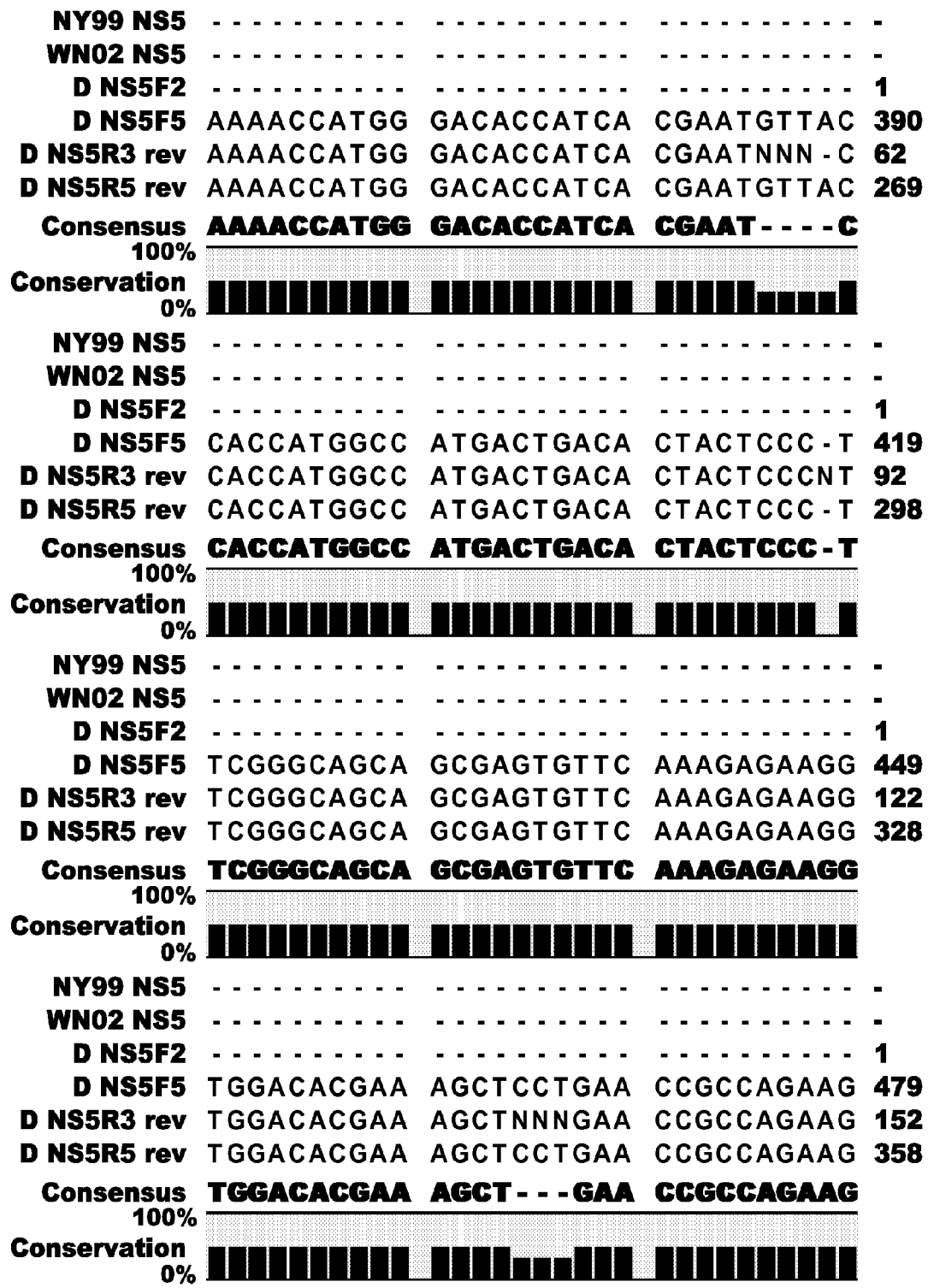
Figure 12E:
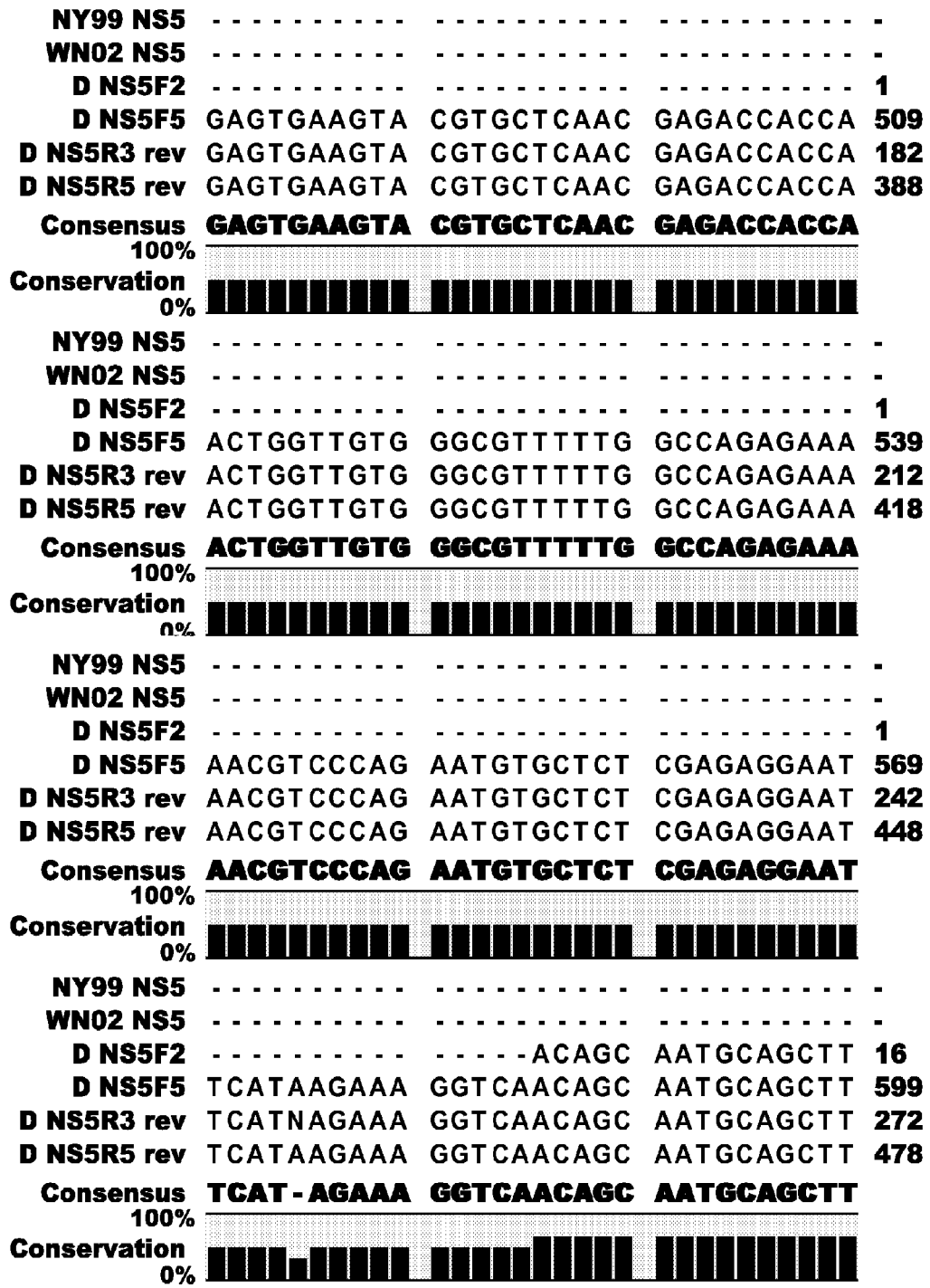
Figure 12H:
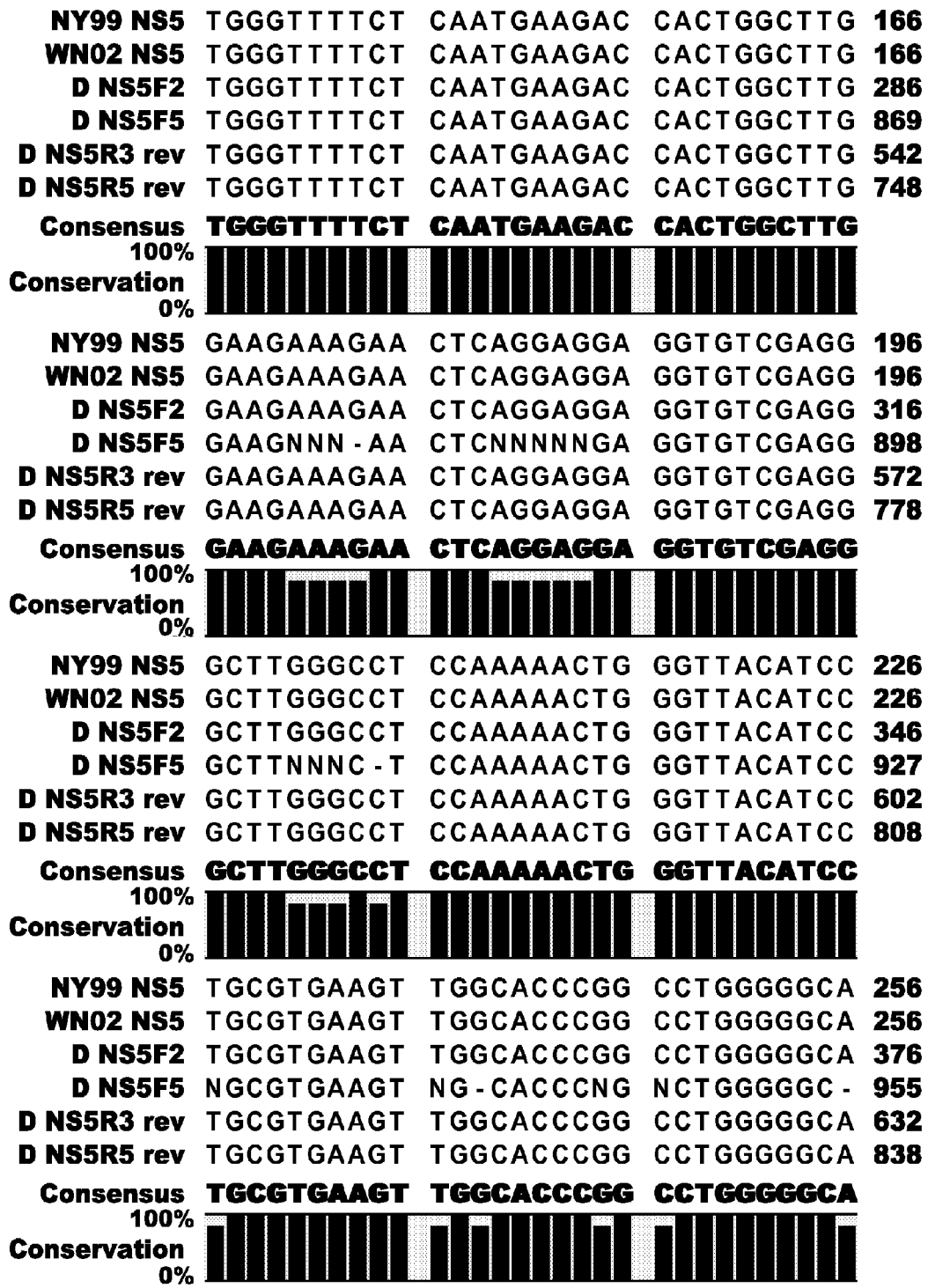
Figure 12M:
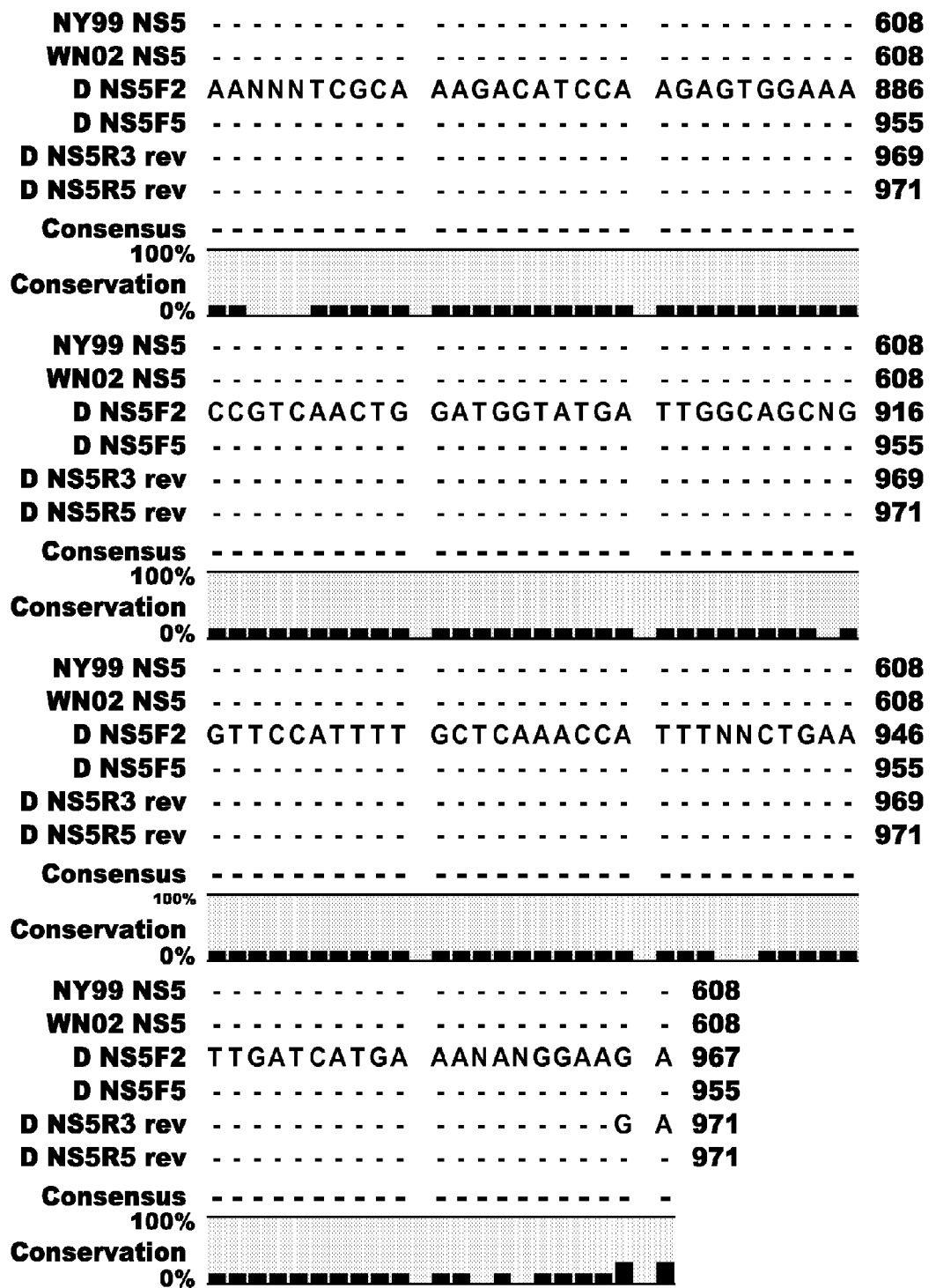
Figure 13A:
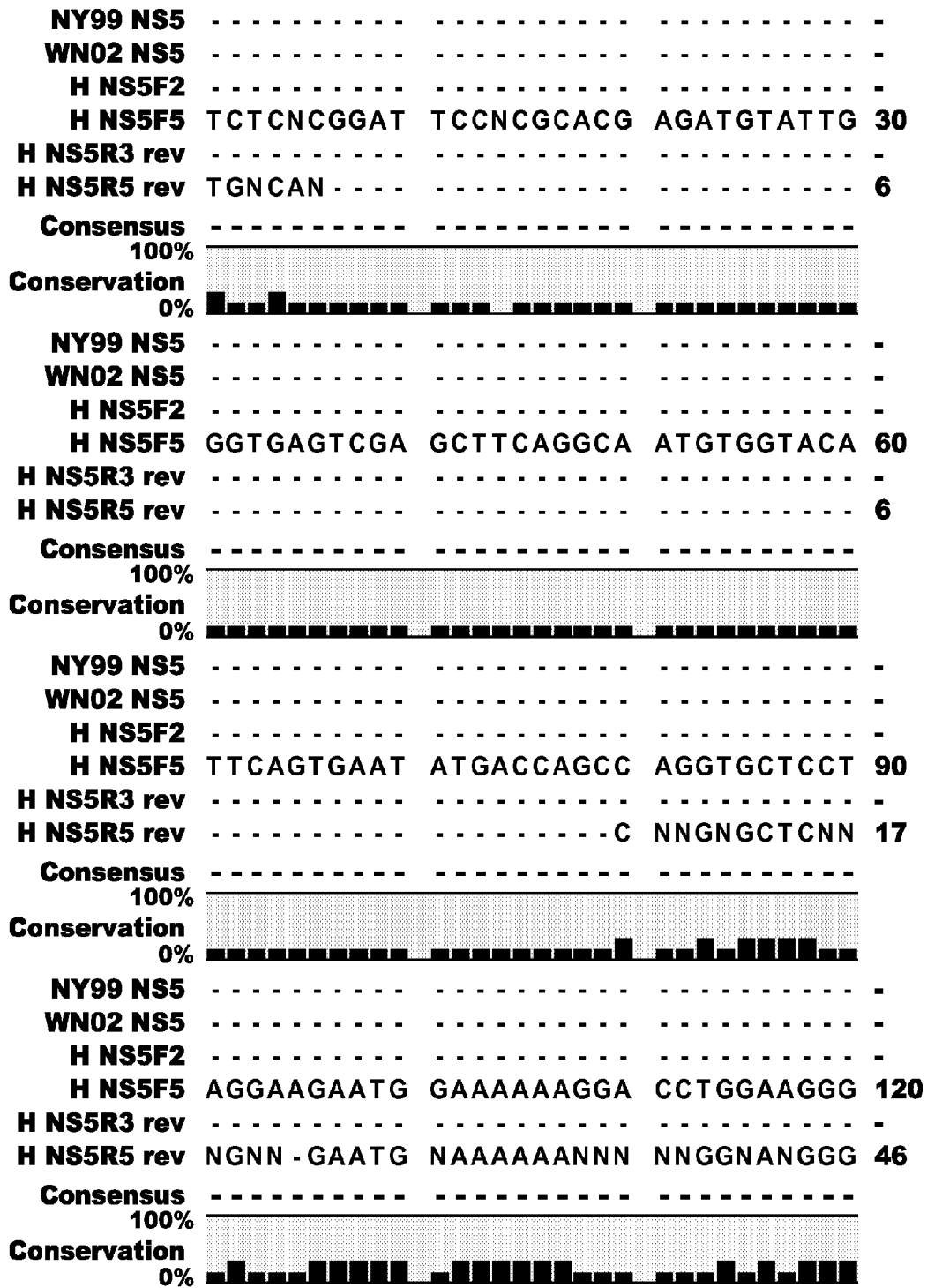
FIG. 13 is a nucleotide alignment of the H NS5 region of WNV isolates.
Figure 13B:
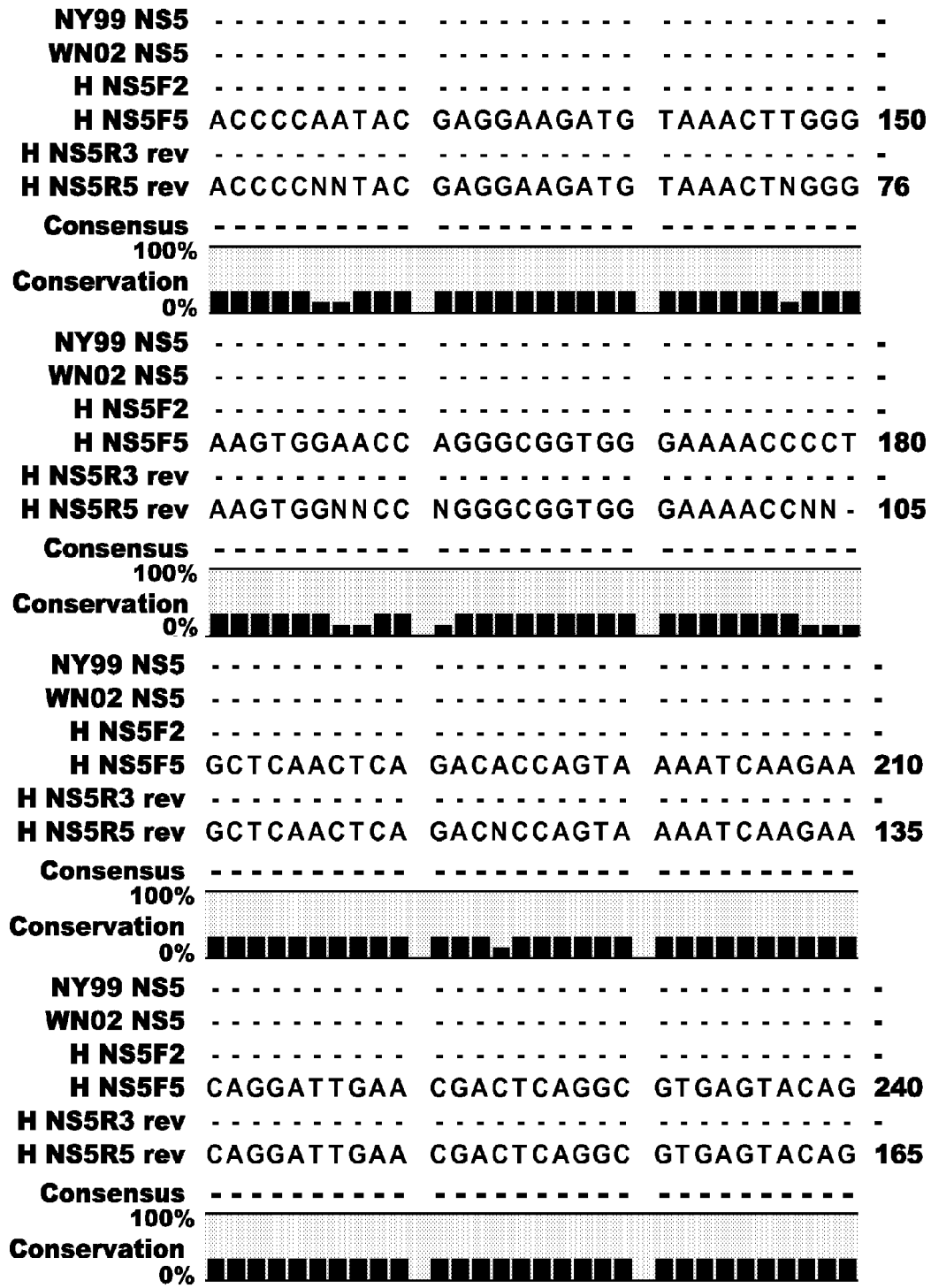
Figure 13C:
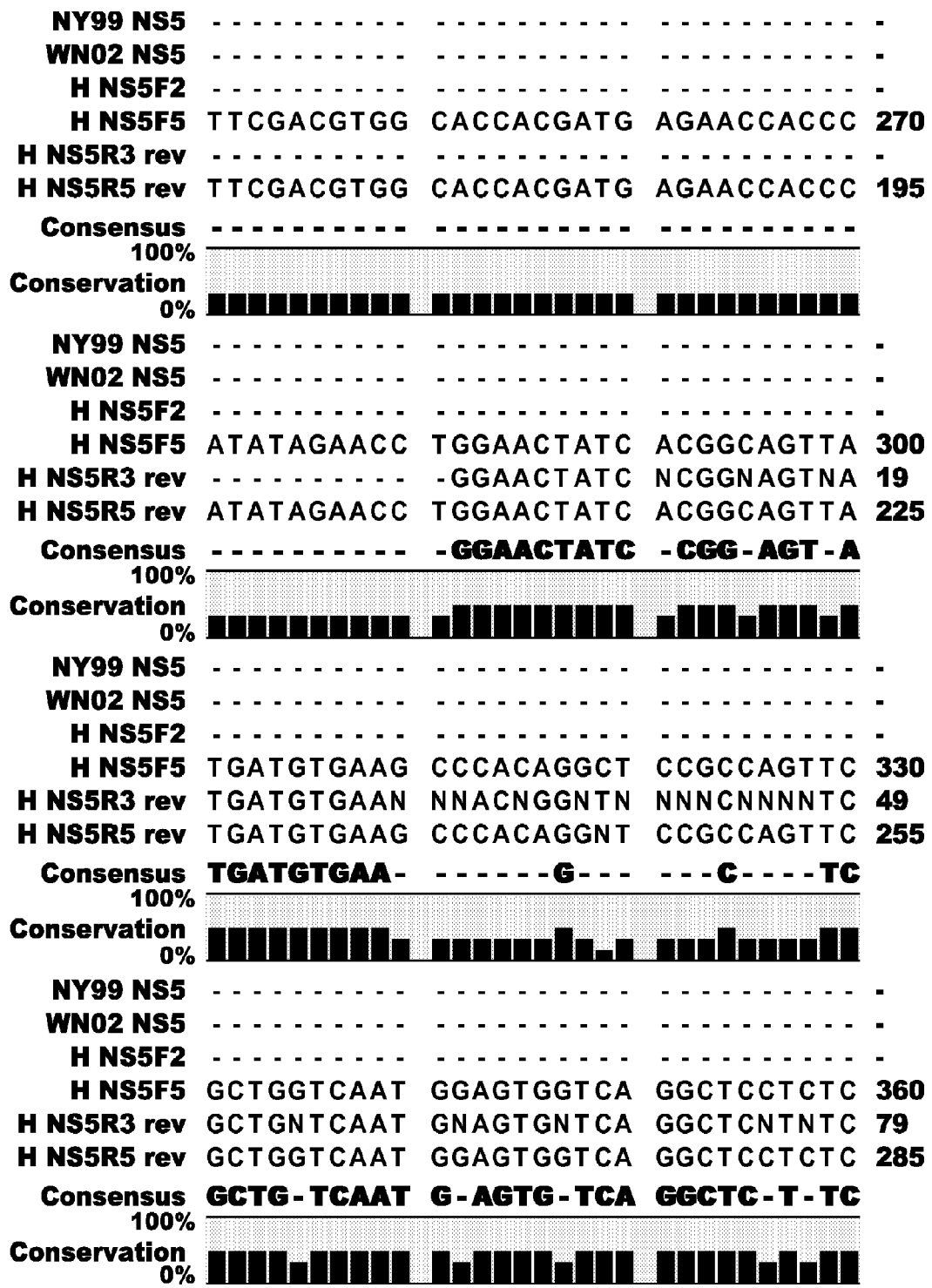
Figure 13F:
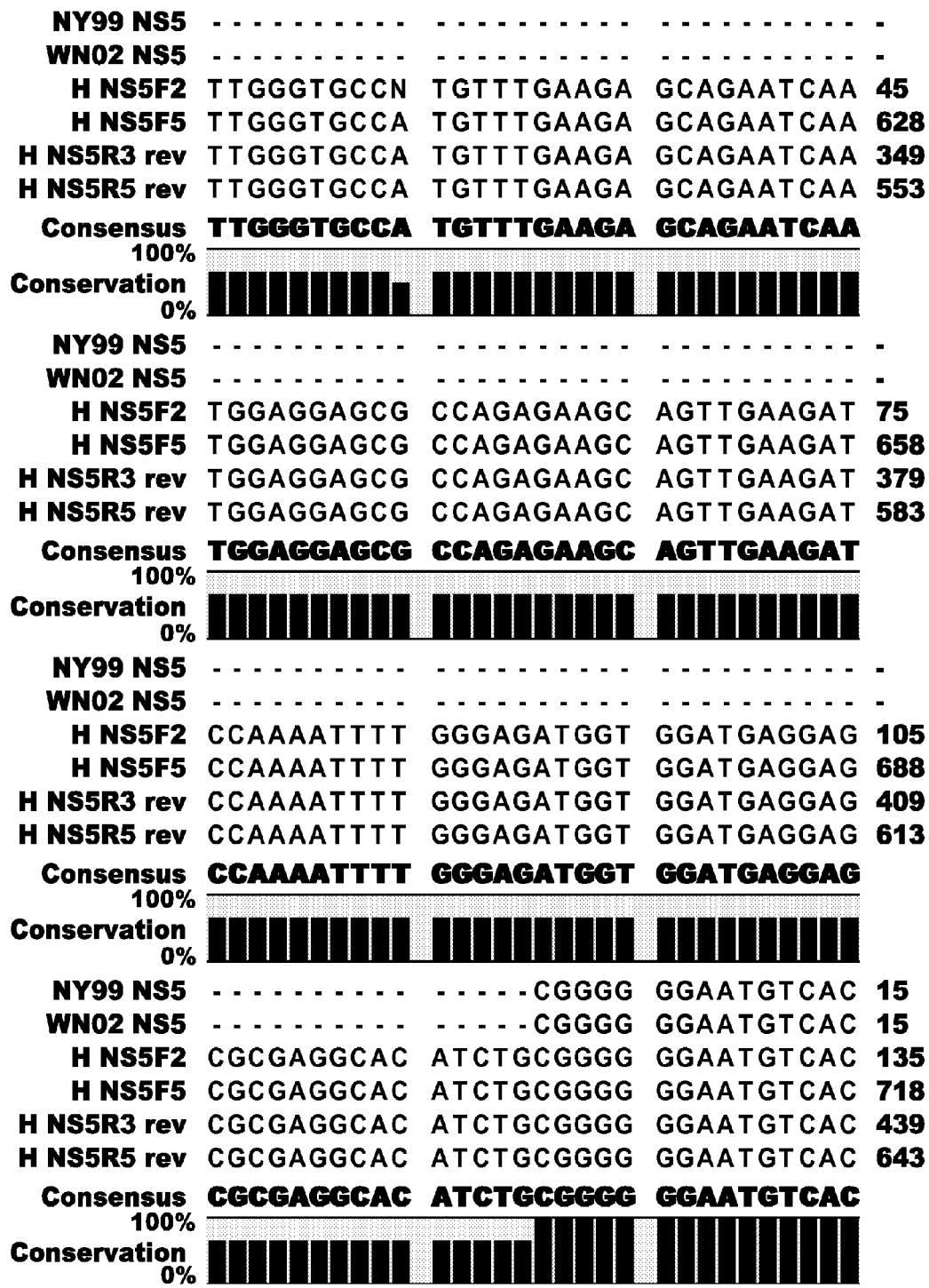
Figure 13G:
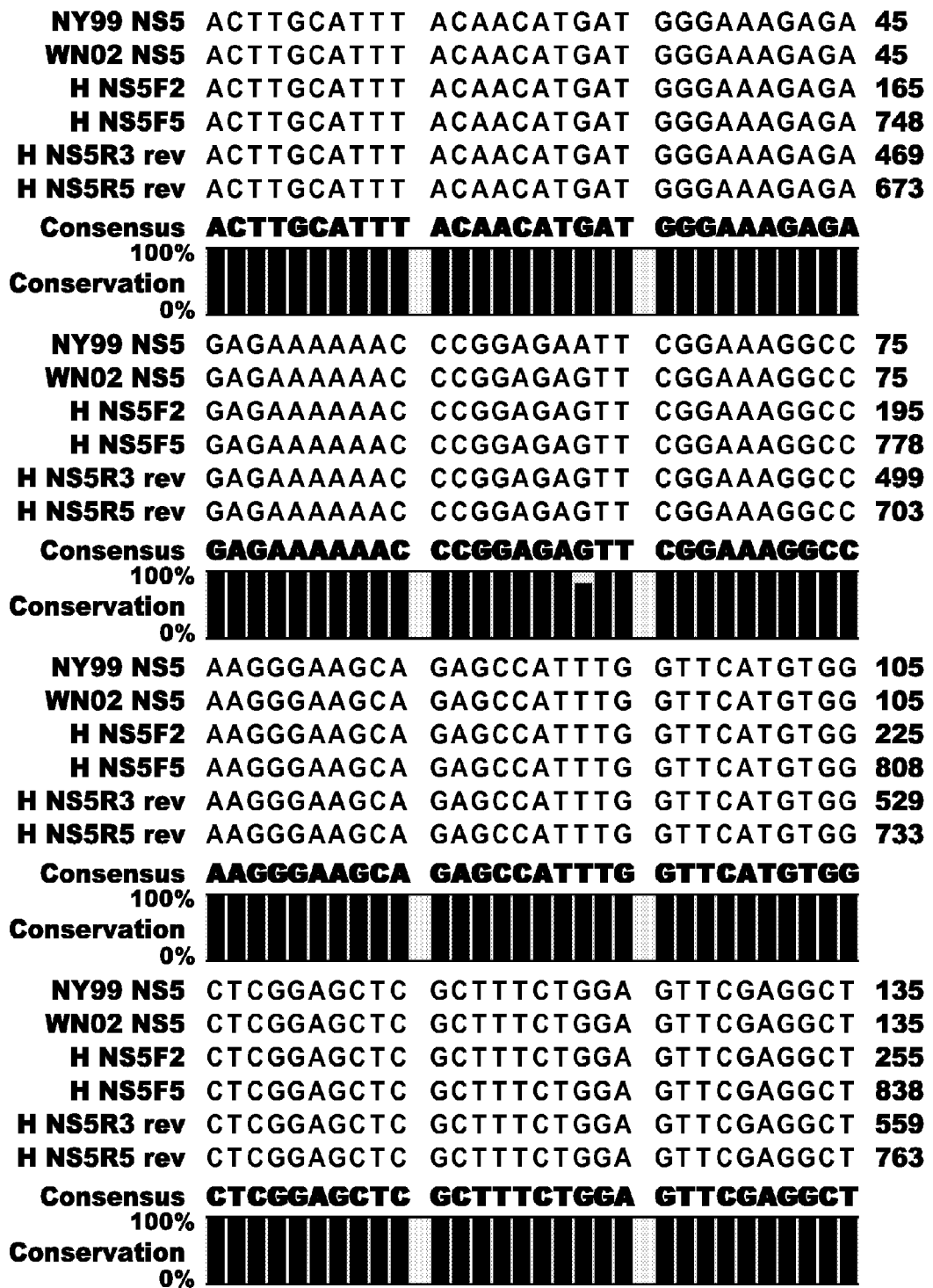
Figure 13I:
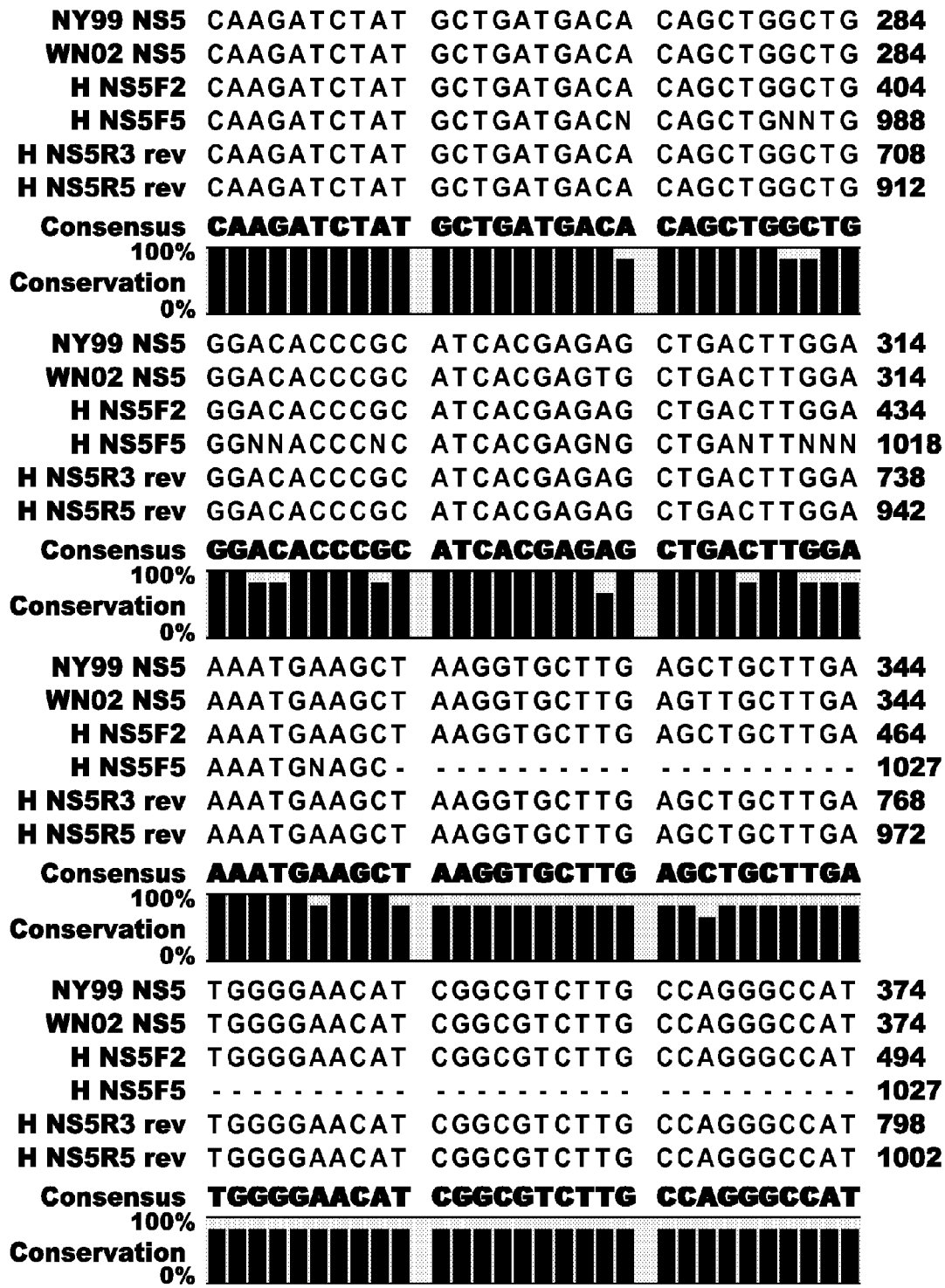
Figure 13J:
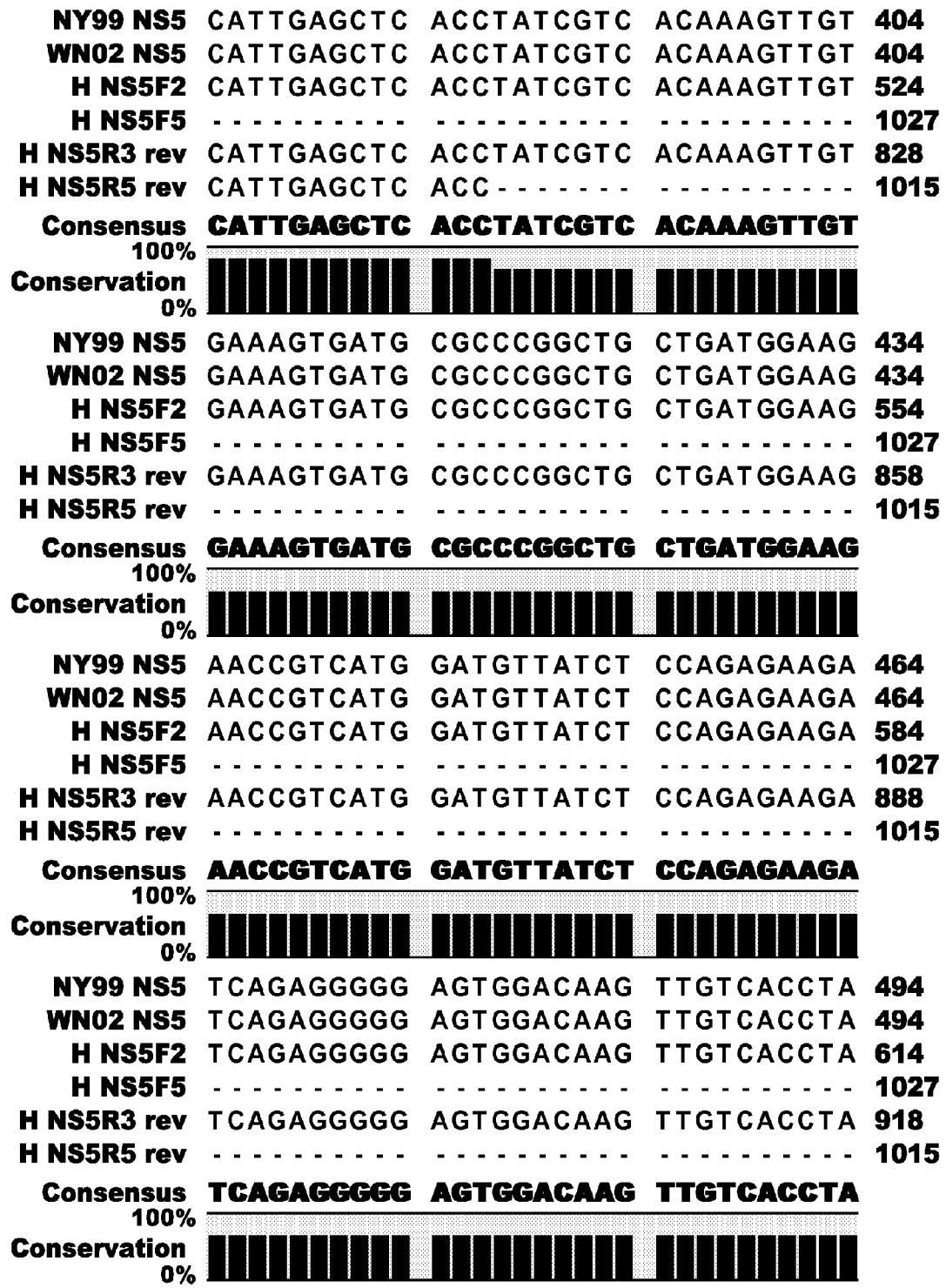
Figure 13L:
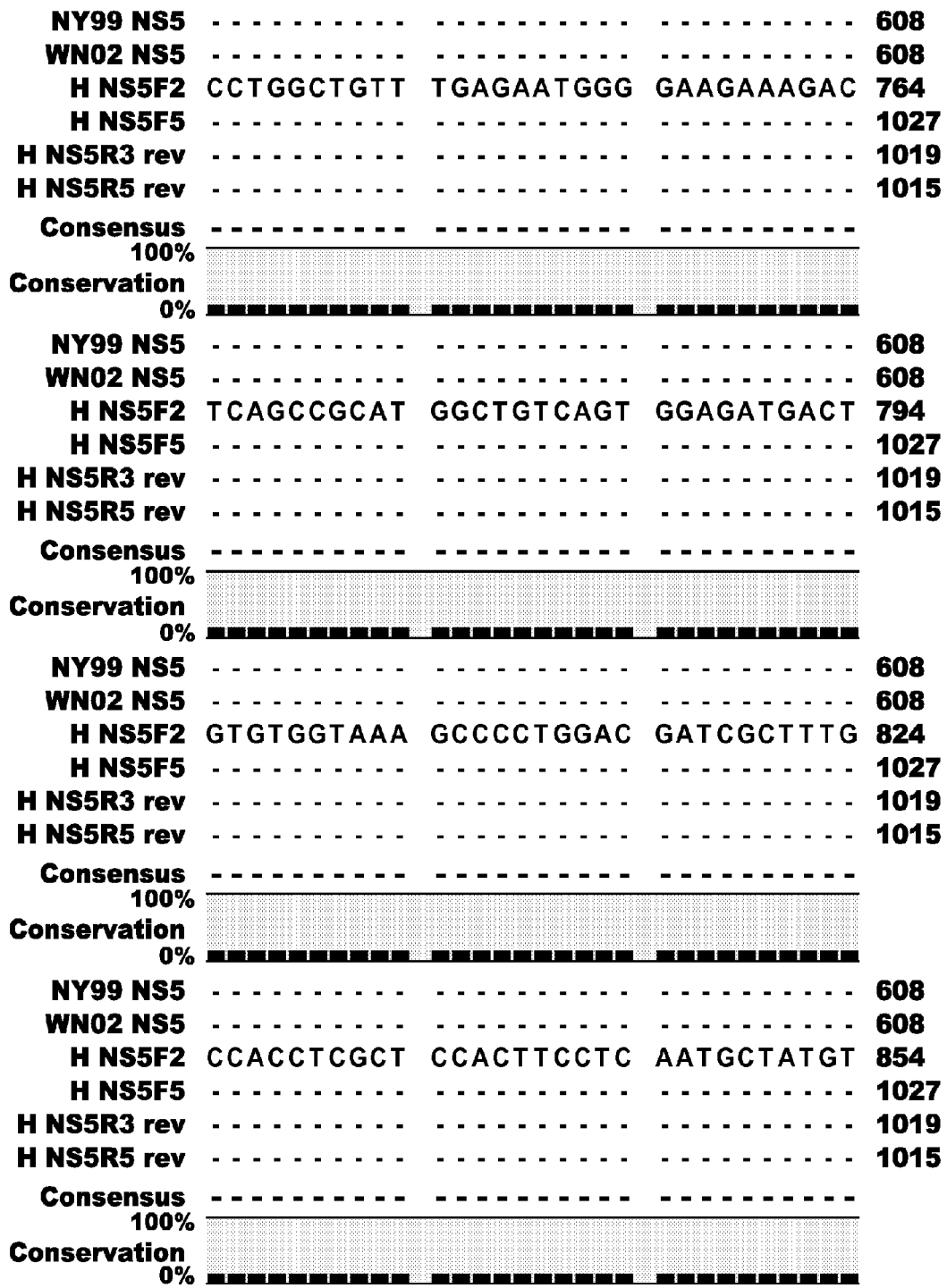
Figure 13M:
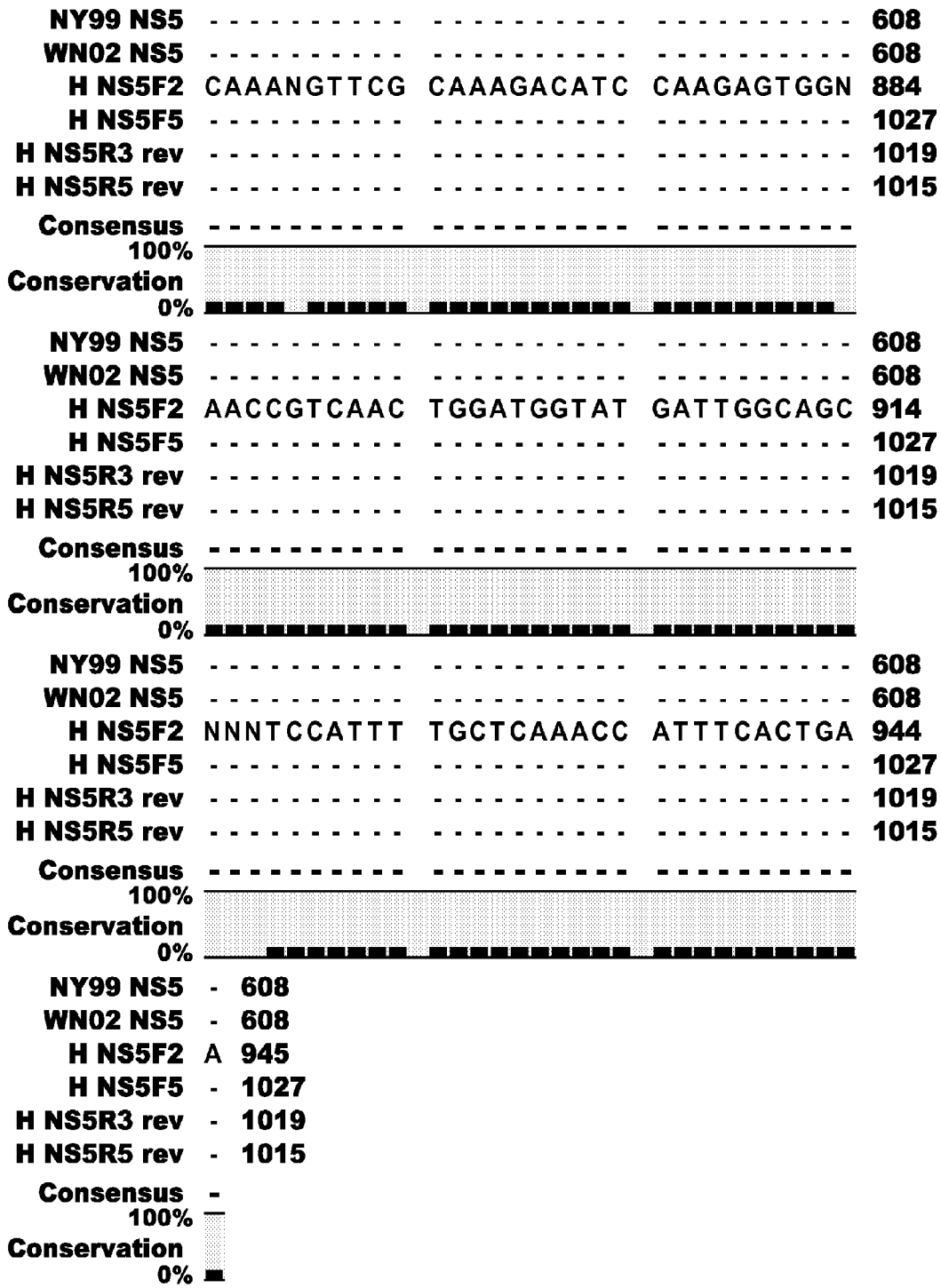
Figure 14E:
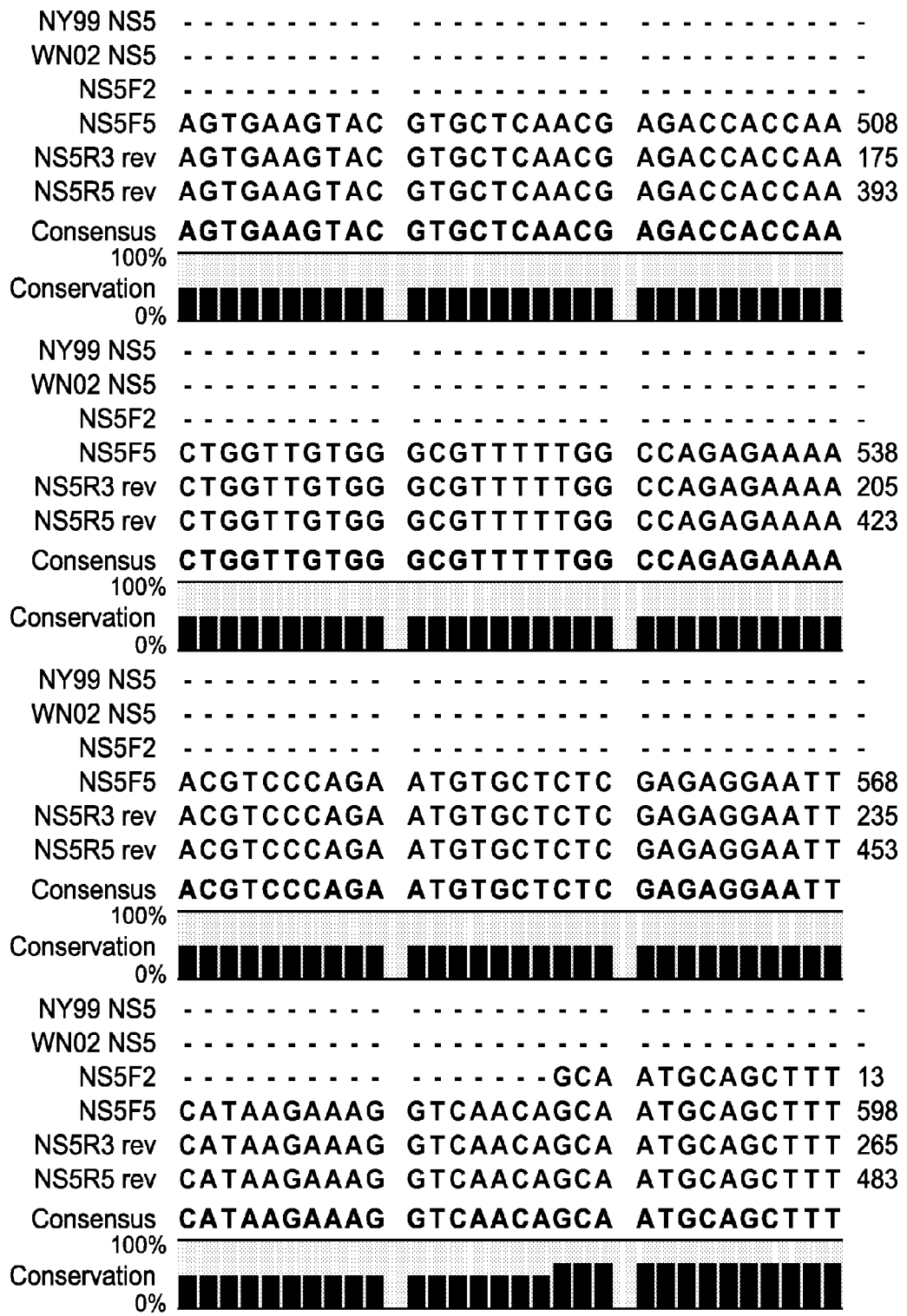
FIG. 14 is a nucleotide alignment of the H WN05 E NS5 region of WNV isolates.
Figure 14J:
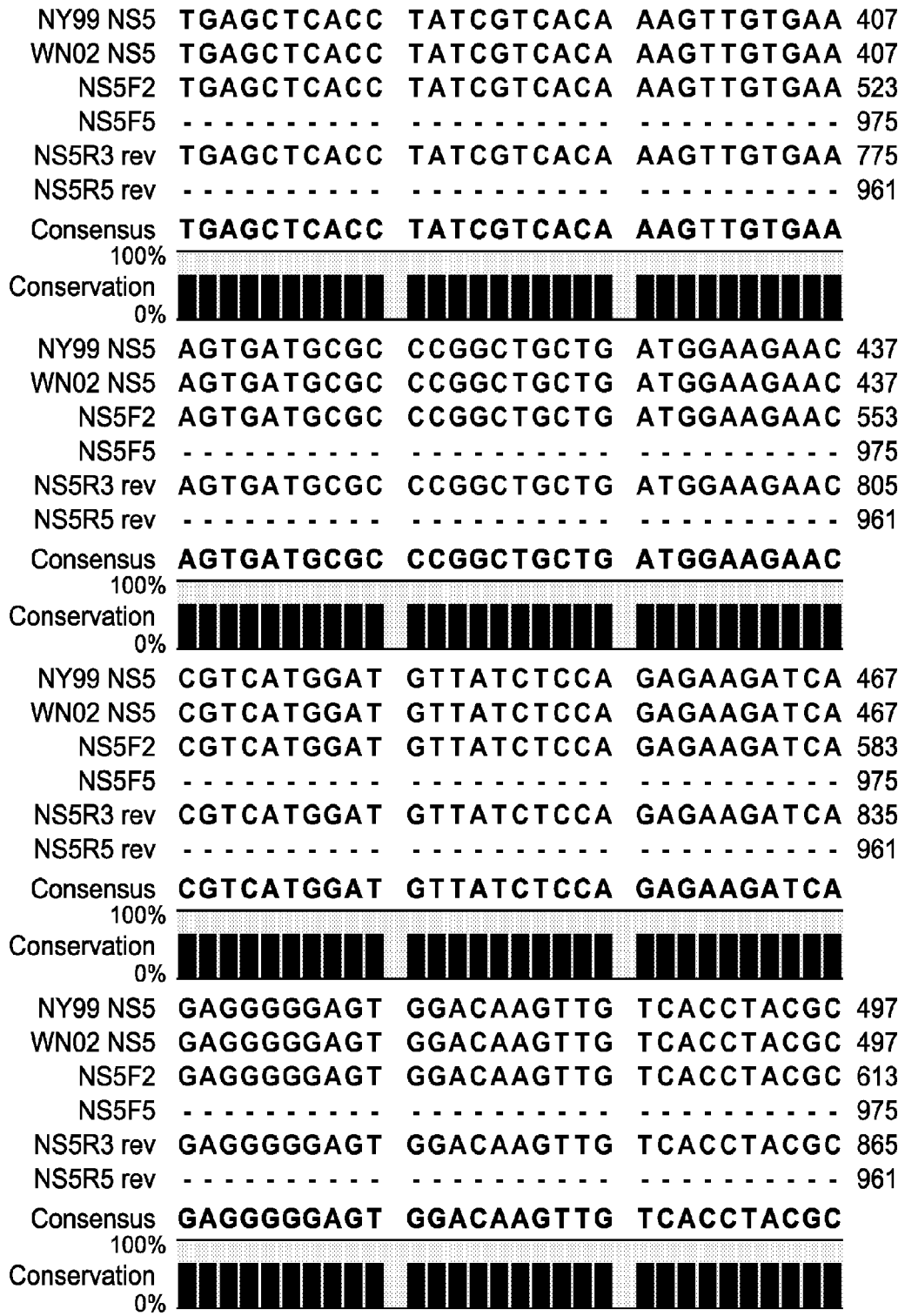
Figure 14K:
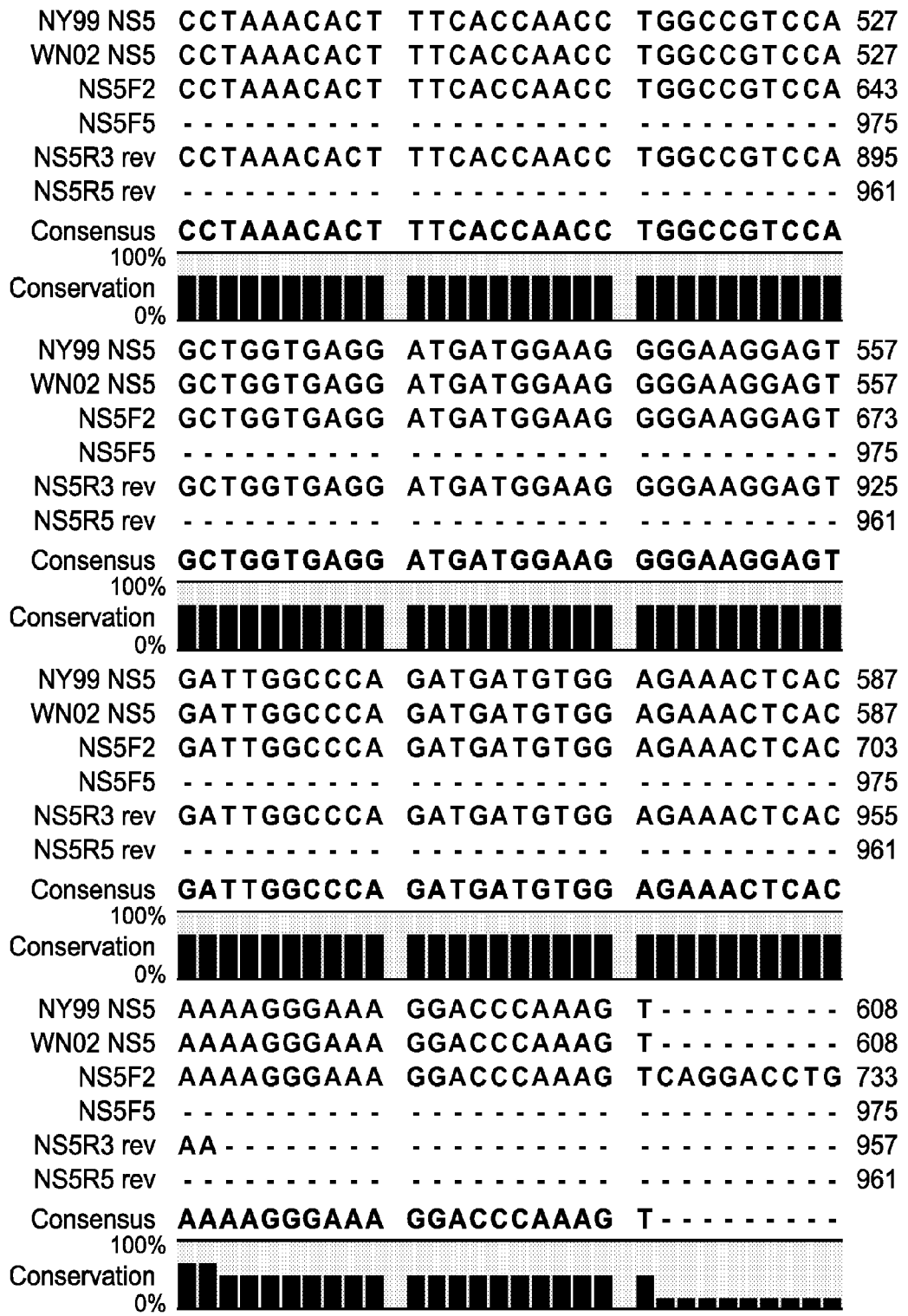
Figure 14L:
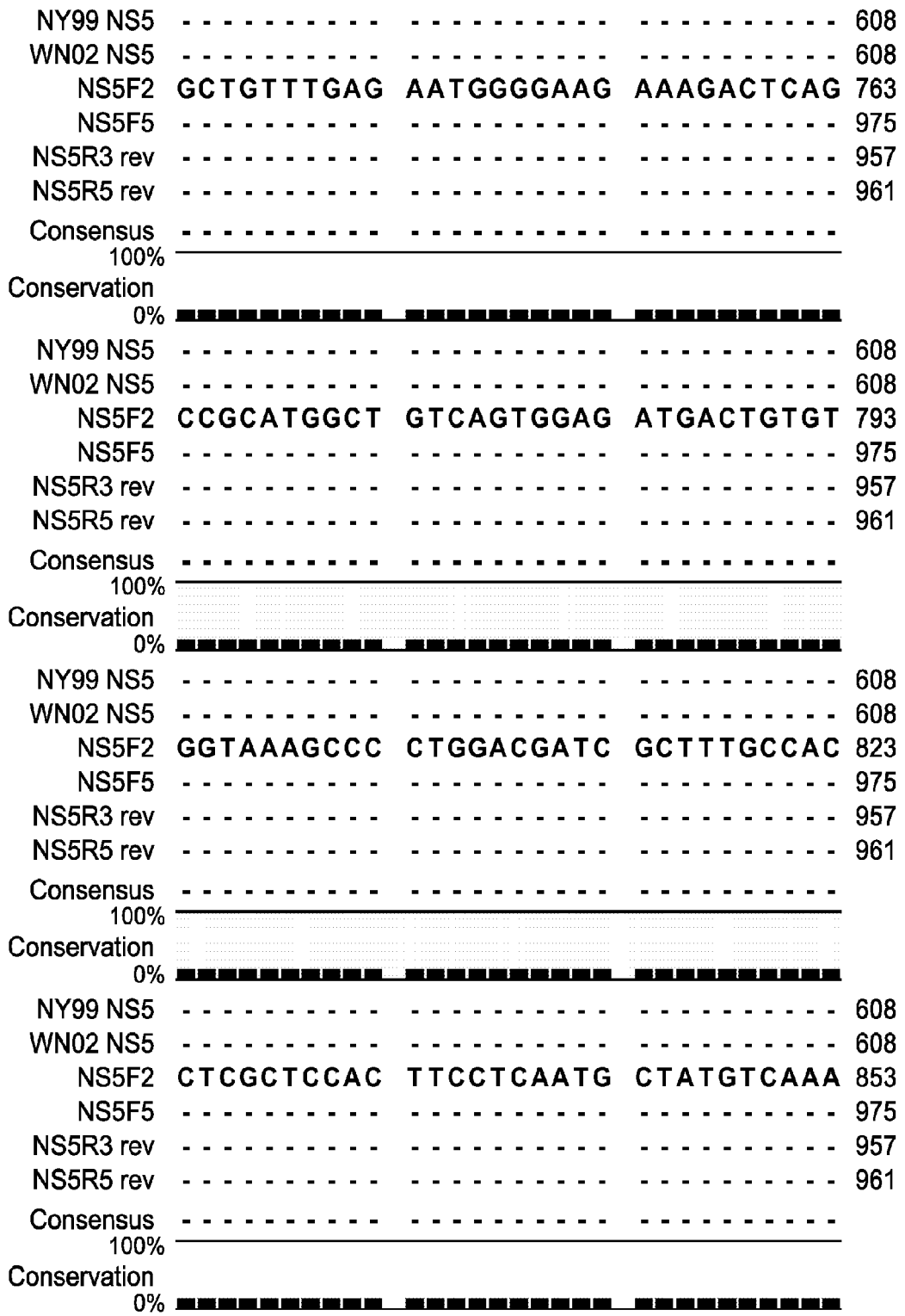
Figure 15C:
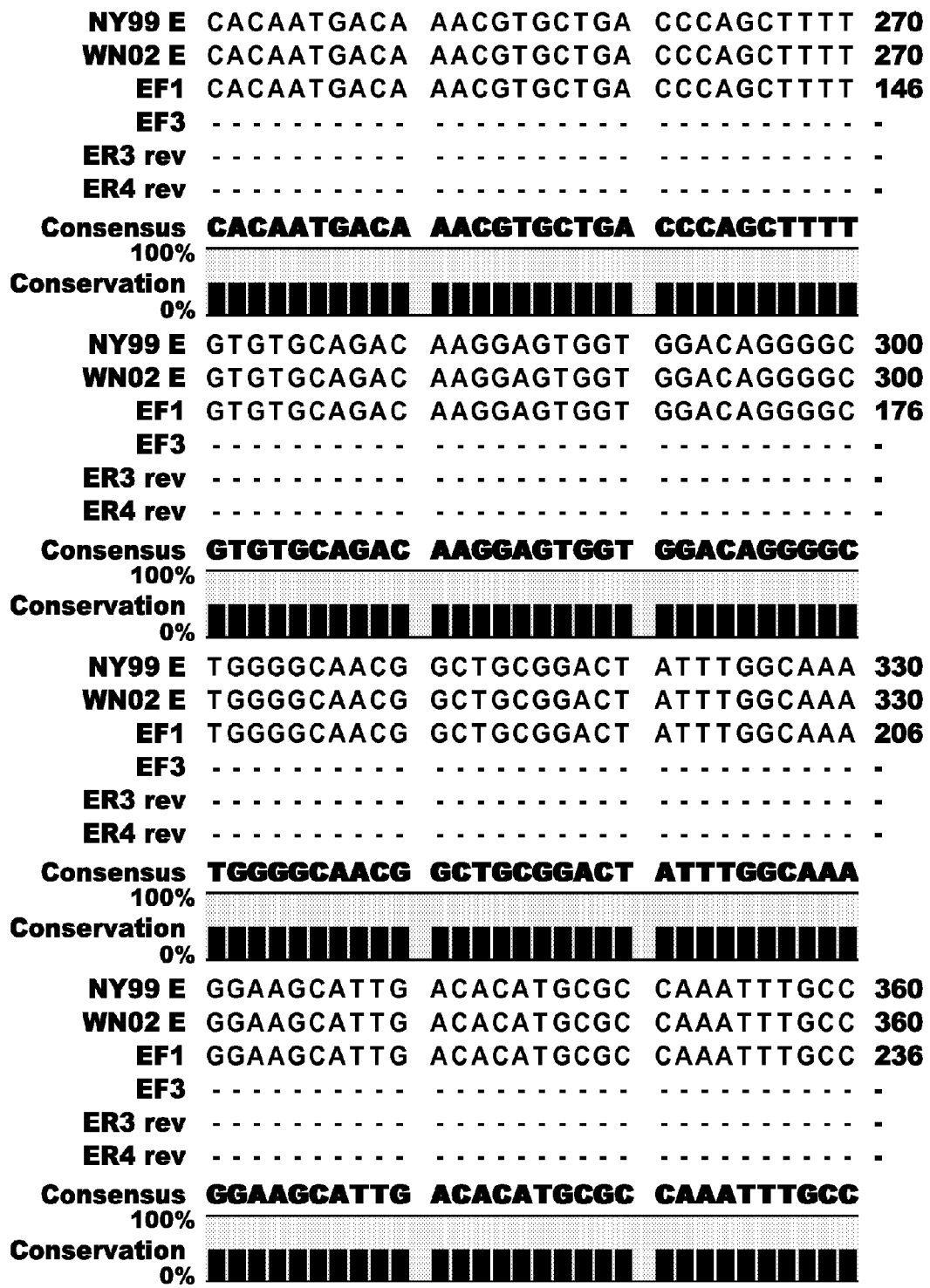
FIG. 15 is a nucleotide alignment of the H WN05 region of WNV isolates.
Figure 15F:
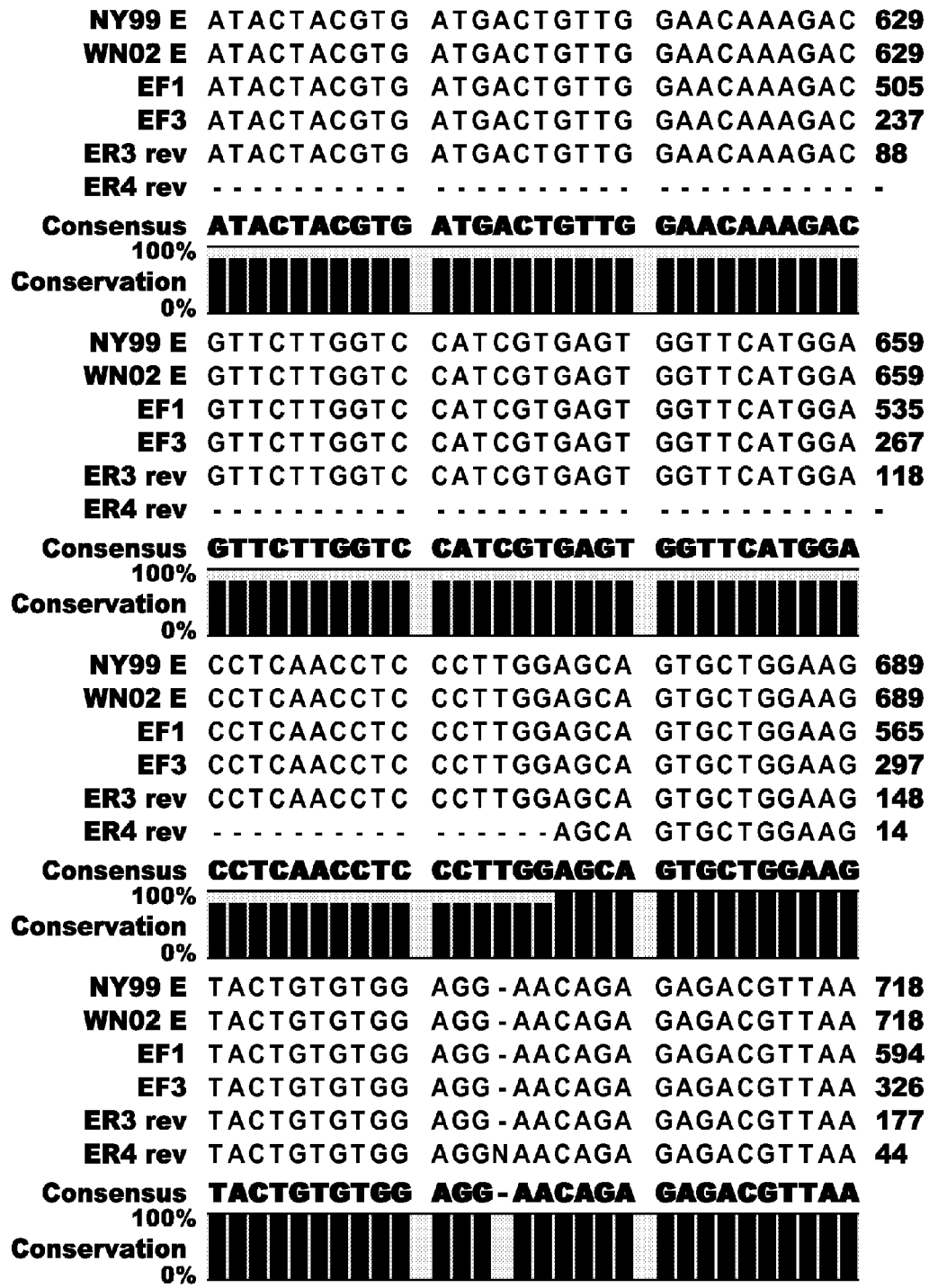
Figure 15M:
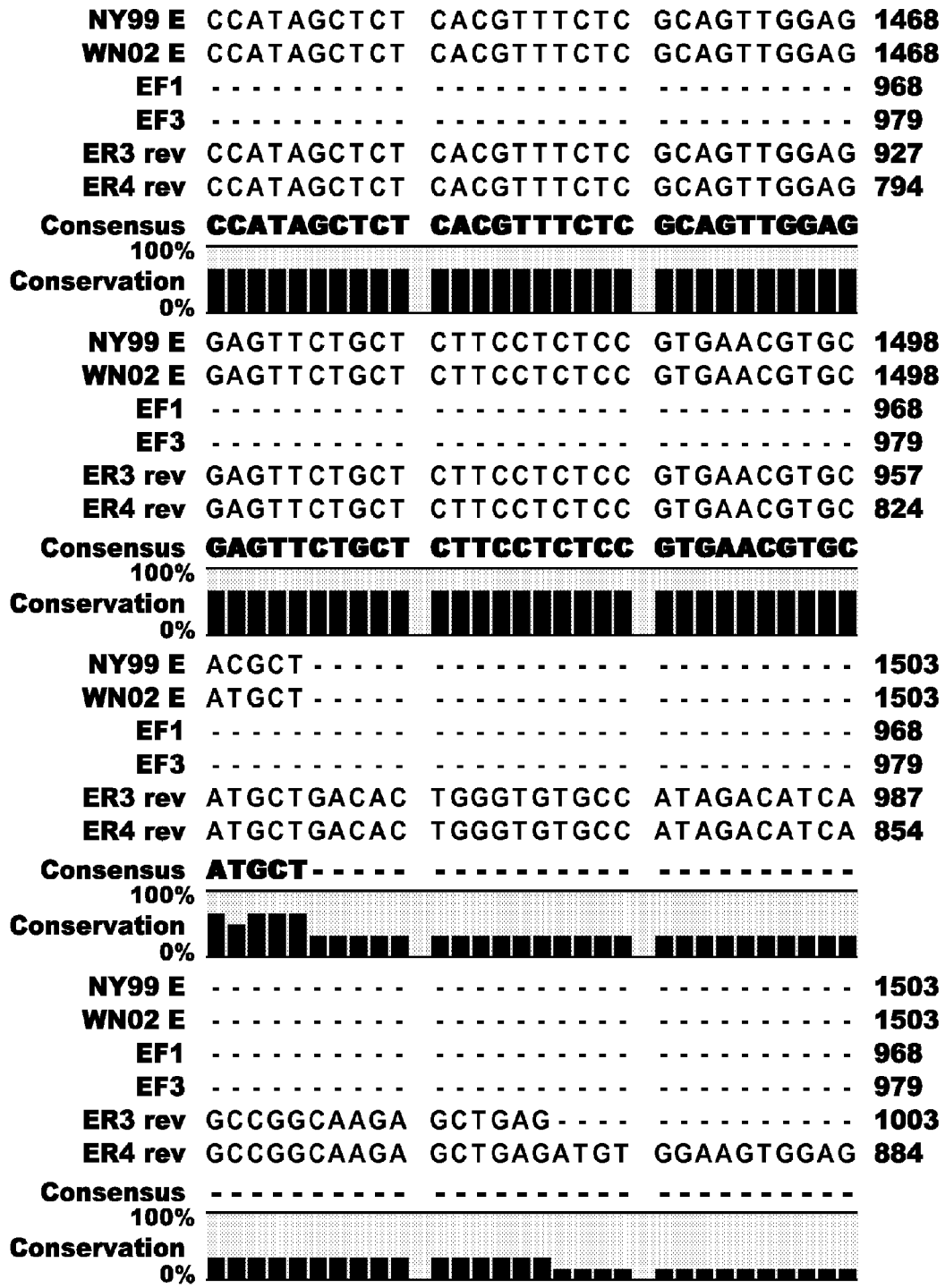
Figure 16B:
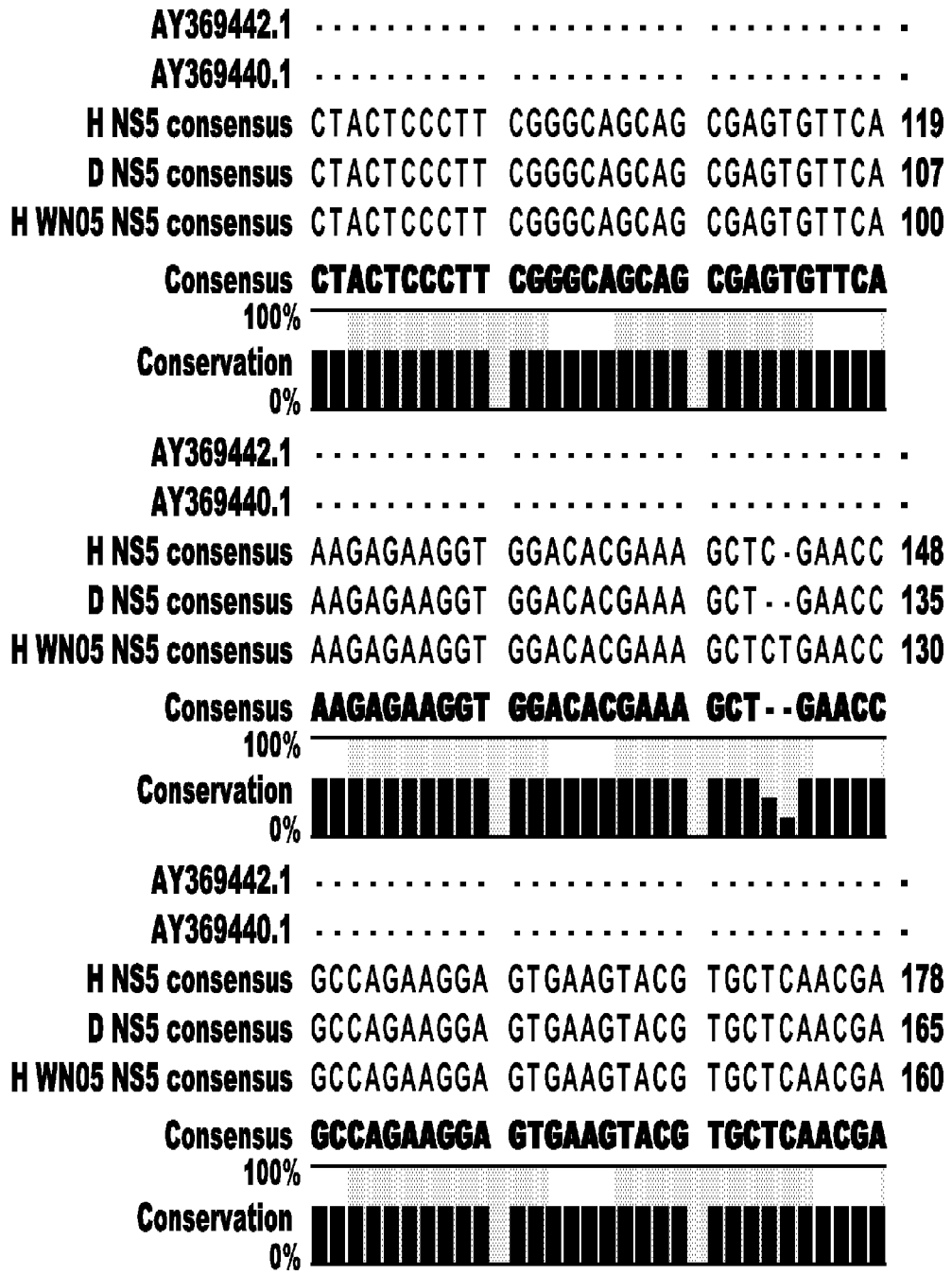
FIG. 16 is a nucleotide alignment of the NS5 region of WNV isolates.
Figure 16F:
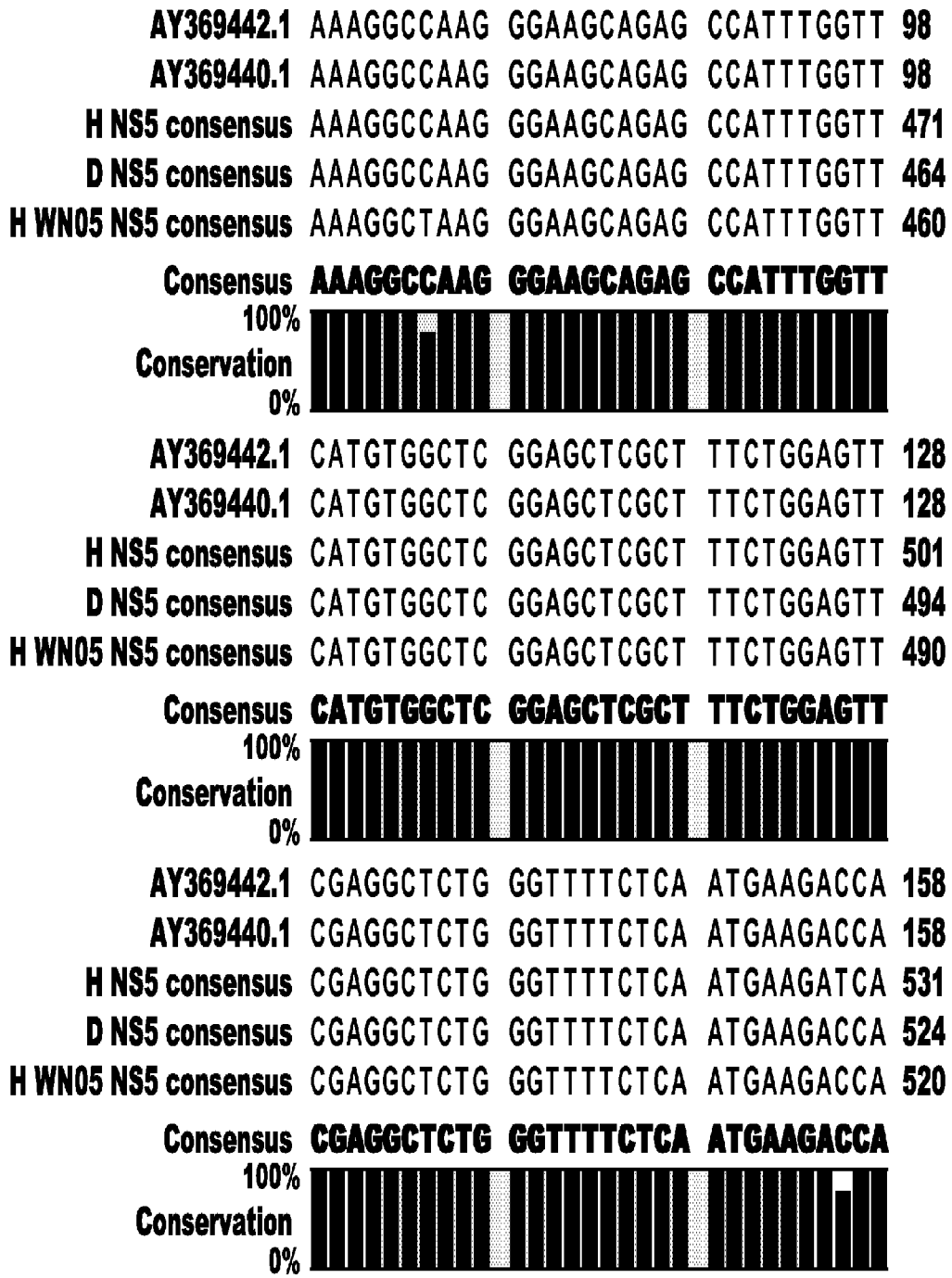
Figure 16H:
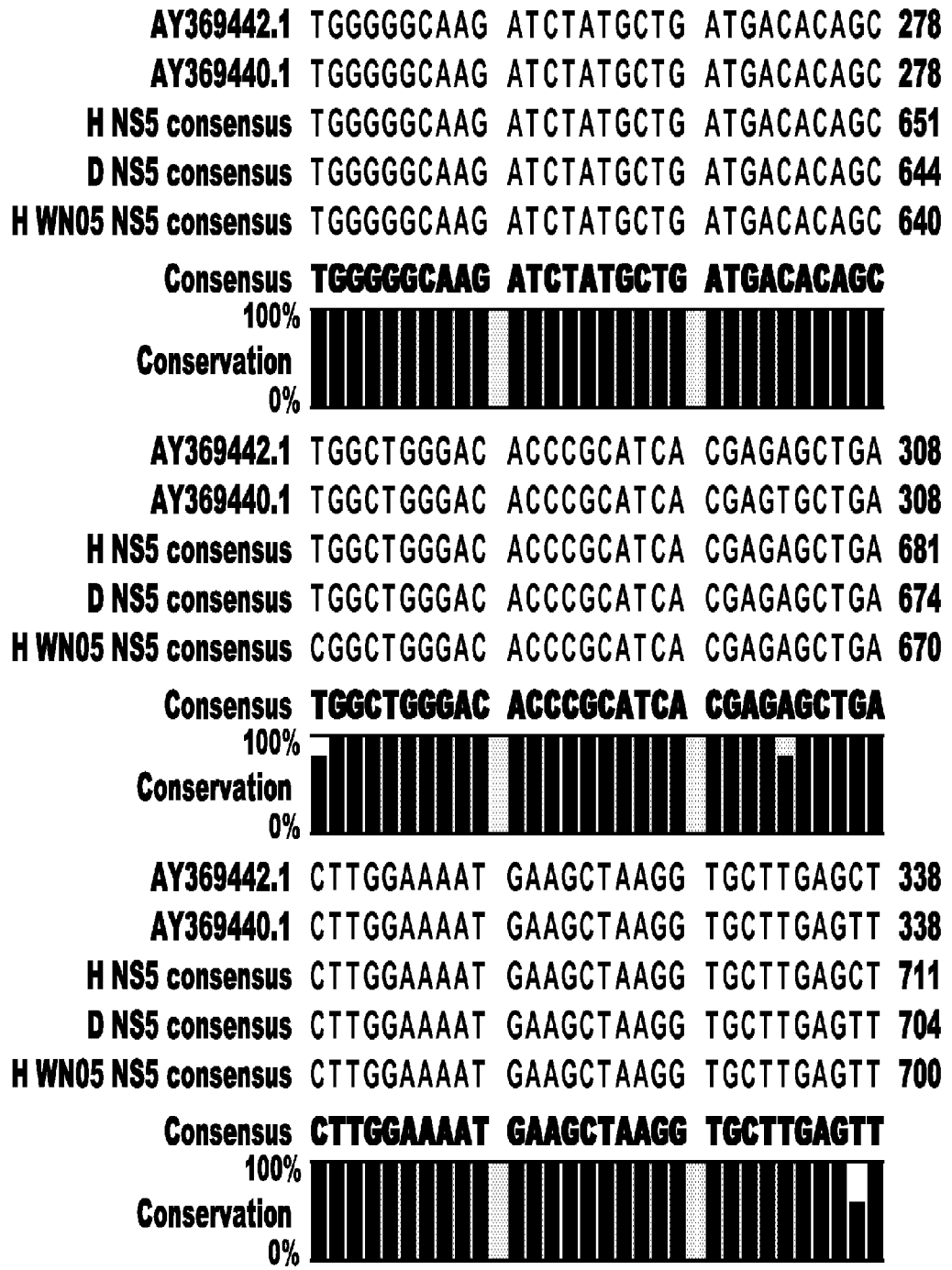
Figure 16I:
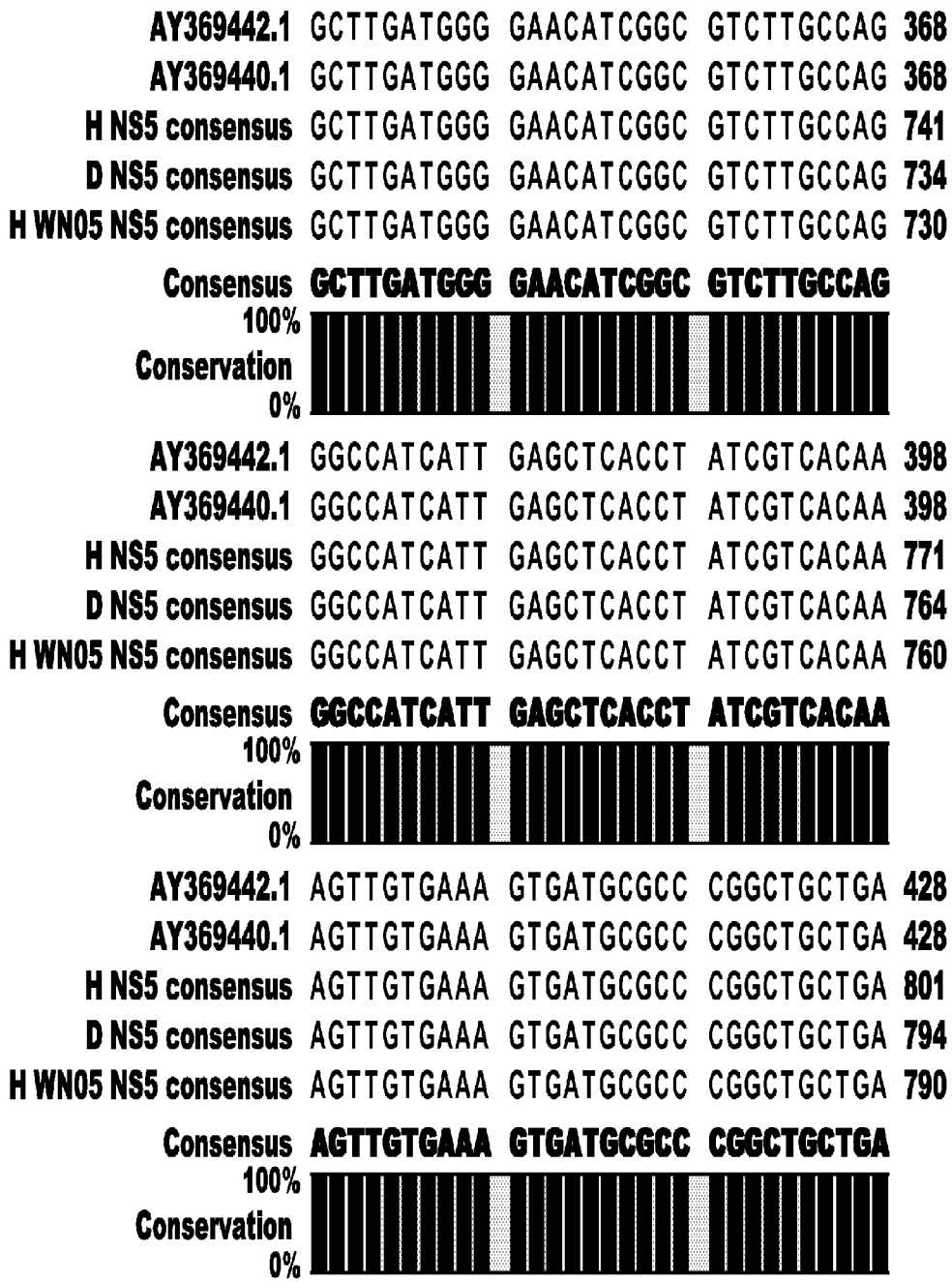
Figure 17C:
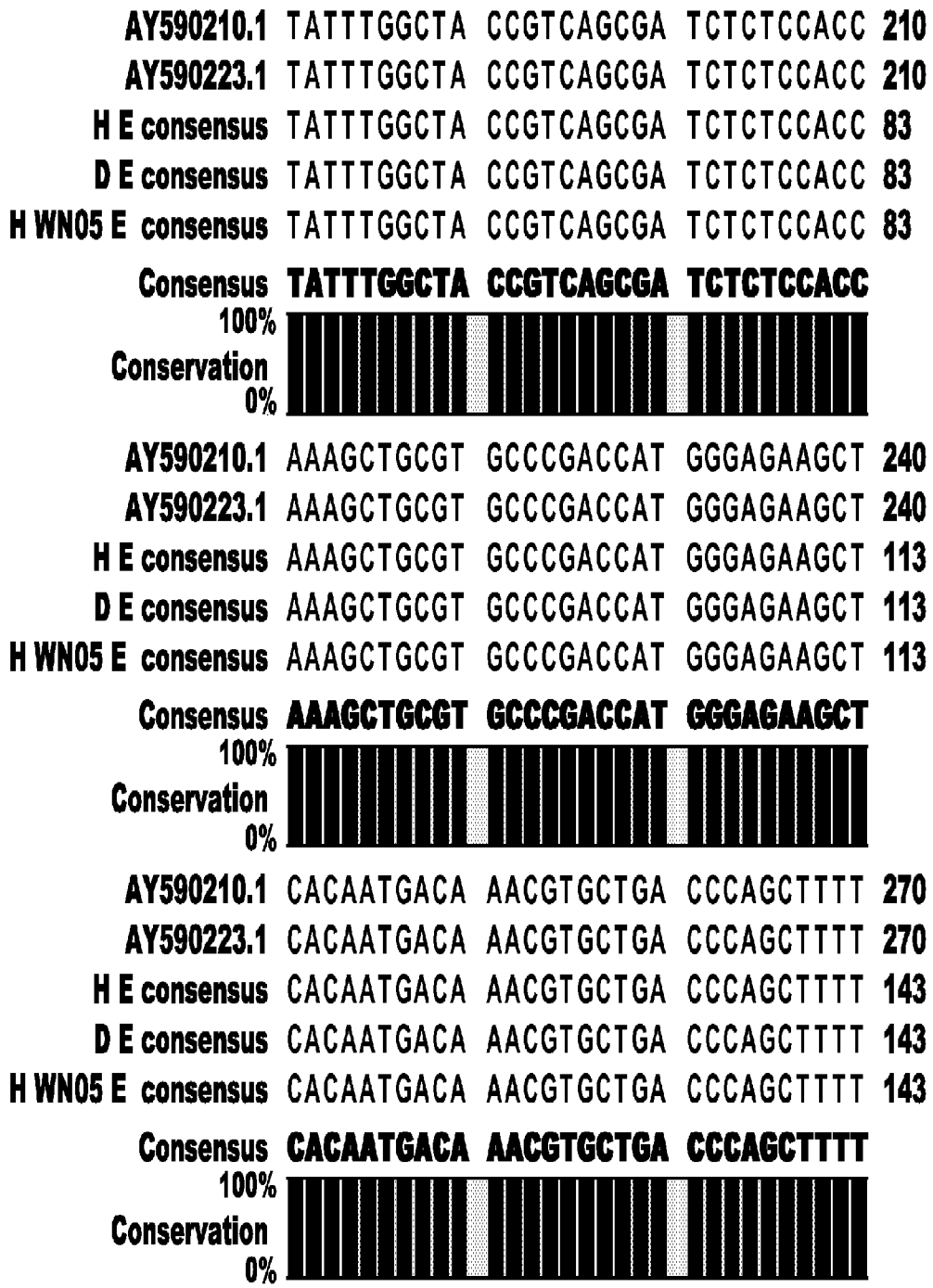
FIG. 17 is a nucleotide alignment of the E region of WNV isolates.
Figure 17D:
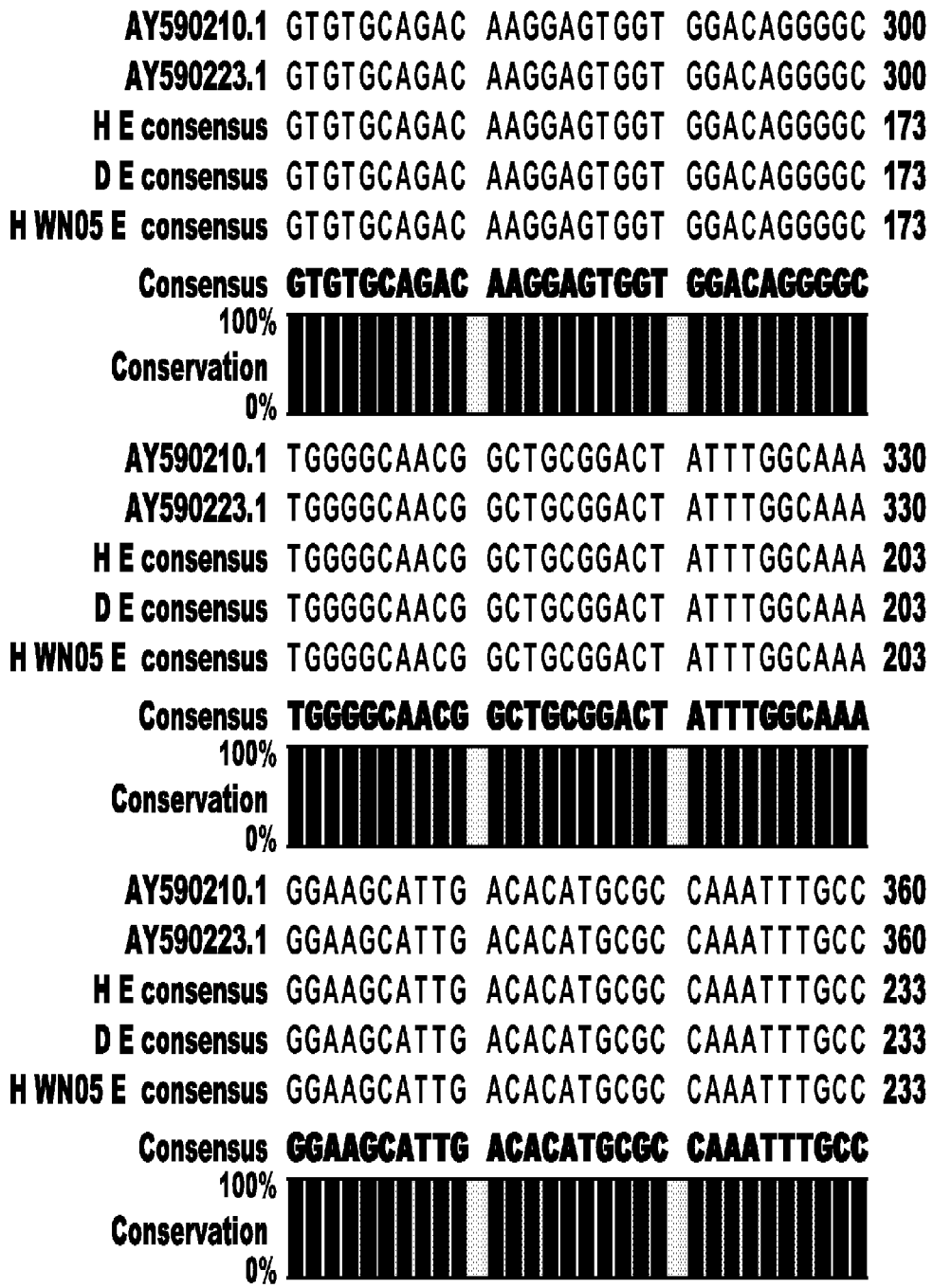
Figure 17F:
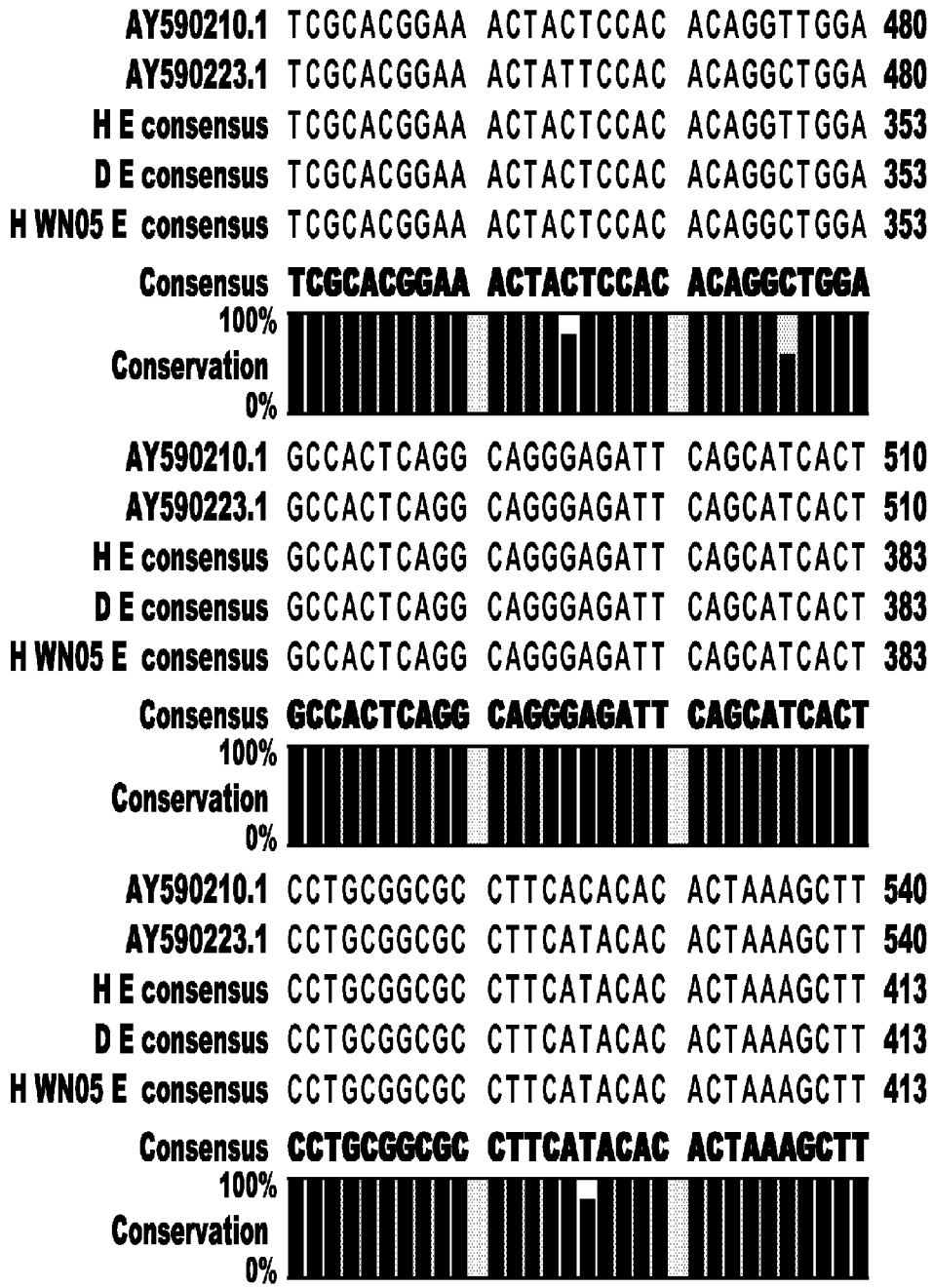
Figure 17G:
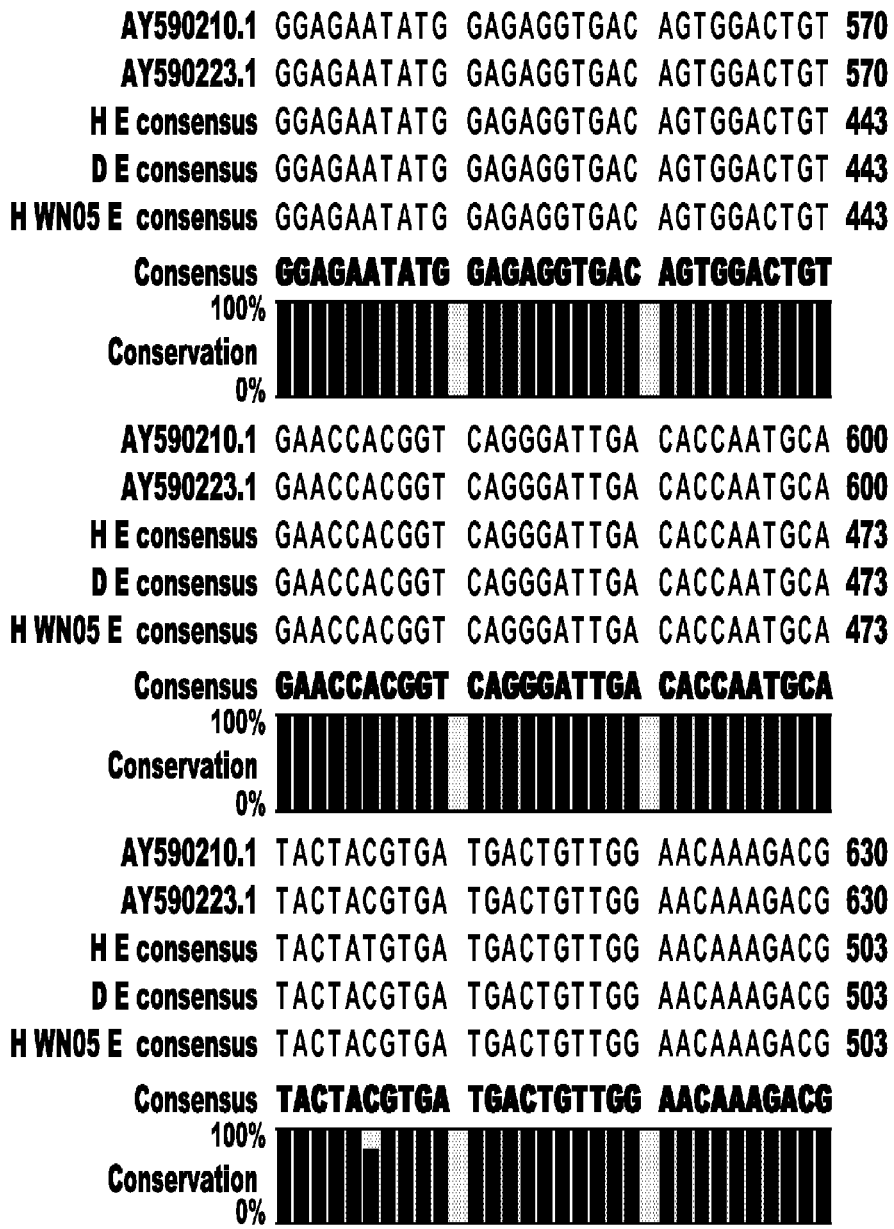
Figure 17H:
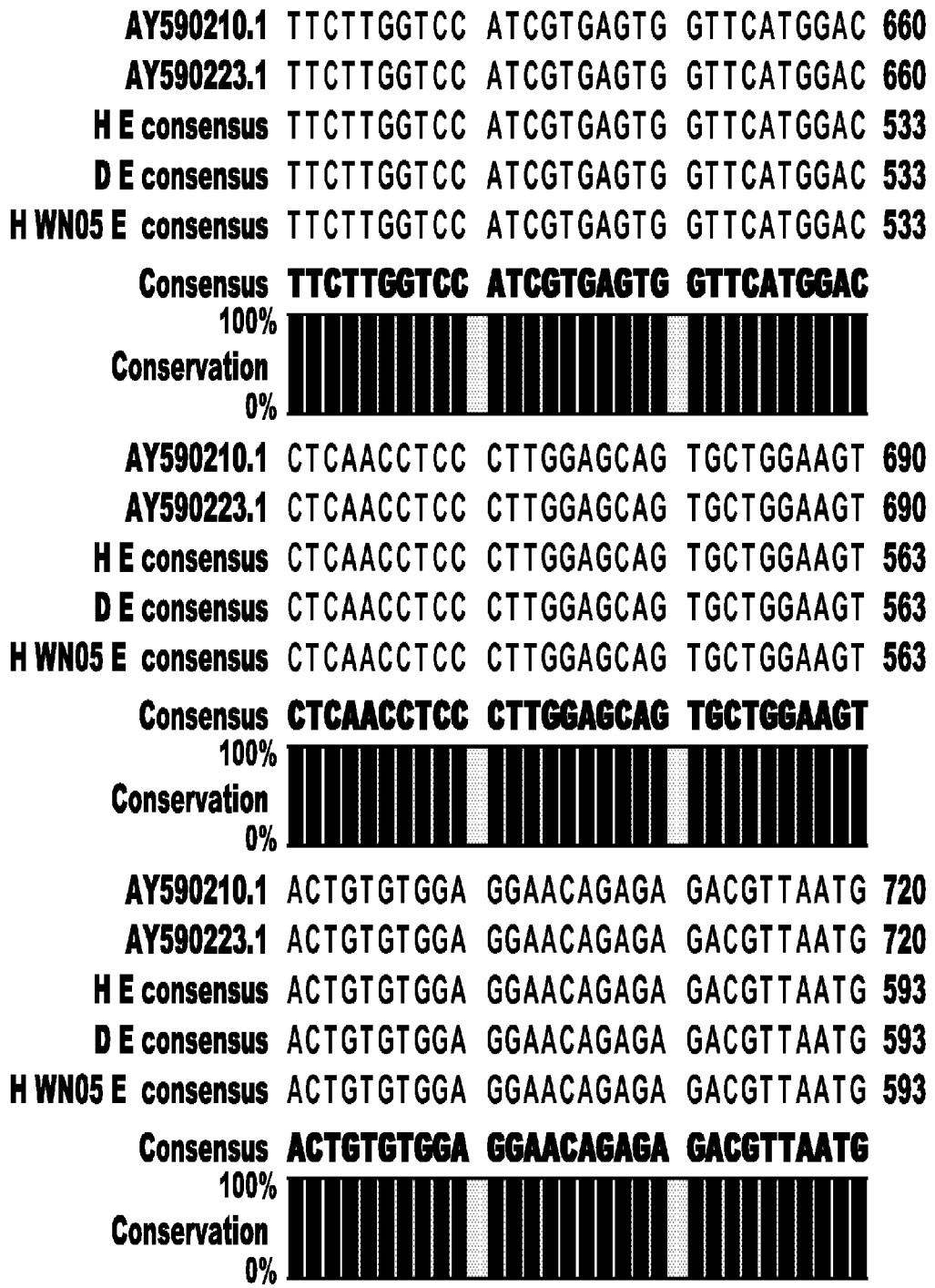
Figure 17I:
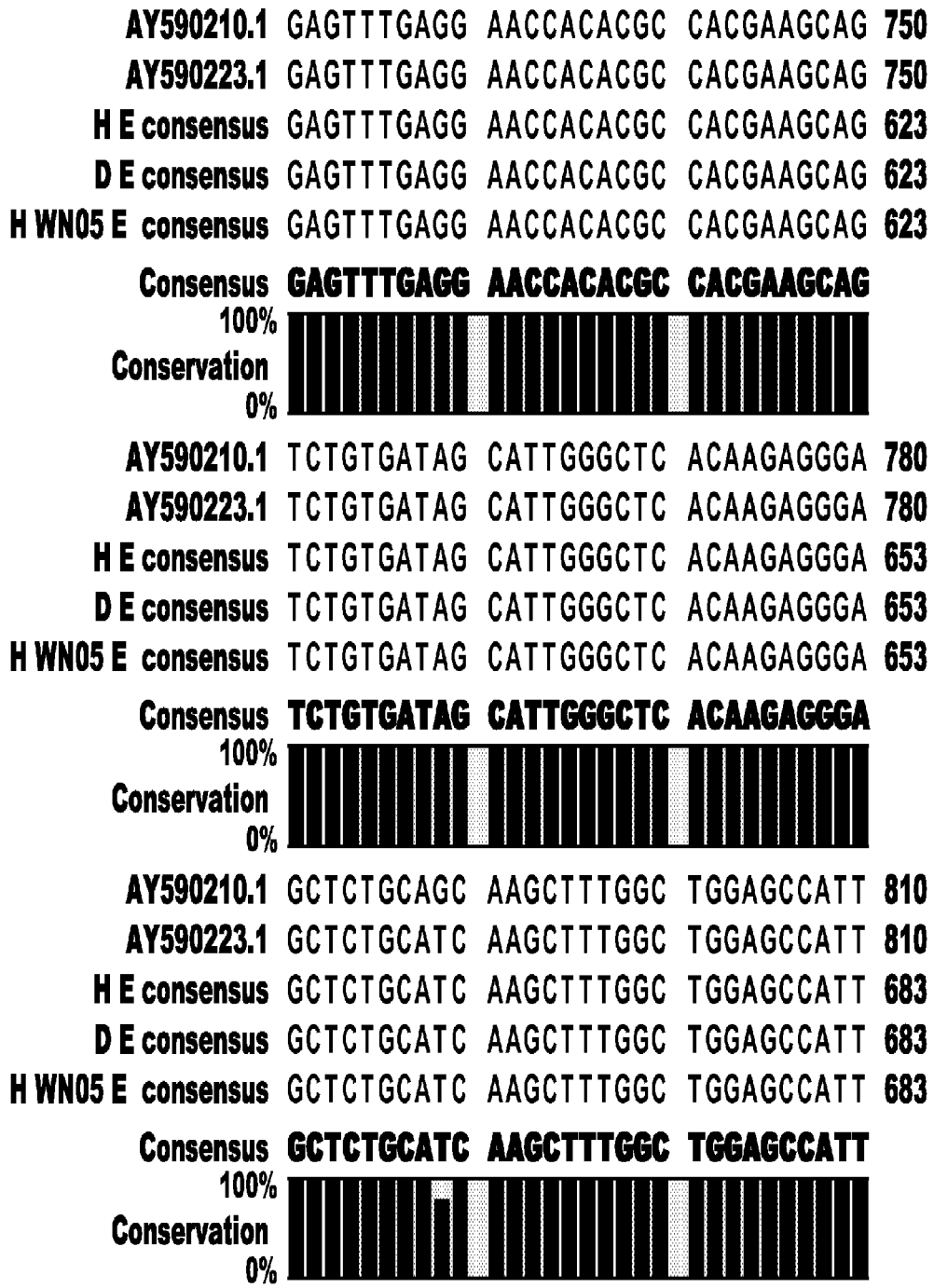
Figure 17J:
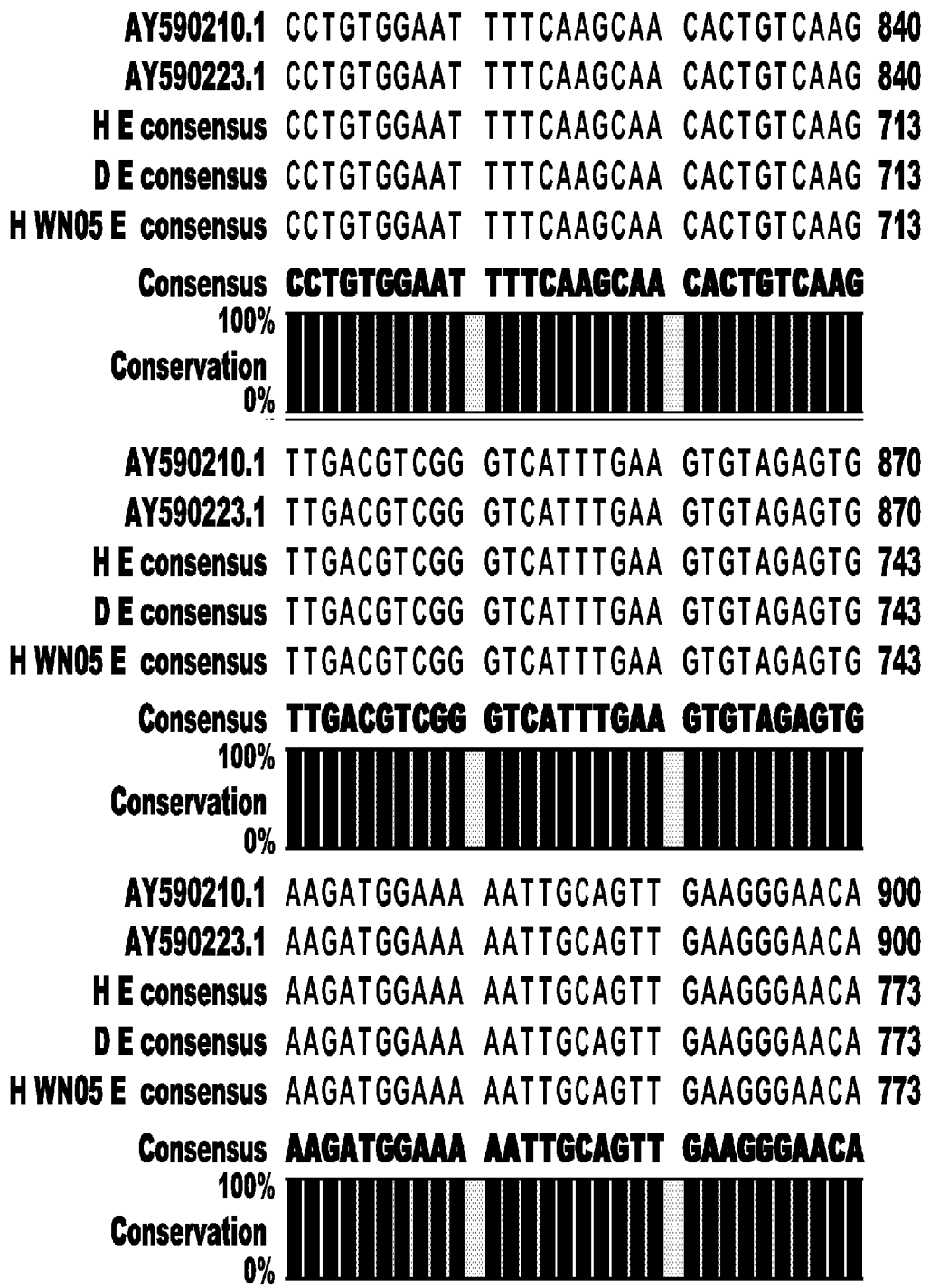
Figure 17K:
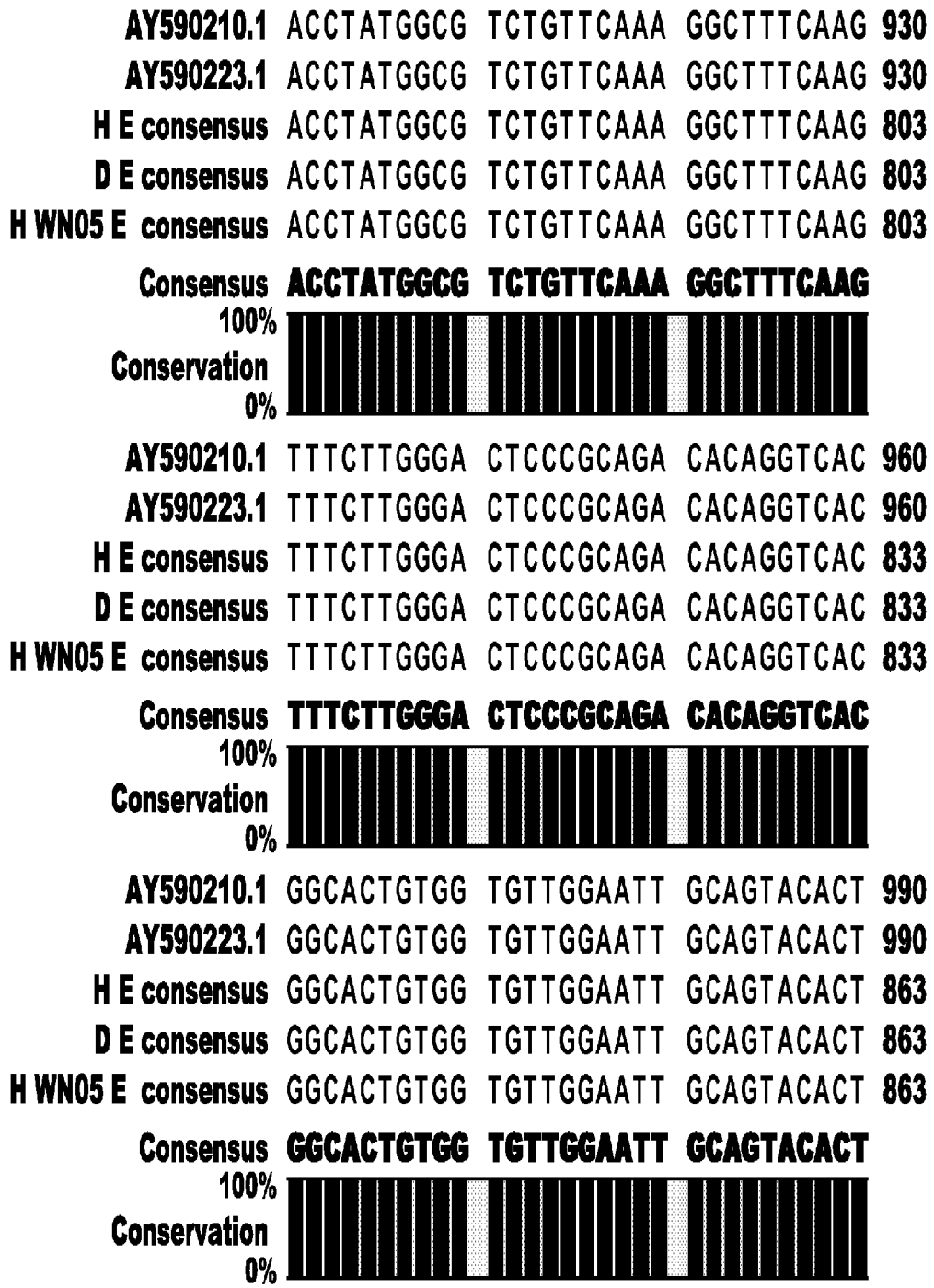
Figure 17L:
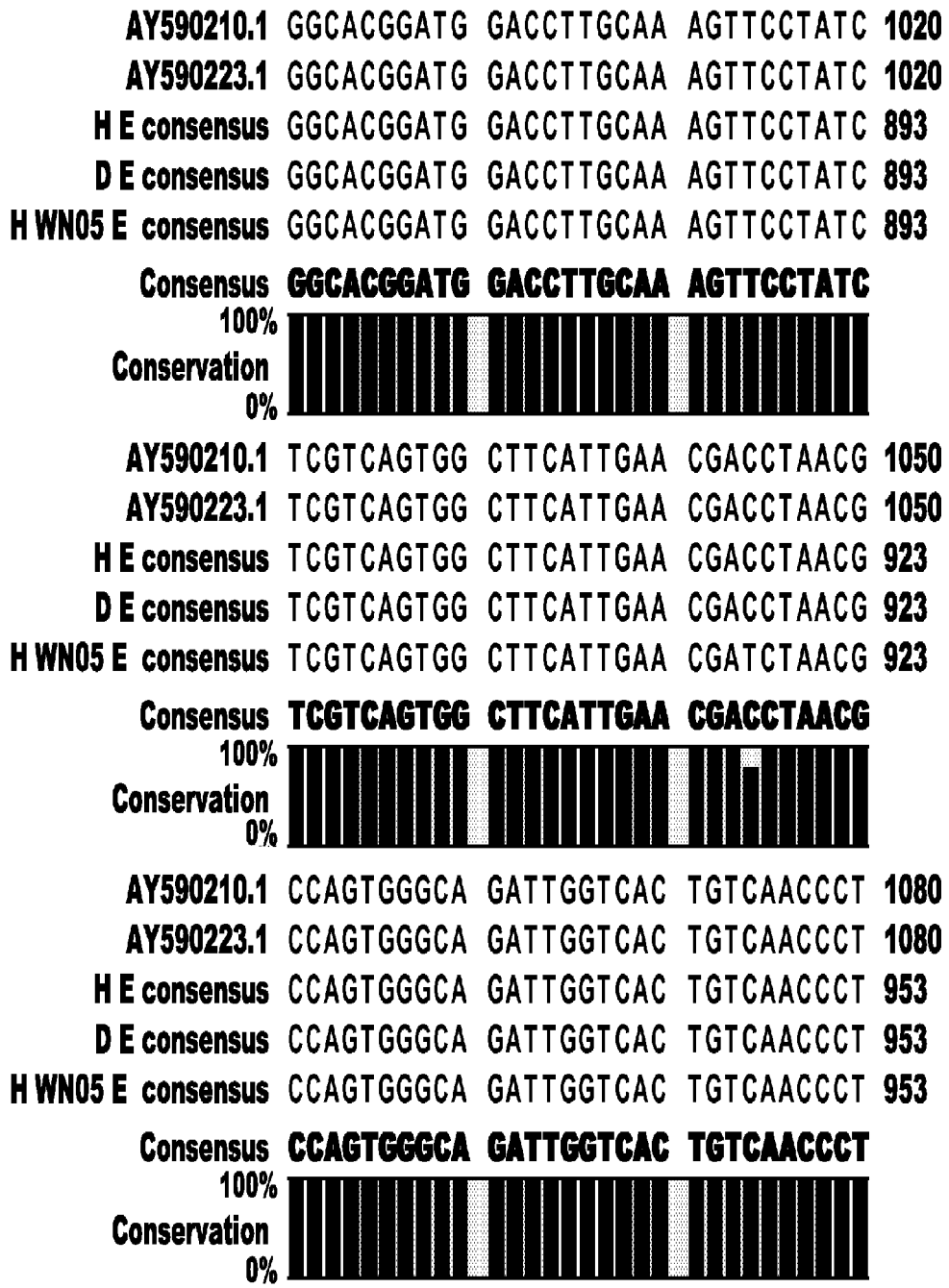
Figure 17O:
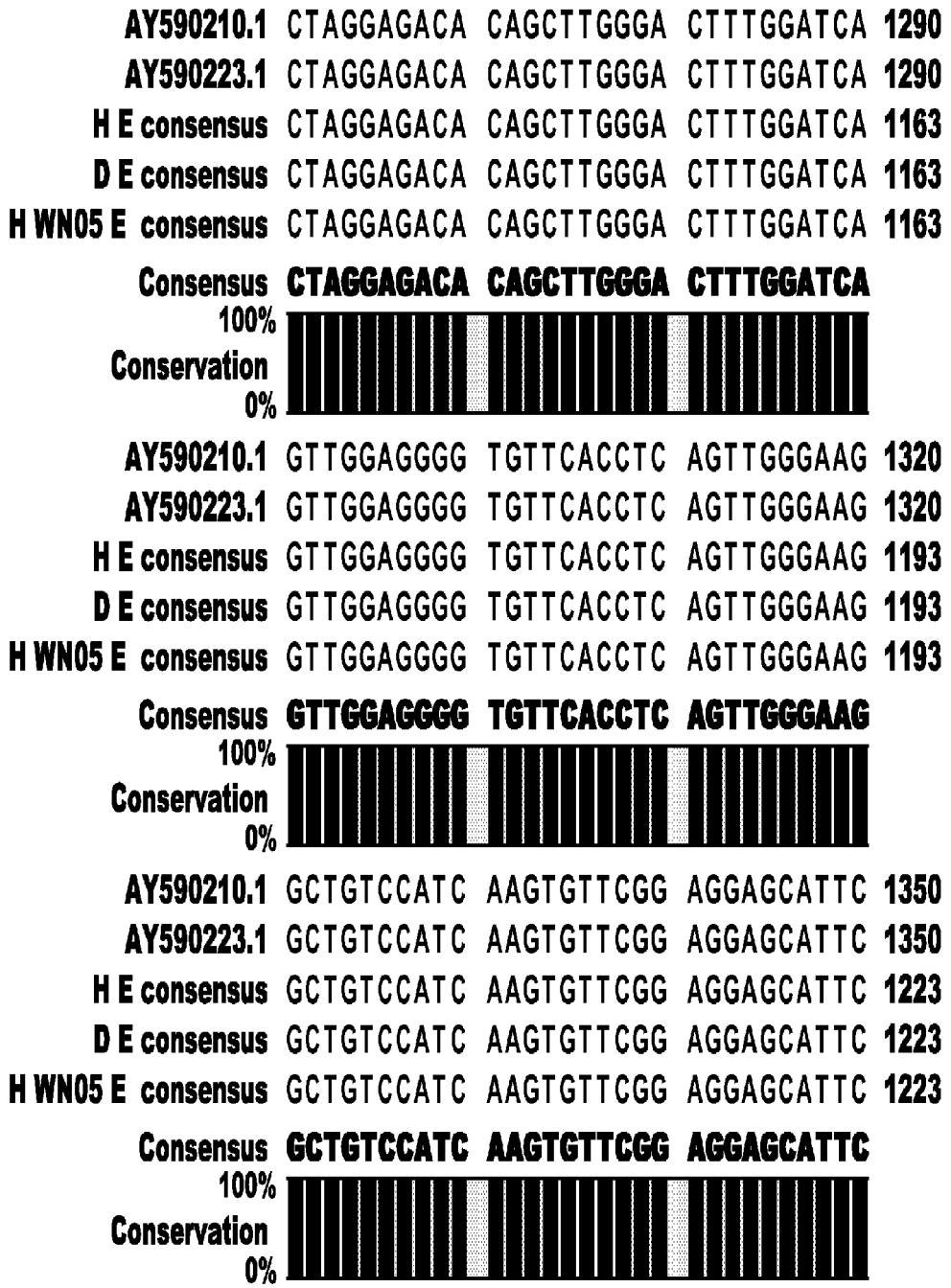
Figure 17P:
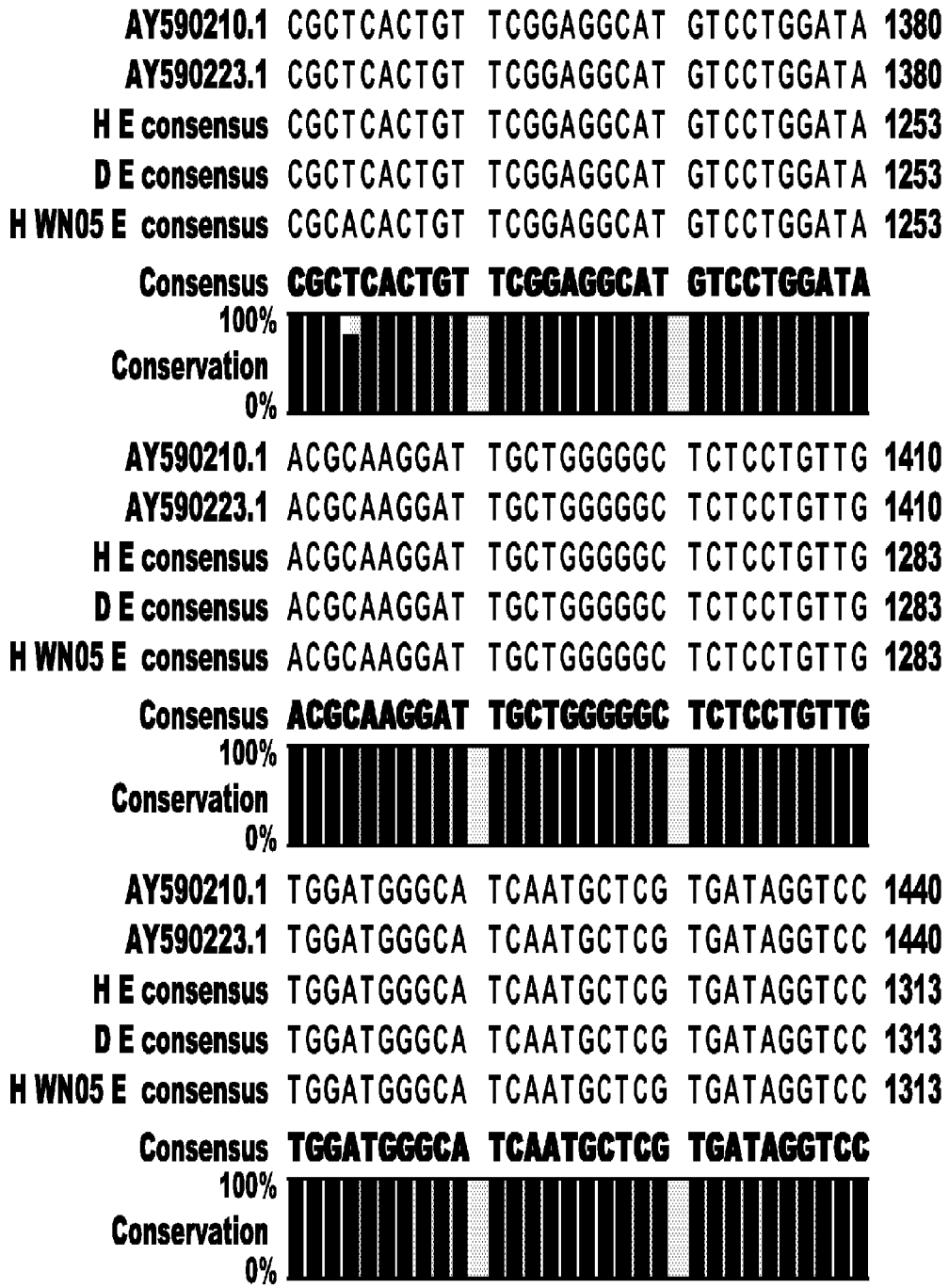

The critical Envelope (E) protein and Non-Structural 5 (NS5) protein was sequenced in these WNV isolates using standard laboratory techniques to determine genetic differences in nucleotide sequence as contrasted with WNV NY99. Notably, the North American Dominant isolates, of which specific examples are North American Equine E159 (NAEE159) and North American Donkey E159(NADE159), displayed the changes which characterize North American Dominant WNV isolates and distinguish them from NY99 WNV, namely, the U to C mutation and C to U mutation at positions 1442 and 2466, respectively, of the nucleotide sequence encoding the E protein and the C to U mutation at position 9352 in the sequence encoding the NS5 protein. FIGS. 10-17 show the sequence alignments of various regions of isolates. The alignments in the E region are relative to publically available reference sequences for a NY 99 isolate (deposited in GenBank as AY590210) and a North American Dominant isolate (WN 02 isolate) deposited in GenBank as AY590223. The alignments in the NS5 region are also relative to publically available reference sequences for a NY 99 isolate (deposited in GenBank as AY369442) and a North American Dominant isolate (WN 02 isolate) deposited in GenBank as AY369440). As shown by these alignments, North American Dominant WNV isolates have the same sequence changes relative to the NY 99 isolate as those defined in the definition for a North American Dominant WNV isolate. These sequences are provided herein as SEQ ID NOS. 1-22, the full length genome of a WN99 isolate is provided as SEQ ID NO. 23, and the protein encoded by the full length genome of SEQ ID NO. 23 is provided as SEQ ID NO. 24.

SEQUENCE LISTING

<160> NUMBER OF SEQ ID NOS: 24

<210> SEQ ID NO 1
<211> LENGTH: 608
<212> TYPE: DNA
<213> ORGANISM: West Nile virus

<400> SEQUENCE: 1 cgggggggaat gtcacacttg catttacaac atgatgggaa agagagagaa aaacccggga     60
gaattcggaa aggccaaggg aagcagagcc atttggttca tgtggctcgg agctcgcttt    120
ctggagttcg aggctctggg ttttctcaat gaagaccact ggcttggaag aaagaactca    180
ggaggaggtg tcgagggctt gggcctccaa aaactgggtt acatcctgcg tgaagttggc    240
acccggcctg ggggcaagat ctatgctgat gacacagctg gctgggacac ccgcatcacg    300
agagctgact tggaaaatga agctaaggtg cttgagctgc ttgatgggga acatcggcgt    360
cttgccaggg ccatcattga gctcacctat cgtcacaaag ttgtgaaagt gatgcgcccg    420
gctgctgatg aagaaccgt catggatgtt atctccagag aagatcagag ggggagtgga     480
caagttgtca cctacgccct aaacactttc accaacctgg ccgtccagct ggtgaggatg    540
atggaagggg aaggagtgat tggcccagat gatgtggaga aactcacaaa agggaaagga    600
cccaaagt                                                             608

<210> SEQ ID NO 2
<211> LENGTH: 608
<212> TYPE: DNA
<213> ORGANISM: West Nile virus

<400> SEQUENCE: 2 cgggggggaat gtcacacttg catttacaac atgatgggaa agagagagaa aaacccggga     60
gagttcggaa aggccaaggg aagcagagcc atttggttca tgtggctcgg agctcgcttt    120
ctggagttcg aggctctggg ttttctcaat gaagaccact ggcttggaag aaagaactca    180
ggaggaggtg tcgagggctt gggcctccaa aaactgggtt acatcctgcg tgaagttggc    240
acccggcctg ggggcaagat ctatgctgat gacacagctg gctgggacac ccgcatcacg    300
agtgctgact tggaaaatga agctaaggtg cttgagttgc ttgatgggga acatcggcgt    360
cttgccaggg ccatcattga gctcacctat cgtcacaaag ttgtgaaagt gatgcgcccg    420
gctgctgatg aagaaccgt catggatgtt atctccagag aagatcagag ggggagtgga     480
caagttgtca cctacgccct aaacactttc accaacctgg ccgtccagct ggtgaggatg    540
atggaagggg aaggagtgat tggcccagat gatgtggaga aactcacaaa agggaaagga    600
cccaaagt                                                             608

<210> SEQ ID NO 3
<211> LENGTH: 909
<212> TYPE: DNA
<213> ORGANISM: West Nile virus
<220> FEATURE:
<221> NAME/KEY: misc_feature
<222> LOCATION: (57)..(57)
<223> OTHER INFORMATION: n is a, c, g, or t

<400> SEQUENCE: 3
gcaatgcagc tttgggtgcc atgtttgaag agcagaatca atggaggagc gccaganaag     60
cagttgaaga tccaaaattt tgggagatgg tggatgagga gcgcgaggca catctgcggg    120
gggaatgtca cacttgcatt tacaacatga tgggaaagag agagaaaaaa cccggagagt    180

```
tcggaaaggc taagggaagc agagccattt ggttcatgtg gctcggagct cgctttctgg    240
agttcgaggc tctgggtttt ctcaatgaag accactggct tggaagaaag aactcaggag    300
gaggtgtcga gggcttgggc ctccaaaaac tgggttacat cctgcgtgaa gttggcaccc    360
gacctggggg caagatctat gctgatgaca cagccggctg gacaccgc atcacgagag      420 ctgacttgga aaatgaagct aaggtgcttg agttgcttga tggggaacat cggcgtcttg    480
ccagggccat cattgagctc acctatcgtc acaaagttgt gaaagtgatg cgcccggctg    540
ctgatggaag aaccgtcatg gatgttatct ccagagaaga tcagaggggg agtggacaag    600
ttgtcaccta cgccctaaac actttcacca acctggccgt ccagctggtg aggatgatgg    660
aaggggaagg agtgattggc ccagatgatg tggagaaact cacaaaaggg aaaggaccca    720
aagtcaggac ctggctgttt gagaatgggg aagaaagact cagccgcatg gctgtcagtg    780
gagatgactg tgtggtaaag cccctggacg atcgctttgc cacctcgctc cacttcctca    840
atgctatgtc aaaggttcgc aaagacatcc aagagtggaa accgtcaact ggatggtatg    900
attggcagc                                                            909

<210> SEQ ID NO 4
<211> LENGTH: 975
<212> TYPE: DNA
<213> ORGANISM: West Nile virus
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t
<220> FEATURE:
<221> NAME/KEY: misc_feature
<222> LOCATION: (881)..(882)
<223> OTHER INFORMATION: n is a, c, g, or t

<400> SEQUENCE: 4
tcncggattc cncgcacgag atgtattggg tgagtcgagc ttcaggcaat gtggtacatt    60
cagtgaatat gaccagccag gtgctcctag aagaatgga aaaaaggacc tggaagggac    120
cccaatacga ggaagatgta aacttgggaa gtggaaccag gcggtgggaa aacccctgc    180 tcaactcaga caccagtaaa atcaagaaca ggattgaacg actcaggcgt gagtacagtt    240
cgacgtggca ccacgatgag aaccacccat atagaacctg gaactatcac ggcagttatg    300
atgtgaagcc cacaggctcc gccagttcgc tggttaatgg agtggtcagg ctcctctcaa    360
aaccatggga caccatcacg aatgttacca ccatggccat gactgacact actcccttcg    420
ggcagcagcg agtgttcaaa gagaaggtgg acacgaaagc tcctgaaccg ccagaaggag    480
tgaagtacgt gctcaacgag accaccaact ggttgtgggc gttttggcc agagaaaaac    540 gtcccagaat gtgctctcga gaggaattca taagaaaggt caacagcaat gcagctttgg    600
gtgccatgtt tgaagagcag aatcaatgga ggagcgccag agaagcagtt gaagatccaa    660
aatttgggga gatggtggat gaggagcgcg aggcacatct gcgggggaa tgtcacactt    720 gcatttacaa catgatggga aagagagaga aaaaccccgg agagttcgga aaggctaagg    780
gaagcagagc catttggttc atgtggctcg ganctcgctt tctggagttc gaggctctgg    840
```

```
gttttctcaa tgaagaccac tggcttggaa gaaagaactc nngaggaggt gtcgagggct      900
tgggcctcca aaaactgggt tacatcctgc gtgaagttgg cacccgacct gggggcaaga      960
tctatgctga tgaca                                                       975
```

<210> SEQ ID NO 5
<211> LENGTH: 957
<212> TYPE: DNA
<213> ORGANISM: West Nile virus
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (130)..(130)
<223> OTHER INFORMATION: n is a, c, g, or t

<400> SEQUENCE: 5

```
aatggagngg tcaggctcct ctcaaaaccc ntgggacacc atcacgaatg ntaccaccat       60
ggccatgact gacactactc ccnttcgggc agcagcgagt gttcaaagag aaggtggaca      120
cgaaagctcn tgaaccgcca gaaggagtga agtacgtgct caacgagacc accaactggt      180
tgtgggcgtt tttggccaga gaaaaacgtc ccagaatgtg ctctcgagag gaattcataa      240
gaaaggtcaa cagcaatgca gctttgggtg ccatgtttga agagcagaat caatggagga      300
gcgccagaga agcagttgaa gatccaaaat tttgggagat ggtggatgag gagcgcgagg      360
cacatctgcg gggggaatgt cacacttgca tttacaacat gatgggaaag agagagaaaa      420
aacccggaga gttcggaaag gctaagggaa gcagagccat ttggttcatg tggctcggag      480
ctcgctttct ggagttcgag gctctgggtt ttctcaatga agaccactgg cttggaagaa      540
agaactcagg aggaggtgtc gagggcttgg gcctccaaaa actgggttac atcctgcgtg      600
aagttggcac ccgacctggg ggcaagatct atgctgatga cacagccggc tgggacaccc      660
gcatcacgag agctgacttg gaaaatgaag ctaaggtgct tgagttgctt gatgggggaac      720 atcggcgtct tgccagggcc atcattgagc tcacctatcg tcacaaagtt gtgaaagtga      780
tgcgcccggc tgctgatgga agaaccgtca tggatgttat ctccagagaa gatcagaggg      840
ggagtggaca agttgtcacc tacgccctaa acactttcac caacctggcc gtccagctgg      900
tgaggatgat ggaaggggaa ggagtgattg cccagatga tgtggagaaa ctcacaa       957
```

<210> SEQ ID NO 6
<211> LENGTH: 961
<212> TYPE: DNA
<213> ORGANISM: West Nile virus
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t

```
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t

<400> SEQUENCE: 6
gggaccccaa tacgaggaag atgtaaactn gggaagtgga nccagggcgg tgggaaaacc      60
cnngctcaac tcagacacca gtaaaatcaa gaacaggatt gaacgantca ggcgtgagta     120
cagttcgacg tggcaccacg atgagaacca cccatataga acctggaact atcacggcag     180
ttatgatgtg aagcccacag gctccgccag ttcgctggtt aatggagtgg tcaggctcct     240
ctcaaaacca tgggacacca tcacgaatgt taccaccatg gccatgactg acactactcc     300
cttcgggcag cagcgagtgt tcaaagagaa ggtggacacg aaagctcctg aaccgccaga     360
aggagtgaaa tacgtgctca acgagaccac caactggttg tgggcgtttt tggccagaga     420
aaaacgtccc agaatgtgct ctcgagagga attcataaga aaggtcaaca gcaatgcagc     480
tttgggtgcc atgtttgaag agcagaatca atggaggagc gccagagaag cagttgaaga     540
tccaaaattt tgggagatgg tggatgagga gcgcgaggca catctgcggg gggaatgtca     600
cacttgcatt tacaacatga tgggaaagag agagaaaaaa cccggagagt tcggaaaggc     660
taagggaagc agagccattt ggttcatgtg gctcggagct cgctttctgg agttcgaggc     720
tctgggtttt ctcaatgaag accactggct tggaagaaag aactcaggag gaggtgtcga     780
gggcttgggc ctccaaaaac tgggttacat cctgcgtgaa gttggcaccc gacctggggg     840
caagatctat gctgatgaca cagccggctg ggacacccgc atcacgagag ctgacttgga     900
aaatgaagct aaggtgcttg agttgcttga tggggaacat cggcgtcttg ccagggccat     960
c                                                                     961

<210> SEQ ID NO 7
<211> LENGTH: 1503
<212> TYPE: DNA
<213> ORGANISM: West Nile virus

<400> SEQUENCE: 7
ttcaactgcc ttggaatgag caacagagac ttcttggaag gagtgtctgg agcaacatgg      60
gtggatttgg ttctcgaagg cgacagctgc gtgactatca tgtctaagga caagcctacc     120
atcgatgtga agatgatgaa tatggaggcg gccaacctgg cagaggtccg cagttattgc     180
tatttggcta ccgtcagcga tctctccacc aaagctgcgt gcccgaccat gggagaagct     240
cacaatgaca aacgtgctga cccagctttt gtgtgcagac aaggagtggt ggacaggggc     300
tggggcaacg gctgcggact atttggcaaa ggaagcattg acacatgcgc caaatttgcc     360
tgctctacca aggcaatagg aagaaccatc ttgaaagaga atatcaagta cgaagtggcc     420
attttcgtcc atggaccaac tactgtggag tcgcacggaa actactccac acaggttgga     480
gccactcagg cagggagatt cagcatcact cctgcggcgc cttcacacac actaaagctt     540
ggagaatatg gagaggtgac agtggactgt gaaccacggt cagggattga caccaatgca     600
tactacgtga tgactgttgg aacaaagacg ttcttggtcc atcgtgagtg gttcatggac     660
ctcaacctcc cttggagcag tgctggaagt actgtgtgga ggaacagaga gacgttaatg     720
gagtttgagg aaccacacgc cacgaagcag tctgtgatag cattgggctc acaagaggga     780
```

```
gctctgcagc aagctttggc tggagccatt cctgtggaat tttcaagcaa cactgtcaag    840
ttgacgtcgg gtcatttgaa gtgtagagtg aagatggaaa aattgcagtt gaagggaaca    900
acctatggcg tctgttcaaa ggctttcaag tttcttggga ctcccgcaga cacaggtcac    960
ggcactgtgg tgttggaatt gcagtacact ggcacggatg gaccttgcaa agttcctatc   1020
tcgtcagtgg cttcattgaa cgacctaacg ccagtgggca gattggtcac tgtcaaccct   1080
tttgtttcag tggccacggc caacgctaag gtcctgattg aattggaacc acccttgga   1140
gactcataca tagtggtggg cagaggagaa caacagatca atcaccattg gcacaagtct   1200
ggaagcagca ttggcaaagc ctttacaacc accctcaaag gagcgcagag actagccgct   1260
ctaggagaca cagcttggga ctttggatca gttggagggg tgttcacctc agttgggaag   1320
gctgtccatc aagtgttcgg aggagcattc cgctcactgt tcggaggcat gtcctggata   1380
acgcaaggat tgctgggggc tctcctgttg tggatgggca tcaatgctcg tgataggtcc   1440
atagctctca cgtttctcgc agttggagga gttctgctct cctctccgt gaacgtgcac   1500
gct                                                                 1503

<210> SEQ ID NO 8
<211> LENGTH: 1503
<212> TYPE: DNA
<213> ORGANISM: West Nile virus

<400> SEQUENCE: 8
ttcaactgcc ttggaatgag caacagagac ttcttggaag gagtgtctgg agcaacatgg     60
gtggatttgg ttctcgaagg cgacagctgc gtgactatca tgtctaagga caagcctacc    120
atcgatgtga agatgatgaa tatggaggcg gccaacctgg cagaggtccg cagttattgc    180
tatttggcta ccgtcagcga tctctccacc aaagctgcgt gcccgaccat gggagaagct    240
cacaatgaca acgtgctga cccagctttt gtgtgcagac aaggagtggt ggacaggggc    300
tggggcaacg gctgcggact atttggcaaa ggaagcattg acacatgcgc caaatttgcc    360
tgctctacca aggcaatagg aagaaccatc ttgaaagaga atatcaagta cgaagtggcc    420
attttttgtcc atggaccaac tactgtggag tcgcacggaa actattccac acaggctgga    480
gccactcagg cagggagatt cagcatcact cctgcggcgc cttcatacac actaaagctt    540
ggagaatatg gagaggtgac agtggactgt gaaccacggt cagggattga caccaatgca    600
tactacgtga tgactgttgg aacaaagacg ttcttggtcc atcgtgagtg gttcatggac    660
ctcaacctcc cttggagcag tgctggaagt actgtgtgga ggaacagaga gacgttaatg    720
gagtttgagg aaccacacgc cacgaagcag tctgtgatag cattgggctc acaagaggga    780
gctctgcatc aagctttggc tggagccatt cctgtggaat tttcaagcaa cactgtcaag    840
ttgacgtcgg gtcatttgaa gtgtagagtg aagatggaaa aattgcagtt gaagggaaca    900
acctatggcg tctgttcaaa ggctttcaag tttcttggga ctcccgcaga cacaggtcac    960
ggcactgtgg tgttggaatt gcagtacact ggcacggatg gaccttgcaa agttcctatc   1020
tcgtcagtgg cttcattgaa cgacctaacg ccagtgggca gattggtcac tgtcaaccct   1080
tttgtttcag tggccacggc caacgctaag gtcctgattg aattggaacc acccttgga   1140
gactcataca tagtggtggg cagaggagaa caacagatca atcaccattg gcacaagtct   1200
ggaagtagca ttggcaaagc ctttacaacc accctcaaag gagcgcagag actagccgct   1260
ctaggagaca cagcttggga ctttggatca gttggagggg tgttcacctc agttgggaag   1320
gctgtccatc aagtgttcgg aggagcattc cgctcactgt tcggaggcat gtcctggata   1380
```

```
acgcaaggat tgctgggggc tctcctgttg tggatgggca tcaatgctcg tgataggtcc   1440
atagctctca cgtttctcgc agttggagga gttctgctct tcctctccgt gaacgtgcat   1500
gct                                                                  1503
```

<210> SEQ ID NO 9
<211> LENGTH: 1376
<212> TYPE: DNA
<213> ORGANISM: West Nile virus
<220> FEATURE:
<221> NAME/KEY: misc_feature
<222> LOCATION: (1358)..(1358)
<223> OTHER INFORMATION: n is a, c, g, or t

<400> SEQUENCE: 9

```
gatgtggaga gaatatggag gcggccaacc tggcagaggt ccgcagttat tgctatttgg    60
ctaccgtcag cgatctctcc accaaagctg cgtgcccgac catgggagaa gctcacaatg   120
acaaacgtgc tgacccagct tttgtgtgca gacaaggagt ggtggacagg ggctggggca   180
acggctgcgg actatttggc aaaggaagca ttgacacatg cgccaaattt gcctgctcta   240
ccaaggcaat aggaagaacc atcttgaaag agaatatcaa gtacgaagtg ccattttg     300 tccatggacc aactactgtg gagtcgcacg gaaactactc cacacaggtt ggagccactc   360
aggcagggag attcagcatc actcctgcgg cgccttcata cactaaag cttggagaat    420 atggagaggt gacagtggac tgtgaaccac ggtcagggat tgacaccaat gcatactatg   480
tgatgactgt tggaacaaag acgttcttgg tccatcgtga gtggttcatg gacctcaacc   540
tcccttggag cagtgctgga agtactgtgt ggaggaacag agagacgtta atggagtttg   600
aggaaccaca cgccacgaag cagtctgtga tagcattggg ctcacaagag ggagctctgc   660
atcaagcttt ggctggagcc attcctgtgg aattttcaag caacactgtc aagttgacgt   720
cgggtcattt gaagtgtaga gtgaagatgg aaaaattgca gttgaaggga acaacctatg   780
gcgtctgttc aaaggctttc aagtttcttg ggactcccgc agacacaggt cacggcactg   840
tggtgttgga attgcagtac actggcacgg atggaccttg caaagttcct atctcgtcag   900
tggcttcatt gaacgaccta acgccagtgg gcagattggt cactgtcaac ccttttgttt   960
cagtggccac ggccaacgct aaggtcctga ttgaattgga accacccttt ggagactcat  1020
acatagtggt gggcagagga gaacaacaga tcaatcacca ttggcacaag tctggaagca  1080
gcattggcaa agccttaca accaccctca aggagcgca gagactagcc gctctaggag  1140
acacagcttg ggactttgga tcagttggag gggtgttcac ctcagttggg aaggctgtcc  1200
atcaagtgtt cggaggagca ttccgctcac tgttcggagg catgtcctgg ataacgcaag  1260
gattgctggg ggctctcctg ttgtggatgg gcatcaatgc tcgtgatagg tccatagctc  1320
tcacgtttct cgcagttgga ggagttctgc tcttcctntc cgtgaacgtg cacgct       1376
```

<210> SEQ ID NO 10
<211> LENGTH: 1376
<212> TYPE: DNA
<213> ORGANISM: West Nile virus

<400> SEQUENCE: 10

```
gatgtggaga gaatatggag gcggccaacc tggcagaggt ccgcagttat tgctatttgg    60
ctaccgtcag cgatctctcc accaaagctg cgtgcccgac catgggagaa gctcacaatg   120
acaaacgtgc tgacccagct tttgtgtgca gacaaggagt ggtggacagg ggctggggca   180
```

```
acggctgcgg actatttggc aaaggaagca ttgacacatg cgccaaattt gcctgctcta      240
ccaaggcaat aggaagaacc atcttgaaag agaatatcaa gtacgaagtg gccattttg       300 tccatggacc aactactgtg gagtcgcacg gaaactactc cacacaggct ggagccactc      360
aggcagggag attcagcatc actcctgcgg cgccttcata cactaaaag cttggagaat       420 atggagaggt gacagtggac tgtgaaccac ggtcagggat tgacaccaat gcatactacg      480
tgatgactgt tggaacaaag acgttcttgg tccatcgtga gtggttcatg gacctcaacc      540
tcccttggag cagtgctgga agtactgtgt ggaggaacag agagacgtta atggagtttg      600
aggaaccaca cgccacgaag cagtctgtga tagcattggg ctcacaagag ggagctctgc      660
atcaagcttt ggctggagcc attcctgtgg aattttcaag caacactgtc aagttgacgt      720
cgggtcattt gaagtgtaga gtgaagatgg aaaaattgca gttgaaggga acaacctatg      780
gcgtctgttc aaaggctttc aagtttcttg ggactcccgc agacacaggt cacggcactg      840
tggtgttgga attgcagtac actggcacgg atggaccttg caagttcct atctcgtcag       900 tggcttcatt gaacgaccta acgccagtgg gcagattggt cactgtcaac ccttttgttt      960
cagtggccac ggccaacgct aaggtcctga ttgaattgga accacccttt ggagactcat     1020
acatagtggt gggcagagga gaacaacaga tcaatcacca ttggcacaag tctggaagca     1080
gcattggcaa agcctttaca accaccctca aggagcgca gagactagcc gctctaggag       1140
acacagcttg ggactttgga tcagttgag gggtgttcac ctcagttggg aaggctgtcc       1200
atcaagtgtt cggaggagca ttccgctcac tgttcggagg catgtcctgg ataacgcaag     1260
gattgctggg ggctctcctg ttgtggatgg gcatcaatgc tcgtgatagg tccatagctc     1320
tcacgtttct cgcagttgga ggagttctgc tcttcctctc cgtgaacgtg catgct         1376
```

<210> SEQ ID NO 11
<211> LENGTH: 1376
<212> TYPE: DNA
<213> ORGANISM: West Nile virus

<400> SEQUENCE: 11

```
gatgtggaga gaatatggag gcggccaacc tggcagaggt ccgcagttat tgctatttgg       60
ctaccgtcag cgatctctcc accaaagctg cgtgcccgac catgggagaa gctcacaatg      120
acaaacgtgc tgacccagct tttgtgtgca gacaaggagt ggtggacagg ggctggggca      180
acggctgcgg actatttggc aaaggaagca ttgacacatg cgccaaattt gcctgctcta      240
ccaaggcaat aggaagaacc atcttgaaag agaatatcaa gtacgaagtg gccattttg       300 tccatggacc aactactgtg gagtcgcacg gaaactactc cacacaggct ggagccactc      360
aggcagggag attcagcatc actcctgcgg cgccttcata cactaaaag cttggagaat       420 atggagaggt gacagtggac tgtgaaccac ggtcagggat tgacaccaat gcatactacg      480
tgatgactgt tggaacaaag acgttcttgg tccatcgtga gtggttcatg gacctcaacc      540
tcccttggag cagtgctgga agtactgtgt ggaggaacag agagacgtta atggagtttg      600
aggaaccaca cgccacgaag cagtctgtga tagcattggg ctcacaagag ggagctctgc      660
atcaagcttt ggctggagcc attcctgtgg aattttcaag caacactgtc aagttgacgt      720
cgggtcattt gaagtgtaga gtgaagatgg aaaaattgca gttgaaggga acaacctatg      780
gcgtctgttc aaaggctttc aagtttcttg ggactcccgc agacacaggt cacggcactg      840
tggtgttgga attgcagtac actggcacgg atggaccttg caagttcct atctcgtcag       900 tggcttcatt gaacgatcta acgccagtgg gcagattggt cactgtcaac ccttttgttt      960
```

```
cagtggccac ggccaacgct aaggtcctga ttgaattgga accacccttt ggagactcat    1020
acatagtggt gggcagagga gaacaacaga tcaatcacca ttggcacaag tctggaagca    1080
gcattggcaa agcctttaca accaccctca aaggagcgca gagactagcc gctctaggag    1140
acacagcttg ggactttgga tcagttggag gggtgttcac ctcagttggg aaggctgtcc    1200
atcaagtgtt cggaggagca ttccgcacac tgttcggagg catgtcctgg ataacgcaag    1260
gattgctggg ggctctcctg ttgtggatgg gcatcaatgc tcgtgatagg tccatagctc    1320
tcacgtttct cgcagttgga ggagttctgc tcttcctctc cgtgaacgtg catgct        1376

<210> SEQ ID NO 12
<211> LENGTH: 608
<212> TYPE: DNA
<213> ORGANISM: West Nile virus

<400> SEQUENCE: 12 cgggggggaat gtcacacttg catttacaac atgatgggaa agagagagaa aaacccgga      60 gaattcggaa aggccaaggg aagcagagcc atttggttca tgtggctcgg agctcgcttt    120
ctggagttcg aggctctggg ttttctcaat gaagaccact ggcttggaag aaagaactca    180
ggaggaggtg tcgagggctt gggcctccaa aaactgggtt acatcctgcg tgaagttggc    240
acccggcctg ggggcaagat ctatgctgat gacacagctg ctgggacac ccgcatcacg     300 agagctgact tggaaaatga agctaaggtg cttgagctgc ttgatgggga acatcggcgt    360
cttgccaggg ccatcattga gctcacctat cgtcacaaag ttgtgaaagt gatgcgcccg    420
gctgctgatg gaagaaccgt catggatgtt atctccagag aagatcagag ggggagtgga    480
caagttgtca cctacgccct aaacactttc accaacctgg ccgtccagct ggtgaggatg    540
atggaagggg aaggagtgat tggcccagat gatgtggaga aactcacaaa agggaaagga    600
cccaaagt                                                             608

<210> SEQ ID NO 13
<211> LENGTH: 608
<212> TYPE: DNA
<213> ORGANISM: West Nile virus

<400> SEQUENCE: 13 cgggggggaat gtcacacttg catttacaac atgatgggaa agagagagaa aaacccgga      60 gagttcggaa aggccaaggg aagcagagcc atttggttca tgtggctcgg agctcgcttt    120
ctggagttcg aggctctggg ttttctcaat gaagaccact ggcttggaag aaagaactca    180
ggaggaggtg tcgagggctt gggcctccaa aaactgggtt acatcctgcg tgaagttggc    240
acccggcctg ggggcaagat ctatgctgat gacacagctg ctgggacac ccgcatcacg     300 agtgctgact tggaaaatga agctaaggtg cttgagttgc ttgatgggga acatcggcgt    360
cttgccaggg ccatcattga gctcacctat cgtcacaaag ttgtgaaagt gatgcgcccg    420
gctgctgatg gaagaaccgt catggatgtt atctccagag aagatcagag ggggagtgga    480
caagttgtca cctacgccct aaacactttc accaacctgg ccgtccagct ggtgaggatg    540
atggaagggg aaggagtgat tggcccagat gatgtggaga aactcacaaa agggaaagga    600
cccaaagt                                                             608

<210> SEQ ID NO 14
<211> LENGTH: 981
<212> TYPE: DNA
```

<213> ORGANISM: West Nile virus

<400> SEQUENCE: 14

```
ggaactatcc ggagtatgat gtgaagctcg ctgtcaatga gtgtcaggct cttcaaaacc      60
tgggacccat ccgaaccgcc atgactgcac tactcccttc gggcagcagc gagtgttcaa     120
agagaaggtg gacacgaaag ctcgaaccgc cagaaggagt gaagtacgtg ctcaacgaga     180
ccaccaactg gttgtgggcg ttttggcca gagaaaaacg tcccagaatg tgctctcgag      240
agatagaaag gtcaacagca atgcagcttt gggtgccatg tttgaagagc agaatcaatg     300
gaggagcgcc agagaagcag ttgaagatcc aaaattttgg gagatggtgg atgaggagcg     360
cgaggcacat ctgcgggggg aatgtcacac ttgcatttac aacatgatgg aaagagaga     420
gaaaaaccc ggagagttcg gaaaggccaa gggaagcaga gccatttggt tcatgtggct      480
cggagctcgc tttctggagt tcgaggctct gggttttctc aatgaagatc actggcttgg     540
aagaaagaac tcaggaggag gtgtcgaggg cttgggcctc caaaaactgg gttacatcct     600
gcgtgaagtt ggcacccggc ctgggggcaa gatctatgct gatgacacag ctggctggga     660
cacccgcatc acgagagctg acttggaaaa tgaagctaag gtgcttgagc tgcttgatgg     720
ggaacatcgg cgtcttgcca gggccatcat tgagctcacc tatcgtcaca agttgtgaa      780
agtgatgcgc ccggctgctg atggaagaac cgtcatggat gttatctcca gagaagatca     840
gagggggagt ggacaagttg tcacctacgc cctaaacact ttcaccaacc tggccgtcca     900
gctggtgagg atgatggaag gggaaggagt gattggccca gatgatgtgg agaaactcac     960
aaaagggaaa ggacccaaag t                                              981
```

<210> SEQ ID NO 15
<211> LENGTH: 974
<212> TYPE: DNA
<213> ORGANISM: West Nile virus

<400> SEQUENCE: 15

```
ttcgctgtca atggagtgtc aggctcctct caaaaccatg gacaccatc acgaatccac       60
catggccatg actgacacta ctcccttcgg cagcagcga gtgttcaaag agaaggtgga     120
cacgaaagct gaaccgccag aaggagtgaa gtacgtgctc aacgagacca ccaactggtt     180
gtgggcgttt ttggccagag aaaaacgtcc cagaatgtgc tctcgagagg aattcataga     240
aaggtcaaca gcaatgcagc tttgggtgcc atgtttgaag agcagaatca atggaggagc     300
gccagagaag cagttgaaga tccaaaattt tgggagatgg tggatgagga gcgcgaggca     360
catctgcggg gggaatgtca cacttgcatt tacaacatga tgggaaagag agagaaaaaa     420
cccggagagt tcgaaaggc caagggaagc agagccattt ggttcatgtg gctcggagct     480
cgctttctgg agttcgaggc tctgggtttt ctcaatgaag accactggct tggaagaaag     540
aactcaggag gaggtgtcga gggcttgggc ctccaaaaac tgggttacat cctgcgtgaa     600
gttggcaccc ggcctggggg caagatctat gctgatgaca cagctggctg gacacccgc      660
atcacgagag ctgacttgga aaatgaagct aaggtgcttg agttgcttga tggggaacat     720
cggcgtcttg ccagggccat cattgagctc acctatcgtc acaaagttgt gaaagtgatg     780
cgcccggctg ctgatggaag aaccgtcatg gatgttatct ccagagaaga tcagaggggg     840
agtggacaag ttgtcaccta cgccctaaac actttcacca acctggccgt ccagctggtg     900
aggatgatga aggggaagg agtgattggc ccagatgatg tggagaaact cacaaaaggg     960
aaaggaccca agt                                                        974
```

<210> SEQ ID NO 16
<211> LENGTH: 970
<212> TYPE: DNA
<213> ORGANISM: West Nile virus

<400> SEQUENCE: 16

```
aatggagggt caggctcctc tcaaaacctg ggacaccatc acgaatgtac caccatggcc      60
atgactgaca ctactccctt cgggcagcag cgagtgttca agagaaggt ggacacgaaa     120
```

```
aatggagggt caggctcctc tcaaaacctg ggacaccatc acgaatgtac caccatggcc      60
atgactgaca ctactccctt cgggcagcag cgagtgttca agagaaggt  ggacacgaaa    120
gctctgaacc gccagaagga gtgaagtacg tgctcaacga daccaccaac tggttgtggg    180
cgttttggc cagagaaaaa cgtcccagaa tgtgctctcg agaggaattc ataagaaagg     240
tcaacagcaa tgcagctttg ggtgccatgt tgaagagca gaatcaatgg aggagcgcca     300
gagaagcagt tgaagatcca aaattttggg agatggtgga tgaggagcgc gaggcacatc    360
tgcgggggga atgtcacact tgcatttaca acatgatggg aaagagagag aaaaaacccg    420
gagagttcgg aaaggctaag ggaagcagag ccatttggtt catgtggctc ggagctcgct    480
ttctggagtt cgaggctctg gtttttctca tgaagacca ctggcttgga agaaagaact    540
caggaggagg tgtcgagggc ttgggcctcc aaaaactggg ttacatcctg cgtgaagttg    600
gcacccgacc tggggcaag atctatgctg atgacacagc cggctgggac acccgcatca    660
cgagagctga cttggaaaat gaagctaagg tgcttgagtt gcttgatggg aacatcggc    720
gtcttgccag ggccatcatt gagctcacct atcgtcacaa agttgtgaaa gtgatgcgcc    780
cggctgctga tggaagaacc gtcatggatg ttatctccag agaagatcag agggggagtg    840
gacaagttgt cacctacgcc ctaaacactt tcaccaacct ggccgtccag ctggtgagga    900
tgatggaagg ggaaggagtg attggcccag atgatgtgga gaaactcaca aaagggaaag    960
gacccaaagt                                                            970
```

<210> SEQ ID NO 17
<211> LENGTH: 1503
<212> TYPE: DNA
<213> ORGANISM: West Nile virus

<400> SEQUENCE: 17

```
ttcaactgcc ttggaatgag caacagagac ttcttggaag gagtgtctgg agcaacatgg     60
gtggatttgg ttctcgaagg cgacagctgc gtgactatca tgtctaagga caagcctacc    120
atcgatgtga agatgatgaa tatggaggcg gccaacctgg cagaggtccg cagttattgc    180
tatttggcta ccgtcagcga tctctccacc aaagctgcgt gcccgaccat gggagaagct    240
cacaatgaca aacgtgctga cccagctttt gtgtgcagac aaggagtggt ggacaggggc    300
tggggcaacg gctgcggact atttggcaaa ggaagcattg acacatgcgc caaatttgcc    360
tgctctacca aggcaatagg aagaaccatc ttgaaagaga atatcaagta cgaagtggcc    420
atttttgtcc atggaccaac tactgtggag tcgcacggaa actactccac acaggttgga    480
gccactcagg cagggagatt cagcatcact cctgcggcgc cttcacacac actaaagctt    540
ggagaatatg gagaggtgac agtggactgt gaaccacggt cagggattga caccaatgca    600
tactacgtga tgactgttgg aacaaagacg ttcttggtcc atcgtgagtg gttcatggac    660
ctcaacctcc cttggagcag tgctggaagt actgtgtgga ggaacagaga gacgttaatg    720
gagtttgagg aaccacacgc cacgaagcag tctgtgatag cattgggctc acaagaggga    780
gctctgcagc aagcttggc tggagccatt cctgtggaat tttcaagcaa cactgtcaag    840
```

```
ttgacgtcgg gtcatttgaa gtgtagagtg aagatggaaa aattgcagtt gaagggaaca      900
acctatggcg tctgttcaaa ggctttcaag tttcttggga ctcccgcaga cacaggtcac      960
ggcactgtgg tgttggaatt gcagtacact ggcacggatg gaccttgcaa agttcctatc     1020
tcgtcagtgg cttcattgaa cgacctaacg ccagtgggca gattggtcac tgtcaaccct     1080
tttgtttcag tggccacggc caacgctaag gtcctgattg aattggaacc acccttggga     1140
gactcataca tagtggtggg cagaggagaa caacagatca atcaccattg gcacaagtct     1200
ggaagcagca ttggcaaagc ctttacaacc accctcaaag gagcgcagag actagccgct     1260
ctaggagaca cagcttggga ctttggatca gttggagggg tgttcacctc agttgggaag     1320
gctgtccatc aagtgttcgg aggagcattc cgctcactgt tcggaggcat gtcctggata     1380
acgcaaggat tgctgggggc tctcctgttg tggatgggca tcaatgctcg tgataggtcc     1440
atagctctca cgtttctcgc agttggagga gttctgctct tcctctccgt gaacgtgcac     1500
gct                                                                   1503

<210> SEQ ID NO 18
<211> LENGTH: 1503
<212> TYPE: DNA
<213> ORGANISM: West Nile virus

<400> SEQUENCE: 18
ttcaactgcc ttggaatgag caacagagac ttcttggaag gagtgtctgg agcaacatgg       60
gtggatttgg ttctcgaagg cgacagctgc gtgactatca tgtctaagga caagcctacc      120
atcgatgtga agatgatgaa tatggaggcg gccaacctgg cagaggtccg cagttattgc      180
tatttggcta ccgtcagcga tctctccacc aaagctgcgt gcccgaccat gggagaagct      240
cacaatgaca aacgtgctga cccagctttt gtgtgcagac aaggagtggt ggacaggggc      300
tggggcaacg gctgcggact atttggcaaa ggaagcattg acacatgcgc caaatttgcc      360
tgctctacca aggcaatagg aagaaccatc ttgaaagaga atatcaagta cgaagtggcc      420
attttgtcc atggaccaac tactgtggag tcgcacggaa actattccac acaggctgga      480
gccactcagg cagggagatt cagcatcact cctgcggcgc ttcatacac actaaagctt      540
ggagaatatg gagaggtgac agtggactgt gaaccacggt cagggattga caccaatgca      600
tactacgtga tgactgttgg aacaaagacg ttcttggtcc atcgtgagtg gttcatggac      660
ctcaacctcc cttggagcag tgctggaagt actgtgtgga ggaacagaga gacgttaatg      720
gagtttgagc aaccacacgc cacgaagcag tctgtgatag cattgggctc aagagggga      780
gctctgcatc aagctttggc tggagccatt cctgtggaat tttcaagcaa cactgtcaag      840
ttgacgtcgg gtcatttgaa gtgtagagtg aagatggaaa aattgcagtt gaagggaaca      900
acctatggcg tctgttcaaa ggctttcaag tttcttggga ctcccgcaga cacaggtcac      960
ggcactgtgg tgttggaatt gcagtacact ggcacggatg gaccttgcaa agttcctatc     1020
tcgtcagtgg cttcattgaa cgacctaacg ccagtgggca gattggtcac tgtcaaccct     1080
tttgtttcag tggccacggc caacgctaag gtcctgattg aattggaacc acccttggga     1140
gactcataca tagtggtggg cagaggagaa caacagatca atcaccattg gcacaagtct     1200
ggaagtagca ttggcaaagc ctttacaacc accctcaaag gagcgcagag actagccgct     1260
ctaggagaca cagcttggga ctttggatca gttggagggg tgttcacctc agttgggaag     1320
gctgtccatc aagtgttcgg aggagcattc cgctcactgt tcggaggcat gtcctggata     1380
acgcaaggat tgctgggggc tctcctgttg tggatgggca tcaatgctcg tgataggtcc     1440
```

```
atagctctca cgtttctcgc agttggagga gttctgctct tcctctccgt gaacgtgcat 1500
gct 1503

<210> SEQ ID NO 19
<211> LENGTH: 968
<212> TYPE: DNA
<213> ORGANISM: West Nile virus
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (941)..(942)
<223> OTHER INFORMATION: n is a, c, g, or t
<400> SEQUENCE: 19
gatgtgngan gangaatatg gaggcggcca acctggcaga ggtccgcagt tattgctatt 60
tggctaccgt cagcgatctc tccaccaaag ctgcgtgccc gaccatggga gaagctcaca 120
atgacaaacg tgctgaccca gcttttgtgt gcagacaagg agtggtggac aggggctggg 180
gcaacggctg cggactattt ggcaaaggaa gcattgacac atgcgccaaa tttgcctgct 240
ctaccaaggc aataggaaga accatcttga aagagaatat caagtacgaa gtggccattt 300
ttgtccatgg accaactact gtggagtcgc acggaaacta ctccacacag gctggagcca 360
ctcaggcagg gagattcagc atcactcctg cggcgccttc atacacacta aagcttggag 420
aatatggaga ggtgacagtg gactgtgaac cacggtcagg gattgacacc aatgcatact 480
acgtgatgac tgttggaaca aagacgttct tggtccatcg tgagtggttc atggacctca 540
acctcccttg gagcagtgct ggaagtactg tgtggaggaa cagagagacg ttaatggagt 600
ttgaggaacc acacgccacg aagcagtctg tgatagcatt gggctcacaa gagggagctc 660
tgcatcaagc tttggctgga gccattcctg tggaattttc aagcaacact gtcaagttga 720
cgtcgggtca tttgaagtgt agagtgaaga tggaaaaatt gcagttgaag ggaacaacct 780
atggcgtctg ttcaaaggct ttcaagtttc ttgggactcc cgcagacaca ggtcacggca 840
ctgtggtgtt ggaattgcag tacactggca cggatggacc ttgcaaagtt cctatctcgt 900
cagtggcttc attgaacgat ctaacgccag tgggcagatt nntcactgtc aacccttttg 960
tttcagtg 968

<210> SEQ ID NO 20
<211> LENGTH: 979
<212> TYPE: DNA
<213> ORGANISM: West Nile virus
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (10)..(10)

```
<223> OTHER INFORMATION: n is a, c, g, or t
<220> FEATURE:
<221> NAME/KEY: misc_feature
<222> LOCATION: (974)..(974)
<223> OTHER INFORMATION: n is a, c, g, or t

<400> SEQUENCE: 20
cttnanagan atcaagtacg aagtggccat ttttgtccat ggaccaacta ctgtggagtc      60
gcacggaaac tactccacac aggctggagc cactcaggca gggagattca gcatcactcc     120
tgcggcgcct tcatacacac taaagcttgg agaatatgga gaggtgacag tggactgtga     180
accacggtca gggattgaca ccaatgcata ctacgtgatg actgttggaa caaagacgtt     240
cttggtccat cgtgagtggt tcatggacct caacctccct tggagcagtg ctggaagtac     300
tgtgtggagg aacagagaga cgttaatgga gtttgaggaa ccacacgcca cgaagcagtc     360
tgtgatagca ttgggctcac aagagggagc tctgcatcaa gctttggctg gagccattcc     420
tgtggaattt tcaagcaaca ctgtcaagtt gacgtcgggt catttgaagt gtagagtgaa     480
gatgaaaaaa ttgcagttga agggaacaac ctatggcgtc tgttcaaagg ctttcaagtt     540
tcttgggact cccgcagaca caggtcacgg cactgtggtg ttggaattgc agtacactgg     600
cacggatgga ccttgcaaag ttcctatctc gtcagtggct tcattgaacg atctaacgcc     660
agtgggcaga ttggtcactg tcaacccttt tgtttcagtg gccacggcca acgctaaggt     720
cctgattgaa ttggaaccac cctttggaga ctcatacata gtggtgggca gaggagaaca     780
acagatcaat caccattggc acaagtctgg aagcagcatt ggcaaagcct ttacaaccac     840
cctcaaagga gcgcagagac tagccgctct aggagacaca gcttgggact ttggatcagt     900 tggagggtg ttcacctcag ttgggaaggc tgtccatcaa gtgttcggag gagcattccg     960
cacactgttc ggangcatg                                                  979

<210> SEQ ID NO 21
<211> LENGTH: 1004
<212> TYPE: DNA
<213> ORGANISM: West Nile virus
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t

<400> SEQUENCE: 21
agantatgga gngnnngncag tggactgtga anccncggtc agggattgac accaatgcat      60
actacgtgat gactgttgga acaaagacgt tcttggtcca tcgtgagtgg ttcatggacc     120
tcaacctccc ttggagcagt gctggaagta ctgtgtggag gaacagagag acgttaatgg     180
```

```
agtttgagga accacacgcc acgaagcagt ctgtgatagc attgggctca caagagggag        240
ctctgcatca agctttggct ggagccattc ctgtggaatt ttcaagcaac actgtcaagt        300
tgacgtcggg tcatttgaag tgtagagtga agatggaaaa attgcagttg aagggaacaa        360
cctatggcgt ctgttcaaag gctttcaagt ttcttggac tcccgcagac acaggtcacg         420
gcactgtggt gttggaattg cagtacactg gcacggatgg accttgcaaa gttcctatct        480
cgtcagtggc ttcattgaac gatctaacgc cagtgggcag attggtcact gtcaacccctt       540 ttgtttcagt ggccacggcc aacgctaagg tcctgattga attggaacca cccctttggag      600 actcatacat agtggtgggc agaggagaac aacagatcaa tcaccattgg cacaagtctg        660
gaagcagcat tggcaaagcc tttacaacca ccctcaaagg agcgcagaga ctagccgctc        720
taggagacac agcttgggac tttggatcag ttggaggggt gttcacctca gttgggaagg      780
ctgtccatca agtgttcgga ggagcattcc gcacactgtt cggaggcatg tcctggataa      840
cgcaaggatt gctgggggct ctcctgttgt ggatgggcat caatgctcgt gataggtcca      900
tagctctcac gtttctcgca gttggaggag ttctgctctt cctctccgtg aacgtgcatg      960
ctgacactgg gtgtgccata gacatcagcc ggcaagagct gaga                        1004
```

<210> SEQ ID NO 22
<211> LENGTH: 1006
<212> TYPE: DNA
<213> ORGANISM: West Nile virus
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (996)..(996)
<223> OTHER INFORMATION: n is a, c, g, or t
<220> FEATURE:
<221> NAME/KEY: misc_feature
<222> LOCATION: (1004)..(1004)
<223> OTHER INFORMATION: n is a, c, g, or t

<400> SEQUENCE: 22

```
agcagtgctg gaagtactgt gtggaggnaa cagagagacg ttaatggagt ttgaggaacc         60
acacgccacg aagcagtctg tgatagcatt gggctcacaa gagggagctc tgcatcaagc       120
tttggctgga gccattcctg tggaattttc aagcaacact gtcaagttga cgtcgggtca       180
tttgaagtgt agagtgaaga tggaaaaatt gcagttgaag ggaacaacct atggcgtctg       240
ttcaaaggct ttcaagtttc ttgggactcc cgcagacaca ggtcacggca ctgtggtgtt       300
ggaattgcag tacactggca cggatggacc ttgcaaagtt cctatctcgt cagtggcttc       360
attgaacgat ctaacgccag tgggcagatt ggtcactgtc aacccttttg tttcagtggc       420
cacggccaac gctaaggtcc tgattgaatt ggaaccaccc tttggagact catacatagt       480
ggtgggcaga ggagaacaac agatcaatca ccattggcac aagtctggaa gcagcattgg       540
caaagccttt acaaccaccc tcaaaggagc gcagagacta gccgctctag agacacagc       600 ttgggacttt ggatcagttg gagggggtgtt cacctcagtt gggaaggctg tccatcaagt    660
gttcggagga gcattccgca cactgttcgg aggcatgtcc tggataacgc aaggattgct       720
gggggctctc ctgttgtgga tgggcatcaa tgctcgtgat aggtccatag ctctcacgtt       780
tctcgcagtt ggaggagttc tgctcttcct ctccgtgaac gtgcatgctg acactgggtg       840
tgccatagac atcagccggc aagagctgag atgtggaagt ggagtgttca tacacaatga       900
```

| | |
|---|---|
| tgtggaggct tggatggacc ggtacaagta ttaccctgaa acgccacaag gcctagccaa | 960 |
| gatcattcag aaagctcata aggaaggagt gtgcgntcta cganca | 1006 |

<210> SEQ ID NO 23
<211> LENGTH: 11029
<212> TYPE: DNA
<213> ORGANISM: West Nile virus

<400> SEQUENCE: 23

| | |
|---|---|
| agtagttcgc ctgtgtgagc tgacaaactt agtagtgttt gtgaggatta acaacaatta | 60 |
| acacagtgcg agctgtttct tagcacgaag atctcgatgt ctaagaaacc aggagggccc | 120 |
| ggcaagagcc gggctgtcaa tatgctaaaa cgcggaatgc cccgcgtgtt gtccttgatt | 180 |
| ggactgaaga gggctatgtt gagcctgatc gacggcaagg ggccaatacg atttgtgttg | 240 |
| gctctcttgg cgttcttcag gttcacagca attgctccga cccgagcagt gctggatcga | 300 |
| tggagaggtg tgaacaaaca aacagcgatg aaacaccttc tgagttttaa gaaggaacta | 360 |
| gggaccttga ccagtgctat caatcggcgg agctcaaaac aaaagaaaag aggaggaaag | 420 |
| accggaattg cagtcatgat tggcctgatc gccagcgtag gagcagttac cctctctaac | 480 |
| ttccaaggga aggtgatgat gacggtaaat gctactgacg tcacagatgt catcacgatt | 540 |
| ccaacagctg ctggaaagaa cctatgcatt gtcagagcaa tggatgtggg atacatgtgc | 600 |
| gatgatacta tcacttatga atgcccagta ctgtcggctg gtaatgatcc agaagacatc | 660 |
| gactgttggt gcacaaagtc agcagtctac gtcaggtatg aagatgcac caagacacgc | 720 |
| cactcaagac gcagtcggag gtcactgaca gtgcagacac acgagaaaag cactctagcg | 780 |
| aacaagaagg gggcttggat ggacagcacc aaggccacaa ggtatttggt aaaaacagaa | 840 |
| tcatggatct tgaggaaccc tggatatgcc ctggtggcag ccgtcattgg ttggatgctt | 900 |
| gggagcaaca ccatgcagag agttgtgttt gtcgtgctat tgcttttggt ggccccagct | 960 |
| tacagcttca actgccttgg aatgagcaac agagacttct tggaaggagt gtctggagca | 1020 |
| acatgggtgg atttggttct cgaaggcgac agctgcgtga ctatcatgtc taaggacaag | 1080 |
| cctaccatcg atgtgaagat gatgaatatg gaggcggcca acctggcaga ggtccgcagt | 1140 |
| tattgctatt tggctaccgt cagcgatctc tccaccaaag ctgcgtgccc gaccatggga | 1200 |
| gaagctcaca atgacaaacg tgctgaccca gcttttgtgt gcagacaagg agtggtggac | 1260 |
| aggggctggg gcaacggctg cggactattt ggcaaaggaa gcattgacac atgcgccaaa | 1320 |
| tttgcctgct ctaccaaggc aataggaaga accatcttga aagagaatat caagtacgaa | 1380 |
| gtggccattt ttgtccatgg accaactact gtggagtcgc acggaaacta ctccacacag | 1440 |
| gttgagccca tcaggcagg gagactcagc atcactcctg cggcgccttc atacacacta | 1500 |
| aagcttggag aatatggaga ggtgacagtg gactgtgaac cacggtcagg gattgacacc | 1560 |
| aatgcatact acgtgatgac tgttggaaca aagacgttct tggtccatcg tgagtggttc | 1620 |
| atggacctca acctcccttg gagcagtgct ggaagtactg tgtggaggaa cagagagacg | 1680 |
| ttaatggagt ttgaggaacc acacgccacg aagcagtctg tgatagcatt gggctcacaa | 1740 |
| gagggagctc tgcatcaagc tttggctgga gccattcctg tggaattttc aagcaacact | 1800 |
| gtcaagttga cgtcgggtca tttgaagtgt agagtgaaga tggaaaaatt gcagttgaag | 1860 |
| ggaacaacct atggcgtctg ttcaaaggct ttcaagtttc ttgggactcc cgcagacaca | 1920 |
| ggtcacggca ctgtggtgtt ggaattgcag tacactggca cggatggacc ttgcaaagtt | 1980 |
| cctatctcgt cagtggcttc attgaacgac ctaacgccag tgggcagatt ggtcactgtc | 2040 |

```
aacccttttg tttcagtggc cacggccaac gctaaggtcc tgattgaatt ggaaccaccc    2100
tttggagact catacatagt ggtgggcaga ggagaacaac agatcaatca ccattggcac    2160
aagtctggaa gcagcattgg caaagccttt acaaccaccc tcaaaggagc gcagagacta    2220
gccgctctag gagacacagc ttgggacttt ggatcagttg gaggggtgtt cacctcagtt    2280
gggaaggctg tccatcaagt gttcggagga gcattccgct cactgttcgg aggcatgtcc    2340
tggataacgc aaggattgct gggggctctc ctgttgtgga tgggcatcaa tgctcgtgat    2400
aggtccatag ctctcacgtt tctcgcagtt ggaggagttc tgctcttcct ctccgtgaac    2460
gtgcacgctg acactgggtg tgccatagac atcagccggc aagagctgag atgtggaagt    2520
ggagtgttca tacacaatga tgtggaggct tggatggacc ggtacaagta ttaccctgaa    2580
acgccacaag gcctagccaa gatcattcag aaagctcata aggaaggagt gtgcggtcta    2640
cgatcagttt ccagactgga gcatcaaatg tgggaagcag tgaaggacga gctgaacact    2700
cttttgaagg agaatggtgt ggaccttagt gtcgtggttg agaaacagga gggaatgtac    2760
aagtcagcac ctaaacgcct caccgccacc acggaaaaat tggaaattgg ctggaaggcc    2820
tggggaaaga gtattttatt tgcaccagaa ctcgccaaca cacctttgt ggttgatggt    2880
ccggagacca aggaatgtcc gactcagaat cgcgcttgga atagcttaga agtggaggat    2940
tttggatttg gtctcaccag cactcggatg ttcctgaagg tcagagagag caacacaact    3000
gaatgtgact cgaagatcat tggaacggct gtcaagaaca acttggcgat ccacagtgac    3060
ctgtcctatt ggattgaaag caggctcaat gatacgtgga agcttgaaag ggcagttctg    3120
ggtgaagtca aatcatgtac gtggcctgag acgcatacct tgtggggcga tggaatcctt    3180
gagagtgact tgataatacc agtcacactg gcgggaccac gaagcaatca caatcggaga    3240
cctgggtaca agacacaaaa ccagggccca tgggacgaag gccgggtaga gattgacttc    3300
gattactgcc caggaactac ggtcaccctg agtgagagct gcggacaccg tggacctgcc    3360
actcgcacca ccacagagag cggaaagttg ataacagatt ggtgctgcag gagctgcacc    3420
ttaccaccac tgcgctacca aactgacagc ggctgttggt atggtatgga gatcagacca    3480
cagagacatg atgaaaagac cctcgtgcag tcacaagtga atgcttataa tgctgatatg    3540
attgaccctt ttcagttggg ccttctggtc gtgttcttgg ccacccagga ggtccttcgc    3600
aagaggtgga cagccaagat cagcatgcca gctatactga ttgctctgct agtcctggtg    3660
tttgggggca ttacttacac tgatgtgtta cgctatgtca tcttggtggg ggcagctttc    3720
gcagaatcta attcgggagg agacgtggta cacttggcgc tcatggcgac cttcaagata    3780
caaccagtgt ttatggtggc atcgtttctc aaagcgagat ggaccaacca ggagaacatt    3840
ttgttgatgt tggcggctgt tttctttcaa atggcttatc acgatgcccg ccaaattctg    3900
ctctgggaga tccctgatgt gttgaattca ctggcggtag cttggatgat actgagagcc    3960
ataacattca caacgacatc aaacgtggtt gttccgctgc tagccctgct aacacccggg    4020
ctgagatgct tgaatctgga tgtgtacagg atactgctgt tgatggtcgg aataggcagc    4080
ttgatcaggg agaagaggag tgcagccgca aaaagaaag gagcaagtct gctatgcttg    4140
gctctagcct caacaggact tttcaacccc atgatccttg ctgctggact gattgcatgt    4200
gatcccaacc gtaaacgcgg atggcccgca actgaagtga tgacagctgt cggcctaatg    4260
tttgccatcg tcgagggct ggcagagctt gacattgact ccatggccat tccaatgact    4320
atcgcggggc tcatgtttgc tgctttcgtg atttctggga aatcaacaga tatgtggatt    4380
```

```
gagagaacgg cggacatttc ctgggaaagt gatgcagaaa ttacaggctc gagcgaaaga   4440
gttgatgtgc ggcttgatga tgatggaaac ttccagctca tgaatgatcc aggagcacct   4500
tggaagatat ggatgctcag aatggtctgt ctcgcgatta gtgcgtacac ccctgggca    4560 atcttgccct cagtagttgg attttggata actctccaat acacaaagag aggaggcgtg   4620
ttgtgggaca ctccctcacc aaaggagtac aaaaagggg acacgaccac cggcgtctac    4680
aggatcatga ctcgtgggct gctcggcagt tatcaagcag gagcgggcgt gatggttgaa   4740
ggtgttttcc acacccttg gcatacaaca aaggagccg ctttgatgag cggagagggc     4800
cgcctggacc catactgggg cagtgtcaag gaggatcgac tttgttacgg aggaccctgg   4860
aaattgcagc acaagtggaa cgggcaggat gaggtgcaga tgattgtggt ggaacctggc   4920
aagaacgtta agaacgtcca gacgaaacca ggggtgttca aaacacctga aggagaaatc   4980
ggggccgtga ctttggactt ccccactgga acatcaggct caccaatagt ggacaaaaac   5040
ggtgatgtga ttgggcttta tggcaatgga gtcataatgc caacggctc atacataagc    5100 gcgatagtgc agggtgaaag gatggatgag ccaatcccag ccggattcga acctgagatg   5160
ctgaggaaaa aacagatcac tgtactggat ctccatcccg gcgccggtaa acaaggagg    5220 attctgccac agatcatcaa agaggccata acagaagac tgagaacagc cgtgctagcg     5280
ccaaccaggg ttgtggctgc tgagatggct gaagcactga gaggactgcc catccggtac    5340
cagacatccg cagtgcccag agaacataat ggaaatgaga ttgttgatgt catgtgtcat    5400
gctaccctca cccacaggct gatgtctcct cacagggtgc cgaactacaa cctgttcgtg    5460
atggatgagg ctcatttcac cgacccagct agcattgcag caagaggtta catttccaca    5520
aaggtcgagc taggggaggc ggcggcaata ttcatgacag ccaccccacc aggcacttca    5580
gatccattcc cagagtccaa ttcaccaatt tccgacttac agactgagat cccggatcga    5640
gcttggaact ctggatacga atggatcaca gaatacaccg ggaagacggt ttggtttgtg    5700
cctagtgtca agatggggaa tgagattgcc ctttgcctac aacgtgctgg aaagaaagta    5760
gtccaattga acagaaagtc gtacgagacg gagtacccaa aatgtaagaa cgatgattgg   5820
gactttgtta tcacaacaga catatctgaa atgggggcta acttcaaggc gagcagggtg    5880
attgacagcc ggaagagtgt gaaaccaacc atcataacag aaggagaagg gagagtgatc    5940 ctggagaac catctgcagt gacagcagct agtgccgccc agagacgtgg acgtatcggt     6000
agaaatccgt cgcaagttgg tgatgagtac tgttatgggg ggcacacgaa tgaagacgac    6060
tcgaacttcg cccattggac tgaggcacga atcatgctgg acaacatcaa catgccaaac    6120
ggactgatcg ctcaattcta ccaaccagag cgtgagaagg tatataccat ggatgggga     6180 taccggctca gaggagaaga gagaaaaac tttctggaac tgttgagga c tgcagatctg    6240 ccagtttggc tggcttacaa ggttgcagcg gctggagtgt cataccacga ccggaggtgg    6300
tgctttgatg gtcctaggac aaacacaatt ttagaagaca caacgaagt ggaagtcatc      6360 acgaagcttg gtgaaaggaa gattctgagg ccgcgctgga ttgatgccag ggtgtactcg    6420
gatcaccagg cactaaaggc gttcaaggac ttcgcctcgg aaaacgttc tcagatagggg    6480 ctcattgagg ttctgggaaa gatgcctgag cacttcatgg ggaagacatg gaagcactt     6540 gacaccatgt acgttgtggc cactgcagag aaaggaggaa gagctcacag aatggccctg   6600
gaggaactgc cagatgctct tcagacaatt gccttgattg ccttattgag tgtgatgacc    6660
atgggagtat tcttcctcct catgcagcgg aagggcattg gaaagatagg tttgggaggc    6720
gctgtcttgg gagtcgcgac ctttttctgt tggatggctg aagttccagg aacgaagatc    6780
```

```
gccggaatgt tgctgctctc ccttctcttg atgattgtgc taattcctga gccagagaag    6840
caacgttcgc agacagacaa ccagctagcc gtgttcctga tttgtgtcat gacccttgtg    6900
agcgcagtgg cagccaacga gatgggttgg ctagataaga ccaagagtga cataagcagt    6960
ttgtttgggc aaagaattga ggtcaaggag aatttcagca tgggagagtt tcttctggac    7020
ttgaggccgg caacagcctg gtcactgtac gctgtgacaa cagcggtcct cactccactg    7080
ctaaagcatt tgatcacgtc agattacatc aacacctcat tgacctcaat aaacgttcag    7140
gcaagtgcac tattcacact cgcgcgaggc ttccccttcg tcgatgttgg agtgtcggct    7200
ctcctgctag cagccggatg ctggggacaa gtcaccctca ccgttacggt aacagcggca    7260
acactccttt tttgccacta tgcctacatg gttcccggtt ggcaagctga ggcaatgcgc    7320
tcagcccagc ggcggacagc ggccggaatc atgaagaacg ctgtagtgga tggcatcgtg    7380
gccacggacg tcccagaatt agagcgcacc acacccatca tgcagaagaa agttggacag    7440
atcatgctga tcttggtgtc tctagctgca gtagtagtga cccgtctgt gaagacagta    7500 cgagaagccg gaattttgat cacggccgca gcggtgacgc tttgggagaa tggagcaagc    7560
tctgtttgga acgcaacaac tgccatcgga ctctgccaca tcatgcgtgg gggttggttg    7620
tcatgtctat ccataacatg gacactcata agaacatgg aaaaaccagg actaaaaga     7680 ggtggggcaa aaggacgcac cttgggagag gtttggaaag aaagactcaa ccagatgaca    7740
aaagaagagt tcactaggta ccgcaaagag gccatcatcg aagtcgatcg ctcagcggca    7800
aaacacgcca ggaaagaagg caatgtcact ggagggcatc cagtctctag ggcacagca    7860 aaactgagat ggctggtcga acggaggttt ctcgaaccgg tcggaaaagt gattgacctt    7920
ggatgtggaa gaggcggttg gtgttactat atggcaaccc aaaaaagagt ccaagaagtc    7980
agagggtaca caaagggcgg tcccggacat gaagagcccc aactagtgca aagttatgga    8040
tggaacattg tcaccatgaa gagtggagtg gatgtgttct acagaccttc tgagtgttgt    8100
gacaccctcc tttgtgacat cggagagtcc tcgtcaagtg ctgaggttga agagcatagg    8160
acgattcggg tccttgaaat ggttgaggac tggctgcacc gagggccaag ggaattttgc    8220
gtgaaggtgc tctgtcccta catgccgaaa gtcatagaga gatggagct gctccaacgc    8280 cggtatgggg ggggactggt cagaaaccca ctctcacgga attccacgca cgagatgtat    8340
tgggtgagtc gagcttcagg caatgtggta cattcagtga atatgaccag ccaggtgctc    8400
ctaggaagaa tggaaaaaag gacctggaag ggaccccaat acgaggaaga tgtaaacttg    8460
ggaagtggaa ccagggcggt gggaaaaccc ctgctcaact cagacaccag taaaatcaag    8520
aacaggattg aacgactcag gcgtgagtac agttcgacgt ggcaccacga tgagaaccac    8580
ccatatagaa cctggaacta tcacggcagt tatgatgtga agcccacagg ctccgccagt    8640
tcgctggtca atggagtggt caggctcctc tcaaaaccat gggacaccat cacgaatgtt    8700
accaccatgg ccatgactga cactactccc ttcgggcagc agcgagtgtt caaagagaag    8760
gtggacacga aagctcctga accgccagaa ggagtgaagt acgtgctcaa cgagaccacc    8820
aactggttgt gggcgttttt ggccagagaa aaacgtccca gaatgtgctc tcgagaggaa    8880
ttcataagaa aggtcaacag caatgcagct ttgggtgcca tgtttgaaga gcagaatcaa    8940
tggaggagcg ccagagaagc agttgaagat ccaaaatttt gggagatggt ggatgaggag    9000
cgcgaggcac atctgcgggg ggaatgtcac acttgcattt acaacatgat gggaaagaga    9060
gagaaaaaac ccgagagtt cggaaaggcc aagggaagca gagccatttg gttcatgtgg    9120
```

```
ctcggagctc gctttctgga gttcgaggct ctgggttttc tcaatgaaga ccactggctt    9180
ggaagaaaga actcaggagg aggtgtcgag ggcttgggcc tccaaaaact gggttacatc    9240
ctgcgtgaag ttggcacccg gcctgggggc aagatctatg ctgatgacac agctggctgg    9300
gacacccgca tcacgagagc tgacttggaa aatgaagcta aggtgcttga gctgcttgat    9360
ggggaacatc ggcgtcttgc cagggccatc attgagctca cctatcgtca caagttgtg    9420
aaagtgatgc gcccggctgc tgatggaaga accgtcatgg atgttatctc cagagaagat    9480
cagaggggga gtggacaagt tgtcacctac gccctaaaca ctttcaccaa cctggccgtc    9540
cagctggtga ggatgatgga aggggaagga gtgattggcc cagatgatgt ggagaaactc    9600
acaaaaggga aaggacccaa agtcaggacc tggctgtttg agaatgggga agaaagactc    9660
agccgcatgg ctgtcagtgg agatgactgt gtggtaaagc ccctggacga tcgctttgcc    9720
acctcgctcc acttcctcaa tgctatgtca aaggttcgca agacatcca agagtggaaa    9780
ccgtcaactg gatggtatga ttggcagcag gttccatttt gctcaaacca tttcactgaa    9840
ttgatcatga aagatggaag aacactggtg gttccatgcc gaggacagga tgaattggta    9900
ggcagagctc gcatatctcc aggggccgga tggaacgtcc gcgacactgc ttgtctggct    9960
aagtcttatg cccagatgtg gctgcttctg tacttccaca aagagaccct gcggctcatg   10020
gccaacgcca tttgctccgc tgtccctgtg aattgggtcc ctaccggaag aaccacgtgg   10080
tccatccatg caggaggaga gtggatgaca acagaggaca tgttggaggt ctggaaccgt   10140
gtttggatag aggagaatga atggatggaa gacaaaaccc cagtggagaa atggagtgac   10200
gtcccatatt caggaaaacg agaggacatc tggtgtggca gcctgattgg cacaagagcc   10260
cgagccacgt gggcagaaaa catccaggtg gctatcaacc aagtcagagc aatcatcgga   10320
gatgagaagt atgtggacta catgagttca ctaaagagat atgaagacac aactttggtt   10380
gaggacacag tactgtagat atttaatcaa ttgtaaatag acaatataag tatgcataaa   10440
agtgtagttt tatagtagta tttagtggtg ttagtgtaaa tagttaagaa aattttgagg   10500
agaaagtcag gccgggaagt tccgccaccg gaagttgag tagacggtgc tgcctgcgac   10560
tcaaccccag gaggactggg tgaacaaagc cgcgaagtga tccatgtaag ccctcagaac   10620
cgtctcggaa ggaggacccc acatgttgta acttcaaagc ccaatgtcag accacgctac   10680
ggcgtgctac tctgcggaga gtgcagtctg cgatagtgcc ccaggaggac tgggttaaca   10740
aaggcaaacc aacgccccac gcggccctag ccccggtaat ggtgttaacc agggcgaaag   10800
gactagaggt tagaggagac cccgcggttt aaagtgcacg gcccagcctg ctgaagctg    10860
taggtcaggg gaaggactag aggttagtgg agacccgtg ccacaaaaca ccacaacaaa    10920
acagcatatt gacacctggg atagactagg agatcttctg ctctgcacaa ccagccacac   10980
ggcacagtgc gccgacaatg gtggctggtg gtgcgagaac acaggatct              11029
```

<210> SEQ ID NO 24  
<211> LENGTH: 3433  
<212> TYPE: PRT  
<213> ORGANISM: West Nile virus

<400> SEQUENCE: 24

Met Ser Lys Lys Pro Gly Gly Pro Gly Lys Ser Arg Ala Val Asn Met  
1               5                   10                  15

Leu Lys Arg Gly Met Pro Arg Val Leu Ser Leu Ile Gly Leu Lys Arg  
            20                  25                  30

Ala Met Leu Ser Leu Ile Asp Gly Lys Gly Pro Ile Arg Phe Val Leu

```
                35                  40                  45
Ala Leu Leu Ala Phe Phe Arg Phe Thr Ala Ile Ala Pro Thr Arg Ala
 50                  55                  60

Val Leu Asp Arg Trp Arg Gly Val Asn Lys Gln Thr Ala Met Lys His
 65                  70                  75                  80

Leu Leu Ser Phe Lys Glu Leu Gly Thr Leu Ser Ala Ile Asn
                 85                  90                  95

Arg Arg Ser Ser Lys Gln Lys Lys Arg Gly Gly Lys Thr Gly Ile Ala
                100                 105                 110

Val Met Ile Gly Leu Ile Ala Ser Val Gly Ala Val Thr Leu Ser Asn
                115                 120                 125

Phe Gln Gly Lys Val Met Met Thr Val Asn Ala Thr Asp Val Thr Asp
                130                 135                 140

Val Ile Thr Ile Pro Thr Ala Ala Gly Lys Asn Leu Cys Ile Val Arg
145                 150                 155                 160

Ala Met Asp Val Gly Tyr Met Cys Asp Asp Thr Ile Thr Tyr Glu Cys
                165                 170                 175

Pro Val Leu Ser Ala Gly Asn Asp Pro Glu Asp Ile Asp Cys Trp Cys
                180                 185                 190

Thr Lys Ser Ala Val Tyr Val Arg Tyr Gly Arg Cys Thr Lys Thr Arg
                195                 200                 205

His Ser Arg Arg Ser Arg Arg Ser Leu Thr Val Gln Thr His Gly Glu
                210                 215                 220

Ser Thr Leu Ala Asn Lys Lys Gly Ala Trp Met Asp Ser Thr Lys Ala
225                 230                 235                 240

Thr Arg Tyr Leu Val Lys Thr Glu Ser Trp Ile Leu Arg Asn Pro Gly
                245                 250                 255

Tyr Ala Leu Val Ala Ala Val Ile Gly Trp Met Leu Gly Ser Asn Thr
                260                 265                 270

Met Gln Arg Val Val Phe Val Val Leu Leu Leu Val Ala Pro Ala
                275                 280                 285

Tyr Ser Phe Asn Cys Leu Gly Met Ser Asn Arg Asp Phe Leu Glu Gly
                290                 295                 300

Val Ser Gly Ala Thr Trp Val Asp Leu Val Leu Glu Gly Asp Ser Cys
305                 310                 315                 320

Val Thr Ile Met Ser Lys Asp Lys Pro Thr Ile Asp Val Lys Met Met
                325                 330                 335

Asn Met Glu Ala Ala Asn Leu Ala Glu Val Arg Ser Tyr Cys Tyr Leu
                340                 345                 350

Ala Thr Val Ser Asp Leu Ser Thr Lys Ala Ala Cys Pro Thr Met Gly
                355                 360                 365

Glu Ala His Asn Asp Lys Arg Ala Asp Pro Ala Phe Val Cys Arg Gln
                370                 375                 380

Gly Val Val Asp Arg Gly Trp Gly Asn Gly Cys Gly Leu Phe Gly Lys
385                 390                 395                 400

Gly Ser Ile Asp Thr Cys Ala Lys Phe Ala Cys Ser Thr Lys Ala Ile
                405                 410                 415

Gly Arg Thr Ile Leu Lys Glu Asn Ile Lys Tyr Glu Val Ala Ile Phe
                420                 425                 430

Val His Gly Pro Thr Thr Val Glu Ser His Gly Asn Tyr Ser Thr Gln
                435                 440                 445

Val Gly Ala Thr Gln Ala Gly Arg Leu Ser Ile Thr Pro Ala Ala Pro
                450                 455                 460
```

Ser Tyr Thr Leu Lys Leu Gly Glu Tyr Gly Glu Val Thr Val Asp Cys
465                 470                 475                 480

Glu Pro Arg Ser Gly Ile Asp Thr Asn Ala Tyr Tyr Val Met Thr Val
            485                 490                 495

Gly Thr Lys Thr Phe Leu Val His Arg Glu Trp Phe Met Asp Leu Asn
        500                 505                 510

Leu Pro Trp Ser Ser Ala Gly Ser Thr Val Trp Arg Asn Arg Glu Thr
    515                 520                 525

Leu Met Glu Phe Glu Glu Pro His Ala Thr Lys Gln Ser Val Ile Ala
530                 535                 540

Leu Gly Ser Gln Glu Gly Ala Leu His Gln Ala Leu Ala Gly Ala Ile
545                 550                 555                 560

Pro Val Glu Phe Ser Ser Asn Thr Val Lys Leu Thr Ser Gly His Leu
                565                 570                 575

Lys Cys Arg Val Lys Met Glu Lys Leu Gln Leu Lys Gly Thr Thr Tyr
            580                 585                 590

Gly Val Cys Ser Lys Ala Phe Lys Phe Leu Gly Thr Pro Ala Asp Thr
        595                 600                 605

Gly His Gly Thr Val Val Leu Glu Leu Gln Tyr Thr Gly Thr Asp Gly
    610                 615                 620

Pro Cys Lys Val Pro Ile Ser Ser Val Ala Ser Leu Asn Asp Leu Thr
625                 630                 635                 640

Pro Val Gly Arg Leu Val Thr Val Asn Pro Phe Val Ser Val Ala Thr
                645                 650                 655

Ala Asn Ala Lys Val Leu Ile Glu Leu Glu Pro Pro Phe Gly Asp Ser
            660                 665                 670

Tyr Ile Val Val Gly Arg Gly Glu Gln Gln Ile Asn His His Trp His
        675                 680                 685

Lys Ser Gly Ser Ser Ile Gly Lys Ala Phe Thr Thr Thr Leu Lys Gly
    690                 695                 700

Ala Gln Arg Leu Ala Ala Leu Gly Asp Thr Ala Trp Asp Phe Gly Ser
705                 710                 715                 720

Val Gly Gly Val Phe Thr Ser Val Gly Lys Ala Val His Gln Val Phe
                725                 730                 735

Gly Gly Ala Phe Arg Ser Leu Phe Gly Gly Met Ser Trp Ile Thr Gln
            740                 745                 750

Gly Leu Leu Gly Ala Leu Leu Leu Trp Met Gly Ile Asn Ala Arg Asp
        755                 760                 765

Arg Ser Ile Ala Leu Thr Phe Leu Ala Val Gly Gly Val Leu Leu Phe
    770                 775                 780

Leu Ser Val Asn Val His Ala Asp Thr Gly Cys Ala Ile Asp Ile Ser
785                 790                 795                 800

Arg Gln Glu Leu Arg Cys Gly Ser Gly Val Phe Ile His Asn Asp Val
                805                 810                 815

Glu Ala Trp Met Asp Arg Tyr Lys Tyr Tyr Pro Glu Thr Pro Gln Gly
            820                 825                 830

Leu Ala Lys Ile Ile Gln Lys Ala His Lys Glu Gly Val Cys Gly Leu
        835                 840                 845

Arg Ser Val Ser Arg Leu Glu His Gln Met Trp Glu Ala Val Lys Asp
    850                 855                 860

Glu Leu Asn Thr Leu Leu Lys Glu Asn Gly Val Asp Leu Ser Val Val
865                 870                 875                 880

-continued

Val Glu Lys Gln Glu Gly Met Tyr Lys Ser Ala Pro Lys Arg Leu Thr
            885                 890                 895

Ala Thr Thr Glu Lys Leu Glu Ile Gly Trp Lys Ala Trp Gly Lys Ser
            900                 905                 910

Ile Leu Phe Ala Pro Glu Leu Ala Asn Asn Thr Phe Val Val Asp Gly
            915                 920                 925

Pro Glu Thr Lys Glu Cys Pro Thr Gln Asn Arg Ala Trp Asn Ser Leu
930                 935                 940

Glu Val Glu Asp Phe Gly Phe Gly Leu Thr Ser Thr Arg Met Phe Leu
945                 950                 955                 960

Lys Val Arg Glu Ser Asn Thr Thr Glu Cys Asp Ser Lys Ile Ile Gly
            965                 970                 975

Thr Ala Val Lys Asn Asn Leu Ala Ile His Ser Asp Leu Ser Tyr Trp
            980                 985                 990

Ile Glu Ser Arg Leu Asn Asp Thr Trp Lys Leu Glu Arg Ala Val Leu
            995                 1000                1005

Gly Glu Val Lys Ser Cys Thr Trp Pro Glu Thr His Thr Leu Trp
        1010                1015                1020

Gly Asp Gly Ile Leu Glu Ser Asp Leu Ile Ile Pro Val Thr Leu
        1025                1030                1035

Ala Gly Pro Arg Ser Asn His Asn Arg Arg Pro Gly Tyr Lys Thr
        1040                1045                1050

Gln Asn Gln Gly Pro Trp Asp Glu Gly Arg Val Glu Ile Asp Phe
        1055                1060                1065

Asp Tyr Cys Pro Gly Thr Thr Val Thr Leu Ser Glu Ser Cys Gly
        1070                1075                1080

His Arg Gly Pro Ala Thr Arg Thr Thr Thr Glu Ser Gly Lys Leu
        1085                1090                1095

Ile Thr Asp Trp Cys Cys Arg Ser Cys Thr Leu Pro Pro Leu Arg
        1100                1105                1110

Tyr Gln Thr Asp Ser Gly Cys Trp Tyr Gly Met Glu Ile Arg Pro
        1115                1120                1125

Gln Arg His Asp Glu Lys Thr Leu Val Gln Ser Gln Val Asn Ala
        1130                1135                1140

Tyr Asn Ala Asp Met Ile Asp Pro Phe Gln Leu Gly Leu Leu Val
        1145                1150                1155

Val Phe Leu Ala Thr Gln Glu Val Leu Arg Lys Arg Trp Thr Ala
        1160                1165                1170

Lys Ile Ser Met Pro Ala Ile Leu Ile Ala Leu Leu Val Leu Val
        1175                1180                1185

Phe Gly Gly Ile Thr Tyr Thr Asp Val Leu Arg Tyr Val Ile Leu
        1190                1195                1200

Val Gly Ala Ala Phe Ala Glu Ser Asn Ser Gly Gly Asp Val Val
        1205                1210                1215

His Leu Ala Leu Met Ala Thr Phe Lys Ile Gln Pro Val Phe Met
        1220                1225                1230

Val Ala Ser Phe Leu Lys Ala Arg Trp Thr Asn Gln Glu Asn Ile
        1235                1240                1245

Leu Leu Met Leu Ala Ala Val Phe Phe Gln Met Ala Tyr His Asp
        1250                1255                1260

Ala Arg Gln Ile Leu Leu Trp Glu Ile Pro Asp Val Leu Asn Ser
        1265                1270                1275

Leu Ala Val Ala Trp Met Ile Leu Arg Ala Ile Thr Phe Thr Thr

-continued

```
            1280            1285            1290
Thr Ser Asn Val Val Pro Leu Leu Ala Leu Leu Thr Pro Gly
    1295            1300            1305
Leu Arg Cys Leu Asn Leu Asp Val Tyr Arg Ile Leu Leu Met
    1310            1315            1320
Val Gly Ile Gly Ser Leu Ile Arg Glu Lys Arg Ser Ala Ala Ala
    1325            1330            1335
Lys Lys Lys Gly Ala Ser Leu Leu Cys Leu Ala Leu Ala Ser Thr
    1340            1345            1350
Gly Leu Phe Asn Pro Met Ile Leu Ala Ala Gly Leu Ile Ala Cys
    1355            1360            1365
Asp Pro Asn Arg Lys Arg Gly Trp Pro Ala Thr Glu Val Met Thr
    1370            1375            1380
Ala Val Gly Leu Met Phe Ala Ile Val Gly Gly Leu Ala Glu Leu
    1385            1390            1395
Asp Ile Asp Ser Met Ala Ile Pro Met Thr Ile Ala Gly Leu Met
    1400            1405            1410
Phe Ala Ala Phe Val Ile Ser Gly Lys Ser Thr Asp Met Trp Ile
    1415            1420            1425
Glu Arg Thr Ala Asp Ile Ser Trp Glu Ser Asp Ala Glu Ile Thr
    1430            1435            1440
Gly Ser Ser Glu Arg Val Asp Val Arg Leu Asp Asp Gly Asn
    1445            1450            1455
Phe Gln Leu Met Asn Asp Pro Gly Ala Pro Trp Lys Ile Trp Met
    1460            1465            1470
Leu Arg Met Val Cys Leu Ala Ile Ser Ala Tyr Thr Pro Trp Ala
    1475            1480            1485
Ile Leu Pro Ser Val Val Gly Phe Trp Ile Thr Leu Gln Tyr Thr
    1490            1495            1500
Lys Arg Gly Gly Val Leu Trp Asp Thr Pro Ser Pro Lys Glu Tyr
    1505            1510            1515
Lys Lys Gly Asp Thr Thr Thr Gly Val Tyr Arg Ile Met Thr Arg
    1520            1525            1530
Gly Leu Leu Gly Ser Tyr Gln Ala Gly Ala Gly Val Met Val Glu
    1535            1540            1545
Gly Val Phe His Thr Leu Trp His Thr Thr Lys Gly Ala Ala Leu
    1550            1555            1560
Met Ser Gly Glu Gly Arg Leu Asp Pro Tyr Trp Gly Ser Val Lys
    1565            1570            1575
Glu Asp Arg Leu Cys Tyr Gly Gly Pro Trp Lys Leu Gln His Lys
    1580            1585            1590
Trp Asn Gly Gln Asp Glu Val Gln Met Ile Val Val Glu Pro Gly
    1595            1600            1605
Lys Asn Val Lys Asn Val Gln Thr Lys Pro Gly Val Phe Lys Thr
    1610            1615            1620
Pro Glu Gly Glu Ile Gly Ala Val Thr Leu Asp Phe Pro Thr Gly
    1625            1630            1635
Thr Ser Gly Ser Pro Ile Val Asp Lys Asn Gly Asp Val Ile Gly
    1640            1645            1650
Leu Tyr Gly Asn Gly Val Ile Met Pro Asn Gly Ser Tyr Ile Ser
    1655            1660            1665
Ala Ile Val Gln Gly Glu Arg Met Asp Glu Pro Ile Pro Ala Gly
    1670            1675            1680
```

-continued

```
Phe Glu Pro Glu Met Leu Arg Lys Lys Gln Ile Thr Val Leu Asp
    1685            1690                1695

Leu His Pro Gly Ala Gly Lys Thr Arg Arg Ile Leu Pro Gln Ile
    1700            1705                1710

Ile Lys Glu Ala Ile Asn Arg Arg Leu Arg Thr Ala Val Leu Ala
    1715            1720                1725

Pro Thr Arg Val Val Ala Ala Glu Met Ala Glu Ala Leu Arg Gly
    1730            1735                1740

Leu Pro Ile Arg Tyr Gln Thr Ser Ala Val Pro Arg Glu His Asn
    1745            1750                1755

Gly Asn Glu Ile Val Asp Val Met Cys His Ala Thr Leu Thr His
    1760            1765                1770

Arg Leu Met Ser Pro His Arg Val Pro Asn Tyr Asn Leu Phe Val
    1775            1780                1785

Met Asp Glu Ala His Phe Thr Asp Pro Ala Ser Ile Ala Ala Arg
    1790            1795                1800

Gly Tyr Ile Ser Thr Lys Val Glu Leu Gly Glu Ala Ala Ala Ile
    1805            1810                1815

Phe Met Thr Ala Thr Pro Pro Gly Thr Ser Asp Pro Phe Pro Glu
    1820            1825                1830

Ser Asn Ser Pro Ile Ser Asp Leu Gln Thr Glu Ile Pro Asp Arg
    1835            1840                1845

Ala Trp Asn Ser Gly Tyr Glu Trp Ile Thr Glu Tyr Thr Gly Lys
    1850            1855                1860

Thr Val Trp Phe Val Pro Ser Val Lys Met Gly Asn Glu Ile Ala
    1865            1870                1875

Leu Cys Leu Gln Arg Ala Gly Lys Lys Val Val Gln Leu Asn Arg
    1880            1885                1890

Lys Ser Tyr Glu Thr Glu Tyr Pro Lys Cys Lys Asn Asp Asp Trp
    1895            1900                1905

Asp Phe Val Ile Thr Thr Asp Ile Ser Glu Met Gly Ala Asn Phe
    1910            1915                1920

Lys Ala Ser Arg Val Ile Asp Ser Arg Lys Ser Val Lys Pro Thr
    1925            1930                1935

Ile Ile Thr Glu Gly Glu Gly Arg Val Ile Leu Gly Glu Pro Ser
    1940            1945                1950

Ala Val Thr Ala Ala Ser Ala Ala Gln Arg Arg Gly Arg Ile Gly
    1955            1960                1965

Arg Asn Pro Ser Gln Val Gly Asp Glu Tyr Cys Tyr Gly Gly His
    1970            1975                1980

Thr Asn Glu Asp Asp Ser Asn Phe Ala His Trp Thr Glu Ala Arg
    1985            1990                1995

Ile Met Leu Asp Asn Ile Asn Met Pro Asn Gly Leu Ile Ala Gln
    2000            2005                2010

Phe Tyr Gln Pro Glu Arg Glu Lys Val Tyr Thr Met Asp Gly Glu
    2015            2020                2025

Tyr Arg Leu Arg Gly Glu Glu Arg Lys Asn Phe Leu Glu Leu Leu
    2030            2035                2040

Arg Thr Ala Asp Leu Pro Val Trp Leu Ala Tyr Lys Val Ala Ala
    2045            2050                2055

Ala Gly Val Ser Tyr His Asp Arg Arg Trp Cys Phe Asp Gly Pro
    2060            2065                2070
```

-continued

```
Arg Thr Asn Thr Ile Leu Glu Asp Asn Asn Glu Val Glu Val Ile
    2075                2080                2085

Thr Lys Leu Gly Glu Arg Lys Ile Leu Arg Pro Arg Trp Ile Asp
    2090                2095                2100

Ala Arg Val Tyr Ser Asp His Gln Ala Leu Lys Ala Phe Lys Asp
    2105                2110                2115

Phe Ala Ser Gly Lys Arg Ser Gln Ile Gly Leu Ile Glu Val Leu
    2120                2125                2130

Gly Lys Met Pro Glu His Phe Met Gly Lys Thr Trp Glu Ala Leu
    2135                2140                2145

Asp Thr Met Tyr Val Val Ala Thr Ala Glu Lys Gly Gly Arg Ala
    2150                2155                2160

His Arg Met Ala Leu Glu Glu Leu Pro Asp Ala Leu Gln Thr Ile
    2165                2170                2175

Ala Leu Ile Ala Leu Leu Ser Val Met Thr Met Gly Val Phe Phe
    2180                2185                2190

Leu Leu Met Gln Arg Lys Gly Ile Gly Lys Ile Gly Leu Gly Gly
    2195                2200                2205

Ala Val Leu Gly Val Ala Thr Phe Phe Cys Trp Met Ala Glu Val
    2210                2215                2220

Pro Gly Thr Lys Ile Ala Gly Met Leu Leu Leu Ser Leu Leu Leu
    2225                2230                2235

Met Ile Val Leu Ile Pro Glu Pro Glu Lys Gln Arg Ser Gln Thr
    2240                2245                2250

Asp Asn Gln Leu Ala Val Phe Leu Ile Cys Val Met Thr Leu Val
    2255                2260                2265

Ser Ala Val Ala Ala Asn Glu Met Gly Trp Leu Asp Lys Thr Lys
    2270                2275                2280

Ser Asp Ile Ser Ser Leu Phe Gly Gln Arg Ile Glu Val Lys Glu
    2285                2290                2295

Asn Phe Ser Met Gly Glu Phe Leu Leu Asp Leu Arg Pro Ala Thr
    2300                2305                2310

Ala Trp Ser Leu Tyr Ala Val Thr Thr Ala Val Leu Thr Pro Leu
    2315                2320                2325

Leu Lys His Leu Ile Thr Ser Asp Tyr Ile Asn Thr Ser Leu Thr
    2330                2335                2340

Ser Ile Asn Val Gln Ala Ser Ala Leu Phe Thr Leu Ala Arg Gly
    2345                2350                2355

Phe Pro Phe Val Asp Val Gly Val Ser Ala Leu Leu Leu Ala Ala
    2360                2365                2370

Gly Cys Trp Gly Gln Val Thr Leu Thr Val Thr Val Thr Ala Ala
    2375                2380                2385

Thr Leu Leu Phe Cys His Tyr Ala Tyr Met Val Pro Gly Trp Gln
    2390                2395                2400

Ala Glu Ala Met Arg Ser Ala Gln Arg Arg Thr Ala Ala Gly Ile
    2405                2410                2415

Met Lys Asn Ala Val Val Asp Gly Ile Val Ala Thr Asp Val Pro
    2420                2425                2430

Glu Leu Glu Arg Thr Thr Pro Ile Met Gln Lys Lys Val Gly Gln
    2435                2440                2445

Ile Met Leu Ile Leu Val Ser Leu Ala Ala Val Val Val Asn Pro
    2450                2455                2460

Ser Val Lys Thr Val Arg Glu Ala Gly Ile Leu Ile Thr Ala Ala
```

-continued

```
              2465                2470                2475

Ala Val Thr Leu Trp Glu Asn Gly Ala Ser Ser Val Trp Asn Ala
    2480                2485                2490

Thr Thr Ala Ile Gly Leu Cys His Ile Met Arg Gly Gly Trp Leu
    2495                2500                2505

Ser Cys Leu Ser Ile Thr Trp Thr Leu Ile Lys Asn Met Glu Lys
    2510                2515                2520

Pro Gly Leu Lys Arg Gly Gly Ala Lys Gly Arg Thr Leu Gly Glu
    2525                2530                2535

Val Trp Lys Glu Arg Leu Asn Gln Met Thr Lys Glu Glu Phe Thr
    2540                2545                2550

Arg Tyr Arg Lys Glu Ala Ile Ile Glu Val Asp Arg Ser Ala Ala
    2555                2560                2565

Lys His Ala Arg Lys Glu Gly Asn Val Thr Gly Gly His Pro Val
    2570                2575                2580

Ser Arg Gly Thr Ala Lys Leu Arg Trp Leu Val Glu Arg Arg Phe
    2585                2590                2595

Leu Glu Pro Val Gly Lys Val Ile Asp Leu Gly Cys Gly Arg Gly
    2600                2605                2610

Gly Trp Cys Tyr Tyr Met Ala Thr Gln Lys Arg Val Gln Glu Val
    2615                2620                2625

Arg Gly Tyr Thr Lys Gly Gly Pro Gly His Glu Glu Pro Gln Leu
    2630                2635                2640

Val Gln Ser Tyr Gly Trp Asn Ile Val Thr Met Lys Ser Gly Val
    2645                2650                2655

Asp Val Phe Tyr Arg Pro Ser Glu Cys Cys Asp Thr Leu Leu Cys
    2660                2665                2670

Asp Ile Gly Glu Ser Ser Ser Ala Glu Val Glu Glu His Arg
    2675                2680                2685

Thr Ile Arg Val Leu Glu Met Val Glu Asp Trp Leu His Arg Gly
    2690                2695                2700

Pro Arg Glu Phe Cys Val Lys Val Leu Cys Pro Tyr Met Pro Lys
    2705                2710                2715

Val Ile Glu Lys Met Glu Leu Leu Gln Arg Arg Tyr Gly Gly Gly
    2720                2725                2730

Leu Val Arg Asn Pro Leu Ser Arg Asn Ser Thr His Glu Met Tyr
    2735                2740                2745

Trp Val Ser Arg Ala Ser Gly Asn Val Val His Ser Val Asn Met
    2750                2755                2760

Thr Ser Gln Val Leu Leu Gly Arg Met Glu Lys Arg Thr Trp Lys
    2765                2770                2775

Gly Pro Gln Tyr Glu Glu Asp Val Asn Leu Gly Ser Gly Thr Arg
    2780                2785                2790

Ala Val Gly Lys Pro Leu Leu Asn Ser Asp Thr Ser Lys Ile Lys
    2795                2800                2805

Asn Arg Ile Glu Arg Leu Arg Arg Glu Tyr Ser Ser Thr Trp His
    2810                2815                2820

His Asp Glu Asn His Pro Tyr Arg Thr Trp Asn Tyr His Gly Ser
    2825                2830                2835

Tyr Asp Val Lys Pro Thr Gly Ser Ala Ser Ser Leu Val Asn Gly
    2840                2845                2850

Val Val Arg Leu Leu Ser Lys Pro Trp Asp Thr Ile Thr Asn Val
    2855                2860                2865
```

-continued

```
Thr Thr Met Ala Met Thr Asp Thr Thr Pro Phe Gly Gln Gln Arg
2870                 2875                 2880

Val Phe Lys Glu Lys Val Asp Thr Lys Ala Pro Glu Pro Pro Glu
2885                 2890                 2895

Gly Val Lys Tyr Val Leu Asn Glu Thr Thr Asn Trp Leu Trp Ala
2900                 2905                 2910

Phe Leu Ala Arg Glu Lys Arg Pro Arg Met Cys Ser Arg Glu Glu
2915                 2920                 2925

Phe Ile Arg Lys Val Asn Ser Asn Ala Ala Leu Gly Ala Met Phe
2930                 2935                 2940

Glu Glu Gln Asn Gln Trp Arg Ser Ala Arg Glu Ala Val Glu Asp
2945                 2950                 2955

Pro Lys Phe Trp Glu Met Val Asp Glu Glu Arg Glu Ala His Leu
2960                 2965                 2970

Arg Gly Glu Cys His Thr Cys Ile Tyr Asn Met Met Gly Lys Arg
2975                 2980                 2985

Glu Lys Lys Pro Gly Glu Phe Gly Lys Ala Lys Gly Ser Arg Ala
2990                 2995                 3000

Ile Trp Phe Met Trp Leu Gly Ala Arg Phe Leu Glu Phe Glu Ala
3005                 3010                 3015

Leu Gly Phe Leu Asn Glu Asp His Trp Leu Gly Arg Lys Asn Ser
3020                 3025                 3030

Gly Gly Gly Val Glu Gly Leu Gly Leu Gln Lys Leu Gly Tyr Ile
3035                 3040                 3045

Leu Arg Glu Val Gly Thr Arg Pro Gly Gly Lys Ile Tyr Ala Asp
3050                 3055                 3060

Asp Thr Ala Gly Trp Asp Thr Arg Ile Thr Arg Ala Asp Leu Glu
3065                 3070                 3075

Asn Glu Ala Lys Val Leu Glu Leu Leu Asp Gly Glu His Arg Arg
3080                 3085                 3090

Leu Ala Arg Ala Ile Ile Glu Leu Thr Tyr Arg His Lys Val Val
3095                 3100                 3105

Lys Val Met Arg Pro Ala Ala Asp Gly Arg Thr Val Met Asp Val
3110                 3115                 3120

Ile Ser Arg Glu Asp Gln Arg Gly Ser Gly Gln Val Val Thr Tyr
3125                 3130                 3135

Ala Leu Asn Thr Phe Thr Asn Leu Ala Val Gln Leu Val Arg Met
3140                 3145                 3150

Met Glu Gly Glu Gly Val Ile Gly Pro Asp Asp Val Glu Lys Leu
3155                 3160                 3165

Thr Lys Gly Lys Gly Pro Lys Val Arg Thr Trp Leu Phe Glu Asn
3170                 3175                 3180

Gly Glu Glu Arg Leu Ser Arg Met Ala Val Ser Gly Asp Asp Cys
3185                 3190                 3195

Val Val Lys Pro Leu Asp Asp Arg Phe Ala Thr Ser Leu His Phe
3200                 3205                 3210

Leu Asn Ala Met Ser Lys Val Arg Lys Asp Ile Gln Glu Trp Lys
3215                 3220                 3225

Pro Ser Thr Gly Trp Tyr Asp Trp Gln Gln Val Pro Phe Cys Ser
3230                 3235                 3240

Asn His Phe Thr Glu Leu Ile Met Lys Asp Gly Arg Thr Leu Val
3245                 3250                 3255
```

-continued

```
Val Pro Cys Arg Gly Gln Asp Glu Leu Val Gly Arg Ala Arg Ile
    3260            3265                3270

Ser Pro Gly Ala Gly Trp Asn Val Arg Asp Thr Ala Cys Leu Ala
    3275            3280                3285

Lys Ser Tyr Ala Gln Met Trp Leu Leu Leu Tyr Phe His Arg Arg
    3290            3295                3300

Asp Leu Arg Leu Met Ala Asn Ala Ile Cys Ser Ala Val Pro Val
    3305            3310                3315

Asn Trp Val Pro Thr Gly Arg Thr Thr Trp Ser Ile His Ala Gly
    3320            3325                3330

Gly Glu Trp Met Thr Thr Glu Asp Met Leu Glu Val Trp Asn Arg
    3335            3340                3345

Val Trp Ile Glu Glu Asn Glu Trp Met Glu Asp Lys Thr Pro Val
    3350            3355                3360

Glu Lys Trp Ser Asp Val Pro Tyr Ser Gly Lys Arg Glu Asp Ile
    3365            3370                3375

Trp Cys Gly Ser Leu Ile Gly Thr Arg Ala Arg Ala Thr Trp Ala
    3380            3385                3390

Glu Asn Ile Gln Val Ala Ile Asn Gln Val Arg Ala Ile Ile Gly
    3395            3400                3405

Asp Glu Lys Tyr Val Asp Tyr Met Ser Ser Leu Lys Arg Tyr Glu
    3410            3415                3420

Asp Thr Thr Leu Val Glu Asp Thr Val Leu
    3425            3430
```

The invention claimed is:

1. An immunogenic composition comprising a killed or inactivated West Nile Virus or any antigen thereof, wherein said West Nile Virus isolate comprises Horse Origin 2005, deposited with the ATCC under accession number PTA-9409.

2. The immunogenic composition according to claim 1, wherein said strain is present in an amount from about $10^{2.0}$ TCID$_{50}$/mL-$10^{10.0}$ TCID$_{50}$/mL per dose.

3. The immunogenic composition according to claim 1, wherein said immunogenic composition further comprises suitable excipients or pharmaceutical carrier.

4. The immunogenic composition according to claim 3, wherein said suitable excipients or pharmaceutical carrier is/are selected from the group consisting of a diluent, adjuvant, antimicrobial agent, inactivating agent, and combinations thereof.

5. The immunogenic composition according to claim 4, wherein said adjuvant is selected from the group consisting of, a polymer of acrylic or methacrylic acid, non-metabolized oil, and combinations thereof.

6. The immunogenic composition according claim 1, wherein said immunogenic composition is administered in one or more doses.

7. The immunogenic composition according to claim 1, wherein one dose of said immunogenic composition is formulated in 0.5 ml to 2.5 ml.

8. The immunogenic composition according to claim 1, wherein said immunogenic composition is safe for use in foals or horses 4 months of age or older.

9. The immunogenic composition according to claim 1, wherein said immunogenic composition further comprises at least one antigenic component of one or more additional viruses selected from the group consisting of Eastern Equine Encephalomyelitis Virus, Western Equine Encephalomyelitis Virus and Venezuelan Equine Encephalomyelitis Virus, Tetanus Toxoid, and combinations thereof.

10. The immunogenic composition according to claim 9, wherein said immunogenic composition comprises at least one antigenic component of Equine Herpes Virus.

11. The immunogenic composition according to claim 10, wherein said Equine Herpes Virus is selected from the group consisting of the strains deposited with the ATCC under accession Nos. PTA-9525 or PTA-9526, and combinations thereof.

12. The immunogenic composition according to claim 9, wherein said immunogenic composition comprises at least one antigenic component of Equine Influenza Virus.

13. The immunogenic composition according to claim 12, wherein said Equine Influenza Virus is selected from the group consisting of Influenza/Equine-2/Ohio/03, Influenza/Equine-2/KY/95, Influenza/Equine-2/New Market/2/93, and combinations thereof.

14. The immunogenic composition according to claim 12, wherein said Equine Influenza Virus is selected from the group consisting of the strains deposited with the ATCC under accession Nos. PTA-9522, PTA-9523 or PTA-9524 and combinations thereof.

15. The immunogenic composition according to claim 9, wherein said Western Equine Encephalomyelitis Virus is the strain deposited with the ATCC under accession number PTA-9410.

16. The immunogenic composition according to claim 9, wherein said Eastern Equine Encephalomyelitis Virus is the strain deposited with the ATCC under accession number PTA-9412.

17. A method for reducing the incidence or lessening the severity of clinical symptoms associated with or caused by West Nile Virus in an equine or a herd of equines comprising the step of administering the immunogenic composition according to claim 1 to an animal in need thereof.

18. The method according to claim 17, wherein said immunogenic composition provides duration of immunity of at least 12 months after the administration of one dose.

\* \* \* \* \*

UNITED STATES PATENT AND TRADEMARK OFFICE
CERTIFICATE OF CORRECTION

Page 1 of 1

PATENT NO. : 8,821,889 B2
APPLICATION NO. : 12/937504
DATED : September 2, 2014
INVENTOR(S) : Hennessy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 537 days.

Signed and Sealed this
Twenty-fifth Day of August, 2015

Michelle K. Lee
*Director of the United States Patent and Trademark Office*